US009730999B2

(12) United States Patent
Hanon et al.

(10) Patent No.: US 9,730,999 B2
(45) Date of Patent: Aug. 15, 2017

(54) ADJUVANTED INFLUENZA VIRUS COMPOSITIONS

(71) Applicant: GlaxoSmithKline Biologicals, sa, Rixensart (BE)

(72) Inventors: Emmanuel Jules Hanon, Rixensart (BE); Jean Stephenne, Rixensart (BE)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 14/465,055

(22) Filed: Aug. 21, 2014

(65) Prior Publication Data
US 2014/0363474 A1    Dec. 11, 2014

Related U.S. Application Data

(60) Division of application No. 13/096,180, filed on Apr. 28, 2011, now abandoned, which is a continuation of application No. 11/909,388, filed as application No. PCT/EP2006/002837 on Mar. 21, 2006, now abandoned.

(51) Int. Cl.
| C07K 14/00 | (2006.01) |
| A61K 39/145 | (2006.01) |
| A61K 39/39 | (2006.01) |
| A61K 39/12 | (2006.01) |
| C12N 7/00 | (2006.01) |
| A61K 39/00 | (2006.01) |

(52) U.S. Cl.
CPC ............ *A61K 39/145* (2013.01); *A61K 39/12* (2013.01); *A61K 39/39* (2013.01); *C12N 7/00* (2013.01); *A61K 2039/55* (2013.01); *A61K 2039/55511* (2013.01); *A61K 2039/55566* (2013.01); *A61K 2039/55572* (2013.01); *A61K 2039/57* (2013.01); *A61K 2039/70* (2013.01); *C12N 2760/16034* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

| 4,436,727 A | 3/1984 | Ribi |
| 4,866,034 A | 9/1989 | Ribi |
| 5,149,531 A | 9/1992 | Youngner |
| 5,376,369 A | 12/1994 | Allison et al. |
| 5,667,784 A | 9/1997 | Lammert et al. |
| 5,858,368 A | 1/1999 | Garcon et al. |
| 5,916,879 A | 6/1999 | Webster |
| 5,969,109 A | 10/1999 | Bona et al. |
| 6,146,632 A | 11/2000 | Momin et al. |
| 6,372,223 B1 | 4/2002 | Kistner et al. ............ 424/209.1 |
| 6,372,227 B1 | 4/2002 | Garcon et al. ............ 424/283.1 |
| 6,451,325 B1 | 9/2002 | Van Nest et al. |
| 6,623,739 B1 | 9/2003 | Momin et al. ............ 424/184.1 |
| 6,861,410 B1 | 3/2005 | Ott et al. |
| 7,029,678 B2 | 4/2006 | Momin et al. |
| 7,238,349 B1 | 7/2007 | D'Hondt et al. |
| 7,316,813 B2 | 1/2008 | Eichhorn |
| 2003/0095974 A1 | 5/2003 | Garcon et al. |
| 2004/0047869 A1 | 3/2004 | Garcon et al. |
| 2004/0071734 A1 | 4/2004 | Garcon et al. |
| 2006/0115489 A1 | 6/2006 | Birkett et al. |
| 2007/0141078 A1* | 6/2007 | D'Hondt et al. .......... 424/204.1 |
| 2008/0171063 A1 | 7/2008 | Hanon et al. |
| 2008/0181911 A1* | 7/2008 | Hanon et al. ............. 424/206.1 |
| 2009/0028903 A1 | 1/2009 | Hanon et al. |
| 2009/0081253 A1 | 3/2009 | Hanon et al. |
| 2009/0136543 A1* | 5/2009 | Ballou et al. ............. 424/206.1 |
| 2009/0263422 A1 | 10/2009 | Hanon et al. ............. 424/209.1 |
| 2010/0183667 A1 | 7/2010 | Ballou et al. |
| 2010/0189741 A1 | 7/2010 | Ballou et al. ............. 424/202.1 |
| 2010/0260797 A1* | 10/2010 | Hanon ....................... 424/209.1 |
| 2011/0123568 A1 | 5/2011 | Hanon et al. ............. 424/210.1 |
| 2011/0243987 A1* | 10/2011 | Hanon et al. ............. 424/209.1 |
| 2011/0287054 A1* | 11/2011 | Hanon et al. ............. 424/209.1 |

FOREIGN PATENT DOCUMENTS

| EP | 0113 665 | 6/1984 |
| EP | 0399643 B | 7/1994 |
| EP | 0870508 | 10/1998 |
| JP | 09-506887 | 7/1997 |
| JP | 11-21253 | 1/1999 |
| WO | WO 90/02562 | 3/1990 |
| WO | WO 90/14837 | 12/1990 |
| WO | WO 91/13261 | 9/1991 |
| WO | WO 92/16231 | 10/1992 |
| WO | WO 93/19780 | 10/1993 |
| WO | WO 94/19013 | 9/1994 |
| WO | WO 95/11700 | 5/1995 |
| WO | WO 95/17210 | 6/1995 |
| WO | WO 95/22989 | 8/1995 |
| WO | WO 95/26204 | 10/1995 |

(Continued)

OTHER PUBLICATIONS

Kodihalli et al. Selection of a single amino acid substitution in the hemagglutinin molecule by chicken eggs can render influenza A virus (H3) candidate vaccine ineffective. J Virol. Aug. 1995;69(8):4888-97.*

(Continued)

Primary Examiner — Michelle S Horning
(74) Attorney, Agent, or Firm — Natalie A. Lissy

(57) ABSTRACT

The present invention relates to influenza vaccine formulations and vaccination regimes for immunising against influenza disease, their use in medicine, in particular their use in augmenting immune responses to various antigens, and to methods of preparation. In particular, the invention relates to multivalent influenza immunogenic compositions comprising an influenza antigen or antigenic preparation thereof from at least two influenza virus strains, at least one strain being associated with a pandemic outbreak or having the potential to be associated with a pandemic outbreak, in combination with an oil-in-water emulsion adjuvant.

21 Claims, 22 Drawing Sheets

(56) References Cited

FOREIGN PATENT DOCUMENTS

Figure 1G:
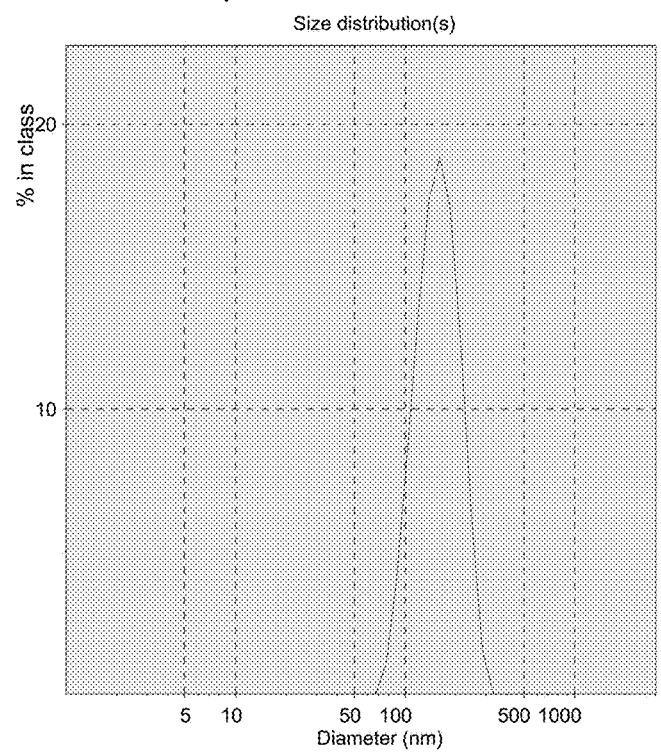

| | | | |
|---|---|---|---|
| WO | WO 98/56414 | 12/1998 | |
| WO | WO 99/11241 | 3/1999 | |
| WO | WO 99/12565 | 3/1999 | |
| WO | WO 99/34850 | 7/1999 | |
| WO | WO 99/56776 | 11/1999 | |
| WO | WO 00/15251 | 3/2000 | |
| WO | WO 00/47222 | 8/2000 | |
| WO | WO 00/50006 | 8/2000 | |
| WO | WO 01/22992 * | 4/2001 | ............ A61K 39/00 |
| WO | WO 01/22992 | 5/2001 | |
| WO | WO 01/54719 | 8/2001 | |
| WO | WO 01/59130 | 8/2001 | |
| WO | WO 02/32454 | 4/2002 | |
| WO | WO 02/38176 | 5/2002 | |
| WO | WO 02/074336 | 9/2002 | |
| WO | WO 02/097072 | 12/2002 | |
| WO | WO 03/011223 | 2/2003 | |
| WO | WO 03/084467 | 10/2003 | |
| WO | WO 03/099195 | 12/2003 | |
| WO | WO 2004/075829 | 9/2004 | |
| WO | WO 2005/107797 | 11/2005 | |
| WO | WO 2008/009309 | 1/2006 | |
| WO | WO 2006/100109 | 9/2006 | |
| WO | WO 2006 100110 | 9/2006 | |
| WO | WO 2007/006939 | 1/2007 | |
| WO | WO 2007/052155 | 5/2007 | |
| WO | WO 2007/080308 | 7/2007 | |
| WO | WO2007/130330 | 11/2007 | |
| WO | WO 2008/043774 | 4/2008 | |

OTHER PUBLICATIONS

Ott et al. Enhancement of humoral response against human influenza vaccine with the simple submicron oil/water emulsion adjuvant MF59. Vaccine. Nov. 1995;13(16):1557-62.*
Levandowski, et al., Cross-Reactive Antibodies Induced by a Monovalent Influenza B Virus Vaccine, 1991, Journal of Clinical Microbiology, vol. 29, No. 7, pp. 1530-1532.
Lu, et al., "Cross-protective immunity in mice induced by live-attenuated or inactivated vaccines against highly pathogenic influenza A (H5N1) viruses", Vaccine, 24:6588-6593 (2006).
Bloom, et al., "Permissive secondary mutations enable the evolution of influena oseltamivir resistance", Science, 328:1272-1274, 2010.
Encarta Dictonary, <http://encarta.msn.com/encnet/features/dictonary/DictonaryResults.aspx?refid=1861736387>, accessed on Jul. 16, 2008.
European Centre for Disease Prevention and Control (ECDC) Technical Report, Expert Advisory Groups on Human H5N1 Vaccines, Aug. 2007.
Goji, et al., "Immune Responses of healthy subjects to a single dose of intramusclar inactivated influenza A/Vietnam/1203/2004 (H5N1) vaccine after priming with an antigenic variant", The Journal of Infectious Diseases 198-635-41, 2008.
Govorkova, et al., "Cross-protection of mice immunized with different influenza A(H2) strains and challenged with viruses of the same HA subtype", Acta Virologica, 4:251-257, 1997.
Govorkova, et al., "Immunization with reverse-genetics-produced H5N1 influenza vaccine protects ferrets aganist homologous and heterologous challenge", The Journal of Infectious Diseases 194:159-67, 2006.
Influenza team (ECDC), "Human influenza A/H5N1 ("pre-pandemic") vaccines: informing policy development in Europe", Eurosurveillance, vol. 12, issue 38, Sep. 20, 2007, Available at : http://www.eurosurveillance.org/ViewArticle.
aspx?ArticleId=3272uh.
Kistner, et al., "Cell culture (Vero) derived whole virus (H5N1) vaccine based on wild-type virus strain induces cross-protective immune responses", Vaccine 25:6028-6036, 2007.
Li, et al., Development of vaccines aganist Influenza A Virus (H5N1), Chang Gung Med J.,30(4):294-304, 2007.

NIH press release "Updates on Pandemic Flu Vaccine Trials to be presented at 44th Annual IDSA meeting", NIH News dated Oct. 12, 2006.
Stephenson, et al., "Are we ready for pandemic influenza H5N1?", Expert Rev. Vaccines, 4(2):151-155, 2005.
Treanor, et al., "Safety and immunogenicity of a recombinant hemagglutinin vaccine for H5 influenza in humans", Vaccine 19:1732-1737, 2001.
Early Trial Show H5N1 Influenza Vaccine Safe and Effective in Humans at Low Doses, *The Lancet Press Release*, 2006.
Edwards, "Safety efficacy and use of inactivated influenza vaccine in children", Proceedings, Advanced Studies in Medicine, 2:301-305 (2002).
Meiklejohn, et al., "Antigenic drift and efficacy of influenza virus vaccines, 1976-1977", The Journal of Infectious Diseases, 138:618-624 (1978).
Treanor, "Influenza vaccine Outmaneuvering antigenic shift and drift", The New England Journal of Medicine, 350:218-220 (2004).
Tumpey et al. Pathogenicity of Influenza Viruses with Genes from the 1918 Pandemic Virus: Functional Roles of Alveolar Macrophages and Neutrophils in Limiting Virus Replication and Mortality in Mice. J. Viral. Dec. 2005 vol. 79 No. 23 14933-14944.
Stephenson et al. Influenza: vaccination and treatment. ERJ Jun. 1, 2001 vol. 17 No. 6 1282-1293.
Yin, "Early Trial Show H5N1 Influenza Vaccine Safe and Effective in Humans at Low Doses," *The Lancet Press Release*, 2006.
Dalsgaard , et al, "Saponin adjuvants", Archiv. für die gesamte Virusforschung, vol. 44, Springer Verlag, Berlin, p. 243-254 (1974).
Edwards, et al., "Safety, Efficacy, and Use of Inactivated influenza vaccine in children", Advanced Studies In Medicine, 2:301-305 (2002).
GlaxoSmithKline, "Briefing document: GSK's strategy against pandemic threat: Pre-pandemic and pandemic vaccines", May 2006.
Nakajima, et al., "Genetic Relationship between the HA genes of typs A influenza viruses isolated in off-seasons and later epidemic seasons", Epidemiol. Infect. 106, 383-395 (1991).
Sabroe, et al, "Toll-Like Receptors in Health and Disease: Complex Questions Remain," J. Immunol., p. 1630 (2003).
Iinuma, et al., "Characteristics of cytotoxic T lynphocytes directed to influenza virus haemagglutinin elicted by immunization with muramyldipeptide-influenza lipsome vaccine", Scand J Immunol., Jan; 41(1):1-10 (1995) Abstract Only.
Rieberdy, et al., "Protection aganist a Lethal Avian Influenza A Virus in a Mammalian System", Journal of Virology, 73(2):1453-1459 (1999).
Rimmelzwaan, et al., "ISCOM Vaccine Induced Protection Aganist a Lethal Challenge with a Human H5N1 Influenza Virus", Vaccine, 17: 1355-1358 (1999).
Ruat et al., "Vaccination of Macaques with Adjuvanted Formula in-Inactivated Influenza A Virus (H5N1) Vaccines . Protection aganist H5N1 Challenge without Disease Enhancement", Journal of Virology, 2565-2569 (Mar. 2008).
Ruf, et al., "Open randomized study to compare the immunogenicity and reactiogenicity of an influenza split vaccine with an MG59-adjuvanted subunit vaccine and a virosome-based subunit in elderly," Infection, vol. 32, No. 4, pp. 191-198, 2004.
Rumke, et al., "Safety and reactogenicity profile of an adjuvanted H5N1 pandemic vaccine candidate in adults within a phase III safety trial", Vaccine, 26:2378-88 (2008).
Squarcione, et al., "Comparison of the reactiogenicity and immunogenicity of a split and a subunit-adjuvanted influenza vaccine in elderly," Vaccine, vol. 21, pp. 1268-1274, 2003.
Stephenson, et al., "Controning the avian influenza threat: vaccine development for a potential pandemic", Lancet Infectious Disease, 4:499-509 (2004).
Stephenson, et al., "Boosting Immunity of influenza HSN1 with MF59-adjuvanted H5N3 A/Duck/Singapore/97 vaccine in a primed human population," Vaccine, vol. 21, pp. 1687-1693, 2003.
Stephenson, et al., "Cross-reactivity to highly pathogenic avian influenza H5N1 viruses after vaccination with non-adjuvanted and MF59-adjuvanted influenza A/Duck/Singapore/97 (H5N3) vaccine, a potential priming strategy," J. of Infect. Dis., vol. 191, pp. 1210-1215, 2005.

(56) References Cited

OTHER PUBLICATIONS

Stephenson, et al., "Development of Vaccines Against influenza H5," The Lancet, 2006. 6:458-460.
Stephenson, et al., "Safety and antigenicity of whole virus and subunit influenza A/Hong Kong/1073/99 (H9N2) vaccine in healthy adults: phase I randomised trial," Lancet, vol. 362, pp. 1959-1966, 2003.
Stephenson, I., "H5N1 Vaccines: How Prepared are we for a Pandemic?" The Lancet, 2006, 368:965-966.
Tamura, et al., "Mechanisms of Broad Cross-Protection Provided by Influenza Virus infection and Their Application to Vaccines", Jpn J. of Infect. Dis., 58: 195-207 (2005).
Thomas, et al., "Cell-mediated protection in influenza infection," Influenza Pathogenesis, vol. 12, No. 1, pp. 48-54, 2006.
Treanor, et al., "Safety and Immunogenicity of an Inactivated Subvirion Influenza A (H5N1) Vaccine", The New England Journal of Medicine, 354(13).1343-1351 (2006).
Walls, at al., "Characterization and evaluation of monoclonal antibodies developed for typing influenza A and influenza B viruses," J. Clin. Microbiol , vol. 23, No. 2, pp. 240-245 (1986).
White, et al., Characterization of Aluminum-Containing Adjuvants, Developmental Biology, 2000, 103:217-228.
Wood, et al., "A Sensitive, single-radial diffusion autoradiographic zone size enhancement technique form the assay of influenza haemagglutinin," J. Gen Virol., vol. 47, pp. 355-363 (1980).
Yalamati, et al., "Synthetic monophosphoryl lipid A. A promising TLR 4 ligand," Abstracts of Papers American Chemical Society, vol. 229, No. Part 1, 2005.
Zahn, et al. "CD4 Help-Independent Induciton of Cytotoxic CD8 Cells to Allogeneic P815 Tumor Cells is absolutely dependent on costimulaton", J. Immunol., 165:3612-3619 (2000).
Wood et al., "International collaborative study of single radial dillusion and immunoelectrophoresis techniques for the assay ol haemagglutinin antigen of influenza virus". J. Biol. Stand. 9 (1981) 317.
Wood et al., "An improved single radial immunodiffusion technique for the assay of influenza haemagglutinin antigen: adaption for potency determincation of inactivated whole virus and subunit vaccines", J. Biol. Stand. 5 (1977) 237.
Kistner, et al., "Development of a Vero Cell-Derived influenza Whole Virus Vaccine," Developments in Biological Standardization, 1999, 98:101-110.
Puig-Barbera et al., "Effectiveness of the MF592004", Vaccine 23, 283-259 (2004).
Rinella, et al., "Effect of Anions on Model Aluminum-Adjuvant-Containing Vaccines," Journal of Colloid and Interface Science, 1996, 172:121-130.
Vaccines for pandemic influenza, summary report. Nov. 11-12, 2004 World Health Organization (WHO).
Ansaldi, et al., "Cross-protection by MF59TM-adjuvanted vaccine • Neutralizing and haemagglutination-inhibiting antibody activity aganist A (H3N2) drifted influenza viruses," Vaccine, vol. 20, pp. 1525-1529 (2008).
Atmar, et al., "Safety and Immunogenicity of Nonadjuvanted and MF59-Adjuvanted influenza A/H9N2 Vaccines Preparations", Clinical Infectious Diseases, 43:1135-1142 (2006).
Banzhoff, et al., "A new MF59-adjuvanted influenza vaccine enhances the immune response in the elderly with chronic diseases: result from an immunogenicity meta-analysis," Gerontology, vol. 49, pp. 177-184, 2003.
Baras, et al., "Cross-Protection aganist Lethal H5N1 Challenge in Ferrets with an Adjuvanted Pandemic influenza Vaccine", PLoS One, Issue 1, e1404: 1-4 (2006).
Bardiya. et al., "Influenza vaccines: recent advances in production technologies", Applied Microbiology and Biotechnology. 67:299-305(2005).
Bernstein, et al., "Effects of Adjuvants on the Safety and Immunogenicty of an Avian Influenza H5N1 Vaccine in Adults", The Journal of Infectous Diseases, vol. 197 pp. 667-675 (2008).

Boger, et al., "Subcutaneous and Intradermal Vaccination with Asian influenza Vaccine," J.A.M.A., 1957, 165(13):1687-1689.
Bresson, et al., "Safety and immunogenicity of an inactivated split-virion influenza A/Vietnam/1194/2004 H5N1 vaccine phase I randomized trial". The Lancet. 2006:367 (9523):1657.
Brown. et al., "CD4 cell response to influenza infection," Seminars in Immunology, vol. 16, pp. 171-177, 2004.
Chaloupka, et al., "Comparative Analysis of Six European Influenza Vaccines", Eur J. Clin. Microbiol. Infect. Dis., 15(2):121-127 (1996).
Cinatl, et al., "The threat of avian influenza A (H5N1). Part IV: development of vaccines", Medical Microbiology and Immunology, 196:213-225 (2007).
Coller, et al., "Development of Primed Animal Models to Assess the Immunogenicity of Influenza Vaccines", Research and Development, Viral Vaccines, GlaxoSmithKline Biologicals, Rue de l'Institut 89, 1330 Rixensart, Belgium, 1 page.
Couch, et al., "Improvement of Inactivated Influenza Virus Vaccines", The Journal of Infectious Diseases, 176:S38-S44 (1997).
De Donato, at al., "Safety and immunogenicity of MF59-adjuvanted influenza vaccine in the elderly," Vaccine, vol. 17, pp. 3094-3101, 1999.
Del Giudice, et al., "An MF59-adjuvanted inactivated influenza vaccine containing A/Panama/199 (H3N2) Induced broader serological protection against heterovariant influenza virus strain A/Fujian/2002 than a subunit and a split influenza vaccine,"Vaccine, vol. 24, pp. 3063-3065, 2006.
Frey, et al., "Comparison of the safety, tolerability and immunogenicity of a MF59-adjuvanted influenza vaccine and a non-adjuvanted influenza vaccine in non-elderly adults," Vaccine, vol. 21, pp. 4234-4237, 2003.
Fukuda, et al., "Inactivated Influenza Vaccines," Vaccines, Fourth Edition, Plotkin, Orenstetin, Chapter 17, pp. 339-370 (2004).
Garçon, et al., "GlaxoSmithKline Adjuvant Systems in Vaccines: Concepts, Achievements and Perspectives", Expert Rev. Vaccines, 6(5):723-739 (2007).
Gasparini, et al., "Increased Immunogenicity of the MF59-adjuvanted vaccine compared to a conventional subunit vaccine in elderly subjects," European J. of Epidemiology, vol. 17, pp. 135-140, 2001.
Gelder, et al., Six unrelated HLA-DR-matched adults recognize identical CD4+ T Cell epitopes from influenze A haemagglutinin that are not simple peptides with high HLA-DR binding affinities, Int Immunol (1998) 10(2):211-22.
Gelder, et al., "Human CD4+ T-cell repertoire of responses to influenza virus hemagglutinin after recent natural infection", J Virol. 1995 69(12):7497-506).
Gelder, et al., "Human CD4+ T-cell recognition of Influenza A virus hemagglutinin after subunit vaccination", J Virol. 70(7):4787-90 (1996).
Goji, "Immune Responses of Healthy Subjects to a Single Dose of Intramuscular Inactivated Influenza A", Abstract LB-4, 44th Annual Meeting of IDSA, Oct. 12-15, 2006.
Guarnaccia, et al., "Comparative Immunogenicity-Reactogenicity dose-response study of influenza vaccine", Annals of Allergy, US, American College of Allergy and Immunology, vol. 65, No. 3, pp. 218-221 (1990).
Hehme, et al., "Immunogenicity of a Monovalent, Aluminum-Adjuvanted Influenza Whole Virus Vaccine for Pandemic Use", Virus Research, 103: 163-171 (2004).
Hehme, et al., "Pandemic Preparedness: Lessons Learnt from: H2N2 and H9N2 Candidate Vaccines", Med. Microbiology Immunol., 191: 203-208 (2002).
Hehme, "GSK's Pandemic Flu Vaccine Project: Evaluation of H2N2 and H9N2 Candidate Vaccines" GlaxoSmithKline Biologicals, Who Meeting on Development and Evaluation of Influenza Pandemic Vaccines, Geneva, 2005, pp. 1-20.
Iorio, et al., "Antibody responses and HIV-1 viral load in HIV-1-seropositive subjects immunised with either the MF59-adjuvanted influenza vaccine or a conventional non-adjuvanted subunit vaccine during highly active antiretroviral therapy," Vaccine, vol. 21, pp. 3629-3637, 2003.

(56) References Cited

OTHER PUBLICATIONS

Johansen, et al., "Toll-like receptor ligands as adjuvants in allergen-specific immunotherapy", Clin. Exp. Allergy, 35(12):1591-8 (2005).
Keitel et al., "Preparing for a possible pandemic : Influenza A/H5N1 vaccine development", Current Opinion in Pharmacology, vol. 7 : 484-490 (2007).
Kistner, et al., "Development of a Mammalian Cell (Vero) Derived Candidate Influenza Virus Vaccine", Vaccine, 16(9/10)960-966 (1998).
Künzel, et al., "Kinetics of humoral antibody response to trivalent inactivated split influenza vaccine in subjects previously vaccinated or vaccinated for thr first time," Vaccine, vol. 14, No. 12, 1996.
La Montagne, et al., "Summary of Clinical Trials of Inactivated Influenza Vaccine," Reviews of Infectous Disease, 1983, 5(4):723-736.
Lee, et al., "CD4 T Cell-Independnet antibody response promotes resolution of primary influenza infection and helps to prevent reinlsetion", J. Immunol . 175:5827-5838 (2005).
Leroux-Roels, "Prepandemic H5N1 Influenza Vaccine Adjuvanted with AS03: A Review of the Pre-Clinical and Clinical Data", Expert Opin. Biol. Ther., 9(8):1-15 (2009).
Leroux-Roels, et al., "Antigen Sparing and Cross-Reactive Immunity with an Adjuvanted rH5N1 Prototype Pandemic Influenza Vaccine: a Randomized Controlled Trial", The Lancet, 370:580-589 (2007).
Leroux-Roels, et al., "Broad Clade 2 Cross-Reactive Immunity by an Adjuvanted Clade 1 rH5N1 Pandemic Influenza Vaccine", PLoS One, 3(2):1-5 (2008).
Lin, et al., "Safety and Immunogenicity of an Inactivated Adjuvanted Whole-Virion Influenza A (H5N1) Vaccine: A Phase I Randomised Controlled Trial," The Lancet, 2006, 368:991-997.
Lu, et al., "A mouse model for the evaluation of pathogenesis and immunity to Influenza A (H5N1) viruses isolated from humans", Journal of Virology, vol. 73, No. 7, pp. 5903-5911 (1999).
Merten, et al., "Production of Influenza Virus in Cell Cultures for Vaccine Preparation," Advances in Experimental Medicine and Biology, 1996, 397:141-151.
Murasko, et al., "Role of humoral and cell-mediated immunity in protection from influenza disease after immunization of healthy elderly," Experimental Gerontology, vol. 37, pp. 427-433, 2002.
Nichol, et al., "Vaccines for seasonal and pandemic influenza," J. of Infect. Dis., Vaccines and Prevention of Influenza, vol. 194, pp. S111-1118, 2006.
Nichol, et al., Influenza vaccination and reduction in hospitalizatons for cardiac disease and stroke among the elderly, New England Journal of Medicine, 348:1322-1332 (2003).
Nicholson, et al., "Safety and Antigenicity of Non-Adjuvanted and MF59-Adjuvanted Influenza A/Duck/Singapore/97 (H5N3) Vaccine: A Randomized Trial of Two Potential Vaccines Against H5N1 Influenza", The Lancet, 357.1937-1943 (2001).
Nicholson, et al., "Clinical Studies of Monovalent Inactivated Whole Virus and Subunit A/USSR/77 (H1N1) Vaccine: Serological Responses and Clinical Reactions", Journal of Biological Standardization, 7:123-136 (1979).
Offit, et al., "Addressing Parents' Concerns: Do Vaccines Contain Harmful Preservatives, Adjuvants, Additives, or Residuals?" Pediatrics, 2003, 112(6):1394-1401.
Paschke, et al., Increased immunogenicity with an MF59-adjuvanted Journal of Preventive Medicine and Hygiene, 44:78-84 (2003).
Patel et al., "A randomized open-label phase I clinical trial comparing the safety, reactogeneicity, and immunogenicity of booster immunization with inactivated influenza A/H5N1 vaccine administered by the intradermal (ID) or intramuscular (IM) route among healthy adults". Abstract LB-5, 44th Annual Meeting of IDSA, Oct. 12-15, 2006.
Pooda, "The adjuvanted influenza vaccines with novel adjuvants: experience with the MF59-adjuvanted vaccine," Vaccine, vol. 19, pp. 2878-2880, 2001.
Baras, et al., "Cross-protection in ferrets after vaccination with adjuvanted influenza split vaccine", IVW Oct. 18-20, 2006, Vienna, Austria.
Barr, et al., "Circulation and antigenic drift in human influenza B viruses in SE Asia and Oceania since 2000", Communicable Diseases Intelligence, 30(3):350-357 (2006).
EMEA/28737312008, "CHMP Assessment Report for Prepandrix" (2008).
EMEA/CHMP/62736/2008 Committee for Medicinal Products for Human Use Summary of Positive Opinion* for Prepandrix, Feb. 2008.
Kojimahara, et al., "Cross-reactivity of influenza A (H3N2) hemagglutination-inhibition antibodies induced by an inactivated influenza vaccine", Vaccine, 24:5966-5969 (2006).
Leroux-Roels, et al., "Adjuvanted influenza vaccines improve anti-influenza humoral immunity impaired in elderly", IVW, Oct. 18-20, 2006, Vienna Austria.
Lipatov, et al., "Cross-protectiveness and immunogenicity of influenza A/Duck/Singapore/3/97(H5) vaccines against infection with A/Vietnam/1203/04(H5N1) virus in ferrets", JID, 194:1040-1043, (2006).
McElhaney, et al., "T Cell responses are better correlates of vaccine protection in the elderly", The Journal of Immunology, 176:6333-6339 (2006).
Oh, et al., "Local and systemic influenza haemagglutinin-specific antibody responses following aerosol and subcutaneous administration of inactivated split influenza vaccine", Vaccine, 10(8):506-511 (1992).
Salerno-Goncaives, et al., "Cell-mediated immunity and the challenges for vaccine development", Trends in Microbiology, 14(12):536-542 (2006).
Sanger, et al., "Immunogenicity and persistence of response to an alum-adjuvanted monovalent (H9N2) whole virus influenza vaccine in healthy adults aged 60 years and older", IVW Oct. 18-20, 2006, Vienna, Austria.
WHO "Report of the second meeting on the development of influenza vaccines that induce broad-spectrum and long lasting immune responses, Geneva Switzerland Dec. 6-7, 2005", Vaccine 24:4897-4900 (2006).
WHO "What is the pandemic (H1N1) 2009 virus?", Feb. 24, 2010, http://www.who.int/csr/disease/swineflu/frequently_asked_questions/about_disease/en/ . . . Dec. 3, 2010.
CDC Avian Influenza (Bird Flu) fact sheet, 2005.
Prepandrix suspension and emulsion for injection: Summary of product characteristics. Date of first authorization: May 16, 2008.
Blow, "Polyvalent Influenza Vaccine in General Practice", Br. Med. J. 2:943 (1964).
Eigaku No Ayumu, "Generation and Maintenance of Memory T Cells", J Clin Exp Med 211:628 (2004) (in Japanese) and English translation of JP office action (dated Dec. 13, 2011).
Kodihalli et al, "Selection of a Single Amino Acid Substitution in the Hemagglutinin Molecule by Chicken Eggs Can Render Influenza A Virus (H3) Candidate Vaccine Ineffective", J. Virology 69:4888 (1995).
Leroux-Roels, et al., "Reactogenicity and safety of adjuvanted influenza vaccines administered in elderly", IVW, Oct. 18-20, 2006, Vienna Austria.

* cited by examiner

FIG. 1A
Dilution A
Rec22

| Size(nm) | Intensity | Volume |
|---|---|---|
| 27.9 | 0.0 | 0.0 |
| 32.2 | 0.0 | 0.0 |
| 37.3 | 0.0 | 0.0 |
| 43.1 | 0.0 | 0.0 |
| 49.8 | 0.0 | 0.0 |
| 57.6 | 0.0 | 0.0 |
| 66.6 | 0.0 | 1.1 |
| 77.0 | 1.0 | 4.8 |
| 89.1 | 4.0 | 10.3 |
| 103.0 | 8.4 | 14.7 |
| 119.1 | 13.3 | 16.6 |
| 137.7 | 17.3 | 15.9 |
| 159.3 | 18.8 | 13.4 |
| 184.2 | 17.1 | 10.2 |
| 212.9 | 12.3 | 7.0 |
| 246.2 | 6.2 | 4.0 |
| 284.7 | 1.5 | 1.7 |
| 329.2 | 0.0 | 0.4 |
| 380.6 | 0.0 | 0.0 |
| 440.1 | 0.0 | 0.0 |
| 508.9 | 0.0 | 0.0 |
| 588.5 | 0.0 | 0.0 |
| 680.4 | 0.0 | 0.0 |
| 786.8 | 0.0 | 0.0 |

Peak Analysis by intensity

| Peak | Area | Mean | Width |
|---|---|---|---|
| 1 | 100.0 | 160.0 | 122.3 |

Peak Analysis by volume

| Peak | Area | Mean | Width |
|---|---|---|---|
| 1 | 100.0 | 141.3 | 116.6 |

Peak Analysis by number

| Peak | Area | Mean | Width |
|---|---|---|---|
| 1 | 100.0 | 109.8 | 62.5 |

FIG. 1B
Rec23

| Size(nm) | Intensity | Volume |
|---|---|---|
| 23.0 | 0.0 | 0.0 |
| 27.0 | 0.0 | 0.0 |
| 31.7 | 0.0 | 0.0 |
| 37.3 | 0.0 | 0.0 |
| 43.9 | 0.0 | 0.0 |
| 51.5 | 0.0 | 0.0 |
| 60.6 | 0.0 | 1.2 |
| 71.2 | 1.1 | 5.3 |
| 83.7 | 3.8 | 10.9 |
| 98.4 | 8.0 | 15.0 |
| 115.6 | 13.0 | 16.4 |
| 135.9 | 17.2 | 15.4 |
| 159.7 | 19.2 | 12.9 |
| 187.7 | 17.7 | 9.9 |
| 220.7 | 12.8 | 6.9 |
| 259.4 | 6.1 | 4.1 |
| 304.8 | 1.2 | 1.8 |
| 358.3 | 0.0 | 0.4 |
| 421.1 | 0.0 | 0.0 |
| 495.0 | 0.0 | 0.0 |
| 581.8 | 0.0 | 0.0 |
| 683.8 | 0.0 | 0.0 |
| 803.7 | 0.0 | 0.0 |
| 944.6 | 0.0 | 0.0 |

Peak Analysis by intensity

| Peak | Area | Mean | Width |
|---|---|---|---|
| 1 | 100.0 | 161.7 | 135.3 |

Peak Analysis by volume

| Peak | Area | Mean | Width |
|---|---|---|---|
| 1 | 100.0 | 139.8 | 128.6 |

Peak Analysis by number

| Peak | Area | Mean | Width |
|---|---|---|---|
| 1 | 100.0 | 102.0 | 59.8 |

FIG. 1C
Rec24

| Size(nm) | Intensity | Volume |
|---|---|---|
| 20.2 | 0.0 | 0.0 |
| 24.0 | 0.0 | 0.0 |
| 28.6 | 0.0 | 0.0 |
| 34.0 | 0.0 | 0.0 |
| 40.4 | 0.0 | 0.0 |
| 48.0 | 0.0 | 0.0 |
| 57.1 | 0.0 | 0.5 |
| 67.9 | 0.4 | 3.5 |
| 80.7 | 2.9 | 9.5 |
| 95.9 | 7.6 | 15.4 |
| 114.0 | 13.7 | 18.1 |
| 135.6 | 19.2 | 17.4 |
| 161.2 | 21.3 | 14.4 |
| 191.7 | 18.9 | 10.6 |
| 227.9 | 12.0 | 6.7 |
| 271.0 | 3.9 | 3.2 |
| 322.2 | 0.0 | 0.8 |
| 383.1 | 0.0 | 0.0 |
| 455.5 | 0.0 | 0.0 |
| 541.5 | 0.0 | 0.0 |
| 643.9 | 0.0 | 0.0 |
| 765.5 | 0.0 | 0.0 |
| 910.2 | 0.0 | 0.0 |
| 1082.2 | 0.0 | 0.0 |

Peak Analysis by intensity

| Peak | Area | Mean | Width |
|---|---|---|---|
| 1 | 100.0 | 160.2 | 130.1 |

Peak Analysis by volume

| Peak | Area | Mean | Width |
|---|---|---|---|
| 1 | 100.0 | 139.1 | 126.2 |

Peak Analysis by number

| Peak | Area | Mean | Width |
|---|---|---|---|
| 1 | 100.0 | 104.2 | 63.0 |

FIG. 1D
Dilution B
Rec28

| Size(nm) | Intensity | Volume |
|---|---|---|
| 22.2 | 0.0 | 4.1 |
| 26.2 | 0.2 | 9.7 |
| 30.9 | 0.1 | 7.1 |
| 36.4 | 0.0 | 1.5 |
| 42.9 | 0.0 | 0.0 |
| 50.5 | 0.0 | 0.0 |
| 59.6 | 0.0 | 0.0 |
| 70.2 | 0.0 | 1.2 |
| 82.7 | 1.8 | 5.1 |
| 97.5 | 6.2 | 10.4 |
| 114.9 | 13.1 | 14.3 |
| 135.5 | 20.1 | 15.3 |
| 159.7 | 23.5 | 13.4 |
| 188.2 | 20.9 | 9.9 |
| 221.8 | 12.0 | 5.6 |
| 261.4 | 2.1 | 2.0 |
| 308.1 | 0.0 | 0.3 |
| 363.2 | 0.0 | 0.0 |
| 428.1 | 0.0 | 0.0 |
| 504.5 | 0.0 | 0.0 |
| 594.6 | 0.0 | 0.0 |
| 700.9 | 0.0 | 0.0 |
| 826.1 | 0.0 | 0.0 |
| 973.6 | 0.0 | 0.0 |

Peak Analysis by intensity

| Peak | Area | Mean | Width |
|---|---|---|---|
| 1 | 99.7 | 159.3 | 111.5 |

Peak Analysis by volume

| Peak | Area | Mean | Width |
|---|---|---|---|
| 1 | 22.5 | 27.6 | 10.3 |
| 2 | 77.5 | 143.3 | 116.1 |

Peak Analysis by number

| Peak | Area | Mean | Width |
|---|---|---|---|
| 1 | 96.4 | 27.2 | 9.8 |
| 2 | 3.6 | 115.4 | 68.8 |

FIG. 1E
Rec29

| Size(nm) | Intensity | Volume |
|---|---|---|
| 28.1 | 0.0 | 0.0 |
| 32.5 | 0.0 | 0.0 |
| 37.6 | 0.0 | 0.0 |
| 43.4 | 0.0 | 0.0 |
| 50.2 | 0.0 | 0.0 |
| 58.1 | 0.0 | 0.3 |
| 67.1 | 0.2 | 2.1 |
| 77.6 | 1.5 | 5.9 |
| 89.7 | 4.2 | 10.6 |
| 103.7 | 8.3 | 14.2 |
| 119.9 | 12.8 | 15.6 |
| 138.6 | 16.6 | 14.9 |
| 160.2 | 18.3 | 12.8 |
| 185.2 | 17.0 | 10.0 |
| 214.1 | 12.6 | 7.0 |
| 247.6 | 6.7 | 4.3 |
| 286.2 | 1.9 | 2.0 |
| 330.9 | 0.0 | 0.5 |
| 382.5 | 0.0 | 0.0 |
| 442.2 | 0.0 | 0.0 |
| 511.2 | 0.0 | 0.0 |
| 591.0 | 0.0 | 0.0 |
| 683.2 | 0.0 | 0.0 |
| 789.8 | 0.0 | 0.0 |

Peak Analysis by intensity

| Peak | Area | Mean | Width |
|---|---|---|---|
| 1 | 100.0 | 161.7 | 127.0 |

Peak Analysis by volume

| Peak | Area | Mean | Width |
|---|---|---|---|
| 1 | 100.0 | 141.4 | 124.5 |

Peak Analysis by number

| Peak | Area | Mean | Width |
|---|---|---|---|
| 1 | 100.0 | 105.8 | 62.6 |

FIG. 1F
Rec30

| Size(nm) | Intensity | Volume |
|---|---|---|
| 29.1 | 0.0 | 0.0 |
| 33.5 | 0.0 | 0.0 |
| 38.6 | 0.0 | 0.0 |
| 44.4 | 0.0 | 0.0 |
| 51.2 | 0.0 | 0.0 |
| 58.9 | 0.0 | 0.3 |
| 67.9 | 0.2 | 2.1 |
| 78.2 | 1.5 | 6.0 |
| 90.1 | 4.3 | 10.7 |
| 103.7 | 8.3 | 14.2 |
| 119.5 | 12.8 | 15.6 |
| 137.6 | 16.5 | 14.9 |
| 158.5 | 18.1 | 12.8 |
| 182.6 | 16.9 | 10.0 |
| 210.3 | 12.6 | 7.0 |
| 242.3 | 6.8 | 4.2 |
| 279.1 | 2.0 | 1.9 |
| 321.5 | 0.0 | 0.4 |
| 370.3 | 0.0 | 0.0 |
| 426.5 | 0.0 | 0.0 |
| 491.3 | 0.0 | 0.0 |
| 565.9 | 0.0 | 0.0 |
| 651.8 | 0.0 | 0.0 |
| 750.8 | 0.0 | 0.0 |

Peak Analysis by intensity

| Peak | Area | Mean | Width |
|---|---|---|---|
| 1 | 100.0 | 159.8 | 123.3 |

Peak Analysis by volume

| Peak | Area | Mean | Width |
|---|---|---|---|
| 1 | 100.0 | 139.6 | 119.8 |

Peak Analysis by number

| Peak | Area | Mean | Width |
|---|---|---|---|
| 1 | 100.0 | 106.0 | 62.1 |

Record 22, intensity

Record 23, intensity

FIG.3

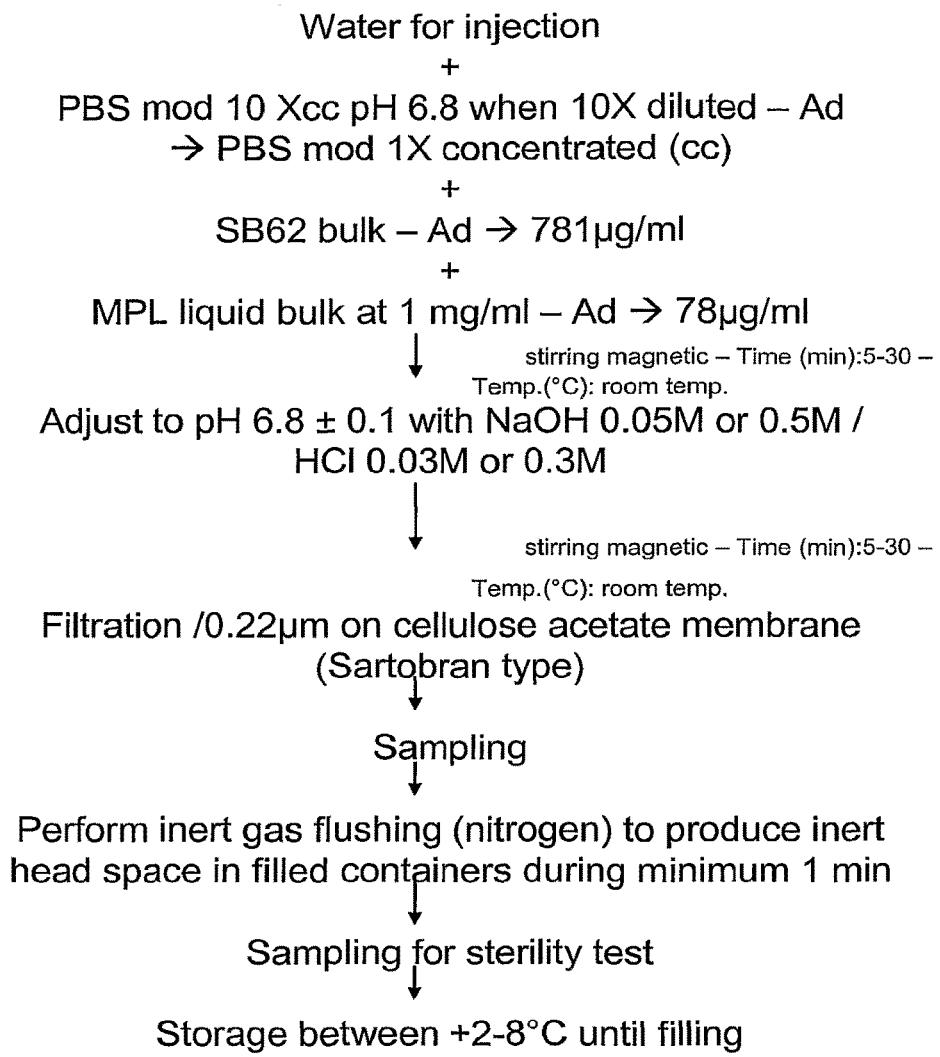

Water for injection
+
PBS mod 10 Xcc pH 6.8 when 10X diluted – Ad
→ PBS mod 1X concentrated (cc)
+
SB62 bulk – Ad → 781µg/ml
+
MPL liquid bulk at 1 mg/ml – Ad → 78µg/ml
↓ stirring magnetic – Time (min):5-30 – Temp.(°C): room temp.

Adjust to pH 6.8 ± 0.1 with NaOH 0.05M or 0.5M / HCl 0.03M or 0.3M
↓ stirring magnetic – Time (min):5-30 – Temp.(°C): room temp.

Filtration /0.22µm on cellulose acetate membrane (Sartobran type)
↓
Sampling
↓
Perform inert gas flushing (nitrogen) to produce inert head space in filled containers during minimum 1 min
↓
Sampling for sterility test
↓
Storage between +2-8°C until filling Remark: the vaccine bulk is maintained under stirring during entire formulation process

| | D-1 AM | D-1 PM | Priming AM | Priming PM | D+1 AM | D+1 PM | D+2 AM | D+2 PM | D+3 AM | D+3 PM | D+6 AM | D+6 PM |
|---|---|---|---|---|---|---|---|---|---|---|---|---|
| Trivalent Plain | 38.6 | 38.7 | 38.6 | 38.7 | 38.7 | 38.6 | 39.0 | 39.0 | 38.9 | 38.6 | 38.3 | 38.4 |
| Trivalent AS03 | 38.8 | 38.8 | 38.7 | 38.8 | 38.8 | 38.7 | 38.9 | 39.2 | 38.9 | 38.8 | 38.4 | 38.4 |
| Trivalent AS03 + 3D-MPL | 38.6 | 38.6 | 38.6 | 38.6 | 38.6 | 38.5 | 38.7 | 39.0 | 38.8 | 38.6 | 38.3 | 38.3 |
| PBS | 38.7 | 38.7 | 38.6 | 38.6 | 38.6 | 38.7 | 38.6 | 39.1 | 38.9 | 38.7 | 38.4 | 38.3 |

| | D-2 PM | D-1 AM | D-1 PM | challenge AM | challenge PM | D+1 AM | D+1 PM | D+2 AM | D+2 PM | D+3 AM | D+3 PM | D+4 AM | D+4 PM |
|---|---|---|---|---|---|---|---|---|---|---|---|---|---|
| Trivalent Plain | 37.8 | 37.7 | 37.8 | 37.6 | 37.9 | 38.0 | 38.4 | 38.3 | 37.9 | 38.1 | 37.9 | 38.0 | 37.7 |
| Trivalent Split AS03 | 37.9 | 37.7 | 37.8 | 37.7 | 37.8 | 38.2 | 38.3 | 38.3 | 38.0 | 37.9 | 38.0 | 38.1 | 37.8 |
| Trivalent Split AS03 + 3D-MPL | 37.9 | 37.8 | 37.9 | 37.6 | 37.7 | 37.7 | 37.6 | 37.7 | 37.9 | 37.7 | 37.9 | 37.9 | 38.0 |
| PBS | 37.7 | 37.8 | 37.8 | 37.7 | 37.8 | 38.0 | 38.4 | 38.3 | 38.1 | 37.9 | 37.9 | 37.8 | 37.7 |

ADJUVANTED INFLUENZA VIRUS COMPOSITIONS

CROSS-REFERENCES TO RELATED APPLICATIONS

This application is a divisional of pending U.S. application Ser. No. 13/096,180, filed Apr. 28, 2011, which is a continuation of U.S. application Ser. No. 11/909,388, filed Sep. 21, 2007 and now abandoned, which is the 371 Application of the National Stage of PCT Application No. PCT/EP2006/002837, filed 21 Mar. 2006, the disclosure of which is incorporated herein by reference. This application also claims benefit of the filing dates of the Great Britain Applications No. 0505998.5, filed 23 Mar. 2005, No. 0506000.9, filed 23 Mar. 2005, No. 0506001.7, filed 23 Mar. 2005, No. 0505989.4, filed 23 Mar. 2005, No. 0506004.1, filed 23 Mar. 2005, No. 0510589.5, filed 24 May 2005, No. 0510591.1, filed 24 May 2005, No. 0510593.7, filed 24 May 2005, No. 0510596.0, filed 24 May 2005, No. 0510598.6, filed 24 May 2005, No. 0603789.9, filed 24 Feb. 2006, No. 0603788.1, filed 24 Feb. 2006, and No. 0603790.7, filed 24 Feb. 2006.

TECHNICAL FIELD

The present invention relates to influenza vaccine formulations and vaccination regimes for immunising against influenza disease, their use in medicine, in particular their use in augmenting immune responses to various antigens, and to methods of preparation. In particular, the invention relates to multivalent influenza immunogenic compositions comprising an influenza antigen or antigenic preparation thereof from at least two influenza virus strains, at least one strain being associated with a pandemic outbreak or having the potential to be associated with a pandemic outbreak, in combination with an oil-in-water emulsion adjuvant.

TECHNICAL BACKGROUND

Influenza viruses are one of the most ubiquitous viruses present in the world, affecting both humans and livestock. Influenza results in an economic burden, morbidity and even mortality, which are significant.

The influenza virus is an RNA enveloped virus with a particle size of about 125 nm in diameter. It consists basically of an internal nucleocapsid or core of ribonucleic acid (RNA) associated with nucleoprotein, surrounded by a viral envelope with a lipid bilayer structure and external glycoproteins. The inner layer of the viral envelope is composed predominantly of matrix proteins and the outer layer mostly of host-derived lipid material. Influenza virus comprises two surface antigens, glycoproteins neuraminidase (NA) and haemagglutinin (HA), which appear as spikes, 10 to 12 nm long, at the surface of the particles. It is these surface proteins, particularly the haemagglutinin that determine the antigenic specificity of the influenza subtypes.

These surface antigens progressively, sometimes rapidly, undergo some changes leading to the antigenic variations in influenza. These antigenic changes, called 'drifts' and 'shifts' are unpredictable and may have a dramatic impact from an immunological point of view as they eventually lead to the emergence of new influenza strains and that enable the virus to escape the immune system causing the well known, almost annual, epidemics.

The influenza virus strains to be incorporated into influenza vaccine each season are determined by the World Health Organisation in collaboration with national health authorities and vaccine manufacturers.

HA is the most important antigen in defining the serological specificity of the different influenza strains. This 75-80 kD protein contains numerous antigenic determinants, several of which are in regions that undergo sequence changes in different strains (strain-specific determinants) and others in regions which are common to many HA molecules (common to determinants).

Influenza viruses cause epidemics almost every winter, with infection rates for type A or B virus as high as 40% over a six-week period. Influenza infection results in various disease states, from a sub-clinical infection through mild upper respiratory infection to a severe viral pneumonia. Typical influenza epidemics cause increases in incidence of pneumonia and lower respiratory disease as witnessed by increased rates of hospitalization or mortality. The severity of the disease is primarily determined by the age of the host, his immune status and the site of infection.

Elderly people, 65 years old and over, are especially vulnerable, accounting for 80-90% of all influenza-related deaths in developed countries. Individuals with underlying chronic diseases are also most likely to experience such complications. Young infants also may suffer severe disease. These groups in particular therefore need to be protected. Besides these 'at risk'-groups, the health authorities are also recommending to vaccinate healthy adults who are in contact with elderly persons.

Vaccination plays a critical role in controlling annual influenza epidemics. Currently available influenza vaccines are either inactivated or live attenuated influenza vaccine. Inactivated flu vaccines are composed of three possible forms of antigen preparation: inactivated whole virus, sub-virions where purified virus particles are disrupted with detergents or other reagents to solubilise the lipid envelope (so-called "split" vaccine) or purified HA and NA (subunit vaccine). These inactivated vaccines are given intramuscularly (i.m.) or intranasaly (i.n.).

Influenza vaccines, of all kinds, are usually trivalent vaccines. They generally contain antigens derived from two influenza A virus strains and one influenza B strain. A standard 0.5 ml injectable dose in most cases contains 15 μg of haemagglutinin antigen component from each strain, as measured by single radial immunodiffusion (SRD) (J. M. Wood et al.: An improved single radial immunodiffusion technique for the assay of influenza haemagglutinin antigen: adaptation for potency determination of inactivated whole virus and subunit vaccines. J. Biol. Stand. 5 (1977) 237-247; J. M. Wood et al., International collaborative study of single radial diffusion and immunoelectrophoresis techniques for the assay of haemagglutinin antigen of influenza virus. J. Biol. Stand. 9 (1981) 317-330).

Influenza vaccines currently available are considered safe in all age groups (De Donato et al. 1999, Vaccine, 17, 3094-3101). However, there is little evidence that current influenza vaccines work in small children under two years of age. Furthermore, reported rates of vaccine efficacy for prevention of typical confirmed influenza illness are 23-72% for the elderly, which are significantly lower than the 60-90% efficacy rates reported for younger adults (Govaert, 1994, J. Am. Med. Assoc., 21, 166-1665; Gross, 1995, Ann Intern. Med. 123, 523-527). The effectiveness of an influenza vaccine has been shown to correlate with serum titres of hemagglutination inhibition (HI) antibodies to the viral strain, and several studies have found that older adults exhibit lower HI titres after influenza immunisation than do younger adults (Murasko, 2002, Experimental gerontology, 37, 427-439).

New vaccines with an improved immunogenicity are therefore still needed. Formulation of vaccine antigen with potent adjuvants is a possible approach for enhancing immune responses to subvirion antigens.

A sub-unit influenza vaccine adjuvanted with the adjuvant MF59, in the form of an oil-in-water emulsion is commercially available, and has demonstrated its ability to induce a higher antibody titer than that obtained with the non-adjuvanted sub-unit vaccine (De Donato et al. 1999, Vaccine, 17, 3094-3101). However, in a later publication, the same vaccine has not demonstrated its improved profile compared to a non-adjuvanted split vaccine (Puig-Barbera et al., 2004, Vaccine 23, 283-289).

By way of background, during inter-pandemic periods, influenza viruses circulate that are related to those from the preceding epidemic. The viruses spread among people with varying levels of immunity from infections earlier in life. Such circulation, over a period of usually 2-3 years, promotes the selection of new strains that have changed enough to cause an epidemic again among the general population; this process is termed 'antigenic drift'. 'Drift variants' may have different impacts in different communities, regions, countries or continents in any one year, although over several years their overall impact is often similar. In other words, an influenza pandemics occurs when a new influenza virus appears against which the human population has no immunity. Typical influenza epidemics cause increases in incidence of pneumonia and lower respiratory disease as witnessed by increased rates of hospitalisation or mortality. The elderly or those with underlying chronic diseases are most likely to experience such complications, but young infants also may suffer severe disease. At unpredictable intervals, novel influenza viruses emerge with a key surface antigen, the haemagglutinin, of a totally different subtype from strains circulating the season before. Here, the resulting antigens can vary from 20% to 50% from the corresponding protein of strains that were previously circulating in humans. This can result in virus escaping 'herd immunity' and establishing pandemics. This phenomenon is called 'antigenic shift'. It is thought that at least in the past pandemics have occurred when an influenza virus from a different species, such as an avian or a porcine influenza virus, has crossed the species barrier. If such viruses have the potential to spread from person to person, they may spread worldwide within a few months to a year, resulting in a pandemic. For example, in 1957 (Asian Flu pandemic), viruses of the H2N2 subtype replaced H1N1 viruses that had been circulating in the human population since at least 1918 when the virus was first isolated. The H2 HA and N2 NA underwent antigenic drift between 1957 and 1968 until the HA was replaced in 1968 (Hong-Kong Flu pandemic) by the emergence of the H3N2 influenza subtype, after which the N2 NA continued to drift along with the H3 HA (Nakajima et al., 1991, Epidemiol. Infect. 106, 383-395).

The features of an influenza virus strain that give it the potential to cause a pandemic outbreak are: it contains a new haemagglutinin compared to the haemagglutinin in the currently circulating strains, which may or not be accompanied by a change in neuraminidase subtype; it is capable of being transmitted horizontally in the human population; and it is pathogenic for humans. A new haemagglutinin may be one which has not been evident in the human population for an extended period of time, probably a number of decades, such as H2. Or it may be a haemagglutinin that has not been circulating in the human population before, for example H5, H9, H7 or H6 which are found in birds. In either case the majority, or at least a large proportion of, or even the entire population has not previously encountered the antigen and is immunologically naïve to it.

There is still a need for improved influenza vaccines, especially in the case of influenza pandemics and for the elderly population.

STATEMENT OF THE INVENTION

In first aspect of the present invention, there is provided a multivalent influenza immunogenic composition comprising an influenza virus or antigenic preparation thereof from at least two influenza virus strains, at least one strain being associated with a pandemic outbreak or having the potential to be associated with a pandemic outbreak, in combination with an oil-in-water emulsion adjuvant, wherein said oil-in-water emulsion adjuvant comprises a metabolisable oil, a sterol and an emulsifying agent. Suitably said sterol is alpha-tocopherol.

Suitable pandemic strains are, but not limited to: H5N1, H9N2, H7N7, H2N2 and H1N1.

In another aspect the invention provides a method for the production of an influenza immunogenic composition for a pandemic situation which method comprises admixing influenza virus antigen or antigenic preparation from at least two influenza virus strains, at least one of which is associated with a pandemic outbreak or has the potential to be associated with a pandemic outbreak, with an oil-in-water emulsion as herein above defined.

In a third aspect there is provided an immunogenic composition as herein defined for use in medicine.

In another aspect there is provided the use of (a) an influenza virus antigen or antigenic preparation thereof, and (b) an oil-in-water emulsion adjuvant in the manufacture of an immunogenic composition for inducing at least one of i) an improved CD4 T-cell immune response, ii) an improved B cell memory response, against said virus antigen or antigenic composition in a human, preferably in an immunocompromised individual or population, such as a high risk adult or an elderly, which is preferred. Preferably the immunogenic composition is as herein defined.

There is also provided the use of an influenza virus or antigenic preparation thereof and an oil-in-water emulsion adjuvant in the preparation of an immunogenic composition as herein defined for vaccination of human elderly against influenza.

In a specific embodiment, the immunogenic composition is capable of inducing both an improved CD4 T-cell immune response and an improved B-memory cell response compared to that obtained with the un-adjuvanted antigen or antigenic composition.

In a further embodiment, there is provided the use of an influenza virus or antigenic preparation thereof in the manufacture of an immunogenic composition for revaccination of humans previously vaccinated with a multivalent influenza immunogenic composition comprising an influenza antigen or antigenic preparation thereof from at least two influenza virus strains, at least one strain being associated with a pandemic outbreak or having the potential to be associated with a pandemic outbreak, in combination with an oil-in-water emulsion adjuvant as herein defined.

In a specific embodiment, the composition used for the revaccination may be un-adjuvanted or may contain an adjuvant, in particular an oil-in-water emulsion adjuvant. In another specific embodiment, the immunogenic composition for revaccination contains an influenza virus or antigenic preparation thereof which shares common CD4 T-cell epitopes with the influenza virus or virus antigenic preparation thereof used for the first vaccination.

Preferably the revaccination is made in subjects who have been vaccinated the previous season against influenza. Typically revaccination is made at least 6 months after the first vaccination, preferably 8 to 14 months after, more preferably at around 10 to 12 months after.

Preferably said oil-in-water emulsion comprises a metabolisable oil, alpha tocopherol and an emulsifying agent. In a another specific embodiment, said oil-in-water emulsion adjuvant comprises at least one metabolisable oil in an amount of 0.5% to 20% of the total volume, and has oil droplets of which at least 70% by intensity have diameters of less than 1 μm.

In a further aspect of the present invention, there is provided the use of an antigen or antigenic preparation from a first influenza strain in the manufacture of an immunogenic composition as herein defined for protection against influenza infections caused by a variant influenza strain.

In another aspect, there is provided a method of vaccination an immuno-compromised human individual or population such as high risk adults or elderly, influenza immunogenic composition comprising an influenza antigen or antigenic preparation thereof from at least two influenza virus strains, at least one strain being associated with a pandemic outbreak or having the potential to be associated with a pandemic outbreak, in combination with an oil-in-water emulsion adjuvant as herein defined.

In still another embodiment, the invention provides a method for revaccinating humans previously vaccinated with a multivalent influenza immunogenic composition comprising an influenza antigen or antigenic preparation thereof from at least two influenza virus strains, at least one strain being associated with a pandemic outbreak or having the potential to be associated with a pandemic outbreak, in combination with an oil-in-water emulsion adjuvant, said method comprising administering to said human an immunogenic composition comprising an influenza virus, either adjuvanted or un-adjuvanted.

In a further embodiment there is provided a method for vaccinating a human population or individual against one influenza virus strain followed by revaccination of said human or population against a variant influenza virus strain, said method comprising administering to said human (i) a first composition comprising an influenza virus or antigenic preparation thereof from a first influenza virus strain and an oil-in-water emulsion adjuvant, and (ii) a second immunogenic composition comprising a influenza virus strain variant of said first influenza virus strain. In a specific embodiment said first strain is associated with a pandemic outbreak or has the potential to be associated with a pandemic outbreak. In another specific embodiment said variant strain is associated with a pandemic outbreak or has the potential to be associated with a pandemic outbreak.

Other aspects and advantages of the present invention are described further in the following detailed description of the preferred embodiments thereof.

LEGEND TO FIGURES

FIG. 1A-1H: Oil droplet particle size distribution in SB62 oil-in-water emulsion as measured by PCS. FIG. 1A-1F shows SB62 lot 1023 size measurements with the Malvern Zetasizer 3000HS: A =dilution 1/10000 (Rec22 to Rec24) (Analysis in Contin and adapted optical model 1.5/0.01); B =Dilution 1/20000 (Rec28 to Rec30) (Analysis in Contin and adapted optical model 1.5/0.01). FIG. 1G-1H shows a schematic illustration of record 22 (upper part) and record 23 (lower part) by intensity.

FIG. 2: Schematic illustration of the preparation of MPL bulk.

FIG. 3: Schematic illustration of the preparation of AS03+MPL adjuvant.

FIG. 4: Explo Flu-001 clinical trial. CD4 T cell response to split influenza antigen (Q1=first quartile, Q3=third quartile).

FIG. 5: Explo Flu-001 clinical trial. CD8 T cell response to split influenza antigen (Q1=first quartile, Q3=third quartile).

FIG. 6: Explo Flu-001 clinical trial. Cross-reactive CD4 T-cell response to split influenza virus antigen after vaccination with FLUARIX®/α-RIX®/INFLUSPLIT® (Influenza vaccine)+AS03.

FIG. 7: Explo Flu-001 clinical trial. B cell memory response post vaccination.

FIG. 8: Explo Flu-002 clinical trial. CD4 T cell response against split influenza antigen following revaccination.

FIG. 9: Explo Flu-002 clinical trial. Anti-HI titers following revaccination.

FIG. 10: Ferret study I. Temperature monitoring (priming and challenge). FIG. 10A is priming, FIG. 10B is challenge.

FIG. 11: Ferret study I. Viral shedding.

FIG. 12: Ferret study II. Temperature monitoring (priming and challenge). FIG. 12A is priming, FIG. 12B is challenge.

FIG. 13: Ferret study II. Viral shedding.

FIG. 14: Ferret study II. HI titers to H3N2 A/Panama (vaccine strain) (FIG. 14A) and to H3N2 A/Wyoming (challenge strain) (FIG. 14B).

FIG. 15: Mice study. Frequencies of CD4 T cells in C57Bl/6 primed mice using whole inactivated virus as re-stimulating antigen (day 7 post-immunisation).

FIG. 16: Mice study. Frequencies of CD8 T cells in C57Bl/6 primed mice using whole inactivated virus as re-stimulating antigen (day 7 post-immunisation).

FIG. 17A-B: Mice study. Frequencies of CD4 (upper part; FIG. 17A) and CD8 (lower part; FIG. 17B) T cells in C57BI/6 mice primed with heterologous strains, using whole inactivated virus as re- stimulating antigen (day 7 post-immunisation).

FIG. 18: Human clinical trial. B cell memory response post-vaccination of elderly with FLUARIX®, FLUARIX®+AS03, Fluarix FLUARIX®+AS03+MPL (difference between pre- and post-).

FIG. 19: Ferret study III. Temperature monitoring before and after challenge.

FIG. 20: Ferret study III. Viral shedding before and after challenge.

FIG. 21: Ferret study III. HI titers to H3N2 A/Wyoming (vaccine strain).

FIG. 22: Ferret study III. HI titers to H3N2 A/Panama (challenge strain).

FIG. 23: Human clinical trial. HI titers (GMTs) at days 21, 90 and 180 post vaccination (persistence).

FIG. 24: Human clinical trial. CD4 response—all double test—Pool antigen at days 21, 90 and 180 post vaccination (persistence).

FIG. 25: Human clinical trial. HI titers in a revaccination clinical trial with AS03+MPL compared to FLUARIX®.

FIG. 26: Human clinical trial. CMI for CD4 response—all double test—Pool antigen at days 0 and 21.

FIG. 27: Human clinical trial with AS03+MPL at two concentrations. HI titers at days 0 and 21.

Figure 28:
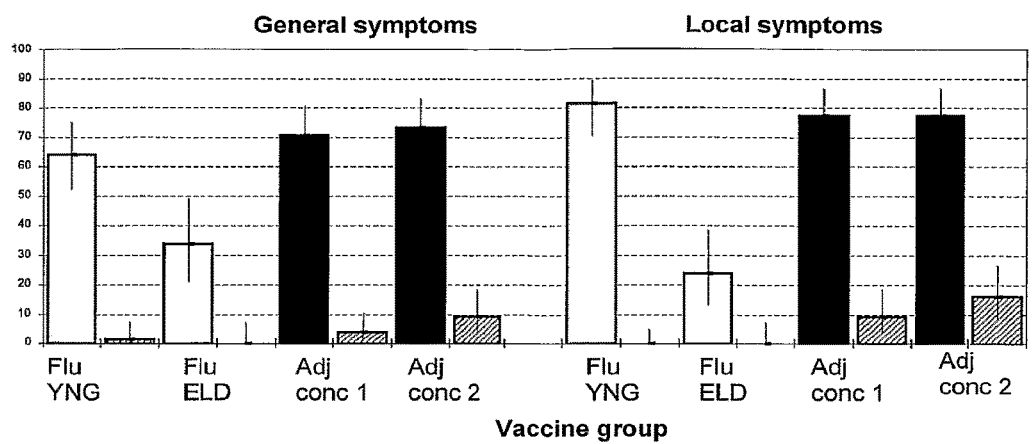

FIG. 28: Human clinical trial with AS03+MPL at two concentrations. Reactogenicity.

DETAILED DESCRIPTION

The present inventors have discovered that an influenza formulation comprising an influenza virus or antigenic preparation thereof together with an oil-in-water emulsion adjuvant comprising a metabolisable oil, a sterol such as alpha tocopherol and an emulsifying agent, was capable of improving the CD4 T-cell immune response and/or B cell memory response against said antigen or antigenic composition in a human compared to that obtained with the un-adjuvanted virus or antigenic preparation thereof. The formulations adjuvanted with an oil-in-water emulsion adjuvant as herein defined will advantageously be used to induce anti-influenza CD4-T cell response capable of detection of influenza epitopes presented by MHC class II molecules. The present Applicant has now found that it is effective to target the cell-mediated immune system in order to increase responsiveness against homologous and drift influenza strains (upon vaccination and infection).

The adjuvanted influenza compositions according to the invention have several advantages:
1) An improved immunogenicity: they will allow to restore weak immune response in the elderly people (over 50 years of age, typically over 65 years of age) to levels seen in young people (antibody and/or T cell responses);
2) An improved cross-protection profile: increased cross-protection against variant (drifted) influenza strains;
3) They will also allow an reduced antigen dosage to be used for a similar response, thus ensuring an increased capacity in case of emergency (pandemics for example).

The compositions for use in the present invention have been able to provide better sero-protection against influenza following revaccination, as assessed by the number of human subjects meeting the influenza correlates of protections. Furthermore, the composition for use in the present invention have also been able to induce a trend for a higher B cell memory response following the first vaccination of a human subject, and a higher humoral response following revaccination, compared to the un-adjuvanted composition.

The Inventors have also been capable of demonstrating that the claimed adjuvanted composition was able to not only induce but also maintain protective levels of antibodies against all three strains present in the vaccine, in more individuals than those obtained with the un-advanted composition (see Table 43 for example).

Thus, in still another embodiment, the claimed composition is capable of ensuring a persistent immune response against influenza related disease. In particular, by persistence it is meant an HI antibody immune response which is capable of meeting regulatory criteria after at least three months, preferably after at least 6 months after the vaccination. In particular, the claimed composition is able to induce protective levels of antibodies in >70% of individuals, suitably in >80% of individuals or suitably in >90% of individuals for at least one influenza strain, preferably for all strains present in the vaccine, after at least three months. In a specific aspect, protective levels of antibodies of >90% are obtained at least 6 months post-vaccination against at least one, suitably two, or all strains present in the vaccine composition.

Influenza Viral Strains and Antigens

An influenza virus or antigenic preparation thereof for use according to the present invention may be a split influenza virus or split virus antigenic preparation thereof. In an alternative embodiment the influenza preparation may contain another type of inactivated influenza antigen, such as inactivated whole virus or purified HA and NA (subunit vaccine), or an influenza virosome. In a still further embodiment, the influenza virus may be a live attenuated influenza preparation.

A split influenza virus or split virus antigenic preparation thereof for use according to the present invention is suitably an inactivated virus preparation where virus particles are disrupted with detergents or other reagents to solubilise the lipid envelope. Split virus or split virus antigenic preparations thereof are suitably prepared by fragmentation of whole influenza virus, either infectious or inactivated, with solubilising concentrations of organic solvents or detergents and subsequent removal of all or the majority of the solubilising agent and some or most of the viral lipid material. By split virus antigenic preparation thereof is meant a split virus preparation which may have undergone some degree of purification compared to the split virus whilst retaining most of the antigenic properties of the split virus components. For example, when produced in eggs, the split virus may be depleted from egg-contaminating proteins, or when produced in cell culture, the split virus may be depleted from host cell contaminants. A split virus antigenic preparation may comprise split virus antigenic components of more than one viral strain. Vaccines containing split virus (called 'influenza split vaccine') or split virus antigenic preparations generally contain residual matrix protein and nucleoprotein and sometimes lipid, as well as the membrane envelope proteins. Such split virus vaccines will usually contain most or all of the virus structural proteins although not necessarily in the same proportions as they occur in the whole virus.

Alternatively, the influenza virus may be in the form of a whole virus vaccine. This may prove to be an advantage over a split virus vaccine for a pandemic situation as it avoids the uncertainty over whether a split virus vaccine can be successfully produced for a new strain of influenza virus. For some strains the conventional detergents used for producing the split virus can damage the virus and render it unusable. Although there is always the possibility to use different detergents and/or to develop a different process for producing a split vaccine, this would take time, which may not be available in a pandemic situation. In addition to the greater degree of certainty with a whole virus approach, there is also a greater vaccine production capacity than for split virus since considerable amounts of antigen are lost during additional purification steps necessary for preparing a suitable split vaccine.

In another embodiment, the influenza virus preparation is in the form of a purified sub-unit influenza vaccine. Sub-unit influenza vaccines generally contain the two major envelope proteins, HA and NA, and may have an additional advantage over whole virion vaccines as they are generally less reactogenic, particularly in young vaccinees. Sub-unit vaccines can be produced either recombinantly or purified from disrupted viral particles.

In another embodiment, the influenza virus preparation is in the form of a virosome. Virosomes are spherical, unilamellar vesicles which retain the functional viral envelope glycoproteins HA and NA in authentic conformation, intercalated in the virosomes' phospholipids bilayer membrane.

Said influenza virus or antigenic preparation thereof may be egg-derived or tissue-culture derived.

For example, the influenza virus antigen or antigenic preparations thereof according to the invention may be derived from the conventional embryonated egg method, by growing influenza virus in eggs and purifying the harvested allantoic fluid. Eggs can be accumulated in large numbers at short notice. Alternatively, they may be derived from any of the new generation methods using tissue culture to grow the virus or express recombinant influenza virus surface antigens. Suitable cell substrates for growing the virus include for example dog kidney cells such as MDCK or cells from a clone of MDCK, MDCK-like cells, monkey kidney cells such as AGMK cells including Vero cells, suitable pig cell lines, or any other mammalian cell type suitable for the production of influenza virus for vaccine purposes. Suitable cell substrates also include human cells e.g. MRC-5 cells. Suitable cell substrates are not limited to cell lines; for example primary cells such as chicken embryo fibroblasts and avian cell lines are also included.

The influenza virus antigen or antigenic preparation thereof may be produced by any of a number of commercially applicable processes, for example the split flu process described in patent no. DD 300 833 and DD 211 444, incorporated herein by reference. Traditionally split flu was produced using a solvent/detergent treatment, such as tri-n-butyl phosphate, or diethylether in combination with TWEEN® (known as "Tween-ether" splitting) (Polyoxyethylenesorbitan monoctleate; Sorbitan monooleate ethoxyate) and this process is still used in some production facilities. Other splitting agents now employed include detergents or proteolytic enzymes or bile salts, for example sodium deoxycholate as described in patent no. DD 155 875, incorporated herein by reference. Detergents that can be used as splitting agents include cationic detergents e.g. cetyl trimethyl ammonium bromide (CTAB), other ionic detergents e.g. laurylsulfate, taurodeoxycholate, or non-ionic detergents such as the ones described above including TRITON X-100™ (Octylphenol ethoxylate) (for example in a process described in Lina et al, 2000, Biologicals 28, 95-103) and TRITON N-101™, or combinations of any two or more detergents.

The preparation process for a split vaccine may include a number of different filtration and/or other separation steps such as ultracentrifugation, ultrafiltration, zonal centrifugation and chromatography (e.g. ion exchange) steps in a variety of combinations, and optionally an inactivation step eg with heat, formaldehyde or β-propiolactone or U.V. which may be carried out before or after splitting. The splitting process may be carried out as a batch, continuous or semi-continuous process. A preferred splitting and purification process for a split immunogenic composition is described in WO 02/097072.

Preferred split flu vaccine antigen preparations according to the invention comprise a residual amount of TWEEN® 80 and/or TRITON X-100™ remaining from the production process, although these may be added or their concentrations adjusted after preparation of the split antigen. Preferably both TWEEN® 80 and TRITON X-100™ are present. The preferred ranges for the final concentrations of these non-ionic surfactants in the vaccine dose are:
TWEEN® 80: 0.01 to 1%, more preferably about 0.1% (v/v)
TRITON X-100™: 0.001 to 0.1 (% w/v), more preferably 0.005 to 0.02% (w/v).

In a specific embodiment, the final concentration for TWEEN® 80 ranges from 0.045%-0.09% w/v. In another specific embodiment, the antigen is provided as a 2 fold concentrated mixture, which has a TWEEN® 80 concentration ranging from 0.045%-0.2% (w/v) and has to be diluted two times upon final formulation with the adjuvanted (or the buffer in the control formulation).

In another specific embodiment, the final concentration for TRITON X-100™ ranges from 0.005%-0.017% w/v. In another specific embodiment, the antigen is provided as a 2 fold concentrated mixture, which has a TRITON X-100™ concentration ranging from 0.005%-0.034% (w/v) and has to be diluted two times upon final formulation with the adjuvanted (or the buffer in the control formulation).

Preferably the influenza preparation is prepared in the presence of low level of thiomersal, or preferably in the absence of thiomersal. Preferably the resulting influenza preparation is stable in the absence of organomercurial preservatives, in particular the preparation contains no residual thiomersal. In particular the influenza virus preparation comprises a haemagglutinin antigen stabilised in the absence of thiomersal, or at low levels of thiomersal (generally 5 μg/ml or less). Specifically the stabilization of B influenza strain is performed by a derivative of alpha tocopherol, such as alpha tocopherol succinate (also known as vitamin E succinate, i.e. VES). Such preparations and methods to prepare them are disclosed in WO 02/097072.

A preferred composition contains three inactivated split virion antigens prepared from the WHO recommended strains of the appropriate influenza season.

Preferably the influenza virus or antigenic preparation thereof and the oil-in-water emulsion adjuvant are contained in the same container. It is referred to as 'one vial approach'. Preferably the vial is a pre-filled syringe. In an alternative embodiment, the influenza virus or antigenic preparation thereof and the oil-in-water emulsion adjuvant are contained in separate containers or vials and admixed shortly before or upon administration into the subject. It is referred to as 'two vials approach'. By way of example, when the vaccine is a 2 components vaccine for a total dose volume of 0.7 ml, the concentrated antigens (for example the concentrated trivalent inactivated split virion antigens) are presented in one vial (335 μl) (antigen container) and a pre-filled syringe contains the adjuvant (360 μl) (adjuvant container). At the time of injection, the content of the vial containing the concentrated trivalent inactivated split virion antigens is removed from the vial by using the syringe containing the adjuvant followed by gentle mixing of the syringe. Prior to injection, the used needle is replaced by an intramuscular needle and the volume is corrected to 530 μl. One dose of the reconstituted adjuvanted influenza vaccine candidate corresponds to 530 μl.

According to the present invention, at least one influenza strain in the multivalent immunogenic composition as herein defined is associated with a pandemic outbreak or have the potential to be associated with a pandemic outbreak. Such strain may also be referred to as 'pandemic strains' in the text below. In particular, when the vaccine is a multivalent vaccine such as a bivalent, or a trivalent or a quadrivalent vaccine, at least one strain is associated with a pandemic outbreak or has the potential to be associated with a pandemic outbreak. Suitable strains are, but not limited to: H5N1, H9N2, H7N7, H2N2 and H1N1.

Said influenza virus or antigenic preparation thereof is suitably multivalent such as bivalent or trivalent or quadrivalent. Preferably the influenza virus or antigenic preparation thereof is trivalent or quadrivalent, having an antigen from three different influenza strains, at least one strain being associated with a pandemic outbreak or having the potential to be associated with a pandemic outbreak.

The features of an influenza virus strain that give it the potential to cause a pandemic outbreak are: it contains a new haemagglutinin compared to the haemagglutinin in the currently circulating strains; it is capable of being transmitted horizontally in the human population; and it is pathogenic for humans. A new haemagglutinin may be one which has not been evident in the human population for an extended period of time, probably a number of decades, such as H2. Or it may be a haemagglutinin that has not been circulating in the human population before, for example H5, H9, H7 or H6 which are found in birds. In either case the majority, or at least a large proportion of, or even the entire population has not previously encountered the antigen and is immunologically naïve to it.

Certain parties are generally at an increased risk of becoming infected with influenza in a pandemic situation. The elderly, the chronically ill and small children are particularly susceptible but many young and apparently healthy people are also at risk. For H2 influenza, the part of the population born after 1968 is at an increased risk. It is important for these groups to be protected effectively as soon as possible and in a simple way.

Another group of people who are at increased risk are travelers. People travel more today than ever before and the regions where most new viruses emerge, China and South East Asia, have become popular travel destinations in recent years. This change in travel patterns enables new viruses to reach around the globe in a matter of weeks rather than months or years.

Thus for these groups of people there is a particular need for vaccination to protect against influenza in a pandemic situation or a potential pandemic situation. Suitable strains are, but not limited to: H5N1, H9N2, H7N7, H2N2 and H1N1.

Optionally the composition may contain more than three valencies, for example two non pandemic strains plus a pandemic strain. Alternatively the composition may contain three pandemic strains. Preferably the composition contains three pandemic strains.

Oil-in-Water Emulsion Adjuvant

The adjuvant composition of the invention contains an oil-in-water emulsion adjuvant, preferably said emulsion comprises a metabolisable oil in an amount of 0.5% to 20% of the total volume, and having oil droplets of which at least 70% by intensity have diameters of less than 1 µm.

In order for any oil in water composition to be suitable for human administration, the oil phase of the emulsion system has to comprise a metabolisable oil. The meaning of the term metabolisable oil is well known in the art. Metabolisable can be defined as 'being capable of being transformed by metabolism' (Dorland's Illustrated Medical Dictionary, W.B. Sanders Company, 25th edition (1974)). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others. A particularly suitable metabolisable oil is squalene. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly preferred oil for use in this invention. Squalene is a metabolisable oil by virtue of the fact that it is an intermediate in the biosynthesis of cholesterol (Merck index, 10th Edition, entry no. 8619).

Oil in water emulsions per se are well known in the art, and have been suggested to be useful as adjuvant compositions (EP 399843; WO 95/17210).

Suitably the metabolisable oil is present in an amount of 0.5% to 20% (final concentration) of the total volume of the immunogenic composition, preferably an amount of 1.0% to 10% of the total volume, preferably in an amount of 2.0% to 6.0% of the total volume.

In a specific embodiment, the metabolisable oil is present in a final amount of about 0.5%, 1%, 3.5% or 5% of the total volume of the immunogenic composition. In another specific embodiment, the metabolisable oil is present in a final amount of 0.5%, 1%, 3.57% or 5% of the total volume of the immunogenic composition.

Preferably the oil-in-water emulsion systems of the present invention have a small oil droplet size in the sub-micron range. Suitably the droplet sizes will be in the range 120 to 750 nm, more preferably sizes from 120 to 600 nm in diameter. Most preferably the oil-in water emulsion contains oil droplets of which at least 70% by intensity are less than 500 nm in diameter, more preferably at least 80% by intensity are less than 300 nm in diameter, more preferably at least 90% by intensity are in the range of 120 to 200 nm in diameter.

The oil droplet size, i.e. diameter, according to the present invention is given by intensity. There are several ways of determining the diameter of the oil droplet size by intensity. Intensity is measured by use of a sizing instrument, suitably by dynamic light scattering such as the Malvern Zetasizer 4000 or preferably the Malvern Zetasizer 3000HS. A detailed procedure is given in Example II.2. A first possibility is to determine the z average diameter ZAD by dynamic light scattering (PCS-Photon correlation spectroscopy); this method additionally give the polydispersity index (PDI), and both the ZAD and PDI are calculated with the cumulants algorithm. These values do not require the knowledge of the particle refractive index. A second mean is to calculate the diameter of the oil droplet by determining the whole particle size distribution by another algorithm, either the Contin, or NNLS, or the automatic "Malvern" one (the default algorithm provided for by the sizing instrument). Most of the time, as the particle refractive index of a complex composition is unknown, only the intensity distribution is taken into consideration, and if necessary the intensity mean originating from this distribution.

The oil in water emulsion according to the invention comprises a sterol. Sterols are well known in the art, for example cholesterol is well known and is, for example, disclosed in the Merck Index, 11th Edn., page 341, as a naturally occurring sterol found in animal fat. Other suitable sterols include β-sitosterol, stigmasterol, ergosterol, alpha-tocopherol and ergocalciferol. Said sterol is suitably present in an amount of 0.01% to 20% (w/v) of the total volume of the immunogenic composition, preferably at an amount of 0.1% to 5% (w/v). Preferably, when the sterol is cholesterol, it is present in an amount of between 0.02% and 0.2% (w/v) of the total volume of the immunogenic composition, more preferably at an amount of 0.02% (w/v) in a 0.5 ml vaccine dose volume, or 0.07% (w/v) in 0.5 ml vaccine dose volume or 0.1% (w/v) in 0.7 ml vaccine dose volume.

Suitably the sterol is alpha-tocopherol or a derivative thereof such as alpha-tocopherol succinate. Preferably alpha-tocopherol is present in an amount of between 0.2% and 5.0% (v/v) of the total volume of the immunogenic composition, more preferably at an amount of 2.5% (v/v) in a 0.5 ml vaccine dose volume, or 0.5% (v/v) in 0.5 ml vaccine dose volume or 1.7-1.9% (v/v), preferably 1.8% in 0.7 ml vaccine dose volume. By way of clarification, concentrations given in v/v can be converted into concentration in w/v by applying the following conversion factor: a 5%

(v/v) alpha-tocopherol concentration is equivalent to a 4.8% (w/v) alpha-tocopherol concentration.

The oil in water emulsion may further comprise an emulsifying agent. The emulsifying agent may be present at an amount of 0.01 to 5.0% by weight of the immunogenic composition (w/w), preferably present at an amount of 0.1 to 2.0% by weight (w/w). Preferred concentration are 0.5 to 1.5% by weight (w/w) of the total composition.

The emulsifying agent may suitably be polyoxyethylene sorbitan monooleate (TWEEN® 80). In a specific embodiment, a 0.5 ml vaccine dose volume contains 1% (w/w) TWEEN® 80, and a 0.7 ml vaccine dose volume contains 0.7% (w/w) TWEEN® 80. In another specific embodiment the concentration of TWEEN® 80 is 0.2% (w/w).

The oil in water emulsion adjuvant may be utilised with other adjuvants or immuno-stimulants and therefore an important embodiment of the invention is an oil in water formulation comprising squalene or another metabolisable oil, alpha tocopherol, and TWEEN® 80. The oil in water emulsion may also contain SPAN 85™ (sorbitan trioleate) and/or Lecithin. Typically the oil in water will comprise from 2 to 10% squalene of the total volume of the immunogenic composition, from 2 to 10% alpha tocopherol and from 0.3 to 3% TWEEN® 80, and may be produced according to the procedure described in WO 95/17210. Preferably the ratio of squalene: alpha tocopherol is equal or less than 1 as this provides a more stable emulsion. Span 85 (polyoxyethylene sorbitan trioleate) may also be present, for example at a level of 1%.

Immunogenic Properties of the Immunogenic Composition Used for the First Vaccination of the Present Invention In the present invention the multivalent influenza composition is capable of inducing an improved CD4 T-cell immune response against at least one of the component antigen(s) or antigenic composition compared to the CD4 T-cell immune response obtained with the corresponding composition which in un-adjuvanted, i.e. does not contain any exogenous adjuvant (herein also referred to as 'plain composition'). In a specific embodiment, said improved CD4 T-cell immune response is against the pandemic influenza strain.

By 'improved CD4 T-cell immune response is meant that a higher CD4 response is obtained in a human patient after administration of the adjuvanted immunogenic composition than that obtained after administration of the same composition without adjuvant. For example, a higher CD4 T-cell response is obtained in a human patient upon administration of an immunogenic composition comprising an influenza virus or antigenic preparation thereof together with an oil-in-water emulsion adjuvant comprising a metabolisable oil, alpha tocopherol and an emulsifying agent, compared to the response induced after administration of an immunogenic composition comprising an influenza virus or antigenic preparation thereof which is un-adjuvanted. Such formulation will advantageously be used to induce anti-influenza CD4-T cell response capable of detection of influenza epitopes presented by MHC class II molecules.

Preferably said immunological response induced by an adjuvanted split influenza composition for use in the present invention is higher than the immunological response induced by any other un-adjuvanted influenza conventional vaccine, such as sub-unit influenza vaccine or whole influenza virus vaccine.

In particular but not exclusively, said 'improved CD4 T-cell immune response' is obtained in an immunologically unprimed patient, i.e. a patient who is seronegative to said influenza virus or antigen. This seronegativity may be the result of said patient having never faced such virus or antigen (so-called 'naive' patient) or, alternatively, having failed to respond to said antigen once encountered. Preferably said improved CD4 T-cell immune response is obtained in an immunocompromised subject such as an elderly, typically at least 50 years of age, typically 65 years of age or above, or an adult below 65 years of age with a high risk medical condition ('high risk' adult), or a child under the age of two.

The improved CD4 T-cell immune response may be assessed by measuring the number of cells producing any of the following cytokines:

cells producing at least two different cytokines (CD40L, IL-2, IFN$\gamma$, TNF$\alpha$)

cells producing at least CD40L and another cytokine (IL-2, TNF$\alpha$, IFN$\gamma$)

cells producing at least IL-2 and another cytokine (CD40L, TNF$\alpha$, IFN$\gamma$)

cells producing at least IFN$\gamma$ and another cytokine (IL-2, TNF$\alpha$, CD40L)

cells producing at least TNF$\alpha$ and another cytokine (IL-2, CD40L, IFN$\gamma$)

There will be improved CD4 T-cell immune response when cells producing any of the above cytokines will be in a higher amount following administration of the adjuvanted composition compared to the administration of the un-adjuvanted composition. Typically at least one, preferably two of the five conditions mentioned herein above will be fulfilled. In a particular embodiment, the cells producing all four cytokines will be present at a higher amount in the adjuvanted group compared to the un-adjuvanted group.

The improved CD4 T-cell immune response conferred by the adjuvanted influenza composition of the present invention may be ideally obtained after one single administration. The single dose approach will be extremely relevant for example in a rapidly evolving outbreak situation. In certain circumstances, especially for the elderly population, or in the case of young children (below 9 years of age) who are vaccinated for the first time against influenza, or in the case of a pandemics, it may be beneficial to administer two doses of the same composition for that season. The second dose of said same composition (still considered as 'composition for first vaccination') may be administered during the on-going primary immune response and is adequately spaced. Typically the second dose of the composition is given a few weeks, or about one month, e.g. 2 weeks, 3 weeks, 4 weeks, 5 weeks, or 6 weeks after the first dose, to help prime the immune system in unresponsive or poorly responsive individuals.

In a specific embodiment, the administration of said immunogenic composition alternatively or additionally induces an improved B-memory cell response in patients administered with the adjuvanted immunogenic composition compared to the B-memory cell response induced in individuals immunized with the un-adjuvanted composition. An improved B-memory cell response is intended to mean an increased frequency of peripheral blood B lymphocytes capable of differentiation into antibody-secreting plasma cells upon antigen encounter as measured by stimulation of in-vitro differentiation (see Example sections, e.g. methods of Elispot B cells memory).

In a still further specific embodiment, the vaccination with the composition for the first vaccination, adjuvanted, has no measurable impact on the CD8 response.

The Applicants have surprisingly found that a composition comprising an influenza virus or antigenic preparation thereof formulated with an oil-in-water emulsion adjuvant, in particular an oil-in-water emulsion adjuvant comprising a metabolisable oil, a sterol such as alpha tocopherol and an emulsifying agent, is effective in promoting T cell responses in an immuno-compromised human population. As the Applicants have demonstrated, the administration of a single dose of the immunogenic composition for first vaccination, as described in the invention is capable of providing better sero-protection, as assessed by the correlates of protection for influenza vaccines, following revaccination against influenza in a human elderly population, than does the vaccination with an un-adjuvanted influenza vaccine. The claimed adjuvanted formulation has also been able to induce an improved CD4 T-cell immune response against influenza virus compared to that obtained with the un-adjuvanted formulation. This finding can be associated with an increased responsiveness upon vaccination or infection vis-à-vis influenza antigenic exposure. Furthermore, this may also be associated with a cross-responsiveness, i.e. a higher ability to respond against variant influenza strains. This improved response may be especially beneficial in an immuno-compromised human population such as the elderly population (65 years of age and above) and in particular the high risk elderly population. This may result in reducing the overall morbidity and mortality rate and preventing emergency admissions to hospital for pneumonia and other influenza-like illness. This may also be of benefit to the infant population (below 5 years, preferably below 2 years of age). Furthermore it allows inducing a CD4 T cell response which is more persistent in time, e.g. still present one year after the first vaccination, compared to the response induced with the un-adjuvanted formulation.

Preferably the CD4 T-cell immune response, such as the improved CD4 T-cell immune response obtained in an unprimed subject, involves the induction of a cross-reactive CD4 T helper response. In particular, the amount of cross-reactive CD4 T cells is increased. By 'cross-reactive' CD4 response is meant CD4 T-cell targeting shared epitopes between influenza strains.

Usually, available influenza vaccines are effective only against infecting strains of influenza virus that have haemagglutinin of similar antigenic characteristics. When the infecting (circulating) influenza virus has undergone minor changes (such as a point mutation or an accumulation of point mutations resulting in amino acid changes in the for example) in the surface glycoproteins in particular haemagglutinin (antigenic drift variant virus strain) the vaccine may still provide some protection, although it may only provide limited protection as the newly created variants may escape immunity induced by prior influenza infection or vaccination. Antigenic drift is responsible for annual epidemics that occur during interpandemic periods (Wiley & Skehel, 1987, Ann. Rev. Biochem. 56, 365-394). The induction of cross-reactive CD4 T cells provides an additional advantage to the composition of the invention, in that it may provide also cross-protection, in other words protection against heterologous infections, i.e. infections caused by a circulating influenza strain which is a variant (e.g. a drift) of the influenza strain contained in the immunogenic composition. This may be advantageous when the circulating strain is difficult to propagate in eggs or to produce in tissue culture, rendering the use of a drifted strain a working alternative. This may also be advantageous when the subject received a first and a second vaccination several months or a year apart, and the influenza strain in the immunogenic composition used for a second immunization is a drift variant strain of the strain used in the composition used for the first vaccination.

The adjuvanted influenza immunogenic composition as herein defined has therefore a higher ability to induce sero-protection and cross-reactive CD4 T cells in vaccinated elderly subjects. This characteristic may be associated with a higher ability to respond against a variant strain of the strain present in the immunogenic composition. This may prove to be an important advantage in a pandemic situation. For example a multivalent influenza immunogenic composition comprising any or several of H5, a H2, a H9, H7 or H6 strain(s) may provide a higher ability to respond against a pandemic variant, i.e. a drift strain of said pandemic strain(s), either upon subsequent vaccination with or upon infection by said drift strain.

Detection of Cross-Reactive CD4 T-Cells Following Vaccination with Influenza Vaccine Following classical trivalent Influenza vaccine administration (3 weeks), there is a substantial increase in the frequency of peripheral blood CD4 T-cells responding to antigenic strain preparation (whole virus or split antigen) that is homologous to the one present in the vaccine (H3N2: A/Panama/2007/99, H1N1: A/New Caledonia /20/99, B: B/Shangdong/7/97) (see Example III). A comparable increase in frequency can be seen if peripheral blood CD4 T-cells are restimulated with influenza strains classified as drifted strains (H3N2: A/Sydney/5/97, H1N1: A/Beijing/262/95, B: B/Yamanashi/166/98).

In contrast, if peripheral blood CD4 T-cells are restimulated with influenza strains classified as shift strains (H2N2: A/Singapore/1/57, H9N2: A/Hongkong/1073/99) by expert in the field, there is no observable increase following vaccination.

CD4 T-cells that are able to recognize both homologous and drifted Influenza strains have been named in the present document "cross-reactive". The adjuvanted influenza compositions as described herein have been capable to show heterosubtypic cross-reactivity since there is observable cross-reactivity against drifted Influenza strains. As said above, the ability of a pandemic vaccine formulation to be effective against drift pandemic strains may prove to be an important characteristic in the case of pandemics.

Consistently with the above observations, CD4 T-cell epitopes shared by different Influenza strains have been identified in human (Gelder C et al. 1998, Int Immunol. 10(2):211-22; Gelder C M et al. 1996 J. Virol. 70(7):4787-90; Gelder C M et al. 1995 J. Virol. 1995 69(12):7497-506).

In a specific embodiment, the adjuvanted composition may offer the additional benefit of providing better protection against circulating strains which have undergone a major change (such as gene recombination for example, between two different species) in the haemagglutinin (antigenic shift) against which currently available vaccines have no efficacy.

Other Adjuvants

The composition may comprise an additional adjuvant, in particular a TRL-4 ligand adjuvant, suitably a non-toxic derivative of lipid A. A suitable TRL-4 ligand is 3 de-O-acylated monophosphoryl lipid A (3D-MPL). Other suitable TLR-4 ligands are lipopolysaccharide (LPS) and derivatives, MDP (muramyl dipeptide) and F protein of RSV.

In one embodiment the composition may additionally include a Toll like receptor (TLR) 4 ligand, such as a non-toxic derivative of lipid A, particularly monophosphoryl lipid A or more particularly 3-Deacylated monophoshoryl lipid A (3D-MPL).

3D-MPL is sold under the trademark MPL® by Corixa corporation (herein MPL) and primarily promotes CD4+ T cell responses with an IFN-γ (Th1) phenotype. It can be produced according to the methods disclosed in GB 2 220 211 A. Chemically it is a mixture of 3-deacylated monophosphoryl lipid A with 3, 4, 5 or 6 acylated chains. Preferably in the compositions of the present invention small particle 3 D-MPL is used. Small particle 3D-MPL has a particle size such that it may be sterile-filtered through a 0.22 μm filter. Such preparations are described in WO94/21292 and in Example II.

3D-MPL can be used, for example, at an amount of 1 to 100 μg (w/v) per composition dose, preferably in an amount of 10 to 50 μg (w/v) per composition dose. A suitable amount of 3D-MPL is for example any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 μg (w/v) per composition dose. More preferably, 3D-MPL amount ranges from 25 to 75 μg (w/v) per composition dose. Usually a composition dose will be ranging from about 0.5 ml to about 1 ml. A typical vaccine dose are 0.5 ml, 0.6 ml, 0.7 ml, 0.8 ml, 0.9 ml or 1 ml. In a preferred embodiment, a final concentration of 50 μg of 3D-MPL is contained per ml of vaccine composition, or 25 μg per 0.5 ml vaccine dose. In other preferred embodiments, a final concentration of 35.7 μg or 71.4 μg of 3D-MPL is contained per ml of vaccine composition. Specifically, a 0.5 ml vaccine dose volume contains 25 μg or 50 μg of 3D-MPL per dose.

The dose of MPL is suitably able to enhance an immune response to an antigen in a human. In particular a suitable MPL amount is that which improves the immunological potential of the composition compared to the unadjuvanted composition, or compared to the composition adjuvanted with another MPL amount, whilst being acceptable from a reactogenicity profile.

Synthetic derivatives of lipid A are known, some being described as TLR-4 agonists, and include, but are not limited to:

OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)

OM 294 DP (3S,9R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO99/64301 and WO 00/0462)

OM197 MP-Ac DP (3S-, 9R)-3-[(R)-dodecanoyloxytetradecanoylamino]-4-oxo-5-aza-9-[(R)-3-hydroxytetradecanoylamino]decan-1,10-diol,1,10-dihydrogenophosphate 10-(6-aminohexanoate) (WO 01/46127)

Other suitable TLR-4 ligands are, for example, lipopolysaccharide and its derivatives, muramyl dipeptide (MDP) or F protein of respiratory syncitial virus.

Another suitable immunostimulant for use in the present invention is Quil A and its derivatives. Quil A is a saponin preparation isolated from the South American tree *Quilaja Saponaria Molina* and was first described by Dalsgaard et al. in 1974 ("Saponin adjuvants", Archiv. für die gesamte Virusforschung, Vol. 44, Springer Verlag, Berlin, p 243-254) to have adjuvant activity. Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of *Quillaja saponaria* Molina, which induces CD8+ cytotoxic T cells (CTLs), Th1 cells and a predominant IgG2a antibody response and is a preferred saponin in the context of the present invention.

Particular formulations of QS21 have been described which are particularly preferred, these formulations further comprise a sterol (WO96/33739). The saponins forming part of the present invention may be in the form of an oil in water emulsion (WO 95/17210).

Revaccination and Composition Used for Revaccination (Boosting Composition)

An aspect of the present invention provides the use of an influenza antigen in the manufacture of an influenza immunogenic composition for revaccination of humans previously vaccinated with an multivalent influenza composition as claimed herein or with said multivalent influenza composition comprising a variant influenza strain, formulated with an oil-in-water emulsion adjuvant as herein defined.

Typically revaccination is made at least 6 months after the first vaccination(s), preferably 8 to 14 months after, more preferably at around 10 to 12 months after.

The immunogenic composition for revaccination (the boosting composition) may contain any type of antigen preparation, either inactivated or live attenuated. It may contain the same type of antigen preparation i.e. split influenza virus or split influenza virus antigenic preparation thereof, a whole virion, a purified HA and NA (sub-unit) vaccine or a virosome, as the immunogenic composition used for the first vaccination. Alternatively the boosting composition may contain another type of influenza antigen, i.e. split influenza virus or split influenza virus antigenic preparation thereof, a whole virion, a purified HA and NA (sub-unit) vaccine or a virosome, than that used for the first vaccination. Preferably a split virus or a whole virion vaccine is used. The boosting composition may be adjuvanted or un-adjuvanted. The un-adjuvanted boosting composition may be Fluarix™/α-Rix®/Influsplit® given intramuscularly. The formulation contains three inactivated split virion antigens prepared from the WHO recommended strains of the appropriate influenza season.

Accordingly, in a preferred embodiment, the invention provides for the use of an influenza virus or antigenic preparation thereof in the manufacture of an immunogenic composition for revaccination of humans previously vaccinated with an immunogenic composition as claimed herein.

The boosting composition may be adjuvanted or un-adjuvanted. In a preferred embodiment, the boosting composition comprises an oil-in-water emulsion adjuvant, in particular an oil-in-water emulsion adjuvant comprising a metabolisable oil, a sterol such as alpha tocopherol and an emulsifying agent. Preferably, said oil-in-water emulsion adjuvant preferably comprises at least one metabolisable oil in an amount of 0.5% to 20% of the total volume, and has oil droplets of which at least 70% by intensity have diameters of less than 1 μm.

In a preferred embodiment, the first vaccination is made with an influenza composition, preferably a split influenza composition, containing at least one influenza strain that could potentially cause a pandemic outbreak and the re-vaccination is made with an influenza composition comprising at least one strain which is a circulating pandemic strain.

In a specific embodiment, the immunogenic composition for revaccination (also called herein below the 'boosting composition') contains an influenza virus or antigenic preparation thereof which shares common CD4 T-cell epitopes with the influenza virus or antigenic preparation thereof used for the first vaccination. A common CD4 T cell epitope is intended to mean peptides/sequences/epitopes from different antigens which can be recognised by the same CD4 cell (see examples of described epitopes in: Gelder C et al. 1998, Int Immunol. 10(2):211-22; Gelder C M et al. 1996 J. Virol. 70(7):4787-90; Gelder C M et al. 1995 J. Virol. 1995 69(12):7497-506).

In an embodiment according to the invention, the boosting composition is a monovalent influenza composition comprising an influenza strain which is associated with a pandemic outbreak or has the potential to be associated with a pandemic outbreak. Suitable strains are, but not limited to: H5N1, H9N2, H7N7, H2N2 and H1N1. Said strain may be the same as that, or one of those, present in the composition used for the first vaccination. In an alternative embodiment said strain may be a variant strain, i.e. a drift strain, of the strain present in the composition used for the first vaccination.

In another specific embodiment, the boosting composition is a multivalent influenza vaccine. In particular, when the boosting composition is a multivalent vaccine such as a bivalent, trivalent or quadrivalent vaccine, at least one strain is associated with a pandemic outbreak or has the potential to be associated with a pandemic outbreak. In a specific embodiment, two or more strains in the boosting composition are pandemic strains. In another specific embodiment, the at least one pandemic strain in the boosting composition is of the same type as that, or one of those, present in the composition used for the first vaccination.

In an alternative embodiment the at least one strain may be a variant strain, i.e. a drift strain, of the at least one pandemic strain present in the composition used for the first vaccination.

Accordingly, in another aspect of the present invention, there is provided the use of an influenza virus or antigenic preparation thereof, from a first pandemic influenza strain, in the manufacture of an immunogenic composition for protection against influenza infections caused by a influenza strain which is a variant of said first influenza strain Accordingly, in another aspect of the present invention, there is provided the use of:
  (a) an influenza virus or antigenic preparation thereof, from a first influenza strain, and
  (b) an oil-in-water emulsion adjuvant as herein defined
in the manufacture of an immunogenic composition for protection against influenza infections caused by a influenza strain which is a variant of said first influenza strain.

The boosting composition may be adjuvanted or not.

Typically a boosting composition, where used, is given at the next influenza season, e.g. approximately one year after the first immunogenic composition. The boosting composition may also be given every subsequent year (third, fourth, fifth vaccination and so forth). The boosting composition may be the same as the composition used for the first vaccination. Suitably, the boosting composition contains an influenza virus or antigenic preparation thereof which is a variant strain of the influenza virus used for the first vaccination. In particular, the influenza viral strains or antigenic preparation thereof are selected according to the reference material distributed by the World Health Organisation such that they are adapted to the influenza strain which is circulating on the year of the revaccination.

The influenza antigen or antigenic composition used in revaccination preferably comprises an adjuvant or an oil-in-water emulsion, suitably as described above. The adjuvant may be an oil-in-water emulsion adjuvant as herein above described, which is preferred, optionally containing an additional adjuvant such as TLR-4 ligand such as 3D-MPL or a saponin, or may be another suitable adjuvant such as alum or alum alternatives such as polyphosphazene for example.

Preferably revaccination induces any, preferably two or all, of the following: (i) an improved CD4 response against the influenza virus or antigenic preparation thereof, or (ii) an improved B cell memory response or (iii) an improved humoral response, compared to the equivalent response induced after a first vaccination with the un-adjuvanted influenza virus or antigenic preparation thereof. Preferably the immunological responses induced after revaccination with the adjuvanted influenza virus or antigenic preparation thereof as herein defined, are higher than the corresponding response induced after the revaccination with the un-adjuvanted composition. Preferably the immunological responses induced after revaccination with an un-adjuvanted, preferably split, influenza virus are higher in the population first vaccinated with the adjuvanted, preferably split, influenza composition than the corresponding response in the population first vaccinated with the un-adjuvanted, preferably split, influenza composition.

As the Applicants have demonstrated, the revaccination of the subjects with a boosting composition comprising an influenza virus and an oil-in-water emulsion adjuvant comprising a metabolisable oil, a sterol such as alpha tocopherol and an emulsifying agent, as defined herein above, shows higher antibody titers than the corresponding values in the group of people first vaccinated with the un-adjuvanted composition and boosted with the un-adjuvanted composition. The effect of the adjuvant in enhancing the antibody response to revaccination is especially of importance in the elderly population which is known to have a low response to vaccination or infection by influenza virus. The adjuvanted composition-associated benefit was also marked in terms of improving the CD4 T-cell response following revaccination.

The adjuvanted composition of the invention is capable of inducing a better cross-responsiveness against drifted strain (the influenza strain from the next influenza season) compared to the protection conferred by the control vaccine. Said cross-responsiveness has shown a higher persistence compared to that obtained with the un-adjuvanted formulation. The effect of the adjuvant in enhancing the cross-responsiveness against drifted strain is of important in a pandemic situation.

Preclinical data given in Example 3 for example show the ability of the composition of the invention to protect against heterotypic influenza infection and disease as assessed by body temperature readouts. The same conclusion holds true for the clinical trials data obtained in revaccination studies.

In a further embodiment the invention relates to a vaccination regime in which the first vaccination is made with an influenza composition, preferably a split influenza composition, containing at least one influenza strain that could potentially cause a pandemic outbreak and the revaccination is made with a circulating strain, either a pandemic strain or a classical strain.

CD4 Epitope in HA

This antigenic drift mainly resides in epitope regions of the viral surface proteins haemagglutinin (HA) and neuraminidase (NA). It is known that any difference in CD4 and B cell epitopes between different influenza strains, being used by the virus to evade the adaptive response of the host immune system, will play a major role in influenza vaccination and is.

CD4 T-cell epitopes shared by different Influenza strains have been identified in human (see for example: Gelder C et al. 1998, Int Immunol. 10(2):211-22; Gelder C M et al. 1996 J. Virol. 70(7):4787-90; and Gelder C M et al. 1995 J. Virol. 1995 69(12):7497-506).

In a specific embodiment, the revaccination is made by using a boosting composition which contains an influenza virus or antigenic preparation thereof which shares common CD4 T-cell epitopes with the influenza virus antigen or antigenic preparation thereof used for the first vaccination. The invention thus relates to the use of the immunogenic composition comprising a pandemic influenza virus or antigenic preparation thereof and an oil-in-water emulsion adjuvant, in particular an oil-in-water emulsion adjuvant comprising a metabolisable oil, a sterol such as alpha tocopherol and an emulsifying agent, in the manufacture of a first vaccination-component of a multi-dose vaccine, the multi-dose vaccine further comprising, as a boosting dose, an influenza virus or antigenic preparation thereof which shares common CD4 T-cell epitopes with the pandemic influenza virus antigen or virus antigenic preparation thereof of the dose given at the first vaccination.

Vaccination Means

The composition of the invention may be administered by any suitable delivery route, such as intradermal, mucosal e.g. intranasal, oral, intramuscular or subcutaneous. Other delivery routes are well known in the art.

The intramuscular delivery route is preferred for the adjuvanted influenza composition.

Intradermal delivery is another suitable route. Any suitable device may be used for intradermal delivery, for example short needle devices such as those described in U.S. Pat. Nos. 4,886,499, 5,190,521, 5,328,483, 5,527,288, 4,270,537, 5,015,235, 5,141,496, 5,417,662. Intradermal vaccines may also be administered by devices which limit the effective penetration length of a needle into the skin, such as those described in WO99/34850 and EP1092444, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556 4,790,824, 4,941,880, 4,940,460, WO 97/37705 and WO 97/13537. Also suitable are ballistic powder/particle delivery devices which use compressed gas to accelerate vaccine in powder form through the outer layers of the skin to the dermis. Additionally, conventional syringes may be used in the classical mantoux method of intradermal administration.

Another suitable administration route is the subcutaneous route. Any suitable device may be used for subcutaneous delivery, for example classical needle. Preferably, a needle-free jet injector service is used, such as that published in WO 01/05453, WO 01/05452, WO 01/05451, WO 01/32243, WO 01/41840, WO 01/41839, WO 01/47585, WO 01/56637, WO 01/58512, WO 01/64269, WO 01/78810, WO 01/91835, WO 01/97884, WO 02/09796, WO 02/34317. More preferably said device is pre-filled with the liquid vaccine formulation.

Alternatively the vaccine is administered intranasally. Typically, the vaccine is administered locally to the nasopharyngeal area, preferably without being inhaled into the lungs. It is desirable to use an intranasal delivery device which delivers the vaccine formulation to the nasopharyngeal area, without or substantially without it entering the lungs.

Preferred devices for intranasal administration of the vaccines according to the invention are spray devices. Suitable commercially available nasal spray devices include BD ACCUSPRAY SCF™ (nasal spray system). Nebulisers produce a very fine spray which can be easily inhaled into the lungs and therefore does not efficiently reach the nasal mucosa. Nebulisers are therefore not preferred.

Preferred spray devices for intranasal use are devices for which the performance of the device is not dependent upon the pressure applied by the user. These devices are known as pressure threshold devices. Liquid is released from the nozzle only when a threshold pressure is applied. These devices make it easier to achieve a spray with a regular droplet size. Pressure threshold devices suitable for use with the present invention are known in the art and are described for example in WO 91/13281 and EP 311 863 B and EP 516 636, incorporated herein by reference. Such devices are commercially available from Pfeiffer GmbH and are also described in Bommer, R. Pharmaceutical Technology Europe, September 1999.

Preferred intranasal devices produce droplets (measured using water as the liquid) in the range 1 to 200 μm, preferably 10 to 120 μm. Below 10 μm there is a risk of inhalation, therefore it is desirable to have no more than about 5% of droplets below 10 μm. Droplets above 120 μm do not spread as well as smaller droplets, so it is desirable to have no more than about 5% of droplets exceeding 120 μm.

Bi-dose delivery is a further preferred feature of an intranasal delivery system for use with the vaccines according to the invention. Bi-dose devices contain two sub-doses of a single vaccine dose, one sub-dose for administration to each nostril. Generally, the two sub-doses are present in a single chamber and the construction of the device allows the efficient delivery of a single sub-dose at a time. Alternatively, a monodose device may be used for administering the vaccines according to the invention.

Alternatively, the epidermal or transdermal vaccination route is also contemplated in the present invention.

In a specific aspect of the present invention, the adjuvanted immunogenic composition for the first administration may be given intramuscularly, and the boosting composition, either adjuvanted or not, may be administered through a different route, for example intradermal, subcutaneous or intranasal. In another specific embodiment, the composition for the first administration may contain a standard HA content of 15 μg per influenza strain, and the boosting composition may contain a low dose of HA, i.e. below 15 μg, and depending on the administration route, may be given in a smaller volume.

Populations to Vaccinate

The target population to vaccinate may be immuno-compromised human. Immuno-compromised humans generally are less well able to respond to an antigen, in particular to an influenza antigen, in comparison to healthy adults.

Preferably the target population is a population which is unprimed against influenza, either being naïve (such as vis à vis a pandemic strain), or having failed to respond previously to influenza infection or vaccination. Preferably the target population is elderly persons suitably aged at least 50, typically at least 55, or at least 60, or 65 years and over, younger high-risk adults (i.e. between 18 and 64 years of age) such as people working in health institutions, or those young adults with a risk factor such as cardiovascular and pulmonary disease, or diabetes. Another target population is all children 6 months of age and over, especially children 6-23 months of age who experience a relatively high influenza-related hospitalization rate. Preferably the target population is elderly above 65 years of age.

Vaccination Regimes, Dosing and Additional Efficacy Criteria Suitably the immunogenic compositions according to the present invention are a standard 0.5 ml injectable dose in most cases, and contains 15 µg of haemagglutinin antigen component from the or each influenza strain, as measured by single radial immunodiffusion (SRD) (J. M. Wood et al.: J. Biol. Stand. 5 (1977) 237-247; J. M. Wood et al., J. Biol. Stand. 9 (1981) 317-330). Suitably the vaccine dose volume will be between 0.5 ml and 1 ml, in particular a standard 0.5 ml, or 0.7 ml vaccine dose volume. Slight adaptation of the dose volume will be made routinely depending on the HA concentration in the original bulk sample.

Suitably said immunogenic composition contains a low dose of HA antigen—e.g any of 1, 2, 3, 4, 5, 6, 7, 8, 9, 10, 11, 12, 13 or 14 µg of HA per influenza strain. A suitable low dose of HA is between 1 to 7.5 µg of HA per influenza strain, suitably between 3.5 to 5 µg such as 3.75 µg of HA per influenza strain, typically about 5 µg of HA per influenza strain.

Advantageously, a vaccine dose according to the invention, in particular a low dose vaccine, may be provided in a smaller volume than the conventional injected split flu vaccines, which are generally around 0.5, 0.7 or 1 ml per dose. The low volume doses according to the invention are preferably below 500 more preferably below 300 µl and most preferably not more than about 200 µl or less per dose.

Thus, a preferred low volume vaccine dose according to one aspect of the invention is a dose with a low antigen dose in a low volume, e.g. about 15 µg or about 7.5 µg HA or about 3.0 µg HA (per strain) in a volume of about 200 µl.

The influenza medicament of the invention preferably meets certain international criteria for vaccines.

Standards are applied internationally to measure the efficacy of influenza vaccines. The European Union official criteria for an effective vaccine against influenza are set out in the Table 1 below. Theoretically, to meet the European Union requirements, an influenza vaccine has to meet only one of the criteria in the table, for all strains of influenza included in the vaccine. The compositions of the present invention suitably meet at least one such criteria.

However in practice, at least two or all three of the criteria will need to be met for all strains, particularly for a new vaccine such as a new vaccine for delivery via a different route. Under some circumstances two criteria may be sufficient. For example, it may be acceptable for two of the three criteria to be met by all strains while the third criterion is met by some but not all strains (e.g. two out of three strains). The requirements are different for adult populations (18-60 years) and elderly populations (>60 years).

TABLE 1

|  | 18-60 years | >60 years |
| --- | --- | --- |
| Seroconversion rate* | >40% | >30% |
| Conversion factor** | >2.5 | >2.0 |
| Protection rate*** | >70% | >60% |

*Seroconversion rate is defined as the percentage of vaccinees who have at least a 4-fold increase in serum haemagglutinin inhibition (HI) titres after vaccination, for each vaccine strain.
**Conversion factor is defined as the fold increase in serum HI geometric mean titres (GMTs) after vaccination, for each vaccine strain.
***Protection rate is defined as the percentage of vaccinees with a serum HI titre equal to or greater than 1:40 after vaccination (for each vaccine strain) and is normally accepted as indicating protection.

In a further aspect the invention provides a method of designing a vaccine for diseases known to be cured or treated through a CD4+ T cell activation, comprising
1) selecting an antigen containing CD4+ epitopes, and
2) combining said antigen with an oil-in-water emulsion adjuvant as defined herein above, wherein said vaccine upon administration in said mammal is capable of inducing an enhanced CD4 T cell response in said mammal.

The teaching of all references in the present application, including patent applications and granted patents, are herein fully incorporated by reference.

For the avoidance of doubt the terms 'comprising', 'comprise' and 'comprises' herein is intended by the inventors to be optionally substitutable with the terms 'consisting of', 'consist of', and 'consists of', respectively, in every instance.

The invention will be further described by reference to the following, non-limiting, examples:

Example I describes immunological read-out methods used in mice, ferret and human studies.

Example II describes the preparation and characterization of the oil in water emulsion and adjuvant formulations used in the studies exemplified.

Example III describes a clinical trial in an elderly population aged over 65 years with a vaccine containing a split influenza antigen preparation and AS03 adjuvant Example IV describes a second clinical trial—revaccination trial—in an elderly population aged over 65 years with a vaccine containing a split influenza antigen preparation and AS03 adjuvant.

Example V shows a pre-clinical evaluation of adjuvanted and un-adjuvanted influenza vaccines in ferrets (study I and study II). The temperature monitoring, viral shedding and CD4 T-cell response were measured.

Example VI shows a pre-clinical evaluation of adjuvanted and un-adjuvanted influenza vaccines in C57Bl/6 naïve and primed mice.

Example VII shows a pre-clinical evaluation of adjuvanted and un-adjuvanted split and sub-unit influenza vaccines in C57Bl/6 mice primed with heterologous strains.

Example VIII describes a clinical trial in an elderly population aged over 65 years with a vaccine containing a split influenza antigen preparation containing AS03 adjuvant, AS03+MPL adjuvant, or no exogeneous adjuvant.

Example IX shows a pre-clinical evaluation of adjuvanted and un-adjuvanted influenza vaccines in ferrets (study III). The temperature monitoring, viral shedding and HI titers were measured.

Example X shows a clinical trial in an elderly population aged over 65 years with a vaccine containing a split influenza antigen preparation containing AS03 with or without MPL adjuvant: immunogenicity persistence data at day 90 and day 180.

Example XI shows a clinical trial in an elderly population aged over 65 years with a vaccine containing a split influenza antigen preparation containing AS03 with MPL adjuvant.

Example XII shows a clinical trial in an elderly population aged over 65 years with a vaccine containing a split influenza antigen preparation containing AS03 with MPL adjuvant at two concentrations.

EXAMPLE I

Immunological Read-out Methods

I.1. Mice Methods
I.1.1. Hemagglutination Inhibition Test
Test Procedure

Anti-Hemagglutinin antibody titers to the three influenza virus strains were determined using the hemagglutination inhibition test (HI). The principle of the HI test is based on the ability of specific anti-Influenza antibodies to inhibit hemagglutination of chicken red blood cells (RBC) by influenza virus hemagglutinin (HA). Heat inactivated sera were previously treated by Kaolin and chicken RBC to remove non-specific inhibitors. After pretreatment, two-fold dilutions of sera were incubated with 4 hemagglutination units of each influenza strain. Chicken red blood cells were then added and the inhibition of agglutination was scored. The titers were expressed as the reciprocal of the highest dilution of serum that completely inhibited hemagglutination. As the first dilution of sera was 1:20, an undetectable level was scored as a titer equal to 10.

Statistical Analysis

Statistical analysis were performed on post vaccination HI titers using UNISTAT. The protocol applied for analysis of variance can be briefly described as follow:

Log transformation of data
Shapiro-Wilk test on each population (group) in order to verify the normality of groups distribution
Cochran test in order to verify the homogenicity of variance between the different populations (groups)
Two-way Analysis of variance performed on groups
Tukey HSD test for multiple comparisons I.1.2. Intracellular Cytokine Staining This technique allows a quantification of antigen specific T lymphocytes on the basis of cytokine production: effector T cells and/or effector-memory T cells produce IFN-γ and/or central memory T cells produce IL-2. PBMCs are harvested at day 7 post-immunization.

Lymphoid cells are re-stimulated in vitro in the presence of secretion inhibitor (Brefeldine). These cells are then processed by conventional immunofluorescent procedure using fluorescent antibodies (CD4, CD8, IFN-γ and IL-2). Results are expressed as a frequency of cytokine positive cell within CD4/CD8 T cells. Intracellular staining of cytokines of T cells was performed on PBMC 7 days after the second immunization. Blood was collected from mice and pooled in heparinated medium RPMI+Add. For blood, RPMI+Add-diluted PBL suspensions were layered onto a Lympholyte-Mammal gradient according to the recommended protocol (centrifuge 20 min at 2500 rpm and R.T.). The mononuclear cells at the interface were removed, washed 2× in RPMI+Add and PBMCs suspensions were adjusted to $2 \times 10^6$ cells/ml in RPMI 5% fetal calf serum.

In vitro antigen stimulation of PBMCs was carried out at a final concentration of $1 \times 10^7$ cells/ml (tube FACS) with Whole FI (1 μgHA/strain) and then incubated 2 hrs at 37° C. with the addition of anti-CD28 and anti-CD49d (1 μg/ml for both).

Following the antigen restimulation step, PBMC are incubated overnight at 37° C. in presence of Brefeldin (1 μg/ml) at 37° C. to inhibit cytokine secretion.

IFN-γ/IL-2/CD4/CD8 staining was performed as follows: Cell suspensions were washed, resuspended in 50 μl of PBS 1% FCS containing 2% Fc blocking reagent (1/50; 2.4 G2). After 10 min incubation at 4° C., 50 μl of a mixture of anti-CD4-PE (2/50) and anti-CD8 perCp (3/50) was added and incubated 30 min at 4° C. After a washing in PBS 1% FCS, cells were permeabilized by resuspending in 200 μl of Cytofix-Cytoperm (Kit BD) and incubated 20 min at 4° C. Cells were then washed with Perm Wash (Kit BD) and resuspended with 50 μl of a mix of anti-IFN-γ APC (1/50)+ anti-IL-2 FITC (1/50) diluted in Perm Wash. After an incubation min 2 h max overnight at 4° C., cells were washed with Perm Wash and resuspended in PBS 1% FCS+1% paraformaldehyde. Sample analysis was performed by FACS. Live cells were gated (FSC/SSC) and acquisition was performed on ~20,000 events (lymphocytes) or 35,000 events on CD4+ T cells. The percentages of IFN-γ+ or IL2+ were calculated on CD4+ and CD8+ gated populations.

I.2. Ferrets Methods

I.2.1. Hemagglutination Inhibition Test (HI)

Test Procedure.

Anti-Hemagglutinin antibody titers to the three influenza virus strains were determined using the hemagglutination inhibition test (HI). The principle of the HI test is based on the ability of specific anti-Influenza antibodies to inhibit hemagglutination of chicken red blood cells (RBC) by influenza virus hemagglutinin (HA). Sera were first treated with a 25% neuraminidase solution (RDE) and were heat-inactivated to remove non-specific inhibitors. After pretreatment, two-fold dilutions of sera were incubated with 4 hemagglutination units of each influenza strain. Chicken red blood cells were then added and the inhibition of agglutination was scored. The titers were expressed as the reciprocal of the highest dilution of serum that completely inhibited hemagglutination. As the first dilution of sera was 1:10, an undetectable level was scored as a titer equal to 5.

Statistical Analysis.

Statistical analysis were performed on HI titers (Day 41, before challenge) using UNISTAT. The protocol applied for analysis of variance can be briefly described as followed:

Log transformation of data.
Shapiro-wilk test on each population (group) in order to verify the normality of groups distribution.
Cochran test in order to verify the homogenicity of variance between the different populations (groups).
Test for interaction of one-way ANOVA.
Tuckey-HSD Test for multiple comparisons.

I.2.2. Body Temperature Monitoring

Individual temperatures were monitored during the challenge period with the transmitters and by the telemetry recording. All implants were checked and refurbished and a new calibration was performed by DSI (Data Sciences International, Centaurusweg 123, 5015 TC Tilburg, The Netherlands) before placement in the intraperitoneal cavity. All animals were individually housed in single cage during these measurements.

Temperatures were recorded every 15 minutes 4 days before challenge until 7 days Post-challenge.

I.2.3. Nasal Washes

The nasal washes were performed by administration of 5 ml of PBS in both nostrils in awoke animals. The inoculum was collected in a Petri dish and placed into sample containers on dry ice.

Viral Titration in Nasal Washes

All nasal samples were first sterile filtered through Spin X filters (Costar) to remove any bacterial contamination. 50 μl of serial ten-fold dilutions of nasal washes were transferred to microtiter plates containing 50 μl of medium (10 wells/ dilution). 100 μl of MDCK cells ($2.4 \times 10^5$ cells/ml) were then added to each well and incubated at 35° C. for 5-7 days.

After 5-7 days of incubation, the culture medium is gently removed and 100 μl of a 1/20 WST-1 containing medium is added and incubated for another 18 hrs.

The intensity of the yellow formazan dye produced upon reduction of WST-1 by viable cells is proportional to the number of viable cells present in the well at the end of the viral titration assay and is quantified by measuring the absorbance of each well at the appropriate wavelength (450 nanometers). The cut-off is defined as the OD average of uninfected control cells—0.3 OD (0.3 OD correspond to +/−3 StDev of OD of uninfected control cells). A positive score is defined when OD is <cut-off and in contrast a negative score is defined when OD is >cut-off. Viral shedding titers were determined by "Reed and Muench" and expressed as Log TCID50/ml.

I.3. Assays for Assessing the Immune Response in Humans

I.3.1. Hemagglutination Inhibition Assay

The immune response was determined by measuring HI antibodies using the method described by the WHO Collaborating Centre for influenza, Centres for Disease Control, Atlanta, USA (1991).

Antibody titre measurements were conducted on thawed frozen serum samples with a standardised and comprehensively validated micromethod using 4 hemagglutination-inhibiting units (4 HIU) of the appropriate antigens and a 0.5% fowl erythrocyte suspension. Non-specific serum inhibitors were removed by heat treatment and receptor-destroying enzyme.

The sera obtained were evaluated for HI antibody levels. Starting with an initial dilution of 1:10, a dilution series (by a factor of 2) was prepared up to an end dilution of 1:20480. The titration end-point was taken as the highest dilution step that showed complete inhibition (100%) of hemagglutination. All assays were performed in duplicate.

I.3.2. Neuraminidase Inhibition Assay

The assay was performed in fetuin-coated microtitre plates. A 2-fold dilution series of the antiserum was prepared and mixed with a standardised amount of influenza A H3N2, H1N1 or influenza B virus. The test was based on the biological activity of the neuraminidase which enzymatically releases neuraminic acid from fetuin. After cleavage of the terminal neuraminic acid β-D-glactose-N-acetyl-galactosamin was unmasked. Horseradish peroxidase (HRP)-labelled peanut agglutinin from *Arachis hypogaea*, which binds specifically to the galactose structures, was added to the wells. The amount of bound agglutinin can be detected and quantified in a substrate reaction with tetra-methylbenzidine (TMB) The highest antibody dilution that still inhibits the viral neuraminidase activity by at least 50% was indicated is the NI titre.

I.3.3. Neutralising Antibody Assay

Neutralising antibody measurements were conducted on thawed frozen serum samples. Virus neutralisation by antibodies contained in the serum was determined in a microneutralization assay. The sera were used without further treatment in the assay. Each serum was tested in triplicate. A standardised amount of virus was mixed with serial dilutions of serum and incubated to allow binding of the antibodies to the virus. A cell suspension, containing a defined amount of MDCK cells was then added to the mixture of virus and antiserum and incubated at 33° C. After the incubation period, virus replication was visualised by hemagglutination of chicken red blood cells. The 50% neutralisation titre of a serum was calculated by the method of Reed and Muench.

I.3.4. Cell-Mediated Immunity was Evaluated by Cytokine Flow Cytometry (CFC)

Peripheral blood antigen-specific CD4 and CD8 T cells can be restimulated in vitro to produce IL-2, CD40L, TNF-alpha and IFN if incubated with their corresponding antigen. Consequently, antigen-specific CD4 and CD8 T cells can be enumerated by flow cytometry following conventional immunofluorescence labelling of cellular phenotype as well as intracellular cytokines production. In the present study, Influenza vaccine antigen as well as peptides derived from specific influenza protein were used as antigen to restimulate Influenza-specific T cells. Results were expressed as a frequency of cytokine(s)-positive CD4 or CD8 T cell within the CD4 or CD8 T cell sub-population.

I.3.5. Statistical Methods

I.3.5.1. Primary Endpoints

Percentage, intensity and relationship to vaccination of solicited local and general signs and symptoms during a 7 day follow-up period (i.e. day of vaccination and 6 subsequent days) after vaccination and overall.

Percentage, intensity and relationship to vaccination of unsolicited local and general signs and symptoms during a 21 day follow-up period (i.e. day of vaccination and 20 subsequent days) after vaccination and overall.

Occurrence of serious adverse events during the entire study.

I.3.5.2. Secondary Endpoints for the Humoral Immune Response:

Observed Variables:
 At days 0 and 21: serum hemagglutination-inhibition (HI) and NI antibody titres, tested separately against each of the three influenza virus strains represented in the vaccine (anti-H1N1, anti-H3N2 & anti-B-antibodies).
 At days 0 and 21: neutralising antibody titres, tested separately against each of the three influenza virus strains represented in the vaccine Derived Variables (with 95% Confidence Intervals):
 Geometric mean titres (GMTs) of serum HI antibodies with 95% confidence intervals (95% CI) pre and post-vaccination
 Seroconversion rates* with 95% CI at day 21
 Conversion factors** with 95% CI at day 21
 Seroprotection rates*** with 95% CI at day 21
 Serum NI antibody GMTs' (with 95% confidence intervals) at all timepoints.
 * Seroconversion rate defined as the percentage of vaccinees who have at least a 4-fold increase in serum HI titres on day 21 compared to day 0, for each vaccine strain.
 **Conversion factor defined as the fold increase in serum HI GMTs on day 21 compared to day 0, for each vaccine strain.
 ***Protection rate defined as the percentage of vaccinees with a serum HI titre=40 after vaccination (for each vaccine strain) that usually is accepted as indicating protection.

for the Cell Mediated Immune (CMI) Response

Observed Variable
 At days 0 and 21: frequency of cytokine-positive CD4/CD8 cells per $10^6$ in different tests. Each test quantifies the response of CD4/CD8 T cell to:
  Peptide Influenza (pf) antigen (the precise nature and origin of these antigens needs to be given/explained
  Split Influenza (sf) antigen
  Whole Influenza (wf) antigen.

Derived Variables:
 cells producing at least two different cytokines (CD40L, IL-2, IFNγ, TNFα)
 cells producing at least CD40L and another cytokine (IL-2, TNFα, IFNγ)
 cells producing at least IL-2 and another cytokine (CD40L, TNFα, IFNγ)
 cells producing at least IFNγ and another cytokine (IL-2, TNFα, CD40L)
 cells producing at least TNFα and another cytokine (IL-2, CD40L, IFNγ)

I.3.5.3. Analysis of Immunogenicity

The immunogenicity analysis was based on the total vaccinated cohort. For each treatment group, the following parameters (with 95% confidence intervals) were calculated:

Geometric mean titres (GMTs) of HI and NI antibody titres at days 0 and 21
Geometric mean titres (GMTs) of neutralising antibody titres at days 0 and 21.
Conversion factors at day 21.
Seroconversion rates (SC) at day 21 defined as the percentage of vaccinees that have at least a 4-fold increase in serum HI titres on day 21 compared to day 0.
Protection rates at day 21 defined as the percentage of vaccinees with a serum HI titre=1:40.
The frequency of CD4/CD8 T-lymphocytes secreting in response was summarised (descriptive statistics) for each vaccination group, at each timepoint (Day 0, Day 21) and for each antigen (Peptide influenza (pf), split influenza (sf) and whole influenza (wf)).
Descriptive statistics in individual difference between timepoint (Post-Pre) responses fore each vaccination group and each antigen (pf, sf, and wf) at each 5 different tests.
A non-parametric test (Kruskall-Wallis test) was used to compare the location differences between the 3 groups and the statistical p-value was calculated for each antigen at each 5 different tests. All significance tests were two-tailed. P-values less than or equal to 0.05 were considered as statistically significant.

EXAMPLE II

Preparation and Characterization of the Oil in Water Emulsion and Adjuvant Formulations Unless otherwise stated, the oil/water emulsion used in the subsequent examples is composed an organic phase made of 2 oils (alpha-tocopherol and squalene), and an aqueous phase of PBS containing TWEEN® 80 as emulsifying agent. Unless otherwise stated, the oil in water emulsion adjuvant formulations used in the subsequent examples were made comprising the following oil in water emulsion component (final concentrations given): 2.5% squalene (v/v), 2.5% alpha-tocopherol (v/v), 0.9% polyoxyethylene sorbitan monooleate (v/v) (TWEEN® 80), see WO 95/17210. This emulsion, termed AS03 in the subsequent examples, was prepared as followed as a two-fold concentrate.

II.1. Preparation of Emulsion SB62

II.1.1. Lab-Scale Preparation

TWEEN® 80 is dissolved in phosphate buffered saline (PBS) to give a 2% solution in the PBS. To provide 100 ml two-fold concentrate emulsion 5 g of DL alpha tocopherol and 5 ml of squalene are vortexed to mix thoroughly. 90 ml of PBS/TWEEN® solution is added and mixed thoroughly. The resulting emulsion is then passed through a syringe and finally microfluidised by using an M110S microfluidics machine. The resulting oil droplets have a size of approximately 120-180 nm (expressed as Z average measured by PCS).

The other adjuvants/antigen components are added to the emulsion in simple admixture.

II.1.2. Scaled-Up Preparation

The preparation of the SB62 emulsion is made by mixing under strong agitation of an oil phase composed of hydrophobic components (α-tocopherol and squalene) and an aqueous phase containing the water soluble components (TWEEN® 80 and PBS mod (modified), pH 6.8). While stirring, the oil phase (1/10 total volume) is transferred to the aqueous phase (9/10 total volume), and the mixture is stirred for 15 minutes at room temperature. The resulting mixture then subjected to shear, impact and cavitation forces in the interaction chamber of a microfluidizer (15000 PSI—8 cycles) to produce submicron droplets (distribution between 100 and 200 nm). The resulting pH is between 6.8±0.1. The SB62 emulsion is then sterilised by filtration through a 0.22 µm membrane and the sterile bulk emulsion is stored refrigerated in Cupac containers at 2 to 8° C. Sterile inert gas (nitrogen or argon) is flushed into the dead volume of the SB62 emulsion final bulk container for at least 15 seconds.

The final composition of the SB62 emulsion is as follows:

TWEEN® 80:1.8% (v/v) 19.4 mg/ml; Squalene: 5% (v/v) 42.8 mg/ml; α-tocopherol: 5% (v/v) 47.5 mg/ml; PBS-mod: NaCl 121 mM, KCl 2.38 mM, Na2HPO4 7.14 mM, KH2PO4 1.3 mM; pH 6.8±0.1.

II.2. Measure of Oil Droplet Size Dynamic Light Scattering

II.2.1. Introduction

The size of the diameter of the oil droplets is determined according to the following procedure and under the following experimental conditions. The droplet size measure is given as an intensity measure and expressed as z average measured by PCS.

I.2.2. Sample Preparation

Size measurements have been performed on the oil-in-water emulsion adjuvant: SB62 prepared following the scaled-up method, AS03 and AS03+MPL (50 µg/ml), the last two being prepared just before use. The composition of the samples is given below (see section II.2.4). Samples were diluted 4000×-8000× in PBS 7.4.

As a control, PL-Nanocal Particle size standards 100 nm (cat n° 6011-1015) was diluted in 10 mM NaCl.

II.2.3. Malvern Zetasizer 3000HS Size Measurements

All size measurements were performed with both Malvern Zetasizer 3000HS.

Samples were measured into a plastic cuvette for Malvern analysis at a suitable dilution (usually at a dilution of 4000× to 20000× depending on the sample concentration), and with two optical models:

either real particle refractive index of 0 and imaginary one of 0.
or real particle refractive index of 1.5 and imaginary one of 0.01 (the adapted optical model for the emulsion, according to the values found in literature).

The technical conditions were:

laser wavelength: 532 nm (Zeta3000HS).
laser power: 50 mW (Zeta3000HS).
scattered light detected at 90° (Zeta3000HS).
temperature: 25° C.,
duration: automatic determination by the soft,
number: 3 consecutive measurements,
z-average diameter: by cumulants analysis
size distribution: by the Contin or the Automatic method.

The Automatic Malvern algorithm uses a combination of cumulants, Contin and non negative least squares (NNLS) algorithms.

The intensity distribution may be converted into volume distribution thanks to the Mie theory.

II.2.4. Results (see Table 2)
Cumulants Analysis (Z Average Diameter):

TABLE 2

| Sample | Dilution | Record | Count rate | ZAD | Polydispersity |
|---|---|---|---|---|---|
| SB62 | 5000 | 1 | 7987 | 153 | 0.06 |
| | | 2 | 7520 | 153 | 0.06 |
| | | 3 | 6586 | 152 | 0.07 |
| | | average | 7364 | 153 | 0.06 |
| SB62 (Example IV) | 8000 | 1 | 8640 | 151 | 0.03 |
| | | 2 | 8656 | 151 | 0.00 |
| | | 3 | 8634 | 150 | 0.00 |
| | | average | 8643 | 151 | 0.01 |
| SB62 + MPL 25 µg (*) | 8000 | 1 | 8720 | 154 | 0.03 |
| | | 2 | 8659 | 151 | 0.03 |
| | | 3 | 8710 | 152 | 0.02 |
| | | average | 8697 | 152 | 0.02 |

(*) Prepared as follows: Water for injection, PBS 10x concentrated, 250 µl of SB62 emulsion and 25 µg of MPL are mixed together to reach a final volume of 280 µl.

The z-average diameter (ZAD) size is weighed by the amount of light scattered by each size of particles in the sample. This value is related to a monomodal analysis of the sample and is mainly used for reproducibility purposes.

The count rate (CR) is a measure of scattered light: it corresponds to thousands of photons per second.

The polydispersity (Poly) index is the width of the distribution. This is a dimensionless measure of the distribution broadness.

Contin and Automatic Analysis:

Two other SB62 preparations (2 fold concentrated AS03) have been made and assessed according to the procedure explained above with the following minor modifications:

Samples were measured into a plastic cuvette for Malvern analysis, at two dilutions determined to obtain an optimal count rate values: 10000× and 20000× for the Zetasizer 3000HS, the same optical models as used in the above example. Results are shown in Table 3.

TABLE 3

| SB62 | Dilution | IR | | Analysis in Contin (mean in nm) | | Analysis in Automatic (mean in nm) | |
|---|---|---|---|---|---|---|---|
| | | Real | Imaginary | Intensity | Volume | Intensity | Volume |
| 1022 | 1/10000 | 0 | 0 | 149 | 167 | 150 | — |
| | | 1.5 | 0.01 | 158 | 139 | 155 | 143 |
| | 1/20000 | 0 | 0 | 159 | 200 | 155 | 196 |
| | | 1.5 | 0.01 | 161 | 141 | 147 | — |
| 1023 | 1/10000 | 0 | 0 | 158 | 198 | 155 | — |
| | | 1.5 | 0.01 | 161 | 140 | 150 | 144 |
| | 1/20000 | 0 | 0 | 154 | 185 | 151 | 182 |
| | | 1.5 | 0.01 | 160 | 133 | 154 | — |

"—" when the obtained values were not coherent.

Figure 1H:
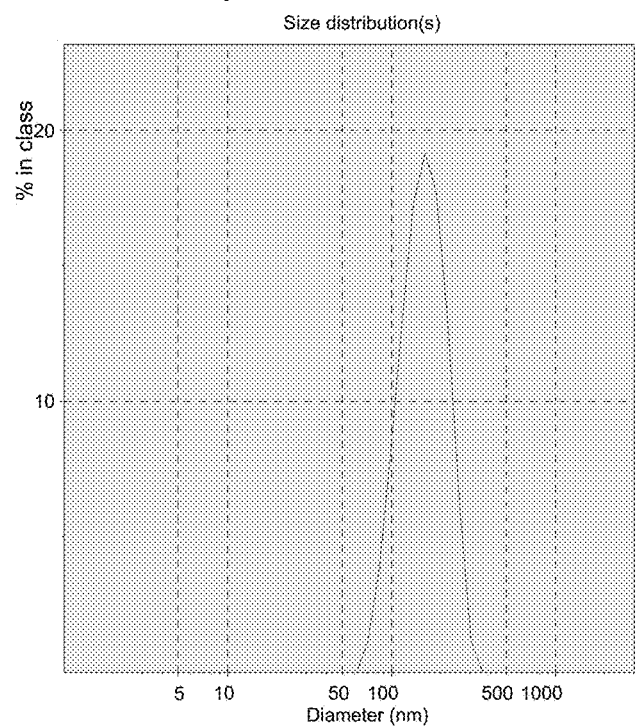

A schematic representation of these results is shown in FIG. 1 for formulation 1023. As can be seen, the great majority of the particles (e.g. at least 80%) have a diameter of less than 300 nm by intensity.

II.2.5. Overall Conclusion

SB62 formulation was measured at different dilutions with the Malvern Zetasizer 3000HS and two optical models. The particle size ZAD (i.e. intensity mean by cumulant analysis) of the formulations assessed above was around 150-155 nm. When using the cumulants algorithm, we observed no influence of the dilution on the ZAD and polydispersity.

Figure 2:
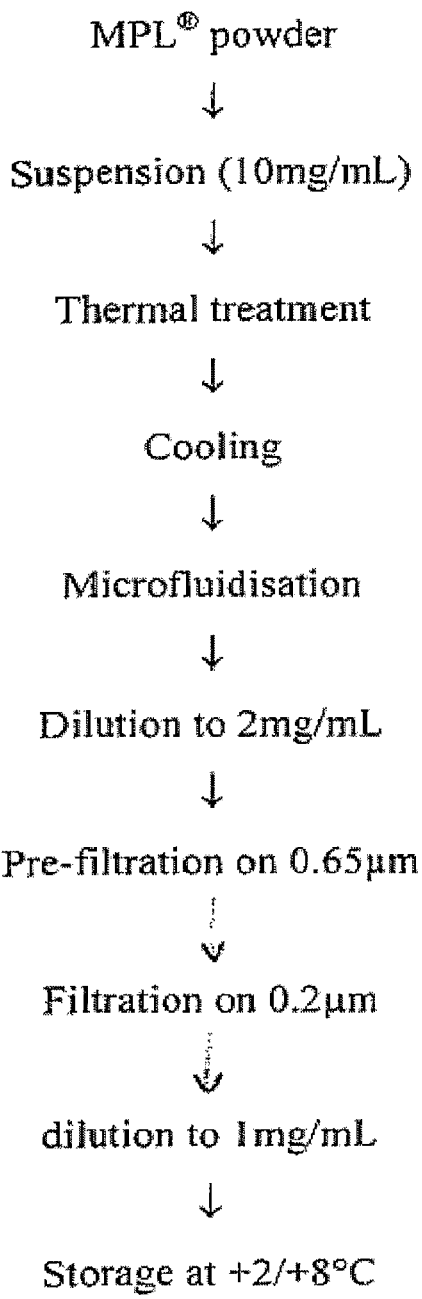

II.3. Preparation of AS03 Comprising MPL
II.3.1. Preparation of MPL Liquid Suspension The MPL (as used throughout the document it is an abbreviation for 3D-MPL, i.e. 3-O-deacylated monophosphoryl lipid A) liquid bulk is prepared from MPL® lyophilized powder. MPL liquid bulk is a stable concentrated (around 1 mg/ml) aqueous dispersion of the raw material, which is ready-to-use for vaccine or adjuvant formulation. A schematic representation of the preparation process is given in FIG. 2.

For a maximum batch size of 12 g, MPL liquid bulk preparation is carried over in sterile glass containers. The dispersion of MPL consists of the following steps:
 suspend the MPL powder in water for injection
 disaggregate any big aggregates by heating (thermal treatment)
 reduce the particle size between 100 nm and 200 nm by microfluidization
 prefilter the preparation on a SARTOCLEAN® Pre-filter unit, 0.8/0.65 µm
 sterile filter the preparation at room temperature (SARTOBRAN® P unit, 0.22 µm)

MPL powder is lyophilized by microfluidisation resulting in a stable colloidal aqueous dispersion (MPL particle size smaller than 200 nm). The MPL lyophilized powder is dispersed in water for injection in order to obtain a coarse 10 mg/ml suspension. The suspension then undergoes a thermal treatment under stirring. After cooling to room temperature, the microfluidization process is started in order to decrease the particle size. Microfluidization is conducted using Microfluidics apparatus M110EH, by continuously circulating the dispersion through a microfluidization interaction chamber, at a defined pressure for a minimum amount of passages (number of cycles: $n_{min}$). The microfluidization duration, representing the number of cycles, is calculated on basis of the measured flow rate and the dispersion volume. On a given equipment at a given pressure, the resulting flow rate may vary from one interaction chamber to another, and throughout the lifecycle of a particular interaction chamber. In the present example the interaction chamber used is of the type F20Y Microfluidics. As the microfluidization efficiency is linked to the couple pressure—flow rate, the processing time may vary from one batch to another. The time required for 1 cycle is calculated on basis of the flow rate. The flow rate to be considered is the flow rate measured with water for injection just before introduction of MPL into the apparatus. One cycle is defined as the time (in minutes) needed for the total volume of MPL to pass once through the apparatus. The time needed to obtain n cycles is calculated as follows:

$n \times$ quantity of MPL to treat (ml)/flow rate (ml/min)

The number of cycles is thus adapted accordingly. Minimum amount of cycles to perform ($n_{min}$) are described for the preferred equipment and interaction chambers used. The total amount of cycles to run is determined by the result of a particle size measurement performed after $n_{min}$ cycles. A particle size limit ($d_{lim}$) is defined, based on historical data. The measurement is realized by photon correlation spectroscopy (PCS) technique, and $d_{lim}$ is expressed as an unimodal result ($Z_{average}$). Under this limit, the microfluidization can be stopped after $n_{min}$ cycles. Above this limit, microfluidization is continued until satisfactory size reduction is obtained, for maximum another 50 cycles.

If the filtration does not take place immediately after microfluidization, the dispersed MPL is stored at +2 to +8° C. awaiting transfer to the filtration area.

After microfluidization, the dispersion is diluted with water for injection, and sterile filtered through a 0.22 μm filter under laminal flow. The final MPL concentration is 1 mg/ml (0.80-1.20 mg/ml).

II.3.2. Preparation of AS03+MPL Adjuvanted Vaccine: 1 Vial Approach

To the AS03 adjuvant formulation, MPL is added at a final concentration of between 10 and 50 μg per vaccine dose.

PBS 10 fold concentrated (pH 7.4 when one fold concentrated) as well as a SB62 mixture containing TWEEN®, TRITON X-100™ and VES (vitamin E succinate) is added to water for injection. The quantities take into account the detergent present in the influenza strains so as to reach a target final concentration of 750 μg/ml TWEEN® 80, 110 μg/ml TRITON X-100™ and 100 μg/ml VES. After 5 min stirring, 15 μg of each influenza strain of interest (for example strain H1N1, H3N2 and B in a classical tri-valent vaccine) are added. After 15 min stirring, 250 μl of SB62 emulsion is added and then 25 μg or 50 μg of MPL.

A schematic representation of the preparation process is given in FIG. 3. The final composition of AS03 comprising MPL per human dose is given the Table 4.

TABLE 4

| Ingredients | | Concentration | Per human dose | |
|---|---|---|---|---|
| Name | Component | | Quantity | Other |
| SB62 | Squalene | 781 μl/ml | 250 μl | |
| | (solution 43 mg/ml) | | 10.68 mg | |
| | Tocopherol | | 11.86 mg | |
| | (solution 48 mg/ml) | | | |
| | TWEEN ® 80 | | 4.85 mg | |
| | (solution 20 mg/ml) | | | |
| MPL** | (solution 1 mg/ml) | 78 μg/ml or 156 μg/ml | 25 μg or 50 μg | |
| PBS mod* | NaCl | 137 mM | 2.56 mg | |
| | KCl | 2.7 mM | 0.064 mg | |
| | Na2HPO4 | 8.1 mM | 0.368 mg | |
| | KH2PO4 | 1.47 mM | 0.064 mg | |
| Water for injection | | | | Ad 320 μl |
| pH | | | | 6.8 +/− 0.1 |

*PBS mod 10x concentrated pH 6.8 = KH2PO4, Na2HPO4, NaCl, KCl—HCl
**MPL is either 25 μg or 50 μg per dose II.3.3. Preparation of AS03+MPL Adjuvanted Vaccine: 2 Vials Approach The same formulation can be prepared from a 2 vials approach by mixing 2 fold concentrated antigen or antigenic preparation with the AS03 (SB62 250 μl) or the AS03+MPL (SB62 250 μl+25 μg or 50 μg MPL) adjuvant. In this instance it is proceeded as follows. The manufacturing of the AS25-adjuvanted influenza vaccine consists of three main steps:
1) Formulation of the trivalent final bulk (2× concentrated) without adjuvant and filling in the antigen container
2) Preparation of the AS03+MPL adjuvant
3) Extemporaneous reconstitution of the AS03+MPL adjuvanted split virus vaccine.
1) Formulation of the Trivalent Final Bulk without Adjuvant and Filling in the Antigen Container The volumes of the three monovalent bulks are based on the HA content measured in each monovalent bulk prior to the formulation and on a target volume of 1100 ml. Concentrated phosphate buffered saline and a pre-mixture of TWEEN® 80, TRITON X-100™ and α-tocopheryl hydrogen succinate are diluted in water for injection. The three concentrated monobulks (A/New Caledonia , A/New York, B/Jiangsu) are then successively diluted in the resulting phosphate buffered saline/TWEEN® 80—TRITON X-100™—α-tocopheryl hydrogen succinate solution (pH 7.4, 137 mM NaCl, 2.7 mMKCl, 8.1 mM Na2HPO4, 1.47 KH2PO4, 990 μg/ml TWEEN® 80, 150 μg/ml TRITON X-100™ and 130 μg/ml α-tocopheryl hydrogen succinate) in order to have a final concentration of 39.47 μg HA of A strains (H1N1, H3N2) per ml of trivalent final bulk (15 μg HA/A strain/380 μl trivalent final bulk) and 46 μg HA of B strain (17.5 μg HA/B strain/380 μl trivalent final bulk). Between addition of each monovalent bulk, the mixture is stirred for 10-30 minutes at room temperature. After addition of the last monovalent bulk and 15-30 minutes of stirring, the pH is checked and adjusted to 7.2±0.2 with HCl or NaOH. The trivalent final bulk of antigens is aseptically filled into 3-ml sterile Type I (Ph.Eur.) glass vials. Each vial contains a volume of 470 μl (380 μl+90 μl overfill).

2) Preparation of AS03/MPL Adjuvant Bulk and Filling in the Adjuvant Container.

The adjuvant AS03/MPL is prepared by mixing of two components: SB62 emulsion (method in section II.1.2) and MPL (method in section II.3.1). One-fold concentrated PBS mod (prepared by diluting 10× concentrated PBS mod in water for injection) with SB62 bulk and MPL liquid bulk at 1 mg/ml. MPL concentration will be determined so as to reach a final content of between 10 to 50 μg, suitably around 25 μg per final human vaccine dose. The mixture is stirred for 5-30 minutes at room temperature, and the pH is adjusted to 6.8±0.1 with NAOH (0.05 or 0.5 M)/HCl (0.03 M or 0.3 M). After another stirring for 5-30 minutes at room temperature the mixture is sterilised by filtration through a 0.22 μm membrane. Sterile inert gas (nitrogen) flushing is performed to produce inert head space in the filled containers during minimum 1 minute. The sterile AS03+MPL adjuvant is stored at +2-8° C. until aseptical filling into 1.25-ml sterile Type I (Ph. Eur.) glass syringes. Each syringe contains a volume overage of 80 μl (320 μl+80 μl overfill).

At the time of injection, the content of the prefilled syringe containing the adjuvant is injected into the vial that contains the concentrated trivalent inactivated split virion antigens. After mixing the content is withdrawn into the syringe and the needle is replaced by an intramuscular needle. One dose of the reconstituted the AS25-adjuvanted influenza candidate vaccine corresponds to 0.7 mL.

II.4. Preparation of Immunogenic Compositions Comprising an Influenza Antigen and Optionally MPL in an Oil in Water Emulsion Formulation To the SB62 emulsion of II.1 an equal volume of twice concentrated split influenza antigen (Fluarix™) (15 μg HA per strain) was added and mixed. This was combined, when appropriate, with 50 μg/ml of MPL to give the final formulation.

EXAMPLE III

Clinical Trial in an Elderly Population Aged Over 65 Years with a Vaccine Containing a Split Influenza Antigen Preparation and AS03 Adjuvant (Explo-Flu-001)

A phase I, open, randomised study was conducted in an elderly population aged over 65 years in 2003 in order to evaluate the reactogenicity and the immunogenicity of GlaxoSmithKline Biologicals influenza candidate vaccine containing the adjuvant AS03.

The humoral immune response (i.e. anti-hemagglutinin, neutralising and anti-neuraminidase antibody titres) and cell mediated immune response (CD4 and/or CD8 T cell responses) was measured 21 days after intramuscular administration of one dose of an AS03 adjuvanted vaccine or a WV vaccine. Fluarix™ was used as reference.

III.1. Study Design

Three groups of subjects in parallel received the following vaccine intramuscularly:
one group of 50 subjects receiving one dose of the reconstituted and adjuvanted SV influenza vaccine (FluAS03)
one group of 50 subjects receiving one dose of whole virus influenza vaccine (FluWVV)
one group of 50 subjects receiving one dose of FLUARIX®=control Vaccination schedule: one injection of influenza vaccine at day 0, blood sample collection, read-out analysis at day 21 (HI antibody determination, NI antibody determination, determination of neutralising antibodies, and CMI analysis) and study conclusion.

The standard trivalent split influenza vaccine—FLUARIX® used in this study, is a commercial vaccine from the year 2003 developed and manufactured by GlaxoSmithKline Biologicals.

III.2. Vaccine Composition and Administration (Table 5)

III.2.1. Vaccine Preparation

AS03 Adjuvanted Influenza Vaccine

The AS03-adjuvanted influenza vaccine candidate is a 2 components vaccine consisting of a concentrated trivalent inactivated split virion antigens presented in a type 1 glass vial (335 μl) (antigen container) and of a pre-filled type I glass syringe containing the SB62 emulsion (335 μl) (adjuvant container). At the time of injection, the content of the antigen container is removed from the with the help of the SB62 emulsion pre-filled syringe, followed by gently mixing of the syringe. Mixing of the SB62 emulsion with the vaccine antigens reconstitute the AS03 adjuvant. Prior to injection, the used needle is replaced by an intramuscular needle and the volume is corrected to 500 μl.

One dose of the reconstituted AS03-adjuvanted influenza vaccine corresponds to 0.5 ml, contains 15 μg HA of each influenza virus strain as in the registered FLUARIX®/α-RIX® vaccine and contains 10.68 mg squalene, 11.86 mg DL-alpha tocopherol, and 4.85 mg polysorbate 80 (TWEEN® 80).

Preparation

The manufacturing of the AS03-adjuvanted influenza vaccine consists of three main steps:

1) Formulation of the Trivalent Final Bulk without Adjuvant and Filling in the Antigen Container. The volumes of the three monovalent bulks are based on the HA content measured in each monovalent bulk prior to the formulation and on a target volume of 800 ml.

Concentrated phosphate buffered saline and a pre-mixture of TWEEN® 80, TRITON X-100™ and α-tocopheryl hydrogen succinate are diluted in water for injection. The three concentrated monobulks (strain A/New Caledonia -, strain A/Panama- and strain B/Shangdong-) are then successively diluted in the resulting phosphate buffered saline/TWEEN® 80—TRITON X-100™-α-tocopheryl hydrogen succinate solution (pH 7.4, 137 mM NaCl, 2.7 mM KCl, 8.1 mM $Na_2HPO_4$, 1.47 mM $KH_2PO_4$, 1500 μg/ml TWEEN® 80, 220 μg/ml TRITON X-100™ and 200 μg/ml α-tocopheryl hydrogen succinate) in order to have a final concentration of 60 μg HA of A strains per ml of trivalent final bulk (15 μg HA/A strain/250 μl trivalent final bulk) and 70 μg HA of B strain (17.5 μg HA/B strain/250 μl trivalent final bulk). Between addition of each monovalent bulk, the mixture is stirred for 10 minutes at room temperature. After addition of the last monovalent bulk and 15 minutes of stirring, the pH is checked and adjusted to 7.2±0.1 with HCl or NaOH.

The trivalent final bulk of antigens is aseptically filled into 3-ml sterile Type I glass vials. Each vial contains a 34% volume overage (335 μl total volume).

2) Preparation of the SB62 Emulsion Sterile Bulk and Filling in the Adjuvant Container.

Aqueous phase: while stirring, 902 ml of TWEEN® 80 is mixed with 44105 ml of PBS-mod buffer (pH=6.8 after adjustment with HCl).

Oil phase: while stirring, 2550 ml of squalene is added to 2550 ml of α-tocopherol.

Mixing of the aqueous and oil phases: while stirring, 5000 ml of oil phase (1/10 total volume) is transferred to 45007 ml of aqueous phase (9/10 total volume). The mixture is stirred for 15 minutes at room temperature.

Emulsification: the resulting mixture is subjected to shear, impact and cavitation forces in the interaction chamber of a microfluidizer (15000 PSI-8 cycles) to produce submicron droplets (distribution between 100 and 200 nm). The resulting pH is between 6.8±0.1.

Sterile filtration: the SB62 emulsion is sterilised by filtration through a 0.22 μm membrane and the sterile bulk emulsion is stored refrigerated in Cupac containers at 2 to 8° C. Sterile inert gas (nitrogen or argon) is flushed into the dead volume of the SB62 emulsion final bulk container for at least 15 seconds.

All quantities of ingredients given are for the preparation of 50 L of emulsion and are given in volumes. In practice, amounts are weighed taking into account the densities of the ingredients. Density of PBS is considered equal to 1.

The final composition of the SB62 emulsion is as follows:

TABLE 5

| TWEEN® 80: | 1.8% (v/v) | 19.4 mg/ml |
|---|---|---|
| Squalene: | 5% (v/v) | 42.8 mg/ml |
| alpha-tocopherol: | 5% (v/v) | 47.5 mg/ml |
| PBS-mod: | | |
| NaCl | | 121 mM |
| KCl | | 2.38 mM |
| $Na_2HPO_4$ | | 7.14 mM |
| $KH_2PO_4$ | | 1.3 mM |
| pH | | 6.8 ± 0.1 |

The sterile SB62 bulk emulsion is then aseptically filled into 1.25-ml sterile Type I glass syringes. Each syringe contains a 34% volume overage (335 μl total volume).

3) Extemporaneous Reconstitution of the AS03 Adjuvanted Split Virus Vaccine.

At the time of injection, the content of the vial containing the concentrated trivalent inactivated split virion antigens is removed from the vial with the help the syringe containing the SB62 emulsion followed by gently mixing of the syringe. Mixing of the SB62 emulsion with the vaccine antigens reconstitutes the AS03 adjuvant.

III.2.2. Vaccine Composition (Table 6) and Administration

TABLE 6

| Vaccine | Formulation | Group |
|---|---|---|
| FLUARIX® | HA from 3 influenza strains (total HA = 45 μg)<br>A/New Caledonia/20/99 (IVR-116): 15 μg<br>A/Panama/2007/99 (RESVIR-17): 15 μg<br>B/Shangdong/7/97: 15 μg<br>Thiomersal content: 5 μg<br>In pre-filled syringes of 0.5 ml | FLUARIX® |
| WVV | HA from 3 influenza strains (total HA = 45 μg)<br>A/New Caledonia/20/99 (IVR-116): 15 μg<br>A/Panama/2007/99 (RESVIR-17): 15 μg<br>B/Shangdong/7/97: 15 μg<br>Thiomersal content: 5 μg<br>In vials of 0.5 ml | FluWVV |
| FLUARIX® + AS03 | HA from 3 influenza strains (total HA = 45 μg)<br>A/New Caledonia/20/99 (IVR-116): 15 μg<br>A/Panama/2007/99 (RESVIR-17): 15 μg<br>B/Shangdong/7/97: 15 μg<br>Thiomersal content: 5 μg<br>In vial of 0.335 ml (2 times concentrated) +<br>syringe (0.335 ml) containing oil-in-water SB62<br>emulsion (scaled-up preparation) | Flu-AS03 |

The vaccines were administered intramuscularly in the deltoid region of the non-dominant arm. The vaccinees were observed closely for at least 30 minutes, with appropriate medical treatment readily available in case of a rare anaphylactic reaction following the administration of vaccine.

III.3. Study Population Results

A total of 148 subjects were enrolled in this study: 49 subjects in the FluAS03 group, 49 subjects in the FLUARIX® group and 50 subjects in the FluWVV group. The mean age of the total vaccinated cohort at the time of vaccination was 71.8 years with a standard deviation of 6.0 years. The mean age and gender distribution of the subjects across the three vaccine groups was similar.

III.4. Safety Conclusions

The administration of the influenza vaccine adjuvanted with AS03 was safe and clinically well tolerated in the study population, i.e. elderly people aged over 65 years.

III.5. Immunogenicity Results

Analysis of immunogenicity was performed on the total vaccinated cohort.

III.5.1. Humoral Immune Response

In order to evaluate the humoral immune response induced by the AS03 adjuvanted vaccine, the following parameters (with 95% confidence intervals) were calculated for each treatment group:

Geometric mean titres (GMTs) of HI and NI antibody titres at days 0 and 21
Geometric mean titres (GMTs) of neutralising antibody titres at days 0 and 21.
Seroconversion rates (SC) at day 21 defined as the percentage of vaccinees that have at least a 4-fold increase in serum HI titres on day 21 compared to day 0.
Conversion factors at day 21 defined as the fold increase in serum HI GMTs on day 21 compared to day 0, for each vaccine strain.
Protection rates at day 21 defined as the percentage of vaccinees with a serum HI titre=1:40.

III.5.1.1 Anti-Hemagglutinin Antibody Response a) HI Geometric Mean Titres (GMT)

The GMTs for HI antibodies with 95% CI are shown in Table 7 (GMT for anti-HI antibody). Pre-vaccination GMTs of antibodies for all vaccine strains were within the same range in the three groups. After vaccination, anti-haemagglutinin antibody levels increased significantly. Post vaccination, there was a trend for higher GMTs of HI antibody for all three vaccine strains in the FluAS03 and FLUARIX® groups although there was some overlap of 95% CI between the FLUARIX® group and the FluWVV group.

TABLE 7

| | | | | GMT | | |
|---|---|---|---|---|---|---|
| | | | | | 95% CI | |
| Antibody | Group | Timing | N | Value | LL | UL |
| A/New Caledonia | FluAS03 | Pre | 49 | 25.6 | 17.3 | 37.9 |
| | FLUARIX® | PI(day 21) | 49 | 317.7 | 219.1 | 460.7 |
| | FluWVV | Pre | 49 | 26.3 | 18.1 | 38.4 |
| | | PI(day 21) | 49 | 358.5 | 244.2 | 526.4 |
| | | Pre | 50 | 19.7 | 13.6 | 28.6 |
| | | PI(day 21) | 50 | 138.2 | 90.3 | 211.7 |
| A/Panama | FluAS03 | Pre | 49 | 52.3 | 35.4 | 77.4 |
| | FLUARIX® | PI(day 21) | 49 | 366.1 | 264.5 | 506.6 |
| | FluWVV | Pre | 49 | 40.9 | 28.1 | 59.5 |
| | | PI(day 21) | 49 | 296.0 | 205.4 | 426.6 |
| | | Pre | 50 | 25.8 | 18.0 | 37.1 |
| | | PI(day 21) | 50 | 165.6 | 116.0 | 236.5 |
| B/Shangdong | FluAS03 | Pre | 49 | 27.5 | 19.0 | 39.8 |
| | FLUARIX® | PI(day 21) | 49 | 317.7 | 226.9 | 444.9 |
| | FluWVV | Pre | 49 | 26.0 | 17.2 | 39.2 |
| | | PI(day 21) | 49 | 270.0 | 187.0 | 389.7 |
| | | Pre | 50 | 32.0 | 20.8 | 49.3 |
| | | PI(day 21) | 50 | 195.6 | 135.2 | 282.9 |

N = number of subjects with available results
95% CI = 95% confidence interval; LL = Lower Limit; UL = Upper Limit
MIN/MAX = Minimum/Maximum
PRE = Prevaccination at Day 0
PI(D 21) = Post-vaccination at Day 21)

b) Conversion Factors of Anti-HI Antibody Titres, Seroprotection Rates and Seroconversion Rates (Correlates for Protection in Human)

Results are presented in Table 8.

The conversion factors represent the fold increase in serum HI GMTs for each vaccine strain on day 21 compared to day 0. The conversion factor varies from 6.1 to 13.6 according to the virus strain and the vaccine. This conversion factor is largely superior to the 2.0 fold increase in GMT required by the European Authorities.

The seroprotection rates represent the proportion of subjects with a serum HI titre≥40 on day 21. At the outset of the study, half of the subjects (range 34.0%-69.4%) in all groups had protective levels of antibodies for all strains At day 21, the seroprotection rates in the three groups ranged from 88.0% to 100% for the different virus strains. In terms of protection, this means that more than 88% of the subjects had a serum HI titre≥40 after vaccination and were deemed to be protected against the three strains. This rate is largely superior to the seroprotection rate of 60% required in the ≥60 years old population, by the European Authorities.

The seroconversion rates represent the proportion of subjects with at least a four-fold increase in serum HI titres on day 21 as compared to day 0. Overall response rates for the three strains were essentially equal in the three groups. To be deemed effective and according to European Union, a vaccine should induce a seroconversion rate greater than 30% in the =60 years old population. In this study, the seroconversion rate was greater than 50% for the three groups.

The conversion factor varies from 6.1 to 13.6 according to the virus strain and the vaccine. This conversion factor is largely superior to the 2.0 fold increase in GMT required by the European Authorities.

At day 21, the seroprotection rates in the three groups ranged from 88.0% to 100% for the different virus strains. This rate is largely superior to the seroprotection rate of 60% required in the ≥60 years old population, by the European Authorities.

In this study, the seroconversion rate was greater than 50% for the three groups. Overall response rates for the three strains were essentially equal in the three groups.

III.5.1.2 Neutralising Antibody Titers

In order to better characterise the immune response to influenza vaccination in the elderly, the serum antibody responses to the neutralising antigens was assessed. Results are shown in Table 9 (Seroprotection rates and geometric mean titres (GMT) for anti-neutralising antibody titres) and Table 10 (Seroconversion rates for anti-neutralising at post vaccination day 21 (fold-increase=4)).

Titres of neutralising antibody against the three influenza strains were measured in pre- and post-immunisation sera. The following parameters were determined:

TABLE 8

| Strains | Group | N | Seroprotection rate EU standard (>60 years) >60% % [95% CI] | Seroconversion rate >30% % [95% CI] | Conversion factor >2.0 GMR [95% CI] |
|---|---|---|---|---|---|
| A/New Caledonia | Flu AS03 | 49 | 98.0 [89.1-99.9] | 69.4 [54.6-81.7] | 12.4 [7.3-21.0] |
|  | FLUARIX ® | 49 | 98.0 [89.1-99.9] | 69.4 [54.6-81.7] | 13.6 [8.0-23.2] |
|  | Flu WVV | 50 | 88.0 [75.7-95.5] | 52.0 [37.4-66.3] | 7.0 [4.0-12.2] |
| A/Panama | Flu AS03 | 49 | 100.0 [92.7-100.0] | 55.1 [40.2-69.3] | 7.0 [4.2-11.6] |
|  | FLUARIX ® | 49 | 91.8 [80.4-97.7] | 65.3 [50.4-78.3] | 7.2 [4.7-11.3] |
|  | Flu WVV | 50 | 90.0 [78.2-96.7] | 56.0 [41.3-70.0] | 6.4 [3.9-10.4] |
| B/shangdong | Flu AS03 | 49 | 100.0 [92.7-100.0] | 73.5 [58.9-85.1] | 11.6 [7.2-18.6] |
|  | FLUARIX ® | 49 | 95.9 [86.0-99.5] | 69.4 [54.6-81.7] | 10.4 [6.5-16.5] |
|  | Flu WVV | 50 | 90.0 [78.2-96.7] | 50.0 [35.5-64.5] | 6.1 [3.6-10.3] |

N = total number of subjects

In conclusion:
Post vaccination, there was a trend for higher GMTs of HI antibody for all three vaccine strains in the FluAS03 and -FLUARIX® groups although there was some overlap of 95% CI between the FLUARIX® group and the FluWVV group.

Geometric mean titres (GMTs) of serum neutralising antibodies with 95% confidence intervals (95% CI) pre and post-vaccination Seroconversion rates with 95% CI at day 21, defined as the percentage of vaccinees with at least a 4-fold increase in HI titres on day 21 compared to day 0, for each vaccine strain.

TABLE 9

| Antibody | Group | Timing | N | n | % | >=18 1/DIL 95% CI LL | 95% CI UL | GMT Value | 95% CI LL | 95% CI UL |
|---|---|---|---|---|---|---|---|---|---|---|
| A/NEW_CALEDONIA | 1 | PRE | 49 | 46 | 93.9 | 83.1 | 98.7 | 106.6 | 77.6 | 146.6 |
|  |  | PI(D 21) | 49 | 49 | 100.0 | 92.7 | 100.0 | 870.2 | 608.5 | 1244.3 |
|  | 2 | PRE | 49 | 48 | 98.0 | 89.1 | 99.9 | 115.6 | 89.4 | 149.5 |
|  |  | PI(D 21) | 49 | 49 | 100.0 | 92.7 | 100.0 | 955.8 | 649.5 | 1406.5 |
|  | 3 | PRE | 50 | 46 | 92.0 | 80.8 | 97.8 | 87.7 | 63.6 | 120.8 |
|  |  | PI(D 21) | 50 | 50 | 100.0 | 92.9 | 100.0 | 375.4 | 271.2 | 519.6 |
| A/PANAMA | 1 | PRE | 49 | 49 | 100.0 | 92.7 | 100.0 | 724.7 | 558.0 | 941.1 |
|  |  | PI(D 21) | 49 | 49 | 100.0 | 92.7 | 100.0 | 2012.8 | 1438.4 | 2816.5 |
|  | 2 | PRE | 49 | 49 | 100.0 | 92.7 | 100.0 | 727.8 | 556.1 | 952.6 |
|  |  | PI(D 21) | 49 | 49 | 100.0 | 92.7 | 100.0 | 1597.7 | 1128.8 | 2261.5 |

TABLE 9-continued

| Antibody | Group | Timing | N | n | % | >=18 1/DIL 95% CI LL | UL | Value | GMT 95% CI LL | UL |
|---|---|---|---|---|---|---|---|---|---|---|
| | 3 | PRE | 50 | 50 | 100.0 | 92.9 | 100.0 | 512.0 | 409.3 | 640.6 |
| | | PI(D 21) | 50 | 50 | 100.0 | 92.9 | 100.0 | 977.8 | 738.2 | 1295.0 |
| B/SHANGDONG | 1 | PRE | 49 | 29 | 59.2 | 44.2 | 73.0 | 25.6 | 18.8 | 35.0 |
| | | PI(D 21) | 49 | 48 | 98.0 | 89.1 | 99.9 | 222.5 | 148.1 | 334.2 |
| | 2 | PRE | 49 | 27 | 55.1 | 40.2 | 69.3 | 29.3 | 20.1 | 42.7 |
| | | PI(D 21) | 49 | 49 | 100.0 | 92.7 | 100.0 | 190.4 | 127.6 | 284.3 |
| B/SHANGDONG | 3 | PRE | 50 | 31 | 62.0 | 47.2 | 75.3 | 33.4 | 23.1 | 48.4 |
| | | PI(D 21) | 50 | 46 | 92.0 | 80.8 | 97.8 | 117.8 | 82.6 | 168.0 |

Group 1: Flu vaccine mix Adjuvant 2× conc Flu vac
Group 2: Flu vaccine Flu vaccine
Group 3: Flu vaccine Flu WVV vaccine
N = number of subjects with available results
n/% = number/percentage of subjects with titre within the specified range
95% CI = 95% confidence interval; LL = Lower Limit; UL = Upper Limit
PRE = Pre-vaccination at Day 0
PI(D 21) = Post-vaccination at Day 21

TABLE 10

| Antibody | Group | N | n | Responders % | 95% CI LL | UL |
|---|---|---|---|---|---|---|
| A/New | 1 | 49 | 29 | 59.2 | 44.2 | 73.0 |
| Caledonia | 2 | 49 | 30 | 61.2 | 46.2 | 74.8 |
| | 3 | 50 | 21 | 42.0 | 28.2 | 56.8 |
| A/Panama | 1 | 49 | 12 | 24.5 | 13.3 | 38.9 |
| | 2 | 49 | 9 | 18.4 | 8.8 | 32.0 |
| | 3 | 50 | 9 | 18.0 | 8.6 | 31.4 |
| B/Shangdong | 1 | 49 | 29 | 59.2 | 44.2 | 73.0 |
| | 2 | 49 | 26 | 53.1 | 38.3 | 67.5 |
| | 3 | 50 | 19 | 38.0 | 24.7 | 52.8 |

Group 1: Flu vaccine (DFLU58A16) mix Adjuvant (D621024A8) 2× conc Flu vac
Group 2: Flu vaccine (18854B9) Flu vaccine
Group 3: Flu vaccine (DFLU59A2) Flu WVV vaccine
N = number of subjects with both pre and post vaccination result available.
n = number of responders
% = Proportion of responders (n/N × 100).
95% CI = exact 95% confidence interval; LL = lower limit, UL = upper limit The main findings are:
For the three vaccines, at day 21, a seroprotection rate of 100% is obtained for both A strains. For the B strain, the seroprotection rates in the three groups ranged from 92% to 100%.
Post vaccination, there was a significant increase of GMT for all strains, in the three groups. However, there was a trend for higher GMTs of neutralising antibody for all three vaccine strains in the FluAS03 and FLUARIX® groups than in the FluWVV although there was some overlap of 95% CI between the FLUARIX® group and the FluWVV group.
For the seroconversion rates, overall response rates for the three strains were essentially equal in the three groups.
In all groups, the results were consistent with those obtained from the analysis performed for anti-hemagglutinin antibodies.

III.5.1.3 Nauraminidase (NA) Antibody Titers

In order to better characterise the immune response to influenza vaccination in the elderly population, the serum antibody responses to the neuraminidase antigens was assessed. Similarly to the HI antibody titre, the following endpoints were determined:
GMT (taking the anti-log of the mean of the log titre transformations)

Seroconversion rate defined as the percentage of vaccinees with at least a 4-fold increase in HI titres on day 21 compared to day 0, for each vaccine strain.

The GMTs and seroconversion rates for NI antibodies with 95% CI are shown in Table 11 (anti-NA antibody GMT) and Table 12 (Seroconversion rates of NA at post—vaccination (day 21) (4-fold-increase)).

TABLE 11

| Antibody | Group | Timing | N | GMT | 95% CI LL | UL |
|---|---|---|---|---|---|---|
| A/New | FluAS03 | PRE | 49 | 77.8 | 61.8 | 97.9 |
| Caledonia | | PI(D 21) | 48 | 270.0 | 212.9 | 342.3 |
| | FLUARIX ® | PRE | 49 | 77.8 | 64.6 | 93.6 |
| | | PI(D 21) | 49 | 249.1 | 190.0 | 326.5 |
| | FluWVV | PRE | 50 | 66.8 | 53.8 | 83.0 |
| | | PI(D 21) | 50 | 159.2 | 122.8 | 206.4 |
| A/Panama | FluAS03 | PRE | 49 | 33.3 | 28.5 | 48.7 |
| | | PI(D 21) | 48 | 156.8 | 124.8 | 196.9 |
| | FLUARIX ® | PRE | 49 | 34.2 | 25.6 | 45.8 |
| | | PI(D 21) | 49 | 133.7 | 100.9 | 177.3 |
| | FluWVV | PRE | 50 | 24.6 | 18.7 | 32.4 |
| | | PI(D 21) | 49 | 78.9 | 59.4 | 104.7 |
| B/Shangdong | FluAS03 | PRE | 49 | 46.7 | 36.5 | 59.9 |
| | | PI(D 21) | 49 | 204.2 | 156.4 | 266.7 |
| | FLUARIX ® | PRE | 49 | 46.1 | 35.3 | 60.1 |
| | | PI(D 21) | 49 | 133.7 | 100.9 | 177.3 |
| | FluWVV | PRE | 50 | 48.6 | 36.4 | 64.7 |
| | | PI(D 21) | 49 | 128.2 | 101.7 | 161.6 |

FluAS03: Flu vaccine (DFLU58A16) mix with AS03 Adjuvant (D621024A8)
FLUARIX ®: Flu vaccine (18854B9)
FluWVV: Flu WVV vaccine (DFLU59A2)
PRE = Pre-vaccination, PI(D 21) = Day 21 post vaccination
95% CI, LL, and UL = 95% confidence interval, lower and upper limit

TABLE 12

| Antibody | Group | N | n | Responders % | 95% CI LL | UL |
|---|---|---|---|---|---|---|
| A/New | FluAS03 | 48 | 25 | 52.1 | 37.2 | 66.7 |
| Caledonia | FLUARIX ® | 49 | 24 | 49.0 | 34.4 | 63.7 |
| | FluWVV | 49 | 18 | 36.7 | 23.2 | 51.7 |

TABLE 12-continued

|  |  |  |  |  | Responders | |
|---|---|---|---|---|---|---|
|  |  |  |  |  | 95% CI | |
| Antibody | Group | N | n | % | LL | UL |
| A/Panama | FluAS03 | 48 | 27 | 56.3 | 41.2 | 70.5 |
|  | FLUARIX ® | 49 | 23 | 46.9 | 32.5 | 61.7 |
|  | FluWVV | 49 | 21 | 42.9 | 28.8 | 57.8 |
| B/Shangdong | FluAS03 | 48 | 26 | 54.2 | 39.2 | 68.6 |
|  | FLUARIX ® | 49 | 23 | 46.9 | 32.5 | 61.7 |
|  | FluWVV | 49 | 16 | 32.7 | 19.9 | 47.5 |

FluAS03: Flu vaccine (DFLU58A16) mix with AS03 Adjuvant (D621024A8),
FLUARIX ®: Flu vaccine (18854B9), FluWVV: Flu WVV vaccine (DFLU59A2)
N = number of subjects with both pre and post vaccination result available, n = number of responders.
% = Proportion of responders (n/N × 100).
95% CI = exact 95% confidence interval; LL = lower limit, UL = upper limit The main findings are:
Higher value of the GMT and seroconversion rates were observed for hemagglutinin than for neuraminidase.
Pre-vaccination GMTs of antibodies for all vaccine strains were within the same range in the three groups. After vaccination, anti-neuraminidase antibody levels increased significantly. As for the HI antibody titres, post vaccination, there was a trend for higher GMTs of HI antibody for all three vaccine strains in the FluAS03 and FLUARIX® groups although there was some overlap of 95% CI between the Fluarix group and the FluWVV group.

Regarding the seroconversion rates, overall response rates for the three strains were essentially equal in the three groups and for the three strains.

Our results show that healthy elderly vaccinated in this study against influenza developed good antibody responses to neuraminidase antigens whatever the influenza vaccine.

However, the response to the neuraminidase antigen is lower than the response to the hemagglutinin antigen.

III.5.2. Cellular Immune Response

Peripheral blood antigen-specific CD4 and CD8 T cells can be restimulated in vitro to produce IL-2, CD40L, TNF-alpha and IFNγ if incubated with their corresponding antigen.

Consequently, antigen-specific CD4 and CD8 T cells can be enumerated by flow cytometry following conventional immunofluorescence labelling of cellular phenotype as well as intracellular cytokines production. In the present study, Influenza vaccine antigen as well as peptides derived from specific influenza protein were used as antigen to restimulate Influenza-specific T cells. Results are presented for the CD4 and CD8 T-cell response in Tables 13 to 18.

TABLE 13

Antigen specific CD4 T-cell responses expressed into cells producing at least two different cytokines: Descriptive Statistics on PRE and POST for CD40L/IL2/TNF-α/IFN-γ (Total vaccinated cohort)

| Secretion | Antigen | Gr | Time point | N | Mean | SD | Min |
|---|---|---|---|---|---|---|---|
| CD40L/IL2/ IFNγ/TNFα in CD4 | Peptide Influenza | 1 | Day 0 | 44 | 33.50 | 139.026 | 1.00 |
|  |  | 1 | Day 21 | 45 | 58.40 | 132.664 | 1.00 |
|  |  | 2 | Day 0 | 42 | 92.10 | 368.790 | 1.00 |
|  |  | 2 | Day 21 | 44 | 88.36 | 272.528 | 1.00 |
|  |  | 3 | Day 0 | 45 | 80.13 | 284.316 | 1.00 |
|  |  | 3 | Day 21 | 47 | 91.40 | 382.967 | 1.00 |
|  | Split Influenza | 1 | Day 0 | 47 | 1901.66 | 1596.203 | 102.00 |
|  |  | 1 | Day 21 | 48 | 6163.75 | 4265.900 | 773.00 |
|  |  | 2 | Day 0 | 45 | 2151.04 | 2622.594 | 265.00 |
|  |  | 2 | Day 21 | 49 | 4150.73 | 3712.469 | 328.00 |
|  |  | 3 | Day 0 | 48 | 1678.44 | 916.329 | 142.00 |
|  |  | 3 | Day 21 | 50 | 3374.60 | 1920.194 | 449.00 |
|  | Whole Influenza | 1 | Day 0 | 48 | 3134.33 | 2568.369 | 507.00 |
|  |  | 1 | Day 21 | 47 | 9332.04 | 6875.403 | 1482.00 |
|  |  | 2 | Day 0 | 47 | 3050.85 | 2654.936 | 486.00 |
|  |  | 2 | Day 21 | 49 | 6760.31 | 6788.258 | 1852.00 |
|  |  | 3 | Day 0 | 48 | 2955.33 | 2019.233 | 473.00 |
|  |  | 3 | Day 21 | 50 | 5661.40 | 4530.321 | 635.00 |

| Secretion | Antigen | Gr | Time point | Q1 | Median | Q3 | Max | Kruskall-Wallis test (P-value) |
|---|---|---|---|---|---|---|---|---|
| CD40L/IL2/ IFNγ/TNFα in CD4 | Peptide Influenza | 1 | Day 0 | 1.00 | 1.00 | 4.00 | 915.00 | 0.7631 |
|  |  | 1 | Day 21 | 1.00 | 1.00 | 56.00 | 733.00 |  |
|  |  | 2 | Day 0 | 1.00 | 1.00 | 54.00 | 2393.00 |  |
|  |  | 2 | Day 21 | 1.00 | 1.00 | 69.50 | 1740.00 |  |
|  |  | 3 | Day 0 | 1.00 | 1.00 | 65.00 | 1908.00 |  |
|  |  | 3 | Day 21 | 1.00 | 1.00 | 63.00 | 2615.00 |  |
|  | Split Influenza | 1 | Day 0 | 957.00 | 1560.00 | 2408.00 | 9514.00 | 0.0002 |
|  |  | 1 | Day 21 | 3468.00 | 4908.00 | 7624.00 | 21324.00 |  |
|  |  | 2 | Day 0 | 930.00 | 1381.00 | 2274.00 | 16289.00 |  |
|  |  | 2 | Day 21 | 2247.00 | 3036.00 | 4744.00 | 21924.00 |  |
|  |  | 3 | Day 0 | 1086.00 | 1502.00 | 2189.00 | 3899.00 |  |
|  |  | 3 | Day 21 | 2312.00 | 3040.00 | 4437.00 | 10431.00 |  |
|  | Whole Influenza | 1 | Day 0 | 1730.00 | 2298.50 | 3876.00 | 15066.00 | 0.0040 |
|  |  | 1 | Day 21 | 4091.00 | 6523.00 | 14045.00 | 29251.00 |  |
|  |  | 2 | Day 0 | 1190.00 | 2031.00 | 4161.00 | 11994.00 |  |
|  |  | 2 | Day 21 | 3573.00 | 4621.00 | 7234.00 | 40173.00 |  |

TABLE 13-continued

Antigen specific CD4 T-cell responses expressed into cells producing at least two different cytokines: Descriptive Statistics on PRE and POST for CD40L/IL2/TNF-α/IFN-γ (Total vaccinated cohort)

| | | | | | |
|---|---|---|---|---|---|
| 3 | Day 0 | 1421.50 | 2668.50 | 3411.50 | 10578.00 |
| 3 | Day 21 | 2459.00 | 4315.00 | 7303.00 | 22053.00 |

Group 1: FluAS03: Flu vaccine Fluarix ™ mixed with AS03 Adjuvant
Group 2: FLUARIX ®: Flu vaccine FLUARIX ®
Group 3: FluWVV: Flu WVV vaccine
SD = Standard Deviation; Min, Max = Minimum, Maximum
Q1 = First quartile; Q3 = Third quartile
N = number of subjects with available results
P-value: Kruskall-Wallis Test (Non-parametric procedure) to test location difference (Wilcoxon rank-sum test) between the 3 groups at Day 21.

TABLE 14

Antigen-specific CD4 T-cell responses expressed into cells producing at least two different cytokines: Descriptive Statistics on difference between PRE and POST (Total vaccinated cohort)

| Secretion | Antigen | Group | N | Mean | SD | Min |
|---|---|---|---|---|---|---|
| CD40L/IFN-γ/ | Peptide | 1 | 44 | 9.57 | 159.363 | −860.00 |
| TNF-α in CD4 | Influenza | 2 | 42 | −40.98 | 386.998 | −2392.00 |
| | | 3 | 45 | −50.73 | 256.596 | −1664.00 |
| | Split | 1 | 47 | 4307.02 | 4468.828 | −8161.00 |
| | Influenza | 2 | 45 | 1982.93 | 3802.332 | −14318.0 |
| | | 3 | 48 | 1555.90 | 1596.216 | −526.00 |
| | Whole | 1 | 47 | 6197.98 | 7220.765 | −11763.0 |
| | Influenza | 2 | 47 | 3791.34 | 5820.894 | −2128.00 |
| | | 3 | 48 | 2535.98 | 3966.345 | −4766.00 |
| CD40L/IFN-γ/ | Peptide | 1 | 42 | −15.95 | 215.710 | −451.00 |
| TNF-α in CD8 | Influenza | 2 | 41 | 50.83 | 264.370 | −614.00 |
| | | 3 | 44 | −52.11 | 243.811 | −684.00 |
| | Split | 1 | 42 | 134.71 | 426.699 | −603.00 |
| | Influenza | 2 | 44 | −65.05 | 822.036 | −4938.00 |
| | | 3 | 45 | 2.49 | 330.700 | −1094.00 |
| | Whole | 1 | 39 | 189.38 | 1394.153 | −2641.00 |
| | Influenza | 2 | 44 | −479.75 | 1790.094 | −9455.00 |
| | | 3 | 44 | −243.73 | 719.269 | −1892.00 |

| Secretion | Antigen | Group | Q1 | Median | Q3 | Max | P-value |
|---|---|---|---|---|---|---|---|
| CD40L/IFN-γ/ | Peptide | 1 | 0.00 | 0.00 | 37.50 | 430.00 | 0.0765 |
| TNF-α in CD4 | Influenza | 2 | −15.00 | 0.00 | 26.00 | 514.00 | |
| | | 3 | −37.00 | 0.00 | 0.00 | 212.00 | |
| | Split | 1 | 1888.00 | 3396.00 | 6634.00 | 19555.00 | <0.0001 |
| | Influenza | 2 | 699.00 | 1490.00 | 2573.00 | 15169.00 | |
| | | 3 | 466.00 | 1183.50 | 2186.50 | 7851.00 | |
| | Whole | 1 | 2170.00 | 4009.00 | 11681.00 | 25570.00 | 0.0003 |
| | Influenza | 2 | 1246.00 | 2382.00 | 3992.00 | 33801.00 | |
| | | 3 | 503.00 | 1382.50 | 3300.50 | 19337.00 | |
| CD40L/IFN-γ/ | Peptide | 1 | −106.00 | 0.00 | 81.00 | 655.00 | 0.0932 |
| TNF-α in CD8 | Influenza | 2 | −58.00 | 13.00 | 202.00 | 703.00 | |
| | | 3 | −160.50 | 0.00 | 53.00 | 567.00 | |
| | Split | 1 | −122.00 | 35.50 | 221.00 | 1387.00 | 0.2121 |
| | Influenza | 2 | −64.50 | 0.00 | 160.50 | 1252.00 | |
| | | 3 | −99.00 | 0.00 | 76.00 | 1060.00 | |
| | Whole | 1 | −420.00 | 49.00 | 591.00 | 5045.00 | 0.0851 |
| | Influenza | 2 | −1016.00 | −263.50 | 180.00 | 3743.00 | |
| | | 3 | −651.00 | −86.50 | 180.00 | 1011.00 | |

TABLE 15

Antigen-specific CD4 T-cell responses expressed into cells producing at least CD40L and another cytokine: Descriptive Statistics on difference between PRE and POST (Total vaccinated cohort)

| Secretion | Antigen | Group | N | Mean | SD | Min |
|---|---|---|---|---|---|---|
| CD40L in CD4 | Peptide | 1 | 44 | 10.09 | 153.007 | −815.00 |
| | Influenza | 2 | 42 | −29.40 | 316.983 | −1921.00 |
| | | 3 | 45 | −43.73 | 251.146 | −1629.00 |

TABLE 15-continued

Antigen-specific CD4 T-cell responses expressed into cells producing
at least CD40L and another cytokine: Descriptive Statistics on
difference between PRE and POST (Total vaccinated cohort)

|  |  |  |  |  |  |  |
|---|---|---|---|---|---|---|
|  | Split | 1 | 46 | 4266.20 | 4470.807 | −8093.00 |
|  | Influenza | 2 | 45 | 2026.42 | 3511.508 | −11482.0 |
|  |  | 3 | 47 | 1512.34 | 1576.133 | −494.00 |
|  | Whole | 1 | 47 | 6071.96 | 7118.132 | −11691.0 |
|  | Influenza | 2 | 47 | 3764.64 | 5740.762 | −2114.00 |
|  |  | 3 | 48 | 2544.27 | 3959.879 | −4390.00 |
| CD40L in CD8 | Peptide | 1 | 44 | −19.41 | 81.675 | −370.00 |
|  | Influenza | 2 | 41 | −3.98 | 100.998 | −399.00 |
|  |  | 3 | 45 | −5.56 | 64.666 | −181.00 |
|  | Split | 1 | 43 | 39.53 | 190.122 | −438.00 |
|  | Influenza | 2 | 44 | 27.61 | 91.173 | −155.00 |
|  |  | 3 | 45 | 30.18 | 191.326 | −291.00 |
|  | Whole | 1 | 41 | −91.24 | 617.077 | −1779.00 |
|  | Influenza | 2 | 44 | −115.91 | 588.424 | −2583.00 |
|  |  | 3 | 45 | −150.89 | 367.300 | −1239.00 |

| Secretion | Antigen | Group | Q1 | Median | Q3 | Max | P-value |
|---|---|---|---|---|---|---|---|
| CD40L in CD4 | Peptide | 1 | 0.00 | 0.00 | 36.50 | 428.00 | 0.1233 |
|  | Influenza | 2 | −8.00 | 0.00 | 27.00 | 494.00 |  |
|  |  | 3 | −35.00 | 0.00 | 3.00 | 230.00 |  |
|  | Split | 1 | 1799.00 | 3156.50 | 6647.00 | 19480.00 | <0.0001 |
|  | Influenza | 2 | 783.00 | 1485.00 | 2546.00 | 15021.00 |  |
|  |  | 3 | 469.00 | 1107.00 | 2035.00 | 7687.00 |  |
|  | Whole | 1 | 2109.00 | 4048.00 | 11472.00 | 25448.00 | 0.0004 |
|  | Influenza | 2 | 1212.00 | 2509.00 | 3957.00 | 33428.00 |  |
|  |  | 3 | 523.00 | 1392.00 | 3261.50 | 19478.00 |  |
| CD40L in CD8 | Peptide | 1 | −2.00 | 0.00 | 0.50 | 100.00 | 0.9721 |
|  | Influenza | 2 | −28.00 | 0.00 | 24.00 | 231.00 |  |
|  |  | 3 | −13.00 | 0.00 | 3.00 | 176.00 |  |
|  | Split | 1 | −35.00 | 0.00 | 140.00 | 608.00 | 0.6175 |
|  | Influenza | 2 | −18.50 | 0.00 | 77.50 | 326.00 |  |
|  |  | 3 | −9.00 | 0.00 | 28.00 | 1188.00 |  |
|  | Whole | 1 | −142.00 | −8.00 | 175.00 | 2087.00 | 0.3178 |
|  | Influenza | 2 | −195.50 | −34.50 | 150.00 | 1258.00 |  |
|  |  | 3 | −270.00 | −103.00 | 88.00 | 588.00 |  |

TABLE 16

Antigen-specific CD4 T-cell responses expressed into cells producing
at least IFNγ and another cytokine: Descriptive Statistics
on difference between PRE and POST (Total vaccinated cohort)

| Secretion | Antigen | Group | N | N missing | Mean | SD | Min |
|---|---|---|---|---|---|---|---|
| IFNγ in CD4 | Peptide | 1 | 44 | 5 | 7.50 | 64.539 | −171.00 |
|  | Influenza | 2 | 42 | 7 | −30.67 | 277.984 | −1766.00 |
|  |  | 3 | 45 | 5 | −27.91 | 103.403 | −639.00 |
|  | Split | 1 | 46 | 3 | 2712.87 | 2905.629 | −4394.00 |
|  | Influenza | 2 | 45 | 4 | 1148.56 | 2526.536 | −10586.0 |
|  |  | 3 | 47 | 3 | 871.00 | 1016.251 | −764.00 |
|  | Whole | 1 | 47 | 2 | 4240.09 | 4811.891 | −8272.00 |
|  | Influenza | 2 | 47 | 2 | 2445.38 | 4030.694 | −3018.00 |
|  |  | 3 | 48 | 2 | 1535.48 | 2456.915 | −3670.00 |
| IFNγ in CD8 | Peptide | 1 | 44 | 5 | 7.75 | 146.412 | −226.00 |
|  | Influenza | 2 | 41 | 8 | 10.68 | 176.026 | −420.00 |
|  |  | 3 | 44 | 6 | −49.80 | 217.214 | −699.00 |
|  | Split | 1 | 43 | 6 | 138.58 | 365.565 | −470.00 |
|  | Influenza | 2 | 44 | 5 | −112.82 | 793.746 | −4919.00 |
|  |  | 3 | 44 | 6 | 29.91 | 238.157 | −708.00 |
|  | Whole | 1 | 41 | 8 | 6.66 | 1642.577 | −5610.00 |
|  | Influenza | 2 | 44 | 5 | −471.55 | 1792.348 | −9586.00 |
|  |  | 3 | 44 | 6 | −189.05 | 685.291 | −1879.00 |

| Secretion | Antigen | Group | Q1 | Median | Q3 | Max | P-value |
|---|---|---|---|---|---|---|---|
| IFNγ in CD4 | Peptide | 1 | −9.50 | 0.00 | 7.50 | 265.00 | 0.1541 |
|  | Influenza | 2 | −5.00 | 0.00 | 24.00 | 222.00 |  |
|  |  | 3 | −20.00 | 0.00 | 0.00 | 51.00 |  |

TABLE 16-continued

Antigen-specific CD4 T-cell responses expressed into cells producing at least IFNγ and another cytokine: Descriptive Statistics on difference between PRE and POST ('Total vaccinated cohort)

|  |  |  |  |  |  |  |  |
|---|---|---|---|---|---|---|---|
|  | Split | 1 | 1273.00 | 1644.00 | 4057.00 | 13296.00 | <0.0001 |
|  | Influenza | 2 | 405.00 | 931.00 | 1757.00 | 9426.00 |  |
|  |  | 3 | 283.00 | 624.00 | 1114.00 | 5031.00 |  |
|  | Whole | 1 | 1610.00 | 2693.00 | 7437.00 | 17489.00 | <0.0001 |
|  | Influenza | 2 | 723.00 | 1487.00 | 2983.00 | 21594.00 |  |
|  |  | 3 | 232.50 | 810.00 | 2218.50 | 11319.00 |  |
| IFNγ in CD8 | Peptide | 1 | −52.50 | 0.00 | 40.00 | 615.00 | 0.3322 |
|  | Influenza | 2 | −1.00 | 0.00 | 72.00 | 610.00 |  |
|  |  | 3 | −172.00 | 0.00 | 90.50 | 424.00 |  |
|  | Split | 1 | −46.00 | 42.00 | 294.00 | 1549.00 | 0.1257 |
|  | Influenza | 2 | −62.00 | 0.00 | 74.00 | 1028.00 |  |
|  |  | 3 | −59.50 | 26.50 | 123.00 | 643.00 |  |
|  | Whole | 1 | −385.00 | 131.00 | 450.00 | 5068.00 | 0.1179 |
|  | Influenza | 2 | −955.50 | −221.00 | 177.00 | 3492.00 |  |
|  |  | 3 | −476.50 | −36.50 | 198.00 | 1299.00 |  |

TABLE 17

Antigen-specific CD4 T-cell responses expressed into cells producing at least IL2 and another cytokine: Descriptive Statistics on difference between PRE and POST ('Total vaccinated cohort)

| Secretion | Antigen | Group | N | Mean | SD | Min |
|---|---|---|---|---|---|---|
| IL2 in CD4 | Peptide | 1 | 44 | 2.82 | 118.164 | −595.00 |
|  | Influenza | 2 | 42 | 0.90 | 84.255 | −167.00 |
|  |  | 3 | 45 | −28.62 | 191.709 | −1222.00 |
|  | Split | 1 | 46 | 3456.15 | 3853.960 | −7009.00 |
|  | Influenza | 2 | 45 | 1738.29 | 2406.045 | −451.00 |
|  |  | 3 | 47 | 1210.02 | 1361.705 | −634.00 |
|  | Whole | 1 | 47 | 4839.02 | 5978.277 | −9178.00 |
|  | Influenza | 2 | 47 | 2891.00 | 4493.387 | −1370.00 |
|  |  | 3 | 48 | 2042.50 | 3123.912 | −3179.00 |
| IL2 in CD8 | Peptide | 1 | 42 | −30.60 | 219.777 | −630.00 |
|  | Influenza | 2 | 41 | 38.85 | 210.715 | −674.00 |
|  |  | 3 | 45 | −44.80 | 197.026 | −526.00 |
|  | Split | 1 | 41 | 54.85 | 250.817 | −336.00 |
|  | Influenza | 2 | 44 | −2.36 | 423.957 | −2272.00 |
|  |  | 3 | 45 | −26.07 | 244.870 | −1004.00 |
|  | Whole | 1 | 39 | 56.21 | 406.262 | −704.00 |
|  | Influenza | 2 | 44 | −151.02 | 822.384 | −4304.00 |
|  |  | 3 | 45 | −63.56 | 359.699 | −1036.00 |

| Secretion | Antigen | Group | Q1 | Median | Q3 | Max | P-value |
|---|---|---|---|---|---|---|---|
| IL2 in CD4 | Peptide | 1 | −1.50 | 0.00 | 31.50 | 324.00 | 0.0806 |
|  | Influenza | 2 | −34.00 | 0.00 | 2.00 | 362.00 |  |
|  |  | 3 | −19.00 | 0.00 | 0.00 | 253.00 |  |
|  | Split | 1 | 1309.00 | 2598.50 | 5926.00 | 16988.00 | <0.0001 |
|  | Influenza | 2 | 453.00 | 1113.00 | 2049.00 | 12273.00 |  |
|  |  | 3 | 331.00 | 806.00 | 1596.00 | 6474.00 |  |
|  | Whole | 1 | 1516.00 | 3341.00 | 8955.00 | 21032.00 | 0.0006 |
|  | Influenza | 2 | 995.00 | 1942.00 | 3007.00 | 26358.00 |  |
|  |  | 3 | 371.50 | 1083.50 | 2624.50 | 14057.00 |  |
| IL2 in CD8 | Peptide | 1 | −111.00 | 0.00 | 103.00 | 412.00 | 0.1684 |
|  | Influenza | 2 | −41.00 | 0.00 | 138.00 | 542.00 |  |
|  |  | 3 | −150.00 | −34.00 | 71.00 | 447.00 |  |
|  | Split | 1 | −76.00 | 26.00 | 133.00 | 803.00 | 0.2311 |
|  | Influenza | 2 | −78.50 | 0.00 | 121.50 | 1064.00 |  |
|  |  | 3 | −93.00 | −1.00 | 30.00 | 705.00 |  |
|  | Whole | 1 | −167.00 | 63.00 | 261.00 | 1302.00 | 0.4586 |
|  | Influenza | 2 | −444.50 | −4.00 | 199.00 | 1398.00 |  |
|  |  | 3 | −198.00 | 9.00 | 131.00 | 838.00 |  |

TABLE 18

Antigen-specific CD4 T-cell responses expressed into cells producing
at least TNFα and another cytokine: Descriptive Statistics
on difference between PRE and POST ('Total vaccinated cohort)

| Secretion | Antigen | Group | N | Mean | SD | Min |
|---|---|---|---|---|---|---|
| TNF-α in CD4 | Peptide | 1 | 44 | 9.48 | 92.992 | −466.00 |
| | Influenza | 2 | 42 | −47.71 | 367.624 | −2333.00 |
| | | 3 | 45 | −37.38 | 179.147 | −1169.00 |
| | Split | 1 | 46 | 2343.11 | 2596.177 | −4450.00 |
| | Influenza | 2 | 45 | 703.87 | 2973.241 | −14260.0 |
| | | 3 | 47 | 732.00 | 740.001 | −611.00 |
| | Whole | 1 | 47 | 3103.74 | 4248.997 | −5146.00 |
| | Influenza | 2 | 47 | 1658.38 | 3639.959 | −1393.00 |
| | | 3 | 48 | 1010.15 | 1689.394 | −1482.00 |
| TNF-α in CD8 | Peptide | 1 | 42 | 11.71 | 201.031 | −453.00 |
| | Influenza | 2 | 41 | 37.46 | 245.241 | −612.00 |
| | | 3 | 44 | −42.95 | 210.185 | −645.00 |
| | Split | 1 | 41 | 138.54 | 362.601 | −329.00 |
| | Influenza | 2 | 44 | −70.27 | 790.309 | −4741.00 |
| | | 3 | 44 | −39.75 | 348.803 | −1044.00 |
| | Whole | 1 | 39 | 279.59 | 1048.352 | −1184.00 |
| | Influenza | 2 | 44 | −280.70 | 1562.095 | −9070.00 |
| | | 3 | 44 | −71.57 | 492.135 | −1574.00 |

| Secretion | Antigen | Group | Q1 | Median | Q3 | Max | P-value |
|---|---|---|---|---|---|---|---|
| TNF-α in CD4 | Peptide | 1 | −1.50 | 0.00 | 39.00 | 239.00 | 0.1836 |
| | Influenza | 2 | −4.00 | 0.00 | 12.00 | 277.00 | |
| | | 3 | −26.00 | 0.00 | 5.00 | 53.00 | |
| | Split | 1 | 862.00 | 1466.50 | 3931.00 | 9267.00 | <0.0001 |
| | Influenza | 2 | 251.00 | 698.00 | 1229.00 | 12275.00 | |
| | | 3 | 191.00 | 540.00 | 1010.00 | 3288.00 | |
| | Whole | 1 | 868.00 | 1607.00 | 5266.00 | 17199.00 | 0.0008 |
| | Influenza | 2 | 367.00 | 871.00 | 1584.00 | 23540.00 | |
| | | 3 | 175.00 | 592.00 | 1385.50 | 8760.00 | |
| TNF-α in CD8 | Peptide | 1 | −80.00 | 0.50 | 70.00 | 772.00 | 0.2759 |
| | Influenza | 2 | −81.00 | 0.00 | 155.00 | 791.00 | |
| | | 3 | −179.00 | 0.00 | 39.50 | 566.00 | |
| | Split | 1 | −23.00 | 60.00 | 178.00 | 1468.00 | 0.0790 |
| | Influenza | 2 | −107.00 | 0.00 | 158.00 | 1286.00 | |
| | | 3 | −185.00 | 0.00 | 78.50 | 1021.00 | |
| | Whole | 1 | −250.00 | 108.00 | 399.00 | 4601.00 | 0.1482 |
| | Influenza | 2 | −392.00 | −56.50 | 205.00 | 3258.00 | |
| | | 3 | −233.50 | −54.00 | 160.00 | 1543.00 | |

Figure 4:
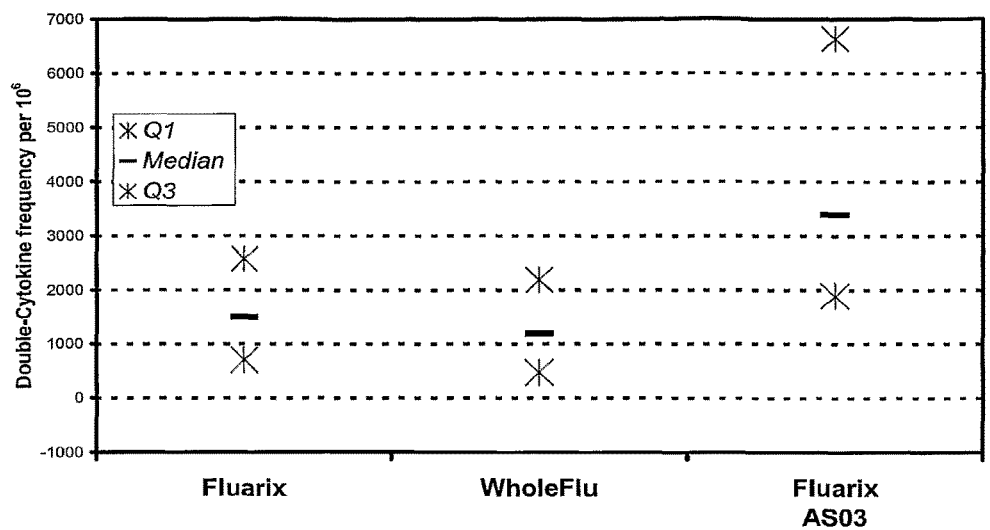
Figure 5:
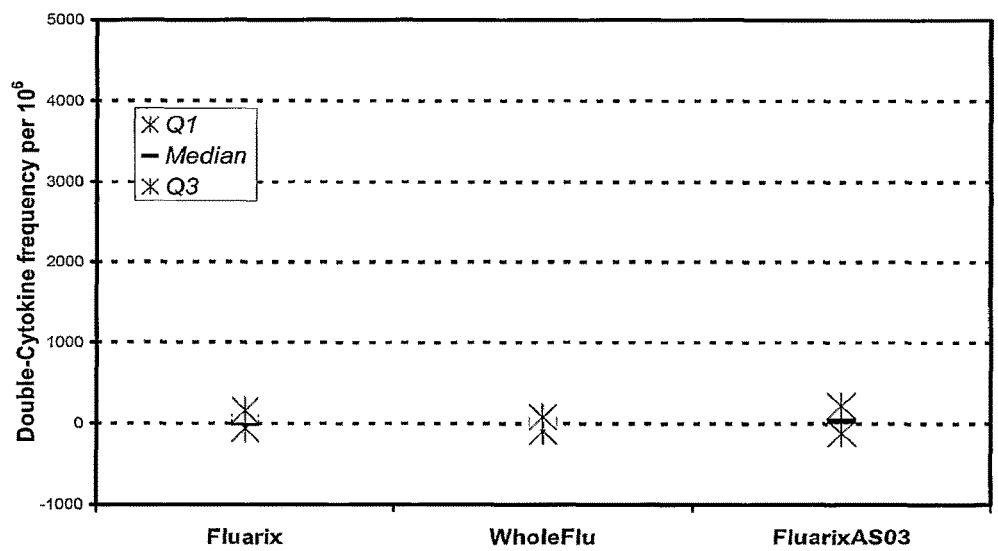

Results were also expressed as a frequency of cytokine(s)-positive CD4 or CD8 T cell within the CD4 or CD8 T cell sub-population and presented in FIG. 4 and FIG. 5.

In a similar analysis, the cross-reactive CD4 T-cells response was evaluated using influenza antigen from drifted strains (A/H1N1/Beijing/262/95 (H1N1d), A/H3N2/Sydney/5/97 (H3N2d), B/Yamanashi/166/98 (Bd)) or shift strains (A/Singapore/1/57 (H2N2), A/Hongkong/1073/99 (H9N2)). Results expressed as a frequency of cytokine(s)-positive CD4 T cells are presented in FIG. 6.

Figure 6:
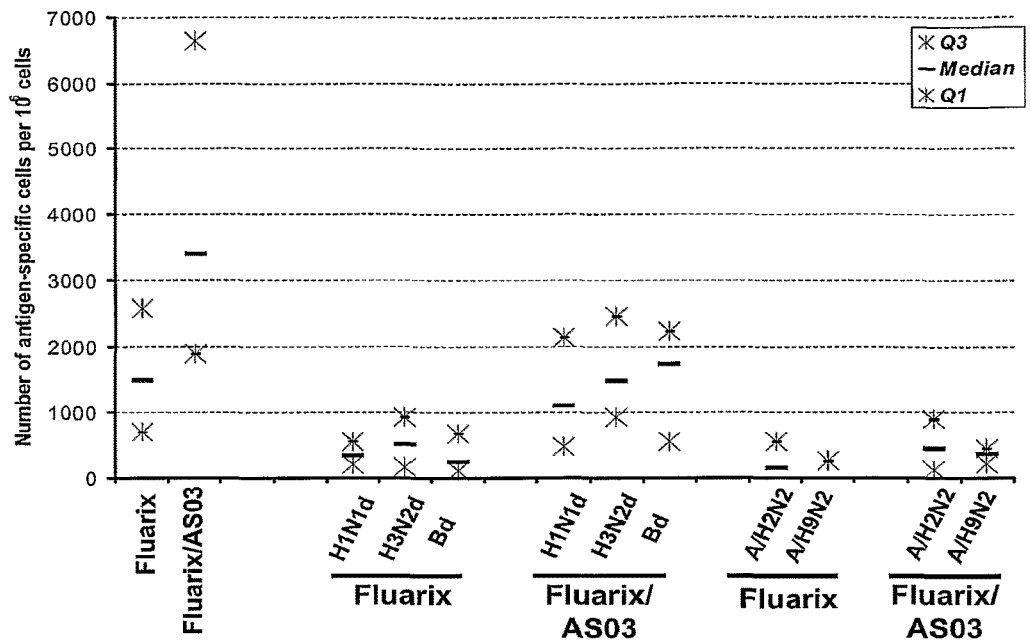

The main findings are:
Vaccination with FLUARIX® or Whole virus slightly boosts the CD4 T-cell response. Vaccination with Flu AS03 induces a strong CD4 T-cell response (FIG. 4), and this is statistically significant. The same conclusion is made after In Vitro stimulation with the split antigen or Whole virus, and this with all cytokines investigated (IL-2, IFNγ, TNFα, and CD40L).
Most individuals have a CD8 T-cell response against the whole flu, however the vaccination has no measurable impact on the CD8 T-cell response (i.e. Pre=post), whatever the group studied (FIG. 5).
Vaccination with FLUARIX® only induces low levels of cross-reactive CD4 T-cell response (FIG. 6). Vaccination with FluAS03 induces a strong CD4 T-cell response against drifted influenza strains and this is statistically significant (FIG. 6). A little response was detected against shift strains.

III.5.3. B-Cells ELISPOT MEMORY

III.5.3.1 Objective

Figure 7:
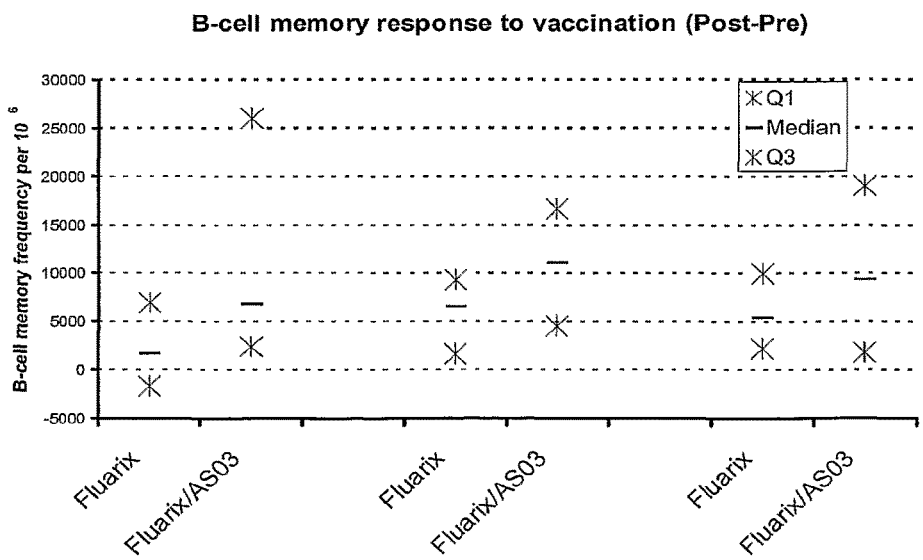

In order to better characterise the CMI response induced by the AS03-adjuvanted influenza vaccine, the B-cells Elispot memory response induced to differentiate into plasma cells in vitro using influenza vaccine strains or anti-human immunoglobulin was evaluate in order to enumerate anti-influenza or IgG secreting plasma. The results are described in Table 19 and Table 20 and in FIG. 7.

A subset of 22 first subjects having received one dose of FluAS03 vaccine and 21 first subjects having received one dose of FLUARIX® vaccine was selected to evaluate the impact of vaccination on influenza-specific memory B-cells using the B-cell memory Elispot technology. The following endpoints were determined At days 0 and 21: Influenza-specific memory B-cells have been measured by B-cell Elispot in all subjects. Results have been expressed as a frequency of Influenza specific-antibody forming cells per million ($10^6$) of antibody forming cells.

Difference between post (day 21) and pre (day 0) vaccination is also expressed as a frequency of Influenza specific-antibody forming cells per million ($10^6$) of antibody forming cells.

III.5.3.2 Statistical Methods

Descriptive statistics for each vaccination group at days 0 and day 21 expressed as a frequency of Influenza specific-antibody forming cells per million ($10^6$) of antibody forming cells. Descriptive statistics in individual difference between day 21 and day 0 (Post-Pre) as a frequency of Influenza specific-antibody forming cells per million ($10^6$) of antibody forming cells.

A Wilcoxon test was used to compare the location of difference between the two groups and the statistical p-value was calculated for each of 3 strains (A/New Caledonia, A/Panama and B/Shangdong).

III.5.3.3 Results

There is a tendency in favour of the influenza adjuvanted AS03 vaccine compared to FLUARIX® group. For A/New Caledonia strain, there is a statistical significant difference (p-value=0.021) in favour of FluAS03 compared to FLU-ARIX®. No statistical difference between the two groups was observed for A/Panama and B/Shangdong strains.

TABLE 19

B-cells Memory: descriptive statistics on pre (Day 0) and post (Day 21) and inferential statistics of post (Day 21) frequency of antigen-plasma within a $10^6$ of IgG-producing plasma cells (subset of subjects)

| STRAIN | Group | Time-point | N | Mean | SD | Min |
|---|---|---|---|---|---|---|
| A/NEW CALEDONIA | 1 | Day 0 | 22 | 9751.58 | 6630.335 | 0.00 |
| | 1 | Day 21 | 22 | 22001.65 | 11308.261 | 3981.90 |
| | 2 | Day 0 | 21 | 9193.61 | 4339.421 | 1300.81 |
| | 2 | Day 21 | 21 | 12263.08 | 7285.698 | 789.47 |
| A/PANAMA | 1 | Day 0 | 22 | 4329.17 | 2923.497 | 0.00 |
| | 1 | Day 21 | 22 | 18066.69 | 14604.842 | 714.29 |
| | 2 | Day 0 | 21 | 4860.41 | 3392.373 | 0.00 |
| | 2 | Day 21 | 21 | 13872.95 | 12052.163 | 0.00 |
| B/SHANDONG | 1 | Day 0 | 22 | 3722.80 | 2347.315 | 0.00 |
| | 1 | Day 21 | 22 | 15949.60 | 12385.965 | 0.00 |
| | 2 | Day 0 | 21 | 3030.39 | 2206.589 | 640.57 |
| | 2 | Day 21 | 21 | 9714.03 | 5656.805 | 0.00 |

| STRAIN | Gr | Time-point | Q1 | Median | Q3 | Max | P-value (Wilcoxon test) |
|---|---|---|---|---|---|---|---|
| A/NEW CALEDONIA | 1 | Day 0 | 4117.65 | 9606.46 | 13430.66 | 25570.78 | 0.0056 |
| | 1 | Day 21 | 11052.63 | 20450.55 | 30234.74 | 40526.32 | |
| | 2 | Day 0 | 6363.64 | 9686.41 | 11698.11 | 19164.84 | |
| | 2 | Day 21 | 7741.05 | 9545.45 | 17069.60 | 32000.00 | |
| A/PANAMA | 1 | Day 0 | 2275.45 | 4003.02 | 5764.55 | 10842.49 | 0.1814 |
| | 1 | Day 21 | 9347.37 | 13176.41 | 21471.39 | 54789.92 | |
| | 2 | Day 0 | 2222.22 | 4545.45 | 7495.74 | 11698.11 | |
| | 2 | Day 21 | 6231.88 | 10147.06 | 20540.54 | 52188.84 | |
| B/SHANDONG | 1 | Day 0 | 2058.82 | 2956.78 | 5972.22 | 7832.17 | 0.1483 |
| | 1 | Day 21 | 6860.47 | 12796.90 | 22947.37 | 48947.37 | |
| | 2 | Day 0 | 1290.32 | 2113.82 | 4770.02 | 7783.25 | |
| | 2 | Day 21 | 6590.91 | 9009.01 | 12774.87 | 21201.72 | |

Group 1: Flu vaccine FLUARIX™ + AS03 oil-in-water emulsion adjuvant
Group 2: Flu vaccine FLUARIX™
SD = Standard Deviation
Min, Max = Minimum, Maximum
Q1 = First quartile
Q3 = Third quartile
N = number of subjects with available results
P-value: Wilcoxon Test (Non-parametric procedure) to test location difference (Wilcoxon rank-sum test) between the 2 groups at Day 21.

TABLE 20

B cells Memory: Descriptive and inferential statistics on difference between POST (Day 21) and PRE (Day 0) frequency of antigen-specific plasma within a 10 6 of IgG-producing plasma cells (subset of subjects)

| STRAIN | Group | N | Mean | SD | Min |
|---|---|---|---|---|---|
| A/NEW CALEDONIA | 1 | 22 | 12250.07 | 12875.755 | −4365.08 |
| | 2 | 21 | 3069.46 | 7309.731 | −10043.4 |
| A/PANAMA | 1 | 22 | 13737.52 | 13677.942 | −188.29 |
| | 2 | 21 | 9012.54 | 11489.012 | −1551.05 |
| B/SHANDONG | 1 | 22 | 12226.81 | 12243.895 | −2222.22 |
| | 2 | 21 | 6683.64 | 6240.312 | −2113.82 |

TABLE 20-continued

B cells Memory: Descriptive and inferential statistics on difference
between POST (Day 21) and PRE (Day 0) frequency of antigen-specific plasma
within a 10 6 of IgG-producing plasma cells (subset of subjects)

| STRAIN | Gr | Q1 | Median | Q3 | Max | P-value (Wilcoxon test) |
|---|---|---|---|---|---|---|
| A/NEW | 1 | 2418.07 | 6776.65 | 26036.01 | 35059.98 | 0.0210 |
| CALEDONIA | 2 | −1762.54 | 1694.51 | 6850.19 | 18579.97 | |
| A/PANAMA | 1 | 4551.30 | 11039.04 | 16614.85 | 49881.94 | 0.1449 |
| | 2 | 1522.85 | 6480.96 | 9214.67 | 47812.47 | |
| B/SHANDONG | 1 | 1788.75 | 9322.70 | 18907.05 | 42134.18 | 0.1895 |
| | 2 | 2117.44 | 5384.41 | 9897.27 | 19801.28 | |

Group 1: Flu vaccine FLUARIX ™ + AS03 oil-in-water emulsion adjuvant
Group 2: Flu vaccine FLUARIX ™
SD = Standard Deviation
Min, Max = Minimum, Maximum
Q1 = First quartile
Q3 = Third quartile
N = number of subjects with available results
P-value: Wilcoxon Test (Non-parametric procedure) to test location difference (Wilcoxon rank-sum test) between the 2 groups at Day 21.

III.6. Overall Conclusions
III.6.1. Reactogenicity and Safety Results
While influenza immunisation significantly reduces the risk of pneumonia and associated deaths, vaccination of elderly only affords 23-72% protection against influenza disease. Formulation of vaccine antigen with potent adjuvants is an attractive approach for enhancing immune responses to subunit antigens. This study was designed to evaluate (1) the safety and reactogenicity in healthy elderly of an influenza vaccine adjuvanted with oil in water emulsion, i.e. AS03, (2) the antibody and cell-mediated immune responses. Reactogenicity data show that the influenza vaccine adjuvanted with AS03 induced more local and general symptoms than the two other vaccines. However regarding unsolicited adverse events, no difference was observed between the three vaccines. From these results, it can be concluded that the reactogenicity and safety profile of the candidate vaccines is satisfactory and clinically acceptable.
III.6.2. Immunogenicity Results
Regarding the immune response, the three vaccines exceeded the requirements of the European authorities for annual registration of split virion influenza vaccines ("Note for Guidance on Harmonisation of Requirements for influenza Vaccines" for the immuno-logical assessment of the annual strain changes—CPMP/BWP/214/96). The three influenza vaccines tested in this study were immunogenic in the healthy elderly, who developed a good antibody response to influenza hemagglutinin and neutralising antigens (Table 21).

TABLE 21

| Variable | EU standard for antibody response | Results |
|---|---|---|
| Conversion factor | >2.0 | >6.1 |
| Seroconversion rate | >30% | >50% |
| Protection rate | >60% | >88% |

Regarding cell-mediated immunity (CMI) response, the influenza vaccine adjuvanted with AS03 induced a significantly stronger CD4 response (included drifted strains) than the two other vaccines (FLUARIX® and whole influenza virus vaccine). However, vaccination has no measurable impact on the CD8 response.

Regarding the B cell memory response, there is a tendency in favour of the influenza adjuvanted vaccine compared to the un-adjuvanted vaccine.

EXAMPLE IV

Clinical Trial in an Elderly Population Aged Over 65 Years with a Vaccine Containing a Split Influenza Antigen Preparation and AS03 Adjuvant—Explo-Flu-002

A phase I/II, open, controlled study has been conducted in order to evaluate the reactogenicity and the immunogenicity of the GlaxoSmithKline Biologicals influenza candidate vaccine containing the adjuvant AS03, in an elderly population aged over 65 years and previously vaccinated in 2003 with the candidate vaccine in the Explo-Flu-001 clinical trial. For immunogenicity and safety evaluations, FLUARIX® vaccine (known as α-RIX® in Belgium) has been used as reference.
IV.1. Objective
The humoral immune response (i.e. anti-hemagglutinin antibody titres) and cell mediated immune response (CD4 and/or CD8 T cell responses) and B memory cell response were measured 21 days after intramuscular administration of one dose of an AS03 adjuvanted vaccine. FLUARIX®/α-RIX® was used as reference.
The objectives were:
1) to determine if AS03 adjuvanted Flu (40 subjects) versus FLUARIX® (18 subjects) confirm his strongest immunostimulating activity on CD4- and/or CD8-mediated immunity of individuals vaccinated with influenza antigens;
2) to investigate, using a longitudinal analysis, the influence of AS03 adjuvanted on the immune response in prevaccination 2004 (so response one year after the first vaccination in 2003).
IV.2. Study Design, Vaccine Composition and End-Points
40 subjects aged>65 years who have previously received one dose of the AS03 adjuvanted influenza vaccine during the Explo-Flu-001 clinical trial in 2003 (FluAS03)
one control group of about 20 subjects aged>65 years who have previously received one dose of FLUARIX® during the Explo-Flu-001 clinical trial in 2003 (FLUARIX®)

IV.2.1. Vaccine Composition

The vaccine composition is similar to that used for the study Explo-Flu-001 except for the influenza strains included in the vaccine (year 2004 vaccine). The strains are as follows:

A/New Caledonia /20/99 (IVR-116) (H1N1)=A/New Caledonia /(H1N1)—like strain

A/Wyoming/3/2003 (X-147) (H3N2)=A/Fujian (H3N2)—like strain

B/Jiangsu/10/2003=B/Shanghai—like strain

IV.2.2. Immunogenicity (HI) End-Points

GMTs (taking the anti-log of the mean of the log titre transformations)

Conversion factors (the fold increase in serum HI GMTs on day 21 compared to day 0)

Seroconversion rate (the percentage of vaccinees with at least a four-fold increases in HI titers on day 21 compared to day 0, for each vaccine strain)

Protection rate (the percentage of vaccinees with a serum HI≥1: 40 at day 21)

IV.2.3. CMI-Endpoints

Observed Variable:

At days 0 and 21: frequency of cytokine-positive CD4/CD8 cells per $10^6$ into 4 different cytokines. Each test quantifies the response of CD4/CD8 T cell to:

Pool of the 3 following antigens

New Caledonia antigen

Wyoming antigen

Jiangsu antigen.

Derived Variables:

Antigen-specific CD4 and CD8-T-cell response expressed into the 5 different tests (cytokines):

1. cells producing at least two different cytokines (CD40L, IL-2, IFNγ, TNFα)
2. cells producing at least CD40L and another cytokine (IL-2, TNFα, IFNγ)
3. cells producing at least IL-2 and another cytokine (CD40L, TNFα, IFNγ)
4. cells producing at least IFNγ and another cytokine (IL-2, TNFα, CD40L)
5. cells producing at least TNFα and another cytokine (IL-2, CD40L, IFNγ)

IV.2.4. CMI Analysis

The first CMI analysis was based on the Total Vaccinated cohort (N=40 subjects for FluAS03 group and N=18 subjects for FLUARIX® group).

A longitudinal analysis was based on the Kinetic cohort of the Explo-Flu-001 (split protein) and Explo-Flu-002 (pool flu antigen) studies:

Pre: N=36 subjects for FluAS03 group and N=15 for FLUARIX® group.

Post-Pre: N=34 subjects for FluAS03 group and N=15 for FLUARIX® group.

(a) The frequency of CD4/CD8 T-lymphocytes secreting in response was summarised by descriptive statistics for each antigen, for each cytokine, for each vaccine group and at each timepoint (pre- and post-vaccination).

(b) Descriptive statistics in individual difference between timepoints (Post-Pre) responses were tabulated for each antigen, for each cytokine and for each vaccine group.

(c) For the timepoints post and (post-pre) vaccination, non-parametric Wilcoxon's test was used to compare the location differences between the two vaccine groups and to calculate the statistical p-value regarding the 4 different cytokines on:

CD4 T-cell response to New Caledonia, Wyoming, Jiangsu and the pool of the 3 strains.

CD8 T-cell response to New Caledonia, Wyoming, Jiangsu and the pool of the 3 strains.

(d) Non-parametric test (Wilcoxon-test) was also used:

To investigate the kinetic of the immune response at Pre (Day 0) in term of frequency of specific CD4 between Explo-Flu-001 and Explo-Flu-002 in each vaccine group To investigate the kinetic of the immune response at Pre (Day 0) in term of frequency of specific CD4 between the 2 vaccine groups in each of the study Explo-Flu-001 and Explo-Flu-002

To investigate the kinetic of the immune response in term of differences (Post-Pre) of frequency of specific CD4 between Explo-Flu-001 and Explo-Flu-002 in each vaccine group.

To investigate the kinetic of the immune response in term of differences (Post-Pre) of frequency of specific CD4 between the 2 vaccine groups in each of the study Explo-Flu-001 and Explo-Flu-002

All significance tests were two-tailed. P-values less than or equal to 0.05 were considered as statistically significant.

IV.3. Results

Results were expressed as a frequency of cytokine(s)-positive CD4 or CD8 T cell within the CD4 or CD8 T cell sub-population.

IV.3.1. Antigen Specific CD4 T-Lymphocytes

The frequency of antigen-specific CD4 T-lymphocytes secreting in response was summarised by descriptive statistics for each antigen, for each cytokine, for each vaccine group and at each timepoint (pre- and post-vaccination).

Descriptive statistics in individual difference between time points (Post-Pre) in CD4 T-lymphocytes responses for each antigen at each 5 different cytokines and for each vaccine group are shown in Table 22.

TABLE 22

Descriptive Statistics on difference between Post-vaccination (at Day 21) and Prevaccination (at Day 0) for the antigen-specific CD4 T-lymphocyte responses (Total vaccinated cohort)

| Antigen | Cytokine | Vaccine Group | N | Mean | SD | Min | Q1 | Median | Q3 | Max |
|---|---|---|---|---|---|---|---|---|---|---|
| Pool Flu | All double | FLUARIX ® | 18 | 1268.67 | 1051.744 | 197.00 | 724.00 | 863.00 | 1561.00 | 4676.00 |
| | | Flu AS03 | 36 | 1781.31 | 1484.860 | −2379.00 | 929.50 | 1664.50 | 2821.00 | 4669.00 |
| | CD40L | FLUARIX ® | 18 | 1260.11 | 1054.487 | 243.00 | 721.00 | 849.00 | 1602.00 | 4743.00 |
| | | Flu AS03 | 36 | 1711.56 | 1433.113 | −2359.00 | 838.00 | 1576.00 | 2759.50 | 4575.00 |
| | IFNγ | FLUARIX ® | 18 | 762.94 | 813.884 | −12.00 | 294.00 | 496.00 | 1061.00 | 3564.00 |
| | | Flu AS03 | 36 | 1179.92 | 881.255 | −817.00 | 692.50 | 1180.50 | 1865.50 | 2831.00 |
| | IL2 | FLUARIX ® | 18 | 1019.06 | 917.905 | −258.00 | 544.00 | 702.00 | 1174.00 | 3850.00 |
| | | Flu AS03 | 36 | 1423.33 | 1359.471 | −2702.00 | 651.00 | 1260.00 | 2200.50 | 4342.00 |

TABLE 22-continued

Descriptive Statistics on difference between Post-vaccination (at Day 21) and Prevaccination (at Day 0) for the antigen-specific CD4 T-lymphocyte responses (Total vaccinated cohort)

| Antigen | Cytokine | Vaccine Group | N | Mean | SD | Min | Q1 | Median | Q3 | Max |
|---|---|---|---|---|---|---|---|---|---|---|
| | TNFα | FLUARIX ® | 18 | 803.39 | 915.838 | 32.00 | 231.00 | 533.00 | 936.00 | 3892.00 |
| | | Flu AS03 | 36 | 1078.28 | 1029.122 | −1816.00 | 446.00 | 983.00 | 1836.00 | 3310.00 |
| A/New Caledonia | All double | FLUARIX ® | 18 | 481.44 | 381.534 | −241.00 | 282.00 | 448.50 | 598.00 | 1412.00 |
| | | Flu AS03 | 36 | 812.78 | 749.192 | −828.00 | 215.50 | 911.50 | 1274.50 | 3206.00 |
| | CD40L | FLUARIX ® | 18 | 450.78 | 360.378 | −239.00 | 291.00 | 447.00 | 580.00 | 1248.00 |
| | | Flu AS03 | 36 | 783.75 | 711.608 | −760.00 | 242.00 | 808.00 | 1161.00 | 3050.00 |
| | IFNγ | FLUARIX ® | 18 | 316.28 | 279.662 | −165.00 | 175.00 | 259.00 | 387.00 | 1111.00 |
| | | Flu AS03 | 36 | 438.22 | 420.770 | −685.00 | 125.00 | 393.00 | 733.50 | 1557.00 |
| | IL2 | FLUARIX ® | 18 | 326.06 | 290.792 | −294.00 | 193.00 | 330.00 | 488.00 | 834.00 |
| | | Flu AS03 | 36 | 634.72 | 616.478 | −557.00 | 179.50 | 678.50 | 952.00 | 2602.00 |
| | TNFα | FLUARIX ® | 18 | 316.44 | 372.492 | −140.00 | 50.00 | 278.00 | 542.00 | 1449.00 |
| | | Flu AS03 | 36 | 449.17 | 591.796 | −916.00 | 100.50 | 343.50 | 848.00 | 2452.00 |
| A/Wyoming | All double | FLUARIX ® | 18 | 609.56 | 559.396 | −176.00 | 257.00 | 510.50 | 957.00 | 1998.00 |
| | | Flu AS03 | 36 | 766.61 | 579.191 | −568.00 | 316.00 | 864.50 | 1221.00 | 1662.00 |
| | CD40L | FLUARIX ® | 18 | 616.33 | 550.853 | −176.00 | 274.00 | 488.00 | 939.00 | 2017.00 |
| | | Flu AS03 | 36 | 728.61 | 570.316 | −670.00 | 260.00 | 789.50 | 1216.00 | 1675.00 |
| | IFNγ | FLUARIX ® | 18 | 407.06 | 424.758 | −311.00 | 129.00 | 370.50 | 723.00 | 1372.00 |
| | | Flu AS03 | 36 | 526.72 | 443.938 | −770.00 | 219.00 | 556.50 | 776.00 | 1342.00 |
| | IL2 | FLUARIX ® | 18 | 495.83 | 503.805 | −187.00 | 88.00 | 540.50 | 801.00 | 1841.00 |
| | | Flu AS03 | 36 | 572.89 | 533.728 | −789.00 | 220.00 | 602.00 | 882.50 | 1512.00 |
| | TNFα | FLUARIX ® | 18 | 424.56 | 485.591 | −260.00 | 110.00 | 359.50 | 461.00 | 1718.00 |
| | | Flu AS03 | 36 | 550.58 | 538.461 | −765.00 | 269.50 | 543.50 | 905.50 | 1678.00 |
| B/Jiangsu | All double | FLUARIX ® | 18 | 698.44 | 793.119 | −306.00 | 233.00 | 433.00 | 961.00 | 2822.00 |
| | | Flu AS03 | 36 | 861.42 | 688.852 | −223.00 | 339.00 | 745.00 | 1325.50 | 2284.00 |
| | CD40L | FLUARIX ® | 18 | 678.39 | 777.259 | −206.00 | 227.00 | 401.50 | 962.00 | 2878.00 |
| | | Flu AS03 | 36 | 825.89 | 674.879 | −223.00 | 305.00 | 722.00 | 1282.00 | 2337.00 |
| | IFNγ | FLUARIX ® | 18 | 431.72 | 489.912 | −95.00 | 191.00 | 272.50 | 382.00 | 1712.00 |
| | | Flu AS03 | 36 | 615.94 | 473.543 | −286.00 | 288.50 | 501.50 | 897.50 | 1740.00 |
| | IL2 | FLUARIX ® | 18 | 552.50 | 666.853 | −234.00 | 155.00 | 278.50 | 833.00 | 2386.00 |
| | | Flu AS03 | 36 | 696.19 | 622.931 | −359.00 | 207.50 | 540.50 | 1146.50 | 2182.00 |
| | TNFα | FLUARIX ® | 18 | 441.39 | 695.792 | −338.00 | 97.00 | 269.50 | 564.00 | 2440.00 |
| | | Flu AS03 | 36 | 500.03 | 448.636 | −166.00 | 107.50 | 436.00 | 745.00 | 1626.00 |

Figure 8:
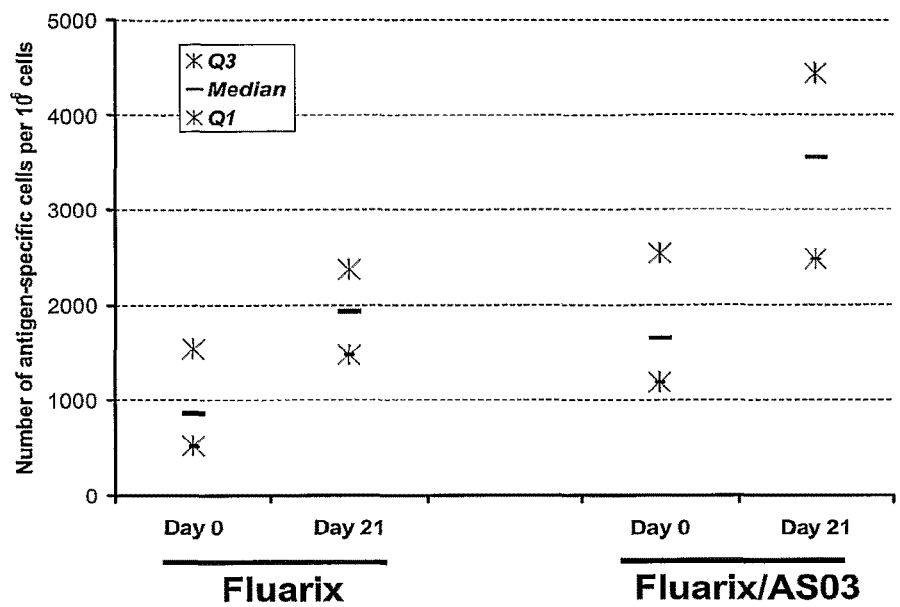

SD = Standard Deviation
Min, Max = Minimum, Maximum
Q1 = First quartile
Q3 = Third quartile
N = number of subjects tested with available results Vaccine-induced CD4 T-cells are shown to be able to persist at least for one year since there is an observable difference in prevaccination levels of CD4 T-cell responses between individuals vaccinated with FLUARIX® has compared to those vaccinated with FLUARIX®/AS03 the year before. The results are also shown in FIG. 8, showing the CD4 T-cell response to split Flu antigen before and after revaccination. D0 corresponds to 12 months after first year vaccination and thus indicates persistence.

Comparing the difference in the frequency of antigen-specific CD4 T-lymphocytes between the 2 groups by Wilcoxon test at post-vaccination, almost all p-values were less than 0.05 and were considered as statistically significant (see Table 23) in favour of the FluAS03 group.

TABLE 23

Inferential statistics: p-values from Wilcoxon rank-sum test between the two vaccine groups at Day 21 for antigen-specific CD4 T-lymphocyte responses (Total vaccinated cohort)

| | P-value | | | |
|---|---|---|---|---|
| Cytokine | Pool | New Caledonia | Wyoming | Jiangsu |
| All double | 0.0014 | 0.0023 | 0.0286 | 0.0133 |
| CD40L | 0.0016 | 0.0014 | 0.0427 | 0.0155 |
| INFγ | 0.0006 | 0.0366 | 0.0400 | 0.0041 |
| IL2 | 0.0037 | 0.0024 | 0.0584 | 0.0162 |
| TNFα | 0.0031 | 0.0103 | 0.0918 | 0.0114 |

P-value: Wilcoxon Test (Non-parametric procedure) to test location difference (Wilcoxon rank-sum test) between the 2 groups at Day 21.

Comparing the difference of the individual difference (Post-Pre) in the frequency of antigen-specific CD4-T-lymphocytes responses between the 2 groups by Wilcoxon test, p-values less than 0.05 and considered as statistically significant occurred for the following antigen-cytokine combinations: pool flu-all double, pool flu-IFNγ and Jiangsu-IFNγ in favour of the FluAS03 group (Table 24).

TABLE 24

Inferential statistics: p-values calculated by Wilcoxon rank-sum test between the different groups on the difference between Post-vaccination (at Day 21) and Prevaccination (at 0) for the antigen-specific CD4 T-lymphocyte responses (Total vaccinated cohort)

| Cytokine | P-value | | | |
|---|---|---|---|---|
| | Pool | New Caledonia | Wyoming | Jiangsu |
| All double | 0.0435 | 0.1124 | 0.2189 | 0.3085 |
| CD40L | 0.0638 | 0.0781 | 0.2831 | 0.2872 |

Comparing the difference of the individual difference (Post-Pre) in the frequency of antigen-specific CD8-T-lymphocytes responses between the 2 groups by Wilcoxon test, all p-values were higher than 0.05 and were not considered as statistically significant.

IV.3.3. Kinetic Analysis: Immune Response at Prevaccination (One Year after the First Vaccination in 2003)

The frequency of antigen-specific CD4 T-lymphocytes secreting in response at prevaccination was summarised by descriptive statistics for each cytokine and for each vaccine group and for each of the two studies in Table 25, for each of the two studies study and for each vaccine group in Table 27. Inferential statistics are given in Table 26 and Table 28.

TABLE 25

Descriptive Statistics on prevaccination (Day 0) for the specific CD4 T-lymphocytes response vaccination (Kinetic)

| Cytokine | Group | Study | N | Mean | SD | Min | Q1 | Median | Q3 | Max |
|---|---|---|---|---|---|---|---|---|---|---|
| All double | Flu AS03 | EXPLO 001 | 36 | 2000.86 | 1783.474 | 102.00 | 911.50 | 1461.50 | 2791.00 | 9514.00 |
| | | EXPLO 002 | 36 | 2028.28 | 1427.000 | 55.00 | 1190.50 | 1647.50 | 2575.00 | 7214.00 |
| | FLUARIX ® | EXPLO 001 | 15 | 2152.87 | 2162.463 | 747.00 | 930.00 | 1354.00 | 2101.00 | 7868.00 |
| | | EXPLO 002 | 15 | 1587.07 | 2123.841 | 192.00 | 468.00 | 735.00 | 1578.00 | 8536.00 |
| CD40L | Flu AS03 | EXPLO 001 | 35 | 1946.66 | 1771.102 | 120.00 | 837.00 | 1340.00 | 2819.00 | 9462.00 |
| | | EXPLO 002 | 35 | 1992.20 | 1440.721 | 77.00 | 1125.00 | 1590.00 | 2587.00 | 7286.00 |
| | FLUARIX ® | EXPLO 001 | 15 | 2094.93 | 2076.632 | 745.00 | 902.00 | 1340.00 | 2077.00 | 7385.00 |
| | | EXPLO 002 | 15 | 1561.73 | 2097.201 | 34.00 | 475.00 | 672.00 | 1579.00 | 8428.00 |
| INFγ | Flu AS03 | EXPLO 001 | 35 | 1068.63 | 1030.745 | 91.00 | 448.00 | 790.00 | 1503.00 | 5425.00 |
| | | EXPLO 002 | 35 | 1259.23 | 890.590 | 312.00 | 725.00 | 984.00 | 1354.00 | 4146.00 |
| | FLUARIX ® | EXPLO 001 | 15 | 1248.07 | 1452.459 | 320.00 | 388.00 | 778.00 | 1227.00 | 5431.00 |
| | | EXPLO 002 | 15 | 974.80 | 1394.044 | 52.00 | 252.00 | 337.00 | 1057.00 | 5576.00 |
| IL2 | Flu AS03 | EXPLO 001 | 35 | 1690.20 | 1524.689 | 37.00 | 688.00 | 1211.00 | 2416.00 | 8235.00 |
| | | EXPLO 002 | 35 | 1883.60 | 1361.337 | 14.00 | 1068.00 | 1413.00 | 2370.00 | 6891.00 |
| | FLUARIX ® | EXPLO 001 | 15 | 1888.40 | 2085.857 | 568.00 | 715.00 | 1136.00 | 1770.00 | 7403.00 |
| | | EXPLO 002 | 15 | 1493.93 | 2037.139 | 58.00 | 444.00 | 755.00 | 1485.00 | 8193.00 |
| TNFα | Flu AS03 | EXPLO 001 | 35 | 1174.74 | 1119.633 | 55.00 | 466.00 | 795.00 | 1720.00 | 5415.00 |
| | | EXPLO 002 | 35 | 1545.40 | 1159.490 | 135.00 | 831.00 | 1203.00 | 1857.00 | 5354.00 |
| | FLUARIX ® | EXPLO 001 | 15 | 1444.20 | 1946.211 | 201.00 | 520.00 | 688.00 | 1254.00 | 7213.00 |
| | | EXPLO 002 | 15 | 1304.73 | 1759.716 | 144.00 | 316.00 | 824.00 | 1171.00 | 7056.00 |

SD = Standard Deviation
Min, Max = Minimum, Maximum
Q1 = First quartile
Q3 = Third quartile
N = number of subjects tested with available results

TABLE 24-continued

Inferential statistics: p-values calculated by Wilcoxon rank-sum test between the different groups on the difference between Post-vaccination (at Day 21) and Prevaccination (at 0) for the antigen-specific CD4 T-lymphocyte responses (Total vaccinated cohort)

| Cytokine | P-value | | | |
|---|---|---|---|---|
| | Pool | New Caledonia | Wyoming | Jiangsu |
| INFγ | 0.0290 | 0.3589 | 0.2553 | 0.0435 |
| IL2 | 0.1024 | 0.0563 | 0.3986 | 0.0435 |
| TNFα | 0.0693 | 0.4090 | 0.1232 | 0.3129 |

P-value: Wilcoxon Test (Non-parametric procedure) to test location difference (Wilcoxon rank-sum test) between the 2 groups.

IV.3.2. Antigen Specific CD8 T-Lymphocytes

The frequency of antigen-specific CD8 T-lymphocytes secreting in response was summarised by descriptive statistics for each antigen, for each cytokine, for each vaccine group and at each timepoint (pre- and post-vaccination), similarly to the procedure followed in respect of CD4 T cell response.

Comparing the difference in the frequency of antigen-specific CD8 T-lymphocytes between the 2 groups by Wilcoxon test at post-vaccination, all p-values were higher than 0.05 and were not considered as statistically significant.

Comparing the difference in the frequency of antigen-specific CD4 T-lymphocytes between the 2 studies by Wilcoxon test for each vaccine group, p-values less than 0.05 and considered as statistically significant (in favour of Explo-Flu-002) occurred only for FluAS03 group and with TNFα cytokine (see Table 26).

TABLE 26

Inferential statistics: p-values from Wilcoxon rank-sum test between the different studies at Day 0 for antigen-specific CD4 T-lymphocyte responses (Kinetic)

| Cytokine | Group | p-value |
|---|---|---|
| ALL DOUBLE | FluAS03 | 0.5209 |
| | FLUARIX ® | 0.0712 |
| CD40L | FluAS03 | 0.4957 |
| | FLUARIX ® | 0.0744 |
| INFγ | FluAS03 | 0.0896 |
| | FLUARIX ® | 0.1103 |
| IL2 | FluAS03 | 0.1903 |
| | FLUARIX ® | 0.1647 |
| TNFα | FluAS03 | 0.0427 |
| | FLUARIX ® | 0.5476 |

P-value: Wilcoxon Test (Non-parametric procedure) to test location difference (Wilcoxon rank-sum test) between the 2 groups at Day 21.

TABLE 27

Descriptive Statistics on Prevaccination (Day 0) for the specific CD4 T-lymphocytes response vaccination (Kinetic)

| Cytokine | Study | Group | N | Mean | SD | Min | Q1 | Median | Q3 | Max |
|---|---|---|---|---|---|---|---|---|---|---|
| All double | EXPLO 001 | Flu AS03 | 36 | 2000.86 | 1783.474 | 102.00 | 911.50 | 1461.50 | 2791.00 | 9514.00 |
| | | FLUARIX ® | 15 | 2152.87 | 2162.463 | 747.00 | 930.00 | 1354.00 | 2101.00 | 7868.00 |
| | EXPLO 002 | Flu AS03 | 36 | 2028.28 | 1427.000 | 55.00 | 1190.50 | 1647.50 | 2575.00 | 7214.00 |
| | | FLUARIX ® | 15 | 1587.07 | 2123.841 | 192.00 | 468.00 | 735.00 | 1578.00 | 8536.00 |
| CD40L | EXPLO 001 | Flu AS03 | 35 | 1946.66 | 1771.102 | 120.00 | 837.00 | 1340.00 | 2819.00 | 9462.00 |
| | | FLUARIX ® | 15 | 2094.93 | 2076.632 | 745.00 | 902.00 | 1340.00 | 2077.00 | 7385.00 |
| | EXPLO 002 | Flu AS03 | 35 | 1992.20 | 1440.721 | 77.00 | 1125.00 | 1590.00 | 2587.00 | 7286.00 |
| | | FLUARIX ® | 15 | 1561.73 | 2097.201 | 34.00 | 475.00 | 672.00 | 1579.00 | 8428.00 |
| INFγ | EXPLO 001 | Flu AS03 | 35 | 1068.63 | 1030.745 | 91.00 | 448.00 | 790.00 | 1503.00 | 5425.00 |
| | | FLUARIX ® | 15 | 1248.07 | 1452.459 | 320.00 | 388.00 | 778.00 | 1227.00 | 5431.00 |
| | EXPLO 002 | Flu AS03 | 35 | 1259.23 | 890.590 | 312.00 | 725.00 | 984.00 | 1354.00 | 4146.00 |
| | | FLUARIX ® | 15 | 974.80 | 1394.044 | 52.00 | 252.00 | 337.00 | 1057.00 | 5576.00 |
| IL2 | EXPLO 001 | Flu AS03 | 35 | 1690.20 | 1524.689 | 37.00 | 688.00 | 1211.00 | 2416.00 | 8235.00 |
| | | FLUARIX ® | 15 | 1888.40 | 2085.857 | 568.00 | 715.00 | 1136.00 | 1770.00 | 7403.00 |
| | EXPLO 002 | Flu AS03 | 35 | 1883.60 | 1361.337 | 14.00 | 1068.00 | 1413.00 | 2370.00 | 6891.00 |
| | | FLUARIX ® | 15 | 1493.93 | 2037.139 | 58.00 | 444.00 | 755.00 | 1485.00 | 8193.00 |
| TNFα | EXPLO 001 | Flu AS03 | 35 | 1174.74 | 1119.633 | 55.00 | 466.00 | 795.00 | 1720.00 | 5415.00 |
| | | FLUARIX ® | 15 | 1444.20 | 1946.211 | 201.00 | 520.00 | 688.00 | 1254.00 | 7213.00 |
| | EXPLO 002 | Flu AS03 | 35 | 1545.40 | 1159.490 | 135.00 | 831.00 | 1203.00 | 1857.00 | 5354.00 |
| | | FLUARIX ® | 15 | 1304.73 | 1759.716 | 144.00 | 316.00 | 824.00 | 1171.00 | 7056.00 |

SD = Standard Deviation
Min, Max = Minimum, Maximum
Q1 = First quartile
Q3 = Third quartile
N = number of subjects tested with available results Comparing the difference in the frequency of antigen-specific CD4 T-lymphocytes between the 2 vaccine groups by Wilcoxon test for each study, all p-values for Explo-Flu-002 were less than 0.05 and were considered as statistically significant (in favour of FluAS03) (see Table 28).

TABLE 28

Inferential statistics: p-values from Wilcoxon rank-sum test between the different groups at Day 21 for antigen-specific CD4 T-lymphocyte responses (Kinetic)

| Cytokine | Study | p-value |
|---|---|---|
| ALL DOUBLE | Explo Flu 001 | 0.9423 |
| | Explo Flu 002 | 0.0300 |
| CD40L | Explo Flu 001 | 0.8989 |
| | Explo Flu 002 | 0.0361 |
| INFγ | Explo Flu 001 | 0.8738 |
| | Explo Flu 002 | 0.0121 |
| IL2 | Explo Flu 001 | 0.9747 |
| | Explo Flu 002 | 0.0216 |
| TNFα | Explo Flu 001 | 0.9916 |
| | Explo Flu 002 | 0.0514 |

P-value: Wilcoxon Test (Non-parametric procedure) to test location difference (Wilcoxon rank-sum test) between the 2 groups at Day 21.

IV.3.4. Kinetic Analysis: Immune Response at Post Minus Prevaccination

The frequency of antigen-specific CD4 T-lymphocytes secreting in response at (post-pre) timepoint was summarised by descriptive statistics for each cytokine and for each vaccine group and for each study in Table 29, for each study and for each vaccine group in Table 31. Inferential statistics are given in Table 30 and Table 32.

TABLE 29

Descriptive Statistics on the difference between Post-vaccination (Day 21) and Prevaccination (Day 0) for the specific CD4 T-lymphocytes response vaccination (Kinetic)

| Cytokine | Group | Study | N | Mean | SD | Min | Q1 | Median | Q3 | Max |
|---|---|---|---|---|---|---|---|---|---|---|
| All double | Flu AS03 | EXPLO 001 | 34 | 4837.56 | 4476.129 | −609.00 | 1888.00 | 3483.50 | 8148.00 | 19555.00 |
| | | EXPLO 002 | 34 | 1737.79 | 1450.177 | −2379.00 | 936.00 | 1664.50 | 2743.00 | 4669.00 |
| | FLUARIX ® | EXPLO 001 | 15 | 3103.53 | 3726.645 | 436.00 | 800.00 | 2283.00 | 3226.00 | 15169.00 |
| | | EXPLO 002 | 15 | 1369.00 | 1127.784 | 197.00 | 725.00 | 869.00 | 1808.00 | 4676.00 |
| CD40L | Flu AS03 | EXPLO 001 | 33 | 4819.06 | 4489.788 | −718.00 | 1799.00 | 3479.00 | 8288.00 | 19480.00 |
| | | EXPLO 002 | 33 | 1694.73 | 1431.082 | −2359.00 | 921.00 | 1659.00 | 2662.00 | 4575.00 |
| | FLUARIX ® | EXPLO 001 | 15 | 3090.00 | 3684.759 | 477.00 | 822.00 | 2189.00 | 3208.00 | 15021.00 |
| | | EXPLO 002 | 15 | 1360.93 | 1131.051 | 243.00 | 725.00 | 860.00 | 1687.00 | 4743.00 |
| IFNγ | Flu AS03 | EXPLO 001 | 33 | 3127.09 | 2974.067 | −453.00 | 1325.00 | 1721.00 | 5162.00 | 13296.00 |
| | | EXPLO 002 | 33 | 1167.85 | 893.363 | −817.00 | 633.00 | 1207.00 | 1803.00 | 2831.00 |
| | FLUARIX ® | EXPLO 001 | 15 | 1660.13 | 1834.023 | −84.00 | 480.00 | 1386.00 | 2284.00 | 7120.00 |
| | | EXPLO 002 | 15 | 851.87 | 859.585 | 148.00 | 294.00 | 501.00 | 1222.00 | 3564.00 |
| IL2 | Flu AS03 | EXPLO 001 | 33 | 3950.18 | 3878.538 | −358.00 | 1309.00 | 2780.00 | 6635.00 | 16988.00 |
| | | EXPLO 002 | 33 | 1404.67 | 1355.665 | −2702.00 | 719.00 | 1341.00 | 2109.00 | 4342.00 |

TABLE 29-continued

Descriptive Statistics on the difference between Post-vaccination (Day 21) and Prevaccination (Day 0) for the specific CD4 T-lymphocytes response vaccination (Kinetic)

| Cytokine | Group | Study | N | Mean | SD | Min | Q1 | Median | Q3 | Max |
|---|---|---|---|---|---|---|---|---|---|---|
| | FLUARIX ® | EXPLO 001 | 15 | 2413.87 | 3027.392 | 263.00 | 674.00 | 1672.00 | 2425.00 | 12273.00 |
| | | EXPLO 002 | 15 | 1117.80 | 975.934 | −258.00 | 575.00 | 714.00 | 1618.00 | 3850.00 |
| TNFα | Flu AS03 | EXPLO 001 | 33 | 2627.36 | 2574.458 | −825.00 | 862.00 | 1475.00 | 4764.00 | 9267.00 |
| | | EXPLO 002 | 33 | 1072.36 | 1044.140 | −1816.00 | 447.00 | 1000.00 | 1752.00 | 3310.00 |
| | FLUARIX ® | EXPLO 001 | 15 | 1460.53 | 3115.174 | −1586.00 | 251.00 | 813.00 | 1314.00 | 12275.00 |
| | | EXPLO 002 | 15 | 904.67 | 974.958 | 32.00 | 338.00 | 752.00 | 965.00 | 3892.00 |

SD = Standard Deviation
Min, Max = Minimum, Maximum
Q1 = First quartile
Q3 = Third quartile
N = number of subjects tested with available results Comparing the difference in the frequency of antigen-specific CD4 T-lymphocytes between the 2 studies by Wilcoxon test for each vaccine group, all p-values for FluAS03 group were less than 0.05 and were considered as statistically significant (in favour of Explo-Flu-001) (see Table 30).

TABLE 30

Inferential statistics on the difference between Post-vaccination (Day 21) and Prevaccination (Day 0): p-values from Wilcoxon rank-sum test between the different studies at Day 21 for antigen-specific CD4 T-lymphocyte responses (Kinetic)

| Cytokine | Group | p-value |
|---|---|---|
| ALL DOUBLE | FluAS03 | 0.0005 |
| | FLUARIX ® | 0.1300 |
| CD40L | FluAS03 | 0.0007 |
| | FLUARIX ® | 0.0890 |
| INFγ | FluAS03 | 0.0012 |
| | FLUARIX ® | 0.1103 |
| IL2 | FluAS03 | 0.0025 |
| | FLUARIX ® | 0.1409 |
| TNFα | FluAS03 | 0.0327 |
| | FLUARIX ® | 0.6936 |

P-value: Wilcoxon Test (Non-parametric procedure) to test location difference (Wilcoxon rank-sum test) between the 2 groups at Day 21.

TABLE 31

Descriptive Statistics on the difference between Post-vaccination (Day 21) and Prevaccination (Day 0) for the specific CD4 T-lymphocytes response vaccination (Kinetic)

| Cytokine | Study | Group | N | Mean | SD | Min | Q1 | Median | Q3 | Max |
|---|---|---|---|---|---|---|---|---|---|---|
| All double | EXPLO 001 | Flu AS03 | 34 | 4837.56 | 4476.129 | −609.00 | 1888.00 | 3483.50 | 8148.00 | 19555.00 |
| | | FLUARIX ® | 15 | 3103.53 | 3726.645 | 436.00 | 800.00 | 2283.00 | 3226.00 | 15169.00 |
| | EXPLO 002 | Flu AS03 | 34 | 1737.79 | 1450.177 | −2379.00 | 936.00 | 1664.50 | 2743.00 | 4669.00 |
| | | FLUARIX ® | 15 | 1369.00 | 1127.784 | 197.00 | 725.00 | 869.00 | 1808.00 | 4676.00 |
| CD40L | EXPLO 001 | Flu AS03 | 33 | 4819.06 | 4489.788 | −718.00 | 1799.00 | 3479.00 | 8288.00 | 19480.00 |
| | | FLUARIX ® | 15 | 3090.00 | 3684.759 | 477.00 | 822.00 | 2189.00 | 3208.00 | 15021.00 |
| | EXPLO 002 | Flu AS03 | 33 | 1694.73 | 1431.082 | −2359.00 | 921.00 | 1659.00 | 2662.00 | 4575.00 |
| | | FLUARIX ® | 15 | 1360.93 | 1131.051 | 243.00 | 725.00 | 860.00 | 1687.00 | 4743.00 |
| IFNγ | EXPLO 001 | Flu AS03 | 33 | 3127.09 | 2974.067 | −453.00 | 1325.00 | 1721.00 | 5162.00 | 13296.00 |
| | | FLUARIX ® | 15 | 1660.13 | 1834.023 | −84.00 | 480.00 | 1386.00 | 2284.00 | 7120.00 |
| | EXPLO 002 | Flu AS03 | 33 | 1167.85 | 893.363 | −817.00 | 633.00 | 1207.00 | 1803.00 | 2831.00 |
| | | FLUARIX ® | 15 | 851.87 | 859.585 | 148.00 | 294.00 | 501.00 | 1222.00 | 3564.00 |
| IL2 | EXPLO 001 | Flu AS03 | 33 | 3950.18 | 3878.538 | −358.00 | 1309.00 | 2780.00 | 6635.00 | 16988.00 |
| | | FLUARIX ® | 15 | 2413.87 | 3027.392 | 263.00 | 674.00 | 1672.00 | 2425.00 | 12273.00 |
| | EXPLO 002 | Flu AS03 | 33 | 1404.67 | 1355.665 | −2702.00 | 719.00 | 1341.00 | 2109.00 | 4342.00 |
| | | FLUARIX ® | 15 | 1117.80 | 975.934 | −258.00 | 575.00 | 714.00 | 1618.00 | 3850.00 |
| TFNα | EXPLO 001 | Flu AS03 | 33 | 2627.36 | 2574.458 | −825.00 | 862.00 | 1475.00 | 4764.00 | 9267.00 |
| | | FLUARIX ® | 15 | 1460.53 | 3115.174 | −1586.00 | 251.00 | 813.00 | 1314.00 | 12275.00 |
| | EXPLO 002 | Flu AS03 | 33 | 1072.36 | 1044.140 | −1816.00 | 447.00 | 1000.00 | 1752.00 | 3310.00 |
| | | FLUARIX ® | 15 | 904.67 | 974.958 | 32.00 | 338.00 | 752.00 | 965.00 | 3892.00 |

SD = Standard Deviation
Min, Max = Minimum, Maximum
Q1 = First quartile
Q3 = Third quartile
N = number of subjects tested with available results Comparing the difference in the frequency of antigen-specific CD4 T-lymphocytes between the 2 vaccine groups by Wilcoxon test for each study, p-value was less than 0.05 only for Explo-Flu-001 and was considered as statistically significant (in favour of FluAS03) (see Table 32).

TABLE 32

Inferential statistics: p-values from Wilcoxon rank-sum test between the different groups at Day 21 for antigen-specific CD4 T-lymphocyte responses (Kinetic)

| Cytokine | Study | p-value |
|---|---|---|
| ALL DOUBLE | Explo Flu 001 | 0.0827 |
| | Explo Flu 002 | 0.0992 |
| CD40L | Explo Flu 001 | 0.0931 |
| | Explo Flu 002 | 0.1391 |
| INFγ | Explo Flu 001 | 0.0543 |
| | Explo Flu 002 | 0.1068 |
| IL2 | Explo Flu 001 | 0.0847 |
| | Explo Flu 002 | 0.2254 |
| TNFα | Explo Flu 001 | 0.0375 |
| | Explo Flu 002 | 0.2009 |

P-value: Wilcoxon Test (Non-parametric procedure) to test location difference (Wilcoxon rank-sum test) between the 2 groups at Day 21.

IV.4. HI Titers

Figure 9:
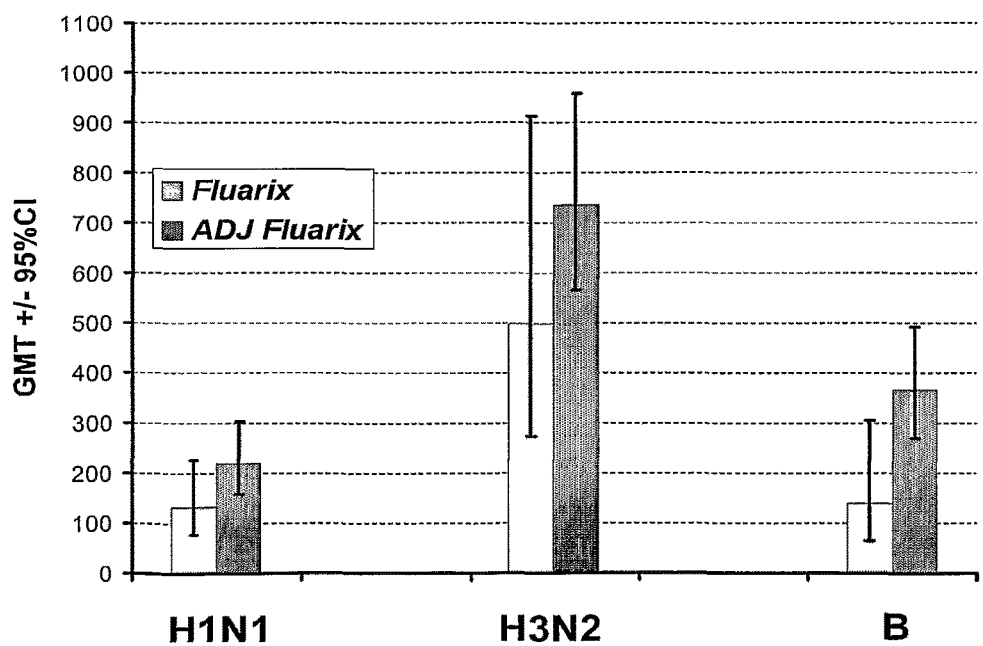
Figure 10A:
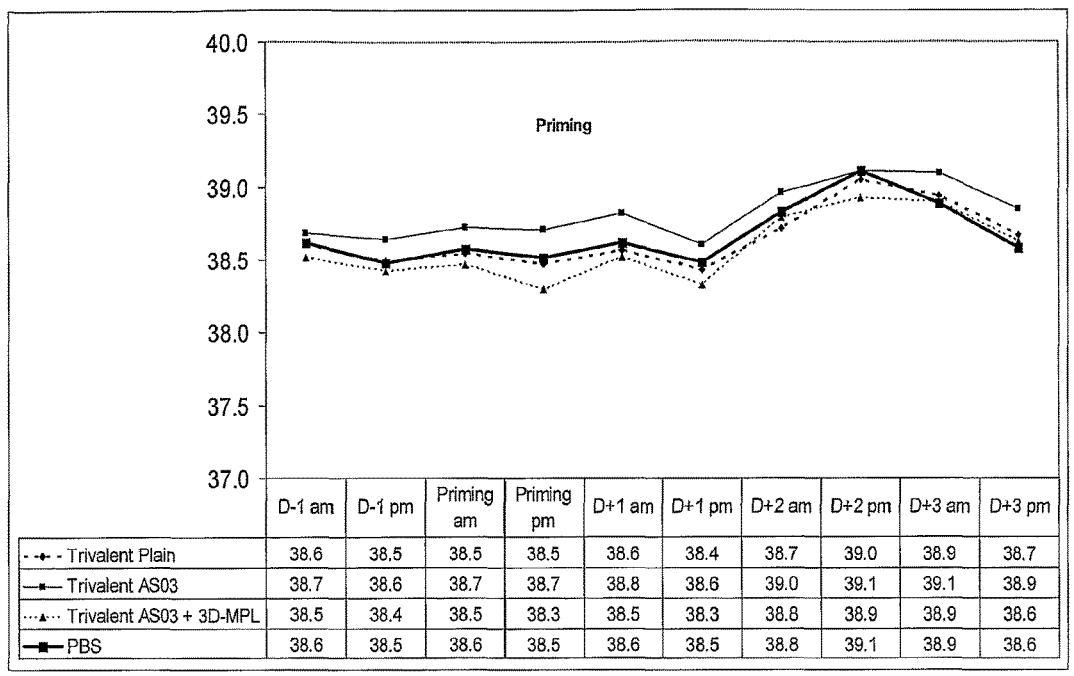
Figure 10B:
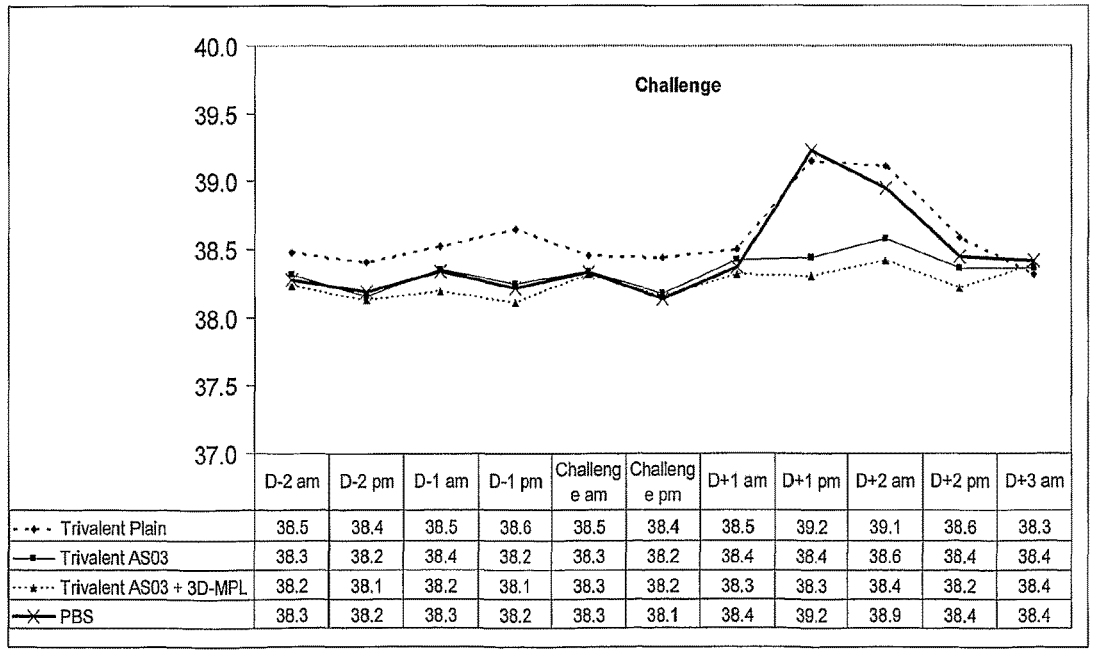
Figure 11:
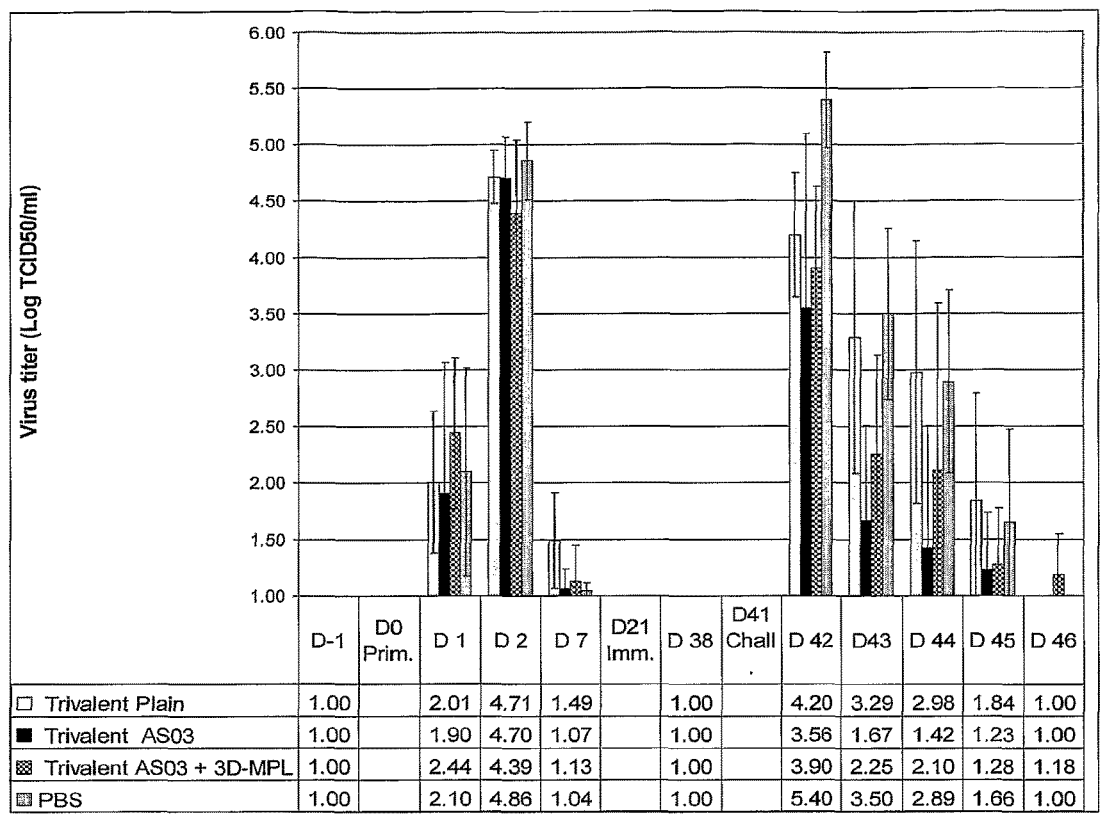
Figure 12A:
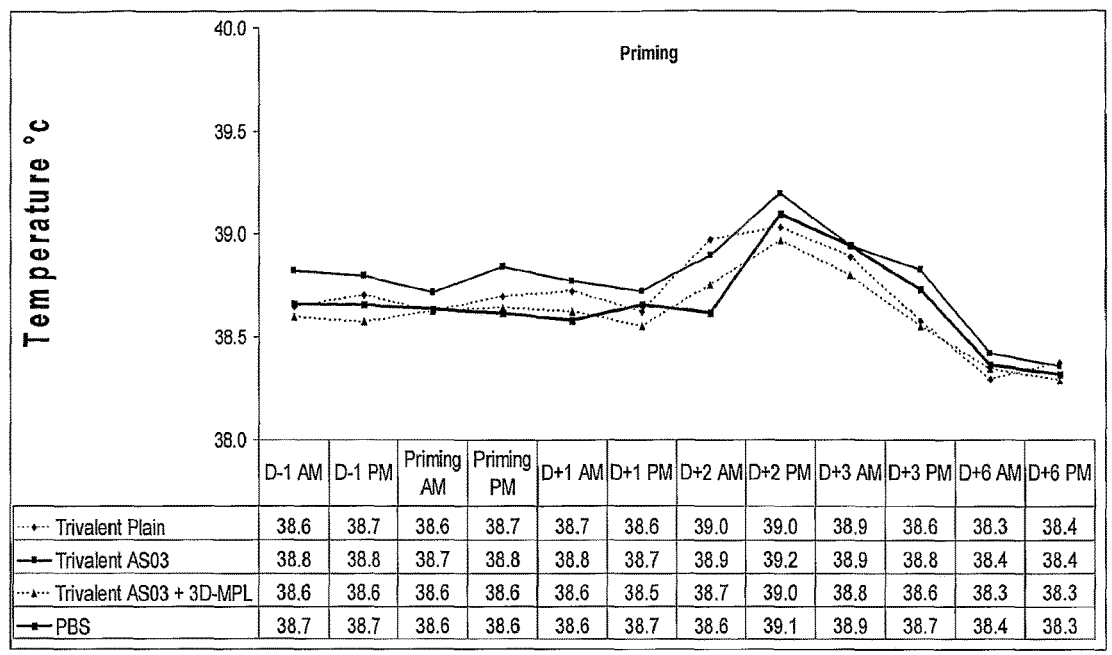
Figure 12B:
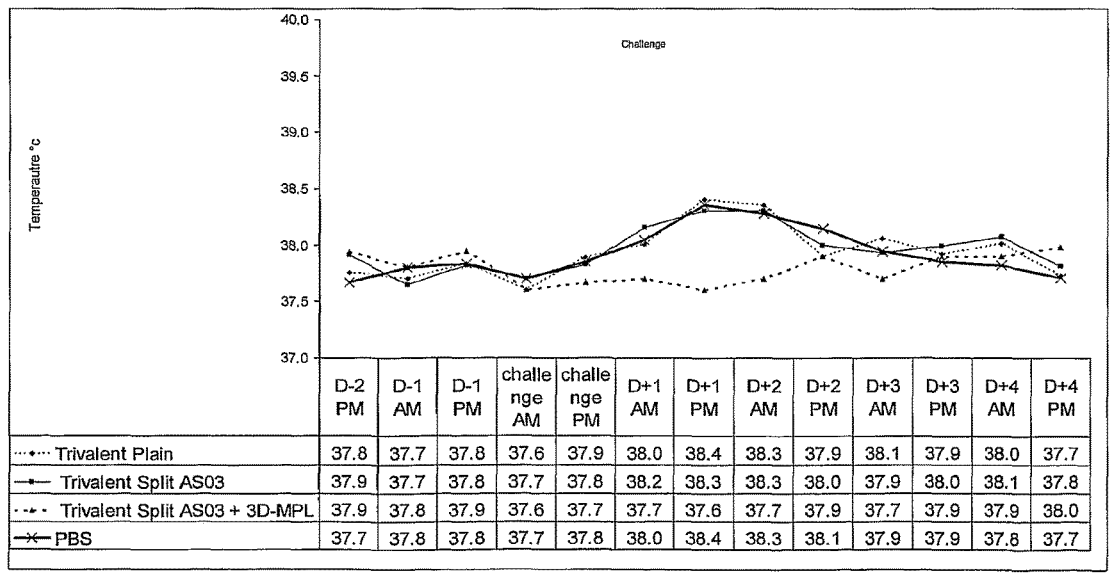

Results are shown in FIG. 9 and in Tables 33 to 36.

TABLE 33

Geometric Mean Titers (GMT) and seropositivity rates of anti-HI titers (GMTs calculated on vaccinated subjects)

| Antibody | Group | Timing | N | S+ | % | 95% CI L.L. | 95% CI U.L. | GMT | 95% CI L.L. | 95% CI U.L. |
|---|---|---|---|---|---|---|---|---|---|---|
| New Caledonia | FLUARIX ® | PRE | 18 | 17 | 94.4 | 72.6 | 99.9 | 63.5 | 38.1 | 105.9 |
| | | PI(D 21) | 18 | 18 | 100 | 81.5 | 100 | 131.9 | 77.1 | 225.6 |
| | FluAS03 | PRE | 40 | 39 | 97.5 | 86.8 | 99.9 | 70.3 | 50.5 | 97.7 |
| | | PI(D 21) | 40 | 40 | 100 | 91.3 | 100 | 218.6 | 158.2 | 302.0 |
| A/Fujian | FLUARIX ® | PRE | 18 | 18 | 100 | 81.5 | 100 | 95.0 | 51.0 | 176.9 |
| | | PI(D 21) | 18 | 18 | 100 | 81.5 | 100 | 498.3 | 272.1 | 912.7 |
| | FluAS03 | PRE | 40 | 40 | 100 | 91.3 | 100 | 94.3 | 71.4 | 124.6 |
| | | PI(D 21) | 40 | 40 | 100 | 91.3 | 100 | 735.1 | 564.4 | 957.5 |
| B/Shanghai | FLUARIX ® | PRE | 18 | 16 | 88.9 | 65.3 | 98.6 | 23.3 | 15.2 | 35.8 |
| | | PI(D 21) | 18 | 17 | 94.4 | 72.6 | 99.9 | 139.8 | 64.0 | 305.0 |
| | FluAS03 | PRE | 40 | 38 | 95.0 | 83.1 | 99.4 | 58.6 | 43.9 | 78.1 |
| | | PI(D 21) | 40 | 40 | 100 | 91.3 | 100 | 364.4 | 269.7 | 492.4 |

PRE = Prevaccination,
PI(D 21) = day 21 post vaccination
95% CI, LL, and UL = 95% confidence interval, lower and upper limit
S+ = number of seropositive subjects

TABLE 34

Conversion factor of anti-HI titers (All vaccinated subjects)

| | A/N-Caledonia | | A/Fujian | | B/Shanghai | |
|---|---|---|---|---|---|---|
| Group | N | GMR [95% CI] | N | GMR [95% CI] | N | GMR [95% CI] |
| FLUARIX ® | 18 | 2.1 [1.4; 3.2] | 18 | 5.2 [3.0; 9.3] | 18 | 6.0 [3.5; 10.2] |
| FluAS03 | 40 | 3.1 [2.4; 4.0] | 40 | 7.8 [5.6; 10.9] | 40 | 6.2 [4.7; 8.2] |

N = total number of subjects
GMR = Geometric Mean Ratio (antilog of the mean log day 21/day 0 titers ratios)
95% CI = 95% confidence interval

TABLE 35

Seroprotection rates of anti-HI titers (All vaccinated subjects)

| | | | | | >=40 | | |
|---|---|---|---|---|---|---|---|
| Antibody | Group | Timing | N | n | % | 95% CI | |
| A/ New Caledonia | FLUARIX ® | PRE | 18 | 14 | 77.8 | 52.4 | 93.6 |
| | | PI(D 21) | 18 | 16 | 88.9 | 65.3 | 98.6 |
| | FluAS03 | PRE | 40 | 32 | 80 | 64.4 | 90.9 |
| | | PI(D 21) | 40 | 39 | 97.5 | 86.8 | 99.9 |
| A/ Fujian | FLUARIX ® | PRE | 18 | 14 | 77.8 | 52.4 | 93.6 |
| | | PI(D 21) | 18 | 18 | 100 | 81.5 | 100 |
| | FluAS03 | PRE | 40 | 36 | 90 | 76.3 | 97.2 |
| | | PI(D 21) | 40 | 40 | 100 | 91.2 | 100 |
| B/ Shanghai | FLUARIX ® | PRE | 18 | 6 | 33.3 | 13.3 | 59.0 |
| | | PI(D 21) | 18 | 14 | 77.8 | 52.4 | 93.6 |
| | FluAS03 | PRE | 40 | 34 | 85 | 70.2 | 94.3 |
| | | PI(D 21) | 40 | 40 | 100 | 91.2 | 100 |

PRE = Prevaccination,
PI(D 21) = day 21 post vaccination
N = number of subjects with available results.
n = number of subjects with titres within the specified range.
% = percentage of subjects with titres within the specified range

TABLE 36

Seroconversion rates at PI day 21(fold-increase = 4) (All vaccinated subjects)

| | | | | Responders | | |
|---|---|---|---|---|---|---|
| | | | | | | 95% CI |
| Antibody | Vaccine Group | N | n | % | LL | UL |
| A/ New Caledonia | FLUARIX ® | 18 | 3 | 16.7 | 3.6 | 41.5 |
| | FluAS03 | 40 | 19 | 47.5 | 31.5 | 63.9 |
| A/ Fujian | FLUARIX ® | 18 | 13 | 72.2 | 46.5 | 90.3 |
| | FluAS03 | 40 | 34 | 85.0 | 70.2 | 94.3 |

TABLE 36-continued

Seroconversion rates at PI day 21(fold-
increase = 4) (All vaccinated subjects)

| Antibody | Vaccine Group | N | Responders n | % | 95% CI LL | 95% CI UL |
|---|---|---|---|---|---|---|
| B/ Shanghai | FLUARIX ® | 18 | 12 | 66.7 | 41.0 | 86.7 |
| | FluAS03 | 40 | 31 | 77.5 | 61.5 | 89.2 |

N = number of subjects with both pre and post vaccination result available.
n = number of responders.
% = Proportion of responders (n/N × 100).
95% CI = exact 95% confidence interval; LL = lower limit, UL = upper limit IV.5. Overall Conclusions From this clinical study it is confirmed that the adjuvanted vaccine Flu-AS03 is superior to the equivalent unadjuvated vaccine FLUARIX® in terms of frequency of influenza specific CD4 T cells, and also in terms of persistence of the immune response elicited by the first Flu-AS03 vaccination (primo-vaccination in Explo Flu 001) until D0 of the revaccination study (Explo Flu 002 i.e. +/−1 year later). Furthermore this response is capable to recognise drifted influenza strains present in the new vaccine and to recognise the strains of the 2004 influenza vaccine.

In contrast to first year vaccination, upon revaccination individuals previously vaccinated with the adjuvanted FLUARIX® showed increased HI titer responsiveness as compared to those vaccinated with un-adjuvanted FLUARIX®. There is an observable trend for 1.5- to 2-fold increase in HI titer directed against H1N1 and H3N2 strains and a demonstrated statistical increase in HI titer directed against B strain.

EXAMPLE V

Pre-Clinical Evaluation of Adjuvanted and Unadjuvanted Influenza Vaccines in Ferrets First Study—Efficacy of New Formulations AS03 and AS03+MPL V.1. Rationale and Objectives Influenza infection in the ferret model closely mimics human influenza, with regards both to the sensitivity to infection and the clinical response.

The ferret is extremely sensitive to infection with both influenza A and B viruses without prior adaptation of viral strains. Therefore, it provides an excellent model system for studies of protection conferred by administered influenza vaccines.

This study investigated the efficacy of various Trivalent Split vaccines, adjuvanted or not, to reduce disease symptoms (body temperature) and viral shedding in nasal secretions of ferrets challenged with homologous strains.

The objective of this experiment was to demonstrate the efficacy of an adjuvanted influenza vaccine compared to the plain (un-adjuvanted) vaccine.

The end-points were:
1) primary end-point: Reduction of viral shedding in nasal washes after homologous challenge:
2) secondary end-points: Analysis of the humoral response by IHA and monitoring of the temperature around the priming and the challenge.

V.2. Experimental Design
V.2.1. Treatment/Group (Table 37)

Female ferrets (*Mustela putorius furo*) (6 ferrets/group) aged 14-20 weeks were obtained from MISAY Consultancy (Hampshire, UK). Ferrets were primed on day 0 with heterosubtypic strain H1N1 A/Stockholm/24/90 (4 Log $TCID_{50}$/ml). On day 21, ferrets were injected intramuscularly with a full human dose (500 µg vaccine dose, 15 µg HA/strain) of a combination of H1N1 A/New Caledonia/20/99, H3N2 A/Panama/2007/99 and B/Shangdong/7/97. Ferrets were then challenged on day 41 by intranasal route with an homotypic strain H3N2 A/Panama/2007/99 (4.51 Log $TCID_{50}$/ml).

TABLE 37

| Group | Antigen(s) + dosage | Formulation + dosage | Comments (schedule/ route/ challenge) | Other treatments |
|---|---|---|---|---|
| 1 | Trivalent Plain | Full HD: 15 µg HA/strain | IM; Day 21 | Priming H1N1 (A/Stockolm/ 24/90) Day 0 |
| 2 | Trivalent AS03 | Full HD: 15 µg HA/strain | IM; Day 21 | Priming H1N1 (A/Stockolm/ 24/90) Day 0 |
| 3 | Trivalent AS03 + MPL | Full HD: 15 µg HA/strain | IM; Day 21 | Priming H1N1 (A/Stockolm/ 24/90) Day 0 |
| 4 | PBS | | IM; Day 21 | Priming H1N1 (A/Stockolm/ 24/90) Day 0 |

V.2.2. Preparation of the Vaccine Formulations
Formulation 1: Trivalent Plain (Un-Adjuvanted) Formulation (500 µl):

PBS 10 fold concentrated (pH 7.4 when one fold concentrated) as well as a mixture containing TWEEN® 80, TRITON X-100™ and VES (quantities taking into account the detergents present in the strains) are added to water for injection. The detergents quantities reached are the following: 750 µg TWEEN® 80, 110 µg TRITON X-100™ and 100 µg VES per 1 ml. After 5 min stirring, 15 µg of each strain H1N1, H3N2 and 17.5 µg of B strain are added in sequence with 10 min stirring between each addition. The formulation is stirred for 15 minutes at room temperature and stored at 4° C. if not administered directly.
Formulation 2: Trivalent Split Influenza Adjuvanted with AS03 (500 µl):

PBS 10 fold concentrated (pH 7.4 when one fold concentrated) as well as a mixture containing TWEEN® 80, TRITON X-100™ and VES (quantities taking into account the detergents present in the strains) is added to water for injection. The detergents quantities reached are the following: 750 µg TWEEN® 80, 110 µg TRITON X-100™ and 100 µg VES per 1 ml. After 5 min stirring, 15 µg of each strain H1N1, H3N2 and 17.5 µg of B strain are added with 10 min stirring between each addition. After 15 min stirring, 250 µl of SB62 emulsion (prepared as in taught in Example II.1) is added. The formulation is stirred for 15 minutes at room temperature and stored at 4° C. if not administered directly.
Formulation 3: Trivalent Split Influenza Adjuvanted with AS03+MPL PBS 10 fold concentrated (pH 7.4 when one fold concentrated) as well as a mixture containing TWEEN® 80, TRITON X-100™ and VES (quantities taking into account the detergents present in the strains) is added to water for injection. The detergents quantities reached are the following: 750 μg TWEEN® 80, 110 μg TRITON X-100™ and 100 μg VES per 1 ml. After 5 min stirring, 15 μg of each strain H1N1, H3N2 and 17.5 μg of B strain are added with 10 min stirring between each addition. After 15 min stirring, 250 μl of SB62 emulsion (prepared as in taught in Example II.1) is added. The mixture is stirred again for 15 min just prior addition of 25 μg of MPL from a suspension prepared as detailed in Example II.3.1. The formulation is stirred for 15 minutes at room temperature and stored at 4° C. if not administered directly.

Remark: In each formulation, PBS 10 fold concentrated is added to reach isotonicity and is 1 fold concentrated in the final volume. H2O volume is calculated to reach the targeted volume.

V.2.3. Read-Outs (Table 38)

TABLE 38

| Readout | Timepoint | Sample-type | I/P | Analysis method |
|---|---|---|---|---|
| Viral shedding | D − 1 to D + 7 Post priming<br>D − 1 to D + 5 Post challenge | Nasal washes | In | Titration |
| T ° monitoring | D − 1 to D + 3 Post priming<br>D − 2 to D + 3 Post challenge | Implant in peritoneal cavity | In | Telemetry |
| IHA | Pre, Post priming, Post imm, Post challenge | Serum | In | IHA |

In = Individual/Po = Pool

V.3. Results

A schematic representation of the results is given in FIG. 10 and FIG. 11.

V.3.1. Temperature Monitoring

Individual temperature were monitored with the transmitters and by the telemetry recording (according to the procedure detailed under I.2.2). All implants were checked and refurbished and a new calibration was performed by DSI before placement in the intraperitoneal cavity. All animals were individually housed in single cage during these measurements.

Temperature were monitored from 3 days Pre-challenge until 5 days Post challenge every 15 minutes and an average has been calculated by mid-day. Results from baseline to baseline body temperature are shown in FIGS. 10A (results from −1 to +3 days are shown) and 10B (results from −2 to +3 days are shown).

Post-challenge, a peak of body temperature only observed after immunization with trivalent split plain or PBS. No peak observed after immunization with trivalent split adjuvanted with AS03 or AS03+MPL.

V.3.2. Viral Shedding (FIG. 11)

Viral titration of nasal washes was performed on 6 animals per group.

The nasal washes were performed by administration of 5 ml of PBS in both nostrils in awake animals. The inoculation was collected in a Petri dish and placed into sample containers at −80° C. (dry ice).

All nasal samples were first sterile filtered through Spin X filters (Costar) to remove any bacterial contamination. 50 μl of serial ten-fold dilutions of nasal washes were transferred to microtiter plates containing 50 μl of medium (10 wells/dilution). 100 μl of MDCK cells ($2.4\times10^5$ cells/ml) were then added to each well and incubated at 35° C. until cell confluence is reached for the control cells, e.g. for 5-7 days. After 6-7 days of incubation, the culture medium is gently removed and 100 μl of a 1/20 WST-1 containing medium is added and incubated for another 18 hrs.

The intensity of the yellow formazan dye produced upon reduction of WST-1 by viable cells is proportional to the number of viable cells present in the well at the end of the viral titration assay and is quantified by measuring the absorbance of each well at the appropriate wavelength (450 nanometers). The cut-off is defined as the OD average of uninfected control cells—0.3 OD (0.3 OD correspond to +/−3 StDev of OD of uninfected control cells). A positive score is defined when OD is <cut-off and in contrast a negative score is defined when OD is >cut-off. Viral shedding titers were determined by "Reed and Muench" and expressed as Log TCID50/ml.

Lower viral shedding was observed Post-challenge with Trivalent Split adjuvanted with AS03 or AS03+MPL compared to Trivalent Split Plain or PBS. The protective effect was slightly better with AS03 compared to AS03+MPL (see Day 2 Post-challenge). Statistical significance could not be determined due to the low number of animals per group.

V.3.3. Conclusion of the Experiment

Higher humoral responses (HI titers) were observed with Trivalent Split adjuvanted with AS03 or AS03+MPL compared to the Trivalent Split Plain for all 3 strains (at least 2-fold for 2 out of 3 strains, i.e. H3N2 and B strains).

AS03 and AS03+MPL formulations showed added benefit in terms of protective efficacy in ferrets (lower viral shedding and temperature) (FIGS. 10 and 11).

Post-challenge, no boost of the humoral response was observed after immunization with Trivalent Split adjuvanted with AS03 or AS03+MPL.

Second Study—Heterotypic Challenge Study in Ferrets: Demonstration of Efficacy of New Formulation Tested V.4. Rationale and Objectives This study investigated the efficacy of various Trivalent Split vaccines, adjuvanted or not, by their ability to reduce disease symptoms (body temperature) and their effects on viral shedding in nasal secretions of immunized ferrets after a heterologuous challenge.

V.5. Experimental Design

Female ferrets (*Mustela putorius furo*) (6 ferrets/group) aged 14-20 weeks were obtained from MISAY Consultancy (Hampshire, UK). Four groups were tested:

FLUARIX® Trivalent Split AS03

Trivalent Split AS03+MPL

PBS

Ferrets were primed on day 0 with heterosubtypic strain H1N1 A/Stockholm/24/90 (4 Log $TCID_{50}$/ml). On day 21, ferrets were injected intramuscularly with a full human dose (500 μg vaccine dose, 15 μg HA/strain) of a combination of H1N1 A/New Caledonia/20/99, H3N2 A/Panama/2007/99 and B/Shangdong/7/97 (17.5 μg HA). Ferrets were then challenged on day 43 by intranasal route with an heterosubtypic strain H3N2 A/Wyoming/3/2003 (4.51 Log $TCID_{50}$/ml).

V.6. Results

A schematic representation of the results is given in FIG. 12 and in FIG. 13.

V.6.1. Temperature Monitoring

Individual temperature were monitored with the transmitters and by the telemetry recording. All implants were checked and refurbished and a new calibration was performed by DSI before placement in the intraperitoneal cavity. All animals were individually housed in single cage during these measurements.

The results (FIG. 12) show that:

A high variability from one group to another was observed around the priming. The baseline seemed to be higher before priming than after priming.

Despite the high variability in the body temperature, a peak was only observed Post-challenge in ferrets immunized with PBS (6/6 ferrets), Trivalent Split Plain (5/6 ferrets) and Trivalent Split adjuvanted with AS03 (2/6 ferrets). No peak was observed after immunization with trivalent split adjuvanted with AS03+MPL (0/6 ferrets).

AS03 seemed to be less efficient than AS03+MPL against heterologous strains in terms of fever prevention. We cannot conclude the possibility that difference between adjuvant is due to different level in pre-challenge antibody levels.

Figure 13:
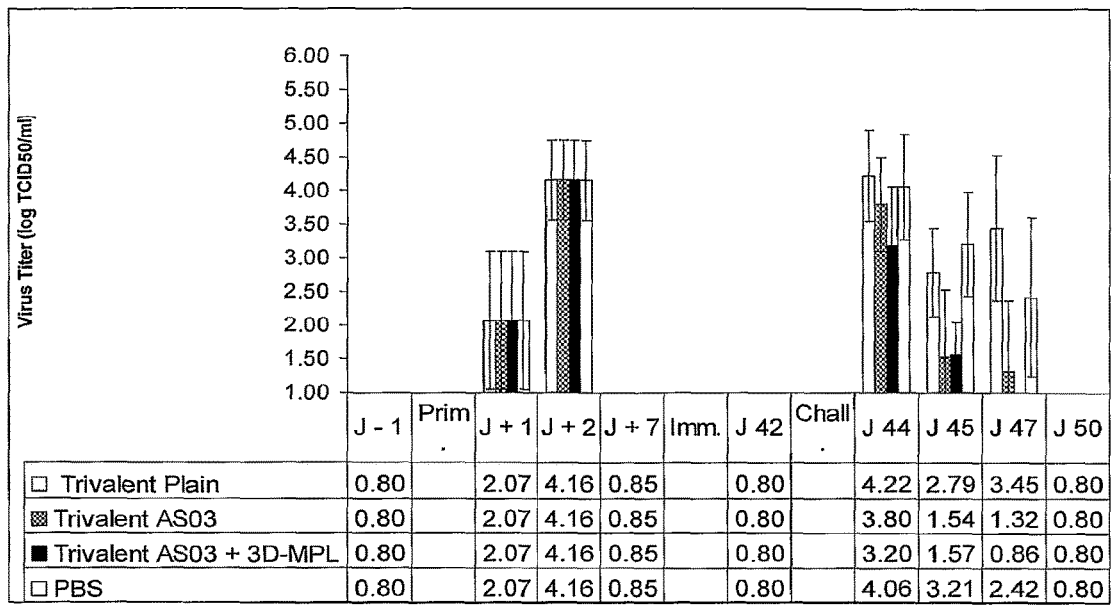

V.6.2. Viral Shedding (FIG. 13)

The nasal washes were performed by administration of 5 ml of PBS in both nostrils in awake animals. The inoculation was collected in a Petri dish and placed into sample containers at −80° C. (dry ice).

All nasal samples were first sterile filtered through Spin X filters (Costar) to remove any bacterial contamination. 50 µl of serial ten-fold dilutions of nasal washes were transferred to microtiter plates containing 50 µl of medium (10 wells/dilution). 100 µl of MDCK cells ($2.4 \times 10^5$ cells/ml) were then added to each well and incubated at 35° C. until cell confluence is reached for the control cells, e.g. for 5-7 days. After 6-7 days of incubation, the culture medium is gently removed and 100 µl of a 1/20 WST-1 containing medium is added and incubated for another 18 hrs.

The intensity of the yellow formazan dye produced upon reduction of WST-1 by viable cells is proportional to the number of viable cells present in the well at the end of the viral titration assay and is quantified by measuring the absorbance of each well at the appropriate wavelength (450 nanometers). The cut-off is defined as the OD average of uninfected control cells—0.3 OD (0.3 OD corresponds to +/−3 St Dev of OD of uninfected control cells). A positive score is defined when OD is <cut-off and in contrast a negative score is defined when OD is >cut-off. Viral shedding titers were determined by "Reed and Muench" and expressed as Log TCID50/ml.

Viral Shedding after Priming

Viral shedding was measured for 12 ferrets from Day 1 Pre-priming to Day 7 Post-priming. Results are expressed in pool.

The viral clearance was observed on Day 7 Post-priming in all ferrets.

Viral Shedding after Challenge

Viral shedding was measured for 6 ferrets/group from Day 1 Pre-challenge to Day 7 Post-challenge.

Two days Post-challenge, statistically significant lower viral titers were observed in ferrets immunized with Trivalent Split adjuvanted with AS03 and AS03+MPL compared to ferrets immunized with Trivalent Split Plain and PBS (difference of 1.25/1.22 log and 1.67/1.64 log with adjuvanted groups AS03/AS03+MPL compared to the Plain vaccine, respectively). On Day 50, no virus was detected in nasal washes.

Figure 14A:
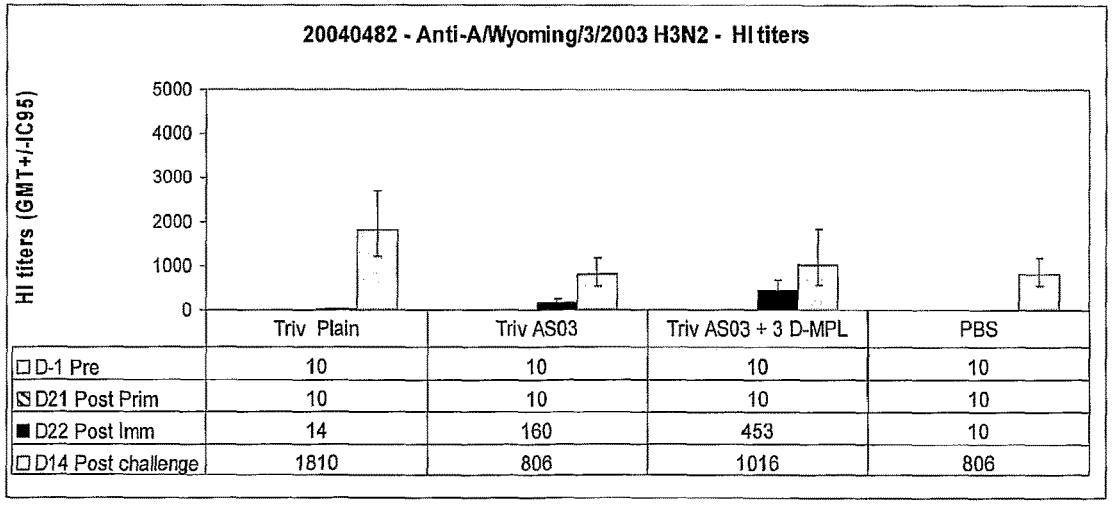

V.6.3. Hemagglutination Inhibition Test (HI Titers) (FIGS. 14A and B)

Serum samples were collected 1 day before priming, 21 days Post-priming, 22 days post-immunization and 14 days post-challenge.

Anti-Hemagglutinin antibody titers to the H3N2 influenza virus (vaccine and challenge strains) were determined using the hemagglutination inhibition test (HI). The principle of the HI test is based on the ability of specific anti-Influenza antibodies to inhibit hemagglutination of chicken red blood cells (RBC) by influenza virus hemagglutinin (HA). Sera were first treated with a 25% neuraminidase solution (RDE) and were heat-inactivated to remove non-specific inhibitors. After pre-treatment, two-fold dilutions of sera were incubated with 4 hemagglutination units of each influenza strain. Chicken red blood cells were then added and the inhibition of agglutination was scored. The titers were expressed as the reciprocal of the highest dilution of serum that completely inhibited hemagglutination. As the first dilution of sera was 1:10, an undetectable level was scored as a titer equal to 5.

Figure 14B:
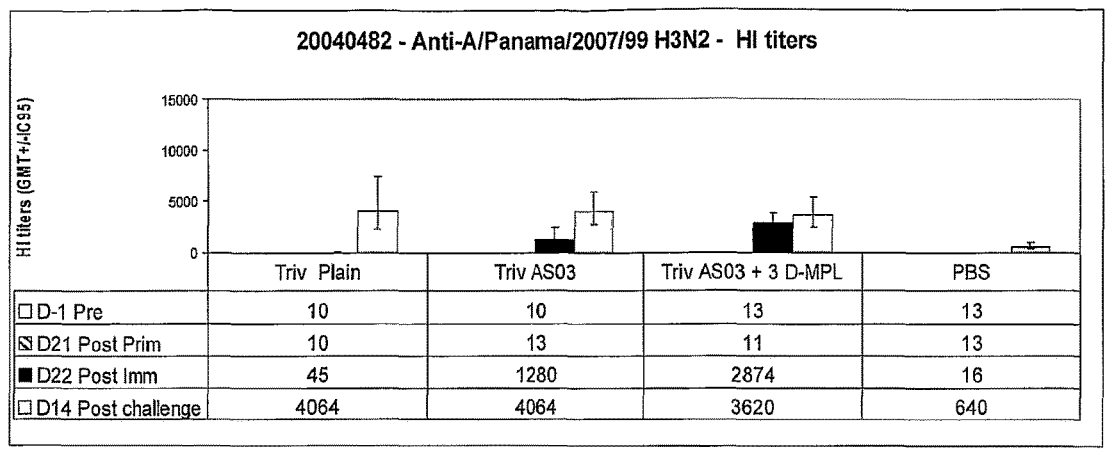

Results:

Results are shown in FIGS. 14A and 14B. After immunization with H3N2 A/Panama, higher humoral responses (HI titers) were observed in ferrets immunized with the trivalent split vaccine adjuvanted with AS03 or AS03+MPL, as compared to the humoral response observed after immunization of ferrets with the un-adjuvanted (plain) trivalent split vaccine FLUARIX®).

Similar HI titers were observed in ferrets immunized with H3N2 A/Panama adjuvanted with AS03 or AS03+MPL.

Cross-reactive HI titers to the heterologous strain A/Wyoming H3N2 was only observed after immunization with A/Panama H3N2 strain containing vaccine adjuvanted with AS03 or AS03+MPL (not observed after immunization with Trivalent Split Plain).

A boost of A/Wyoming-specific HI titers was observed in ferrets immunized with the heterologous strain A/Panama H3N2 and challenged with A/Wyoming H3N2. As expected and contrary to the homologous challenge, the heterologous challenge resulted in an increase of A/Panama-specific HI titers in ferrets immunized with A/Panama H3N2 adjuvanted with AS03 and AS03+MPL.

V.6.4. Conclusion of this Experiment

As expected, a boost of anti-H3N2 HI titers was observed after heterologous challenge compared to the situation after homologous challenge (no boost). However, similar protection (viral shedding) was observed after heterologous and homologous challenge.

EXAMPLE VI

Pre-Clinical Evaluation of Adjuvanted and Unadjuvanted Influenza Vaccines in C57Bl/6 Primed Mice VI.1. Experimental Design and Objective Significant higher CD4 T cell responses were observed, in Explo-Flu-001 clinical study (see Example HI), for Trivalent Flu Split AS03 compared to FLUARIX® Plain (un-adjuvanted). No difference was observed for both CD8 T cell and humoral responses between these two groups.

The purpose was to select readouts to induce in mice similar CMI responses than observed in humans. Particularly, the purpose was to show higher CMI responses in mice by using Split AS03 or split AS03+MPL compared to Split plain.

VI.1.1. Treatment/Group

Female C57Bl/6 mice (15 mice/group) aged 6-8 weeks were obtained from Harlan Horst, Netherland. The groups tested were:

Trivalent Split Plain
Trivalent Split AS03
Trivalent Split AS03+MPL
PBS

Mice were primed on day 0 with heterosubtypic strains (5 µg HA whole inactivated H1N1 A/Johannesburg/82/96, H3N2 A/Sydney/5/97, B/Harbin/7/94). On day 28, mice were injected intramuscularly with 1.5 µg HA Trivalent split (A/New Caledonia/20/99, A/Panama/2007/99, B/Shangdong/7/97) plain or adjuvanted (see groups below).

VI.1.2. Preparation of the Vaccine Formulations

In each formulation, PBS 10 fold concentrated is added to reach isotonicity and is 1 fold concentrated in the final volume. H₂O volume is calculated to reach the targeted volume.

Split Trivalent Plain (Un-Adjuvanted):

Formulation 1 (for 500 µl): PBS 10 fold concentrated (pH 7.4 when one fold concentrated) as well as a mixture containing TWEEN® 80, TRITON X-100™ and VES (quantities taking into account the detergents present in the strains) are added to water for injection. The detergents quantities reached are the following: 750 µg TWEEN® 80, 110 µg TRITON X-100™ and 100 µg VES per 1 ml After 5 min stirring, 15 µg of each strain H1N1, H3N2 and B are added with 10 min stirring between each addition. The formulation is stirred for 15 minutes at room temperature and stored at 4° C. if not administered directly.

Split Trivalent Adjuvanted with the Oil-in-Water Emulsion Adjuvant AS03:

PBS 10 fold concentrated (pH 7.4 when one fold concentrated) as well as a mixture containing TWEEN® 80, TRITON X-100™ and VES (quantities taking into account the detergents present in the strains) is added to water for injection. The detergents quantities reached are the following: 750 µg TWEEN® 80, 110 µg TRITON X-100™ and 100 µg VES per 1 ml. After 5 min stirring, 15 µg of each strain H1N1, H3N2 and B are added with 10 min stirring between each addition. After 15 min stirring, 250 µl of SB62 emulsion (prepared as taught in Example II.1) is added. The formulation is stirred for 15 minutes at room temperature and stored at 4° C. if not administered directly.

Split Trivalent Adjuvanted with AS03+MPL:

PBS 10 fold concentrated (pH 7.4 when one fold concentrated) as well as a mixture containing TWEEN® 80, TRITON X-100™ and VES (quantities taking into account the detergents present in the strains) is added to water for injection. The detergents quantities reached are the following: 750 µg TWEEN® 80, 110 µg TRITON X-100™ and 100 µg VES per 1 ml After 5 min stirring, 15 µg of each strain H1N1, H3N2 and B are added with 10 min stirring between each addition. After 15 min stirring, 250 µl of SB62 emulsion (prepared as taught in Example II.1) is added. The mixture is stirred again for 15 min just prior addition of 25 µg of MPL. The formulation is stirred for 15 minutes at room temperature and stored at 4° C. if not administered directly.

VI.1.3. Read-Outs

CM/Analysis (ICS: CD4/CD8, IL-2/IFNg Staining)

PBMCs from primed mice were harvested 7 days post-immunization. They were tested in pools/group.

VI.2. Results

Figure 15:
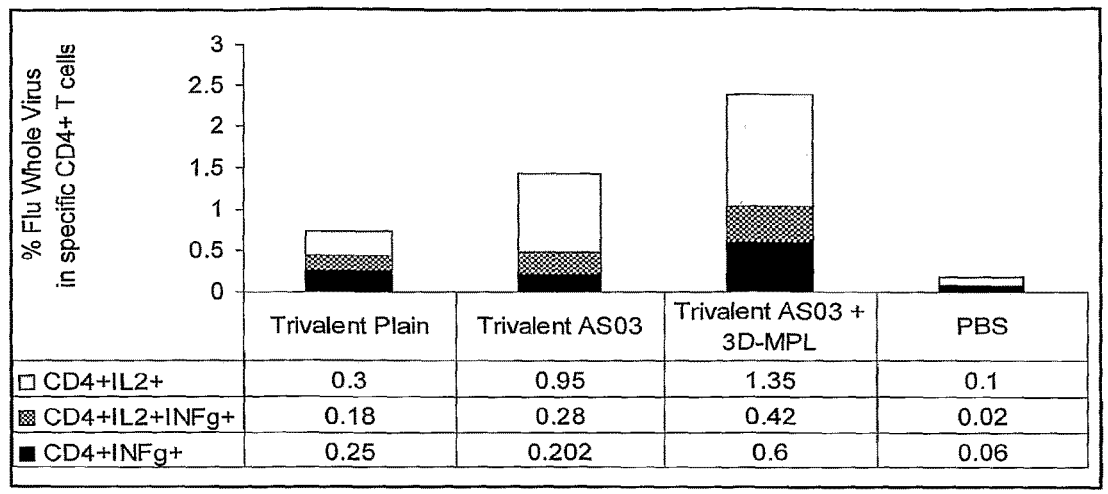
Figure 16:
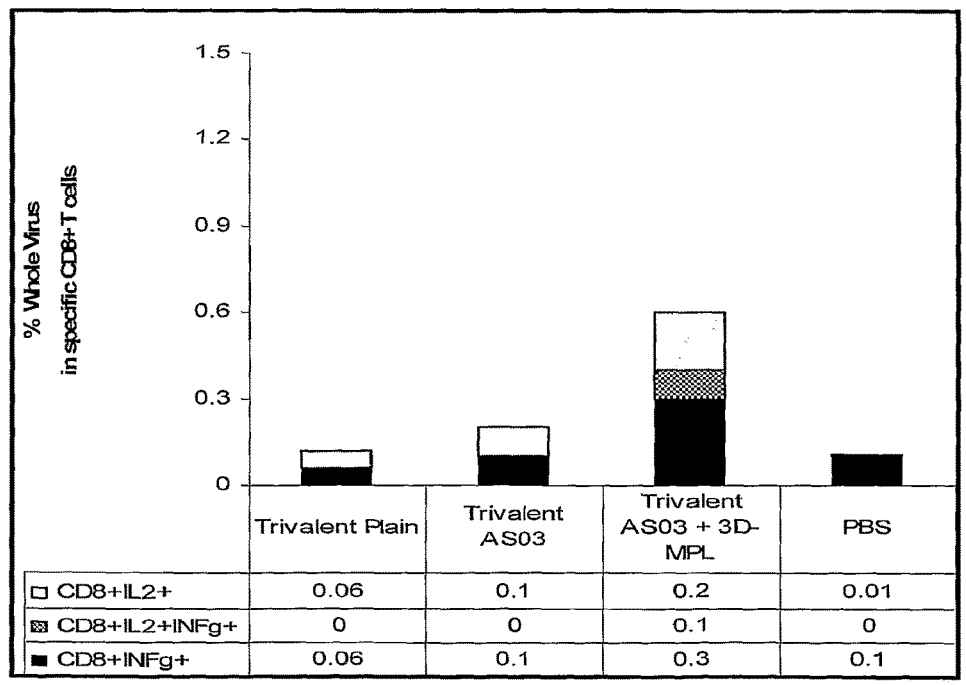

Conditions that showed higher frequencies of CD4 and CD8+ T cells, as well as lower background, were determined by using C57Bl/6 primed mice and whole inactivated virus 1 µg/ml as re-stimulating antigen. Results are shown in FIG. 15 (CD4 T-cell responses) and in FIG. 16 (CD8 T-cell response).

With these conditions, it was possible to induce:
  Higher CD4 T cell responses for Split AS03 compared to Split Plain, as observed in humans.
  Higher CD4 T cell responses for Split AS03+MPL compared to Split Plain.
  Similar CD8 T cell responses between Split Plain and Split AS03, as observed in humans.
  Trend for higher CD8 T cell responses for AS03+MPL compared to Split AS03 or Split Plain

EXAMPLE VII

Pre-Clinical Evaluation of Adjuvanted and Unadjuvanted Split and Sub-Unit Influenza Vaccines in C57Bl/6 Mice Primed with Heterologous Strains VII.1. Experimental Design and Objective Significant higher CD4 T cell responses were observed, in Explo-Flu-001 clinical study (see Example III), for Trivalent Flu Split AS03 compared to FLUARIX® Plain (un-adjuvanted). No difference was observed for both CD8 T cell and humoral responses between these two groups.

An animal model reproducing similar immune profiles than observed in humans was developed by using C57Bl/6 mice primed with heterologous strains. For ICS (intracellular cytokine staining), the re-stimulation is performed with an inactivated whole virus.

The purpose was to compare the CMI response induced by a GlaxoSmithKline commercially available split vaccine (FLUARIX®) versus a subunit vaccine (Chiron's vaccine FLUAD®) as well as the CMI response obtained with these vaccines adjuvanted with AS03, or AS03+MPL or another oil-in-water emulsion adjuvant (OW).

VII.1.1. Treatment/Group

Female C57Bl/6 mice (24 mice/group) aged 6-8 weeks were obtained from Harlan Horst, Netherland. Mice were primed intranasally on day 0 with heterosubtypic strains (5 µg HA whole formaldehyde inactivated H1N1 A/Johannesburg/82/96, H3N2 A/Sydney/5/97, B/Harbin/7/94). On day 29, mice were injected intramuscularly with 1.5 µg HA Trivalent split (A/New Caledonia/20/99, A/Wyoming/3/2003, B/Jiangsu/10/2003) plain or adjuvanted (see groups in Table 39 below).

TABLE 39

| Gr | Antigen/Formulation | Other treatment |
|---|---|---|
| 1 | Trivalent split*/Plain (un-adjuvanted) = FLUARIX ® | Heterologous priming D 0 |
| 2 | Trivalent split*/OW | Heterologous priming D 0 |
| 3 | Trivalent split*/AS03 | Heterologous priming D 0 |
| 4 | Trivalent split*/AS03 + MPL (2.5 µg per dose) | Heterologous priming D 0 |
| 5 | Gripguard (=FLUAD ® = sub-unit in an oil-in-water emulsion | Heterologous priming D 0 |
| 6 | AGGRIPAL ™ (sub-unit)/AS03 | Heterologous priming D 0 |
| 7 | AGGRIPAL ™ (sub-unit)/AS03 + MPL (2.5 µg per dose) | Heterologous priming D 0 |
| 8 | AGGRIPAL ™ (sub-unit)/OW** | Heterologous priming D 0 |
| 9 | AGGRIPAL ™ (sub-unit) | Heterologous priming D 0 |
| 10 | PBS | Heterologous priming D 0 |

*FLUARIX ®
**OW produced as explained in the section below

VII.1.2. Preparation of the Vaccine Formulations
Preparation of OW

An oil-in-water emulsion called OW is prepared following the recipe published in the instruction booklet contained in Chiron Behring FLUAD® vaccine.

Water for injection, 36.67 mg of Citric acid and 627.4 mg of Na Citrate.2H2O are mixed together and the volume is adjusted to 200 ml. 470 mg of TWEEN® 80 is mixed with 94.47 ml of this buffer and this mixture is called "solution A". The oil mixture is prepared by mixing 3.9 g of squalene and 470 mg of SPAN 85™ (sorbitan trioleate) under magnetic stirring. Solution A is then added to the oil mixture and the final volume obtained is 100 ml. The mixture is then first passed trough a 18Gx 1½ needle and is then put in the M110S microfluidiser (from Microfluidics) in two samples to reduce the size of the oil dropplets. When a particle size around 150 nm is obtained for each, the 2 samples are pooled and filtrated on 0.2 μm filter. A z average mean of 143 nm with a polydispersity of 0.10 is obtained for the pooled sample at T0 and of 145 nm with a polydispersity of 0.06 after 4 months storage at 4° C. This size is obtained using the Zetasizer 3000HS (from Malvern), under the following technical conditions:

- laser wavelength: 532 nm (Zeta3000HS).
- laser power: 50 mW (Zeta3000HS).
- scattered light detected at 90° (Zeta3000HS).
- temperature: 25° C.,
- duration: automatic determination by the soft,
- number: 3 consecutive measurements,
- z-average diameter: by cumulants analysis Formulation for Group 1 (for 1 ml):

PBS 10 fold concentrated (pH 7.4 when one fold concentrated) as well as a mixture containing TWEEN® 80, TRITON X-100™ and VES (quantities taking into account the detergents present in the strains) to reach a final concentration of 375 μg/ml TWEEN® 80, 55 μg/ml TRITON X-100™ and 50 μg/ml VES, are added to water for injection. After 5 min stirring, 15 μg of each strain H1N1, H3N2 and B are added with 10 min stirring between each addition. The formulation is stirred for 15 minutes and stored at 4° C. if not administered directly.

Formulation for Group 2 (for 1 ml):

PBS 10 fold concentrated (pH 7.4 when one fold concentrated) as well as a mixture containing TWEEN® 80, TRITON X-100™ and VES (quantities taking into account the detergents present in the strains) to reach a final concentration of 375 μg/ml TWEEN® 80, 55 μg/ml TRITON X-100™ and 50 μg/ml VES, is added to water for injection. After 5 min stirring, 15 μg of each strain H1N1, H3N2 and B are added with 10 min stirring between each addition. After 15 min stirring, 250 μl of OW emulsion is added. The formulation is stirred for 15 minutes and stored at 4° C. if not administered directly.

Formulation for Group 3: For 1 ml:

PBS 10 fold concentrated (pH 7.4 when one fold concentrated) as well as a mixture containing TWEEN® 80, TRITON X-100™ and VES (quantities taking into account the detergents present in the strains) to reach a final concentration of 375 μg/ml TWEEN® 80, 55 μg/ml TRITON X-100™ and 50 μg/ml VES, is added to water for injection. After 5 min stirring, 15 μg of each strain H1N1, H3N2 and B are added with 10 min stirring between each addition. After 15 min stirring, 250 μl of SB62 emulsion is added. The formulation is stirred for 15 minutes and stored at 4° C. if not administered directly.

Formulation for Group 4: For 1 ml:

PBS 10 fold concentrated (pH 7.4 when one fold concentrated) as well as a mixture containing TWEEN® 80, TRITON X-100™ and VES (quantities taking into account the detergents present in the strains) to reach a final concentration of 375 μg/ml TWEEN® 80, 55 μg/ml TRITON X-100™ and 50 μg/ml VES, is added to water for injection. After 5 min stirring, 15 μg of each strain H1N1, H3N2 and B are added with 10 min stirring between each addition. After 15 min stirring, 250 μl of SB62 emulsion is added. The mixture is stirred again for 15 min just prior addition of 25 μg of MPL. The formulation is stirred for 15 minutes and stored at 4° C. if not administered directly.

Formulation for Group 5: For 1 ml:

Equal volume of PBS and FLUAD®/GRIPGUARD™ (commercial vaccine) vaccine are mixed. The formulation is stirred for 15 minutes and stored at 4° C. if not administered directly.

Formulation for Group 6: For 1 ml:

250 μl of PBS mod pH 7.4 are added to a 500 μl dose of AGGRIPAL™ (commercial vaccine). After 15 min stirring, 250 μl of SB62 is added (prepared according to the methodoly detailed for the scaled-up production). The formulation is stirred for 15 minutes and stored at 4° C. if not administered directly.

Formulation for Group 7: For 1 ml:

PBS mod pH 7.4 (to reach a final volume of 1 ml) is added to a 500 μl dose of AGGRIPAL™ (commercial vaccine). After 15 min stirring, 250 μl of SB62 is added (prepared according to the methodoly detailed for the scaled-up production). 25 μg of MPL are then added. The formulation is stirred for 15 minutes and stored at 4° C. if not administered directly.

Formulation for Group 8: For 1 ml:

250 μl of PBS mod pH 7.4 are added to a 500 μl dose of AGGRIPAL™. After 15 min stirring, 250 μl of OW as prepared for group 2 is added and the formulation is stirred 15 min and stored at 4° C. if not administered directly.

Formulation for Group 9: For 1 ml:

Equal volume of PBS mod pH 7.4 and AGGRIPAL™ are mixed. The formulation is stirred for 15 minutes and stored at 4° C. if not administered directly.

VII.1.3. Read-Outs (Table 40)

CMI (ICS): 7 Days Post-immunization.

IHA/neutralization assay: 21 Days Post-immunization.

TABLE 40

| Read-out | Timepoint | Sample type | I/P | Analysis method |
|---|---|---|---|---|
| ICS (CD4, CD8, IL-2, IFN-γ) | D 35 | PBLs | Po | FACS analysis |
| Humoral response | D 14, D 44 | Sera | In | IHA, neutra |

In = Individual/Po = Pool
CMI analysis (ICS: CD4/CD8; IL-2/IFN-gamma staining)
PBMCs from 24 mice/group were harvested 7 days post-immunization and tested in pools/group.

VII.2. Results

VII.2.1. Humoral Immunity

Haemagglutination inhibition activity against the 3 vaccine strains was detected in sera from 24 animals per group at Day 14 after intranasal heterologous priming and at Day 16 Post-immunization.

For the 3 strains and for all groups, a boost of HI titers was observed after immunization.

- For a same adjuvant and for the 3 strains, similar HI titers were induced by the subunit vaccine and the Split vaccine.
- Similar HI titers were observed for FLUAD® compared to AGGRIPAL™ OW for the 3 strains
- No difference was observed between FLUARIX® and AGGRIPAL™ for H1N1 and B strains.
- For the 3 strains, statistically significant higher HI titers were observed when the Flu vaccine (Split or subunit) was adjuvanted with AS03 with or without MPL compared to the plain Flu vaccine.
- HI titers were statistically significant higher for the Flu vaccine (Split or subunit) adjuvanted with OW compared to the Flu vaccine plain only for the A/Wyoming strain.

VII.2.2. Cell-Mediated Immune Response (ICS at Day 7 Post Immunization)

Figure 17A:
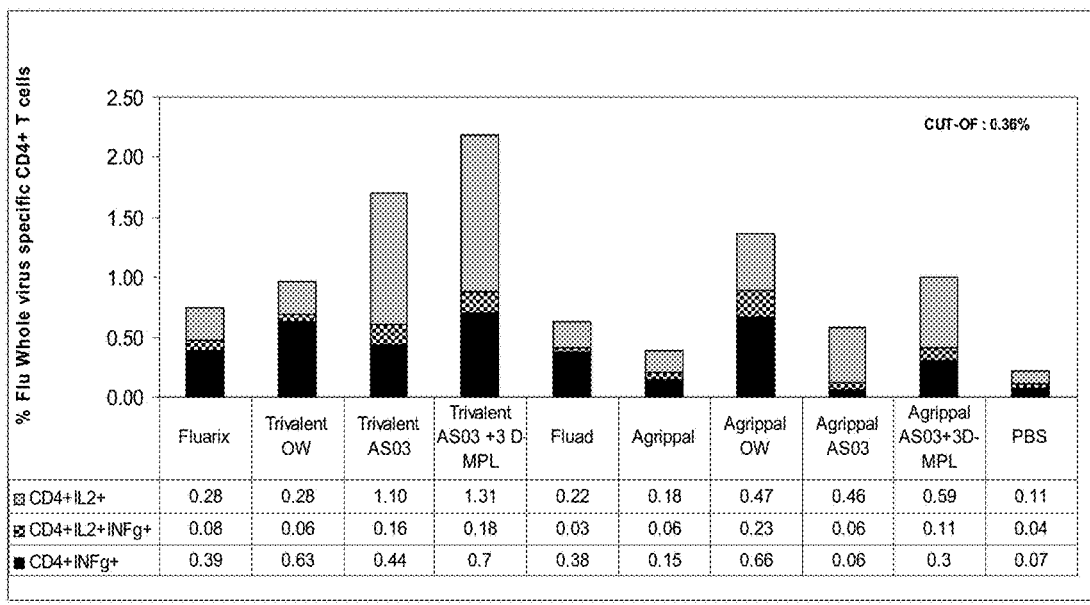
Figure 17B:
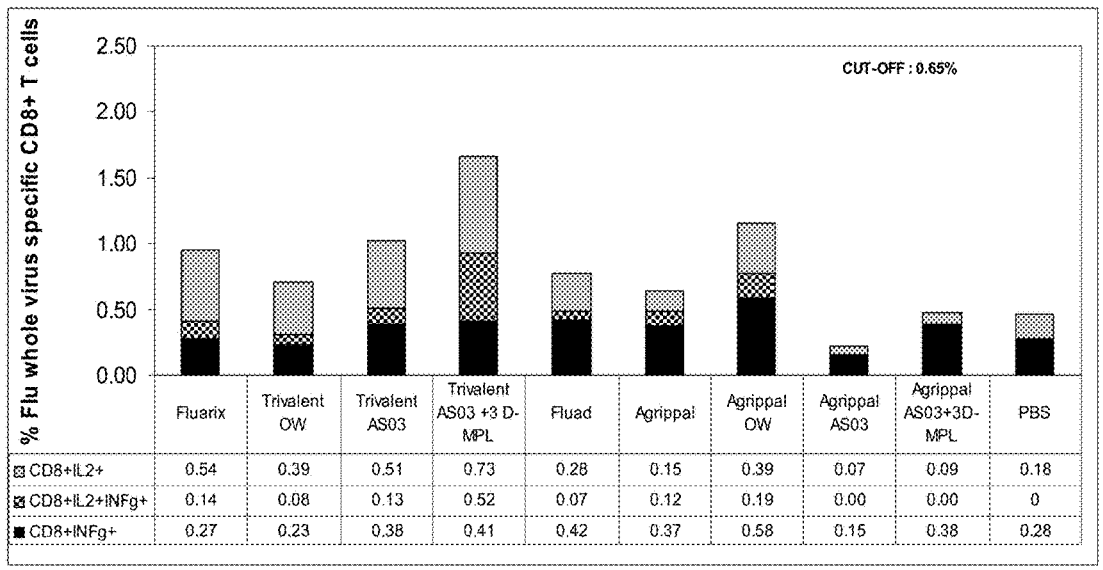

CD4 T Cell Responses—FIG. 17 Upper Part

PBMCs from 24 mice per group were harvested at Day 7 Post-immunization and tested in one pool/group. Inactivated trivalent whole viruses (1 μg/ml) were used as re-stimulating antigen. Results are shown in FIG. 17 upper part.

In terms of Flu whole virus-specific CD4+ T cells expressing IL-2, IFN-γ or both cytokines (FIG. 17 upper part):
1. GSK adjuvants showed the same trend as previously observed (Example VI): AS03+MPL was superior to AS03 which was in turn superior to the result obtained with the plain vaccine. This trend was observed both for the split or the subunit vaccine.
2. Whatever the formulation (Plain, AS03 or AS03+MPL), the split vaccine induced a higher CD4+ T cell responses than the subunit vaccine.
3. FLUAD® (subunit+oil-in-water emulsion OW—see preparation section) seemed to induce similar frequencies than Fluarix Plain.
4. Formulations Trivalent Split/AS03 or Trivalent Split/AS03+MPL induced higher CD4+ T cell responses than the formulation subunit/oil-in-water emulsion OW.

CD8 T Cell Responses—FIG. 17 Lower Part

PBMCs from 24 mice per group were harvested at Day 7 Post-immunization and tested in one pool/group. Inactivated trivalent whole viruses (1 μg/ml) were used as re-stimulating antigen.

In terms of Flu whole virus-specific CD8+ T cells expressing IL-2, IFN-γ or both cytokines (FIG. 17 lower part):
The cut-off of this experiment was relatively high due to the high background observed for the PBS negative control group.
However higher specific CD8 T cell responses were observed for mice immunized with Trivalent Split/AS03+MPL compared to other vaccine formulations.

VII.3. Summary of Results and Conclusions

The following results were obtained:
1) Flu-specific CD4+ T cells obtained by ICS at Day 7 post—immunization showed:
1. Similar responses were obtained for FLUAD® compared to FLUARIX®
2. The adjuvanted formulation induced higher immune response compared to the un-adjuvanted vaccine, both for the split influenza vaccine (as observed in humans) and for the subunit (AGGRIPAL™) vaccine (not assessed in humans). The oil-in-water emulsion adjuvant AS03 supplemented with MPL (groups 4 and 9) gave higher responses than the oil-in-water emulsion adjuvant AS03 (groups 3 and 8).
3. There is a trend of a higher CD4 responses with Split/AS03+MPL compared to Split/AS03 (FIG. 17).
4. The responses induced by the split vaccine were superior to the responses obtained with the subunit vaccine (compare groups 1 to 4 and groups 5 to 9).
5. The split vaccine, whether adjuvanted with AS03 with or without MPL (groups 3 and 4) performed showed higher CD4+ T cell responses than the sub-unit vaccine, either FLUAD® (group 5) or AGGRIPAL™+OW (group 7).

2) Flu-specific CD8+ T cells obtained by ICS at Day 7 post—immunization showed no differences are observed between Split/AS3 and Split Plain (as observed in humans). There was a trend for a higher CD8+ T cell response by using Split/AS03+MPL compared to Split/AS03 or Split Plain.

3) For a same adjuvant and for the 3 strains, similar HI titers were induced by the subunit vaccine and the split vaccine. For the 3 strains, statistically significant higher titers were observed when the Flu vaccine (subunit or split) was adjuvanted with AS03 or AS03+MPL compared to the Flu vaccine plain (Flu vaccine OW>Flu vaccine Plain only for the A/Wyoming strain).

EXAMPLE VIII

Clinical Trial in an Elderly Population Aged Over 65 Years with a Vaccine Containing a Split Influenza Antigen Preparation and AS03 with or without MPL Adjuvant VIII.1. Study Design A phase I, open, randomised, controlled study in an elderly population aged over 65 years 65 years-old) in order to evaluate the reactogenicity and the immunogenicity of GlaxoSmithKline Biologicals influenza candidate vaccines containing the adjuvant AS03 or AS03+MPL, administered intramuscularly as compared to FLUARIX® vaccine (known as a-RIX® in Belgium).

Three parallel groups were assessed:
one group of 50 subjects receiving one dose of the reconstituted and AS03 adjuvanted SV influenza vaccine (Flu AS03)
one group of 50 subjects receiving one dose of the reconstituted and Flu AS03+MPL adjuvanted SV influenza vaccine (Flu AS03+MPL)
one control group of 50 subjects receiving one dose of FLUARIX®

VIII.2. Vaccine Composition and Administration

The strains used in the three vaccines were the ones that had been recommended by the WHO for the 2004-2005 Northern Hemisphere season, i.e. A/New Caledonia /20/99 (H1N1), A/New California/3/2003 (H3N2) and B/Jiangsu/10/2003. Like FLUARIX®/α-RIX®, the commercially available vaccine used as a comparator, the adjuvanted vaccines (AS03, or AS03+MPL) contain 15 μg haemagglutinin (HA) of each influenza virus strain per dose.

The adjuvanted influenza candidate vaccines are 2 component vaccines consisting of a concentrated trivalent inactivated split virion antigens presented in a type I glass vial and of a pre-filled type I glass syringe containing the adjuvant (AS03 or AS03+MPL). They have been prepared as detailed in Example II. The three inactivated split virion antigens (monovalent bulks) used in formulation of the adjuvanted influenza candidate vaccines, are exactly the same as the active ingredients used in formulation of the commercial FLUARIX®/α-RIX®.

AS03 Adjuvanted Vaccine:

The AS03-adjuvanted influenza candidate vaccine is a 2 components vaccine consisting of a concentrated trivalent inactivated split virion antigens presented in a type I glass vial (335 μl) (antigen container) and of a pre-filled type I glass syringe containing the SB62 emulsion (335 μl) (adjuvant container). Description and composition of the AS03 candidate vaccine is explained in Example III.

AS03+MPL Adjuvanted Vaccine:

Briefly, the AS03+MPL-adjuvanted influenza candidate vaccine is a 2 components vaccine consisting of a concentrated trivalent inactivated split virion antigens presented in a type I glass vial (335 μl) (antigen container) and of a pre-filled type I glass syringe containing the AS03+MPL adjuvant (360 μl) (adjuvant container). At the time of injection, the content of the antigen container is removed from the vial by using the syringe containing the AS03+MPL adjuvant, followed by gently mixing of the syringe. Prior to injection, the used needle is replaced by an intramuscular needle and the volume is corrected to 530 μl. One dose of the reconstituted the AS03+MPL-adjuvanted influenza candidate vaccine corresponds to 530 μl. To obtain the 15 μg HA for each influenza strain at reconstitution of the AS03+MPL adjuvanted vaccine, the inactivated split virion antigen are concentrated two-fold in the antigen container (i.e. 60 μg HA/ml) as compared to FLUARIX® (i.e. 30 μg HA/ml).

The composition of one dose of the reconstituted adjuvanted influenza vaccine is identical to that reported in Table 45 (see Example XI) except for the influenza strains. Both vaccines were given intramuscularly.

VIII.3. CMI Objective, End-Points and Results

The CMI objectives were to determine which immunogenic composition between the formulation adjuvanted with AS03, or AS03+MPL versus the composition without any adjuvant has the strongest immunostimulating activity on CD4- and CD8-mediated immunity of individuals vaccinated with influenza antigens.

VIII.3.1. CMI End Points and Results

Observed Variable

At days 0 and 21: frequency of cytokine-positive CD4/CD8 cells per $10^6$ into 5 different cytokines. Each test quantifies the response of CD4/CD8 T cell to:
Pool of the 3 following antigens
New Caledonia antigen
Wyoming antigen
Jiangsu antigen.

Derived Variables:
Antigen-specific CD4 and CD8-T-cell response expressed into the 5 different tests:
(a) cells producing at least two different cytokines (CD40L, IL-2, IFNγ, TNFα)
(b) cells producing at least CD40L and another cytokine (IL-2, TNFα, IFNγ)
(c) cells producing at least IL-2 and another cytokine (CD40L, TNFα, IFNγ)
(d) cells producing at least IFNγ and another cytokine (IL-2, TNFα, CD40L)
(e) cells producing at least TNFα and another cytokine (IL-2, CD40L, IFNγ)

Analysis of the CMI Response:

The CMI analysis was based on the Total vaccinated cohort.
(a) For each treatment group, the frequency of CD4/CD8 T-lymphocytes secreting in response was determined for each vaccination group, at each timepoint (Day 0, Day 21) and for each antigen: New Caledonia, Wyoming and Jiangsu and the pooled of the 3 different strains.
(b) Descriptive statistics in individual difference between timepoint (POST-PRE) responses for each vaccination group and each antigen at each 5 different cytokines.
(c) Comparison of the 3 groups regarding the 5 different cytokines on:
CD4 T-cell response to New Caledonia, Wyoming, Jiangsu and the pool of the 3 strains
CD8 T-cell response to New Caledonia, Wyoming, Jiangsu and the pool of the 3 strains
(d) A non-parametric test (Kruskall-Wallis test) was used to compare the location differences between the 3 groups and the statistical p-value was calculated for each antigen at each 5 different cytokines.
(e) A Wilcoxon test were use to test pairwise comparison of 2 groups respectively between Flu AS03+MPL versus FLUARIX®, Flu AS03+MPL versus Flu AS03 and Flu AS03 versus FLUARIX®

(f) All significance tests were two-tailed. P-values less than or equal to 0.05 were considered as statistically significant.

VIII.3.2. CMI Results

Results were expressed as a frequency of cytokine(s)-positive CD4 or CD8 T cell within the CD4 or CD8 T cell sub-population.

Frequency of Antigen Specific CD4 T-Lymphocytes (a) The frequency of antigen-specific CD4 T-lymphocytes secreting in response was determined for each vaccination group, at each time point (Day 0, Day 21) and for each antigen (Pool, New Caledonia, Wyoming and Jiangsu), similarly to that performed in Example III.
(b) Comparing the difference in the frequency of antigen-specific CD4 T-lymphocytes between the 3 groups by Kruskall-Wallis test, all p-values were less than 0.05 and were considered as statistically significant.
(c) Comparing the difference in the frequency of antigen-specific CD4 T-lymphocytes between Flu AS03+MPL and FLUARIX® groups by the Wilcoxon test, all p-values were less than 0.05 and were considered as statistically significant.
(d) Comparing the difference in the frequency antigen-specific of CD4 T-lymphocytes between Flu AS03 and FLUARIX® groups by the Wilcoxon test, all p-values were less than 0.05 and were considered as statistically significant.
(e) Comparing the difference in the frequency of antigen-specific CD4 T-lymphocytes between Flu AS03 and Flu AS03+MPL groups by the Wilcoxon test, all p-values were more than 0.05 and were considered as no statistically significant.

Individual Difference Between Time Point (Post-Pre) in CD4 T-Lymphocytes (a) Descriptive statistics in individual difference between time point (POST-PRE) in CD4 T-lymphocytes responses was calculated for each vaccination group and for each antigen at each 5 different cytokines, similarly to what has been done in Example III.
(b) Comparing the individual difference POST-PRE in the antigen-specific CD4-T-lymphocytes responses between the 3 groups by Kruskall-Wallis test, all p-values were less than to 0.001 and were considered as highly statistically significant.
(c) Comparing the individual difference POST-PRE in the antigen-specific CD4-T-lymphocytes responses between Flu AS03+MPL and FLUARIX® using Wilcoxon test, all p-values were less than to 0.05 and were considered as statistically significant.
(d) Comparing the individual difference POST-PRE in the antigen-specific CD4-T-lymphocytes responses between Flu AS03 and FLUARIX® using Wilcoxon test, all p-values were less than to 0.001 and were considered as highly statistically significant.
(e) Comparing the individual difference POST-PRE in the antigen-specific CD4-T-lymphocytes responses between Flu AS03+MPL and Flu AS03 using Wilcoxon test, all p-values were more than 0.05 and were considered as no statistically significant.

VIII.4. B Cell Memory Response Objective, End-Points and Results

The objective of the study was to investigate whether the frequency of memory B cell specific to Flu Antigen are significantly induced upon one intramuscular vaccination with the Flu candidate vaccine containing the Adjuvant AS03+MPL or AS03, as compared to FLUARIX® in elderly population. The frequency of memory B cell has been assessed by B cell Elispot assay.

VIII.4.1. B Cell Memory Response End-Points

The end points are:

(a) At days 0, 21: cells generated in vitro cultivated memory B-cells measured by B-cell ELISPOST in all subjects in term of frequency of specific-antigen plasma within a million ($10^6$) of IgG producing plasma cells.

(b) Difference between post (day 21) and pre (day 0) vaccination are also expressed as a frequency of Influenza specific-antibody forming cells per million ($10^6$) of antibody forming cells.

VIII.4.2. B Cell Memory Response Results

The frequency of Influenza-specific antibody forming cells per million ($10^6$) of antibody forming cells were determined. The results showed that the frequency of memory B cell specific to Flu antigen between Flu AS03+MPL and FLUARIX® groups by the Wilcoxon test was significantly ($p<0.05$) higher for B/Jiangsu strain, whilst not for the other two strains (A strains New Caledonia and Wyoming).

The individual difference between time point (post-pre) in memory B cell specific to Flu antigen was also determined. The results showed that individual difference between time point (post-pre) in the frequency of memory B cell specific to Flu antigen between Flu AS03+MPL and FLUARIX® groups by the by the Kruskall-Wallis test was significantly ($p<0.05$) higher for B/Jiangsu strain, whilst not for the other two strains (A strains New Caledonia and Wyoming).

Figure 18:
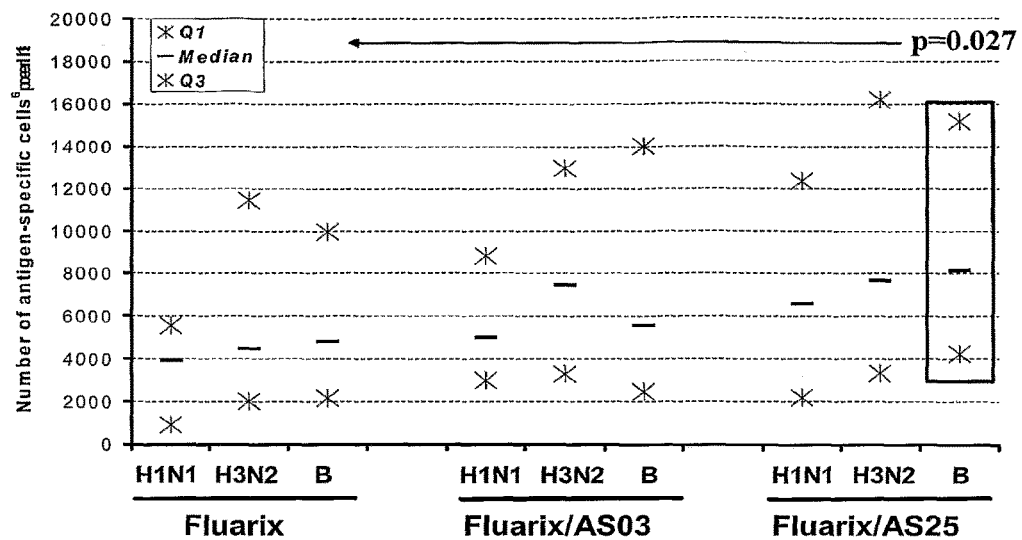

The results are shown in FIG. 18.

EXAMPLE IX

Pre-Clinical Evaluation of Adjuvanted and Unadjuvanted Influenza Vaccines in Ferrets (Study III)

IX.1. Rationale and Objectives

This study compared GSK commercial influenza trivalent split vaccine, either un-adjuvanted (FLUARIX®) or adjuvanted with AS03+MPL, with two other commercially available sub-unit vaccines:

FLUAD®, Chiron's adjuvanted subunit vaccine (the adjuvant is Chiron's MF59 adjuvant), AGRIPPAL™, Chiron un-adjuvanted commercial sub-unit vaccine, which was in the present study adjuvanted with AS03 adjuvant.

The objective of this experiment was to evaluate the ability of these vaccines to reduce disease symptoms (body temperature and viral shedding) in nasal secretions of ferrets challenged with heterologous strains.

The end-points were:

1) Primary end-point: reduction of viral shedding in nasal washes after heterologous challenge:

2) Secondary end-points: analysis of the humoral response by IHA and monitoring of the temperature around the priming and the heterologous challenge.

IX.2. Experimental Design

IX.2.1. Treatment/Group

Female ferrets (*Mustela putorius furo*) aged 14-20 weeks were obtained from MISAY Consultancy (Hampshire, UK). Ferrets were primed intranasally on day 0 with the hetero-subtypic strain H1N1 A/Stockholm/24/90 (4 Log $TCID_{50}$/ml). On day 21, ferrets were injected intramuscularly with a full human dose (1 ml vaccine dose, 15 µg HA/strain) of a combination of H1N1 A/New Caledonia /20/99, H3N2 A/Wyoming/3/2003 and B/Jiangsu/10/2003. Ferrets were then challenged on day 42 by intranasal route with a heterotypic strain H3N2 A/Panama/2007/99 (4.51 Log $TCID_{50}$/ml). The groups (6 ferrets/group) are illustrated in Table 41. The read-out that were performed are detailed in Table 42.

TABLE 41

| Group | Antigen(s) + dosage | Formulation + dosage | Comments (ex: schedule/ route/ challenge) | Other treatments |
|---|---|---|---|---|
| 1 | Trivalent Plain FLUARIX ® | Full HD: 15 µg HA/strain | IM; Day 21 | Priming H1N1 (A/Stockolm/ 24/90) Day 0 |
| 2 | Trivalent AS03 + MPL | Full HD: 15 µg HA/strain | IM; Day 21 | Priming H1N1 (A/Stockolm/ 24/90) Day 0 |
| 3 | FLUAD ® | Full HD: 15 µg HA/strain | IM; Day 21 | Priming H1N1 (A/Stockolm/ 24/90) Day 0 |
| 4 | AGRIPPAL ™ AS03 | Full HD: 15 µg HA/strain | IM; Day 21 | Priming H1N1 (A/Stockolm/ 24/90) Day 0 |

IX.2.2. Preparation of the Vaccine Formulations

Split Trivalent Plain (Un-Adjuvanted): Formulation for 9 ml:

PBS 10 fold concentrated (pH 7.4 when one fold concentrated) as well as a mixture containing TWEEN® 80, TRITON X-100™ and VES (quantities taking into account the detergents present in the strains) are added to water for injection. The detergents quantities reached are the following: 375 µg TWEEN® 80, 55 µg TRITON X-100™ and 50 µg VES per 1 ml. After 5 min stirring, 15 µg of each strain H1N1, H3N2 and 17.5 µg of B strain are added with 10 min stirring between each addition. The formulation is stirred for 15 minutes at room temperature and stored at 4° C. if not administered directly.

Split Trivalent Adjuvanted with AS03+MPL: Formulation for 1 ml:

PBS 10 fold concentrated (pH 7.4 when one fold concentrated) as well as a mixture containing TWEEN® 80, TRITON X-100™ and VES (quantities taking into account the detergents present in the strains) is added to water for injection. The detergents quantities reached are the following: 375 µg TWEEN® 80, 55 µg TRITON X-100™ and 50 µg VES per 1 ml. After 5 min stirring, 15 µg of each strain H1N1, H3N2 and B are added with 10 min stirring between each addition. After 15 min stirring, 250 µl of SB62 emulsion (prepared as detailed in Example II.1) is added. The mixture is stirred again for 15 minutes just prior addition of 25 µg of MPL. The formulation is stirred for 15 minutes at room temperature and stored at 4° C. if not administered directly.

FLUAD® Formulation: Formulation for 1 ml:

A 2 fold dilution of FLUAD® vaccine is made in PBS buffer pH 7.4.

Agrippal™ AS03 Formulation: Formulation for 1 ml:

250 µl of PBS buffer pH 7.4 is added to one dose of AGRIPAL™. After mixing, 250 µl of SB62 emulsion (prepared as detailed in Example II.1) is added. The mixture is stirred at room temperature.

IX.2.2. Read-Outs

TABLE 42

| Readout | Timepoint | Sample-type | I/Po | Analysis method |
|---|---|---|---|---|
| Viral shedding | D − 3 to D + 7 Post priming<br>D + 1 to D + 5 Post challenge | Nasal washes | In | Titration |
| T° monitoring | D − 3 to D + 4 Post priming<br>D − 2 to D + 4 Post challenge | Implant in peritoneal cavity | In | Telemetry |
| IHA | Pre, Post priming, Post imm, Post challenge | Serum | In | IHA |

In = Individual/Po = Pool

IX.3. Results (FIGS. 19 to 22)

IX.3.1. Temperature Monitoring

Figure 19:
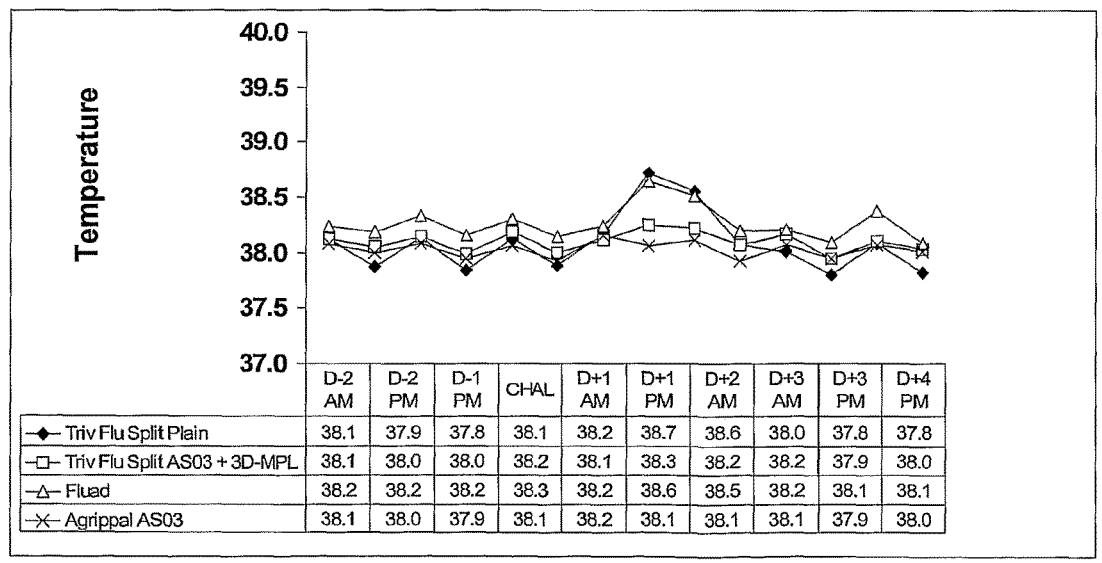

Individual temperatures were monitored with the transmitters and by the telemetry recording. All implants were checked and refurbished and a new calibration was performed by DSI before placement in the intraperitoneal cavity. All animals were individually housed in single cage during these measurements. Temperature was monitored from 2 days Pre-challenge until 4 days Post challenge every 15 minutes and an average temperature calculated by midday. Results are shown in FIG. 19.

Results:

Post-challenge, a peak of body temperature was observed after immunization of ferrets with the un-adjuvanted (plain) trivalent split (FLUARIX®) or the sub-unit vaccine FLUAD® (which contains MF59 oil-in-water emulsion). No peak was observed after immunization of ferrets with the trivalent split vaccine adjuvanted neither with AS03+MPL nor with sub-unit Agrippal™ adjuvanted with AS03. In conclusion, an added value of the AS03-containing vaccines in the prevention of body temperature rise after challenge was shown for both the split and sub-unit tested vaccines, by contrast to the inability of the MF59—containing vaccines to prevent this temperature rise in ferrets after challenge.

IX.3.2. Viral Shedding

Viral titration of nasal washes was performed on 6 animals per group. The nasal washes were performed by the administration of 5 ml of PBS in both nostrils in awake animals. The inoculation was collected in a Petri dish and placed into sample containers on dry ice (−80° C.).

All nasal samples were first sterile filtered through Spin X filters (Costar) to remove any bacterial contamination. 50 µl of serial ten-fold dilutions of nasal washes were transferred to microtiter plates containing 50 µl of medium (10 wells/dilution). 100 µl of MDCK cells ($2.4\times10^5$ cells/ml) were then added to each well and incubated at 35° C. for 5-7 days. After 5-7 days of incubation, the culture medium is gently removed and 100 µl of a 1/20 WST-1 containing medium is added and incubated for another 18 hrs.

The intensity of the yellow formazan dye produced upon reduction of WST-1 by viable cells is proportional to the number of viable cells present in the well at the end of the viral titration assay and is quantified by measuring the absorbance of each well at the appropriate wavelength (450 nanometers). The cut-off is defined as the OD average of uninfected control cells—0.3 OD (0.3 OD corresponds to +/−3 St Dev of OD of uninfected control cells). A positive score is defined when OD is <cut-off and in contrast a negative score is defined when OD is >cut-off. Viral shedding titers were determined by "Reed and Muench" and expressed as Log TCID50/ml.

Figure 20:
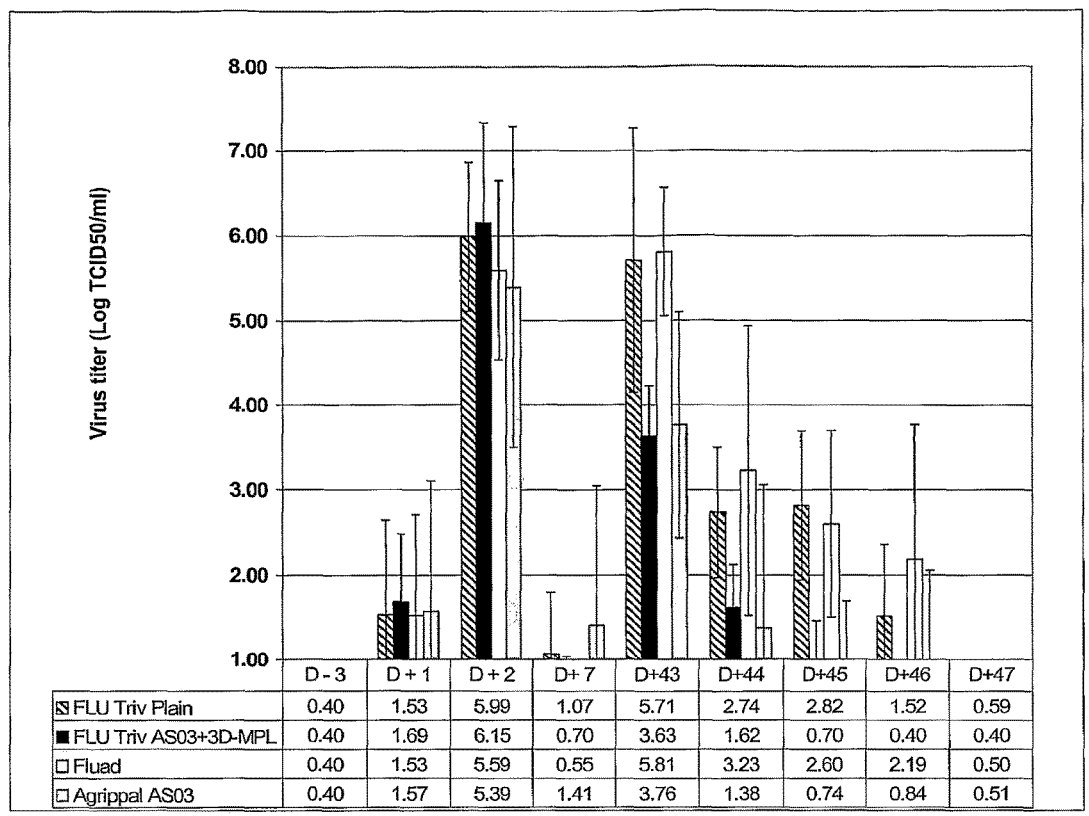

Results:

Results are shown in FIG. 20. Lower viral shedding was observed post-challenge with the trivalent split vaccine adjuvanted with AS03+MPL, or with the Agrippal™ sub-unit vaccine adjuvanted with AS03, as compared to the very low viral shedding reduction observed after immunization of ferrets with the un-adjuvanted (plain) trivalent split vaccine (FLUARIX®) or with FLUAD® sub-unit vaccine.

Similarly to what was discussed in respect of body temperature rise, an added value of the AS03-containing vaccines was observed compared to the MF59-containing vaccines.

IX.3.3. HI Titers

Anti-Hemagglutinin antibody titers to the H3N2 influenza virus strains were determined using the hemagglutination inhibition test (HI). The principle of the HI test is based on the ability of specific anti-Influenza antibodies to inhibit hemagglutination of chicken red blood cells (RBC) by influenza virus hemagglutinin (HA). Sera were first treated with a 25% neuraminidase solution (RDE) and were heat-inactivated to remove non-specific inhibitors. After pre-treatment, two-fold dilutions of sera were incubated with 4 hemagglutination units of each influenza strain. Chicken red blood cells were then added and the inhibition of agglutination was scored. The titers were expressed as the reciprocal of the highest dilution of serum that completely inhibited hemagglutination. As the first dilution of sera was 1:10, an undetectable level was scored as a titer equal to 5.

Figure 21:
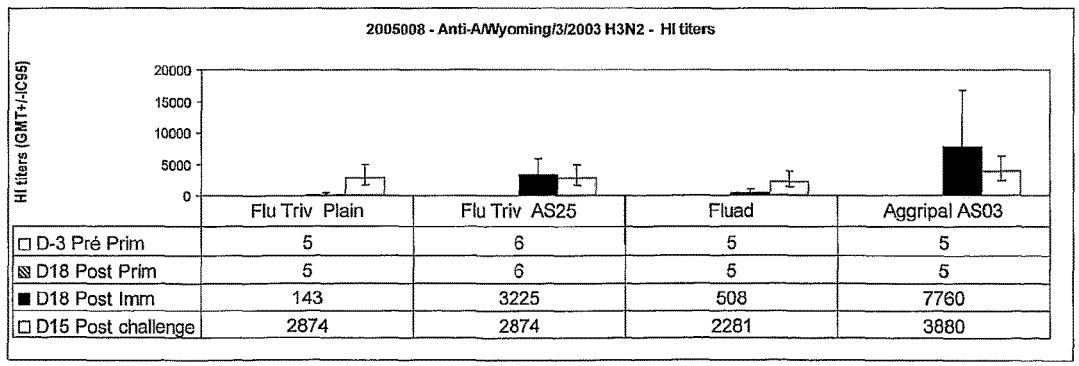

Results:

After immunization with H3N2 A/Wyoming, higher humoral responses (HI titers) were observed in ferrets immunized with the trivalent split vaccine adjuvanted with AS03+MPL or with the Agrippal™ sub-unit vaccine adjuvanted with AS03, as compared to the humoral response observed after immunization of ferrets with the un-adjuvanted (plain) trivalent split vaccine (FLUARIX®) or with FLUAD® sub-unit vaccine (FIG. 21).

Figure 22:
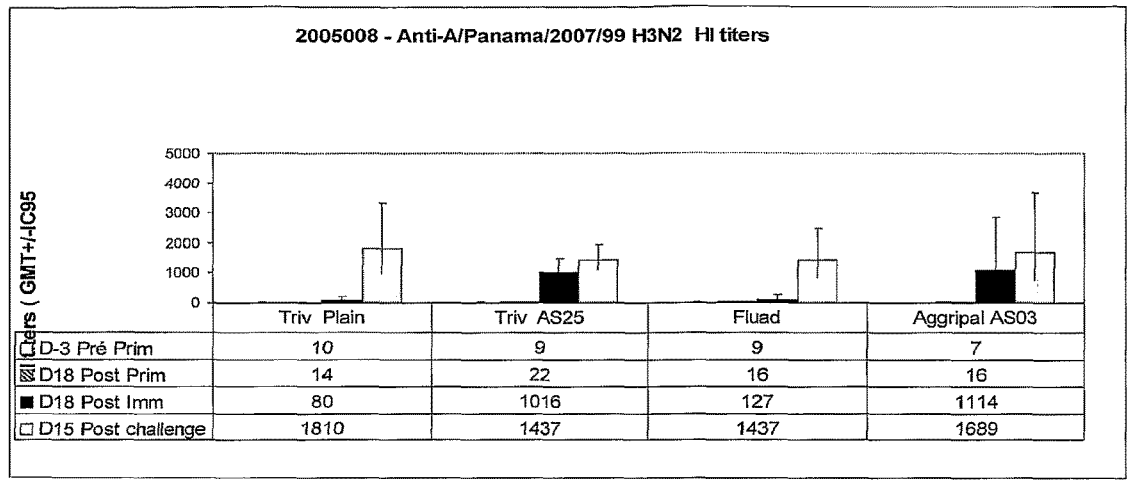

After immunization with H3N2 A/Wyoming, higher humoral responses (HI titers) were also observed against the drift strain H3N2 A/Panama, used as the challenge strain, in ferrets immunized with Trivalent Split adjuvanted with AS03+MPL or Agrippal™ adjuvanted with AS03 compared to ferrets immunized with Trivalent Split Plain or FLUAD® (FIG. 22).

This cross-reaction observed with our adjuvant (AS03 or AS03+MPL) against a heterologous strain correlated with the protection observed in ferrets immunized with the trivalent split vaccine adjuvanted with AS03+MPL or with the AGRIPPAL™ sub-unit vaccine adjuvanted with AS03, and then challenged with this heterologous strain. This cross-reactivity to heterologous strain induced by AS03-containing vaccines was not induced by the MF59's adjuvanted vaccines (FLUAD®).

EXAMPLE X

Clinical Trial in an Elderly Population Aged Over 65 Years with a Vaccine Containing a Split Influenza Antigen Preparation and AS03 with or without MPL Adjuvant: Immunogenicity Persistence Data at Day 90 and 180

X.1. Study Design

A phase I, open, randomised, controlled study in an elderly population aged over 65 years (≥65 years-old) in order to evaluate the reactogenicity and the immunogenicity of GlaxoSmithKline Biologicals influenza candidate vaccines containing the adjuvant AS03 or AS03+MPL, administered intramuscularly as compared to FLUARIX® vaccine (known as α-Rix™ in Belgium). This study follows that reported in Example VIII.

Three parallel groups were assessed:
one group of 50 subjects receiving one dose of the reconstituted and AS03 adjuvanted SV influenza vaccine (Flu AS03)
one group of 50 subjects receiving one dose of the reconstituted and Flu AS03+MPL adjuvanted SV influenza vaccine (Flu AS03+MPL)
one control group of 50 subjects receiving one dose of FLUARIX®

X.2. Immunogenicity Results

X.2.1. Humoral Immune Response Endpoints and Results

In order to evaluate the humoral immune response induced by the AS03 and AS03+MPL adjuvanted vaccines and its persistence, the following parameters were calculated for each treatment group.

At Days 0, 21, 90 and 180: serum haemagglutination-inhibition (HI) antibody titres, tested separately against each of the three influenza virus strains represented in the vaccine (anti-H1N1, anti-H3N2 & anti-B-antibodies).

Serum HI antibody GMTs' with 95% CI at Days 0, 21, 90 and 180
Seroconversion rates with 95% CI at Days 21, 90 and 180
Conversion factors with 95% CI at Day 21
Seroprotection rates with 95% CI at Days 0, 21, 90 and 180

Results

Figure 23:
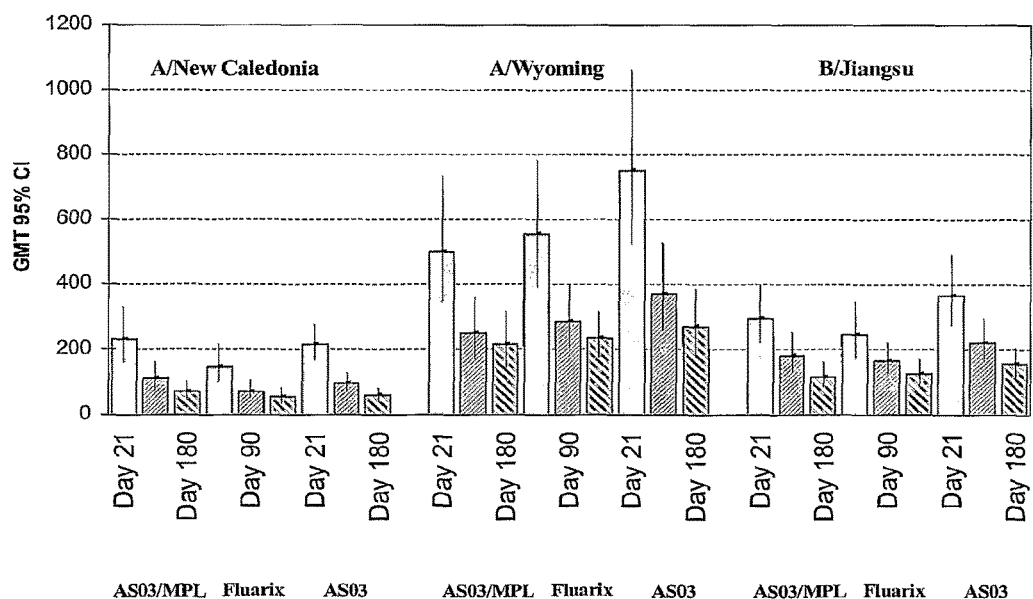

The GMTs for HI antibodies with 95% CI are shown in FIG. 23. Pre-vaccination GMTs of antibodies for all 3 vaccine-strains were within the same range in the 3 groups. After vaccinations, anti-haemagglutinin antibody levels increased significantly. Post-vaccination GMTs of antibodies for the 3 vaccine strains remained however within the same ranges for all vaccines. On Day 21, a slight tendency in favour of the 2 adjuvanted vaccines compared to FLUARIX® was noted for the A/New Caledonia and the B/Jiangsu strains and among the two adjuvanted vaccines, the higher GMTs were observed with FLU AS03 for the A/Wyoming and B/Jiangsu strains.

The same trends were observed at Day 90. On Day 180, GMTs of antibodies for the 3 vaccine strains were within the same ranges for the 3 vaccines.

All influenza vaccines fulfilled the requirements of the European authorities for annual registration of influenza inactivated vaccines ["Note for Guidance on Harmonisation of Requirements for Influenza Vaccines for the immunological assessment of the annual strain changes" (CPMP/BWP/214/96)] in subjects aged over 60 years.

Three months (90 days) and 6 months (180 days) after vaccination, the seroprotection rates were still higher than the minimum rate of 60% required by the European Authorities whatever the study group considered. On Day 90, the minimum seroconversion rate of 30% required by the European Authorities was still achieved for all vaccines strains in the 3 vaccine groups except with FLUARIX® for the A/New Caledonia strain. On Day 180, it was still achieved for the A/Wyoming and B/Jiangsu strains with the 3 vaccines but not for the A/New Caledonia strain (Table 43 and Table 44).

TABLE 43

Seroprotection rates as the percentage of vaccinees with a serum haemagglutination inhibition titre superior or equal to 1:40 (ATP cohort for immunogenicity)

| Antibody | Group | Timing | N | n | ≥1:40 % | 95% CI LL | 95% CI UL |
|---|---|---|---|---|---|---|---|
| A/ New Caledonia | Flu AS03 + MPL | PRE | 50 | 28 | 56.0 | 41.3 | 70.0 |
| | | PI(D 21) | 50 | 46 | 92.0 | 80.8 | 97.8 |
| | | PI(D 90) | 50 | 43 | 86.0 | 73.3 | 94.2 |
| | | PI(D 180) | 50 | 39 | 78.0 | 64.0 | 88.5 |
| | FLUARIX® | PRE | 50 | 26 | 52.0 | 37.4 | 66.3 |
| | | PI(D 21) | 50 | 46 | 92.0 | 80.8 | 97.8 |
| | | PI(D 90) | 50 | 38 | 76.0 | 61.8 | 86.9 |
| | | PI(D 180) | 50 | 34 | 68.0 | 53.3 | 80.5 |
| | FluAS03 | PRE | 49 | 28 | 57.1 | 42.2 | 71.2 |
| | | PI(D 21) | 49 | 48 | 98.0 | 89.1 | 99.9 |
| | | PI(D 90) | 49 | 45 | 91.8 | 80.4 | 97.7 |
| | | PI(D 180) | 49 | 38 | 77.6 | 63.4 | 88.2 |
| A/ Wyoming | Flu AS03 + MPL | PRE | 50 | 33 | 66.0 | 51.2 | 78.8 |
| | | PI(D 21) | 50 | 47 | 94.0 | 83.5 | 98.7 |
| | | PI(D 90) | 50 | 46 | 92.0 | 80.8 | 97.8 |
| | | PI(D 180) | 50 | 45 | 90.0 | 78.2 | 96.7 |
| | FLUARIX® | PRE | 50 | 32 | 64.0 | 49.2 | 77.1 |
| | | PI(D 21) | 50 | 50 | 100 | 92.9 | 100.0 |
| | | PI(D 90) | 50 | 49 | 98.0 | 89.4 | 99.9 |
| | | PI(D 180) | 50 | 50 | 100 | 92.9 | 100.0 |
| | FluAS03 | PRE | 49 | 34 | 69.4 | 54.6 | 81.7 |
| | | PI(D 21) | 49 | 48 | 98.0 | 89.1 | 99.9 |
| | | PI(D 90) | 49 | 46 | 93.9 | 83.1 | 98.7 |
| | | PI(D 180) | 49 | 47 | 95.9 | 86.0 | 99.5 |
| B/ Jiangsu | Flu AS03 + MPL | PRE | 50 | 19 | 38.0 | 24.7 | 52.8 |
| | | PI(D 21) | 50 | 50 | 100 | 92.9 | 100.0 |
| | | PI(D 90) | 50 | 47 | 94.0 | 83.5 | 98.7 |
| | | PI(D 180) | 50 | 46 | 92.0 | 80.8 | 97.8 |
| | FLUARIX® | PRE | 50 | 17 | 34.0 | 21.2 | 48.8 |
| | | PI(D 21) | 50 | 48 | 96.0 | 86.3 | 99.5 |
| | | PI(D 90) | 50 | 47 | 94.0 | 83.5 | 98.7 |
| | | PI(D 180) | 50 | 47 | 94.0 | 83.5 | 98.7 |
| | FluAS03 | PRE | 49 | 25 | 51.0 | 36.3 | 65.6 |
| | | PI(D 21) | 49 | 49 | 100 | 92.7 | 100.0 |
| | | PI(D 90) | 49 | 47 | 95.9 | 86.0 | 99.5 |
| | | PI(D 180) | 49 | 46 | 93.9 | 83.1 | 98.7 |

N = number of subjects with available results
n/% = number/percentage of subjects with titre within the specified range
PRE = pre-vaccination titre
PI (D 21) = post-vaccination blood sampling at Day 21
PI (D 90) = post-vaccination blood sampling at Day 90
PI (D 180) = post-vaccination blood sampling at Day 180

TABLE 44

Seroconversion rate for haemagglutination inhibition (HI) antibody titres defined as the percentage of vaccinees who have at least a 4-fold increase in serum HI titre at each post-vaccination time point compared to Day 0 (ATP cohort for immunogenicity)

| Vaccine strain | Timing | Group | N | n | 4-fold % | 95% CI LL | 95% CI UL |
|---|---|---|---|---|---|---|---|
| A/ NEW | Day 21 | Flu AS03 + MPL | 50 | 30 | 60.0 | 45.2 | 73.6 |
| | | FLUARIX® | 50 | 25 | 50.0 | 35.5 | 64.5 |

TABLE 44-continued

Seroconversion rate for haemagglutination inhibition (HI) antibody titres defined as the percentage of vaccinees who have at least a 4-fold increase in serum HI titre at each post-vaccination time point compared to Day 0 (ATP cohort for immunogenicity)

| Vaccine strain | Timing | Group | N | n | 4-fold % | 95% CI LL | UL |
|---|---|---|---|---|---|---|---|
| CALEDONIA | | Flu AS03 | 49 | 31 | 63.3 | 48.3 | 76.6 |
| | Day 90 | Flu AS03 + MPL | 50 | 19 | 38.0 | 24.7 | 52.8 |
| | | FLUARIX ® | 50 | 14 | 28.0 | 16.2 | 42.5 |
| | | Flu AS03 | 49 | 17 | 34.7 | 21.7 | 49.6 |
| | Day 180 | Flu AS03 + MPL | 50 | 12 | 24.0 | 13.1 | 38.2 |
| | | FLUARIX ® | 50 | 11 | 22.0 | 11.5 | 36.0 |
| | | Flu AS03 | 49 | 10 | 20.4 | 10.2 | 34.3 |
| A/ WYOMING | Day 21 | Flu AS03 + MPL | 50 | 46 | 92.0 | 80.8 | 97.8 |
| | | FLUARIX ® | 50 | 38 | 76.0 | 61.8 | 86.9 |
| | | Flu AS03 | 49 | 40 | 81.6 | 68.0 | 91.2 |
| | Day 90 | Flu AS03 + MPL | 50 | 33 | 66.0 | 51.2 | 78.8 |
| | | FLUARIX ® | 50 | 33 | 66.0 | 51.2 | 78.8 |
| | | Flu AS03 | 49 | 31 | 63.3 | 48.3 | 76.6 |
| | Day 180 | Flu AS03 + MPL | 50 | 27 | 54.0 | 39.3 | 68.2 |
| | | FLUARIX ® | 50 | 23 | 46.0 | 31.8 | 60.7 |
| | | Flu AS03 | 49 | 26 | 53.1 | 38.3 | 67.5 |
| B/ JIANGSU | Day 21 | Flu AS03 + MPL | 50 | 44 | 88.0 | 75.7 | 95.5 |
| | | FLUARIX ® | 50 | 38 | 76.0 | 61.8 | 86.9 |
| | | Flu AS03 | 49 | 43 | 87.8 | 75.2 | 95.4 |
| | Day 90 | Flu AS03 + MPL | 50 | 37 | 74.0 | 59.7 | 85.4 |
| | | FLUARIX ® | 50 | 36 | 72.0 | 57.5 | 83.8 |
| | | Flu AS03 | 49 | 37 | 75.5 | 61.1 | 86.7 |
| | Day 180 | Flu AS03 + MPL | 50 | 32 | 64.0 | 49.2 | 77.1 |
| | | FLUARIX ® | 50 | 29 | 58.0 | 43.2 | 71.8 |
| | | Flu AS03 | 49 | 31 | 63.3 | 48.3 | 76.6 |

N = number of subjects with both pre- and post-vaccination results available
n/% = number/percentage of subjects with at least a 4-fold increase
95% CI = exact 95% confidence interval; LL = lower limit, UL = upper limit

X.2.2. CMI Response Endpoints and Results

In order to evaluate the cellular immune response induced by the adjuvanted vaccines and its persistence, the following parameters were calculated for each treatment group:

At each time point (Days 0, 21, 90 and 180): frequency of cytokine-positive CD4/CD8 cells per $10^6$ in different tests (New Caledonia, Wyoming and Jiangsu antigens considered separately as well as pooled at Days 0 and 21; New Caledonia, Wyoming, Jiangsu and New York antigens considered separately as well as pooled at Days 90 and 180)

- All double: cells producing at least two different cytokines (CD40L, IFN-γ, IL-2, TNF-α).
- CD40L: cells producing at least CD40L and another cytokine (IFN-γ, IL-2, TNF-α).
- IFN-γ: cells producing at least IFN-γ and another cytokine (CD40L, IL-2, TNF-α).
- IL-2: cells producing at least IL-2 and another cytokine (CD40L, IFN-γ, TNF-α).
- TNF-α: cells producing at least TNF-α and another cytokine (CD40L, IFN-γ, IL-2).

Results

Figure 24:
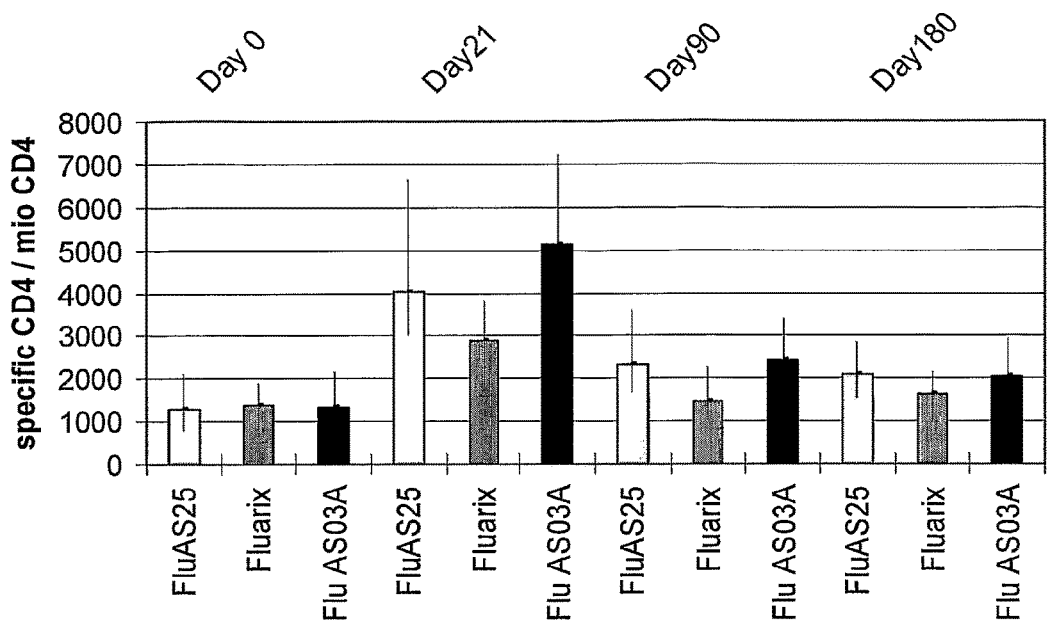

The main findings were (FIG. 24):

(a) Twenty-one days after the vaccination, the frequency of cytokine-positive CD4 T cells (IL-2, CD40L, TNF-α and IFN-γ) was significantly higher in the two adjuvanted vaccine groups compared to the FLUARIX® group. No significant difference was however detected between the two adjuvants.

(b) All statistical differences between adjuvanted vaccines and FLUARIX® were maintained up to Day 90 and Day 180 with the following exceptions at Day 180:

No statistically significant difference was found between FluAS03/MPL and FLUARIX® for all double, CD40L, IFN-γ and IL2 (Wyoming strain only) and for all double, CD40L and TNF-α (New York strain only)

No statistically significant difference was found between FluAS03 and FLUARIX® for IL2 (Jiangsu strain only)

(c) The absence of statistically significant difference between the two adjuvanted vaccines was confirmed up to Day 90 and Day 180.

(d) The difference between pre and post-vaccination (Day 21) in CD4 T-lymphocytes responses for all cytokines investigated (IL-2, CD40L, TNF-α and IFN-γ) was significantly higher with the two adjuvanted vaccines compared to FLUARIX®. No significant difference was however detected between both adjuvants.

(e) The vaccination had no measurable impact on the CD8 response whatever the treatment group.

EXAMPLE XI

Clinical Trial in an Elderly Population Aged Over 65 Years with a Vaccine Containing a Split Influenza Antigen Preparation and AS03 with MPL Adjuvant XI.1. Study Design and Objectives A phase I/II, open, controlled study was conducted in order to evaluate the reactogenicity and the immunogenicity of GlaxoSmithKline Biologicals influenza candidate vaccine containing the AS03+MPL adjuvant in an elderly population aged over 65 years (>65 years-old) previously vaccinated in 2004 with the same candidate vaccine. For immunogenicity and safety evaluations, FLUARIX® (known as α-RIX® in Belgium) vaccine was used as reference.

Two parallel groups were assessed:
One group of about 50 subjects who had previously received one dose of the reconstituted adjuvanted influenza vaccine during the previous clinical trial
One control group (FLUARIX®) of about 50 subjects who had previously received one dose of FLUARIX® during the previous clinical trial One objective of this study was to evaluate the humoral immune response (anti-haemagglutinin and anti-MPL titres) of the revaccination with the adjuvanted influenza vaccine Flu AS03+MPL administered about one year after administration of the first dose. For comparison purposes, subjects who had already received FLUARIX® in the previous trial received a dose of commercial vaccine and formed the control group of this trial.

XI.2. Vaccine Composition and Administration

The strains used in the three vaccines were the ones that had been recommended by the WHO for the 2005-2006 Northern Hemisphere season, i.e. A/New Caledonia /20/99 (H1N1), A/New California/7/2004 (H3N2) and B/Jiangsu/10/2003. Like FLUARIX®/α-RIX®, the commercially available vaccine used as a comparator, the (AS03+MPL— adjuvanted vaccine, hereinafter in short "the adjuvanted vaccine") contains 15 µg haemagglutinin (HA) of each influenza virus strain per dose.

The adjuvanted influenza candidate vaccine is a 2 component vaccine consisting of a concentrated trivalent inactivated split virion antigens presented in a type I glass vial and of a pre-filled type I glass syringe containing the AS03+MPL adjuvant. It has been prepared according the method detailed in Example II.

At the time of injection, the content of the prefilled syringe containing the adjuvant is injected into the vial that contains the concentrated trivalent inactivated split virion antigens. After mixing the content is withdrawn into the syringe and the needle is replaced by an intramuscular needle. One dose of the reconstituted the adjuvanted influenza candidate vaccine corresponds to 0.7 mL. The adjuvanted influenza candidate vaccine is a preservative-free vaccine.

The composition of one dose of the reconstituted adjuvanted influenza vaccine is given in Table 45. Both vaccines were given intramuscularly.

TABLE 45

Composition of the reconstituted vaccine adjuvanted (AS03 + MPL) influenza candidate vaccine

| Component | Quantity per dose |
|---|---|
| Inactivated split virions | |
| A/New Caledonia/20/99 (H1N1) | 15 µg HA |
| A/New California/7/2004 (H3N2) | 15 µg HA |
| B/Jiangsu/10/2003 | 15 µg HA |

TABLE 45-continued

Composition of the reconstituted vaccine adjuvanted (AS03 + MPL) influenza candidate vaccine

| Component | Quantity per dose |
|---|---|
| Adjuvant SB62 emulsion | |
| (squalene) | 10.68 mg |
| (DL-alpha-tocopherol) | 11.86 mg |
| (polysorbate 80 - TWEEN ® 80) | 4.85 mg |
| MPL | 25 µg |

XI.3. Immunogenicity Results
XI.3.1. Anti-HA Humoral Immune Response Endpoints and Results
Observed Variables:

At days 0 and 21: serum haemagglutination-inhibition (HI) antibody titres, tested separately against each of the three influenza virus strains represented in the vaccine (anti-H1N1, anti-H3N2 & anti-B-antibodies).

Derived Variables (with 95% Confidence Intervals):
(f) Geometric mean titres (GMTs) of serum HI antibodies with 95% confidence intervals (95% CI) pre and post-vaccination
(g) Seroconversion rates* with 95% CI at day 21
(h) Seroconversion factors** with 95% CI at day 21
(i) Seroprotection rates*** with 95% CI at day 21

* Seroconversion rate defined as the percentage of vaccinees with either a pre-vaccination HI titre<1:10 and a post-vaccination titre≥1:40, or a pre-vaccination titre≥1:10 and a minimum 4-fold increase at post-vaccination titre, for each vaccine strain.

**Seroconversion factor defined as the fold increase in serum HI GMTs on day 21 compared to day 0, for each vaccine strain.

***Protection rate defined as the percentage of vaccinees with a serum HI titre≥40 after vaccination (for each vaccine strain) that usually is accepted as indicating protection.

Results

Figure 25:
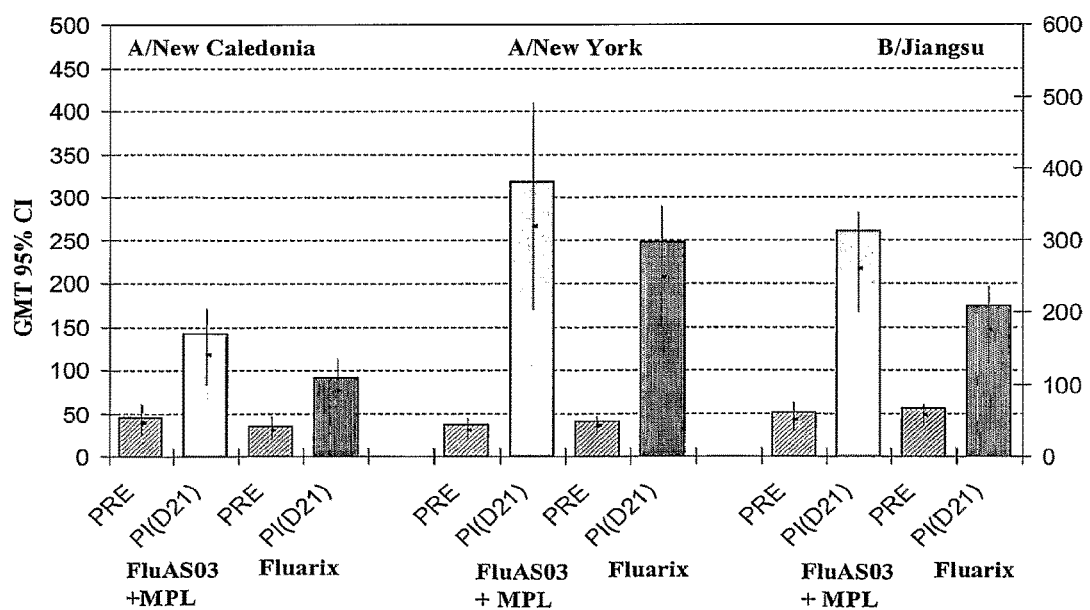

As expected, the vast majority of subjects were already seropositive for the three strains in both groups before vaccination. Pre-vaccination GMTs for all 3 vaccine strains were within the same range in the 2 groups. There was a trend for higher GMTs at post-vaccination for all 3 vaccine strains in the Flu AS03+MPL group compared to the FLUARIX® group, although 95% CI were overlapping (FIG. 25).

The two influenza vaccines fulfilled the requirements of the European authorities for annual registration of influenza inactivated vaccines ["Note for Guidance on Harmonisation of Requirements for Influenza Vaccines for the immunological assessment of the annual strain changes" (CPMP/BWP/214/96)] in subjects aged over 60 years (Table 46).

TABLE 46

Seroprotection rates seroconversion rates and conversion factors at day 21 (ATP cohort for immunogenicity)

| Strains | Group | N | Seroprotection rate (HI titre ≥40) % | Seroconversion rate (≥4-fold increase) [95% CI] | Seroconversion factor [95% CI] |
|---|---|---|---|---|---|
| EU standard (>60) | | | >60% | >30% | >2.0 |
| A/New Caledonia | Flu + MPL – AS03 | 38 | 89.5 [75.20-97.06] | 31.6 [17.5-48.7] | 3.1 [2.2-4.4] |
| | FLUARIX ® | 45 | 82.2 [67.95-92.00] | 31.1 [18.2-46.6] | 2.5 [1.8-3.5] |

TABLE 46-continued

Seroprotection rates seroconversion rates and conversion factors at day 21 (ATP cohort for immunogenicity)

| Strains | Group | N | Seroprotection rate (HI titre ≥40) % | Seroconversion rate (≥4-fold increase) [95% CI] | Seroconversion factor [95% CI] |
|---|---|---|---|---|---|
| A/New York (H3N2) | Flu + MPL – AS03 | 38 | 92.1 [78.62-98.34] | 78.9 [62.7-90.4] | 8.8 [6.1-12.5] |
| | FLUARIX ®* | 45 | 95.6 [84.85-99.46] | 68.9 [53.4-818] | 6.0 [4.4-8.3] |
| B/Jiangsu (B) | Flu + MPL – AS03 | 38 | 100 [90.75-100] | 57.9 [40.8-73.7] | 5.1 [3.7-7.0] |
| | FLUARIX ®* | 45 | 100 [92.13-100] | 37.8 [23.8-53.5] | 3.1 [2.4-4.0] |

N = total number of subject; % = Percentage of subjects with titre at day 21 within the specified range; CI = confidence interval

EXAMPLE XII

Clinical Trial in an Elderly Population Aged Over 65 Years with a Vaccine Containing a Split Influenza Antigen Preparation Adjuvanted with AS03 and MPL at Two Different Concentrations XII.1. Study Design and Objectives An open, randomized phase I/II study to demonstrate the non inferiority in term of cellular mediated immune response of GlaxoSmithKline Biologicals influenza candidate vaccines containing various adjuvants administered in elderly population (aged 65 years and older) as compared to FLUARIX® (known as α-RIX® in Belgium) administered in adults (18-40 years)

Four parallel groups were assigned:
(a) 75 adults (aged 18-40 years) in one control group receiving one dose of FLUARIX® (FLUARIX® group)
(b) 200 elderly subjects (aged 65 years and older) randomized 3:3:2 into three groups:
one group with 75 subjects receiving influenza vaccine adjuvanted with AS03+MPL (concentration 1-25 µg)
One group with 75 subjects receiving influenza vaccine adjuvanted with AS03+MPL (concentration 2-50 µg)
Reference Flu group with 50 subjects receiving one dose of FLUARIX®.

Primary Objective

The primary objective is to demonstrate the non inferiority 21 days post-vaccination of the influenza adjuvanted vaccines administered in elderly subjects (aged 65 years and older) as compared to FLUARIX® administered in adults (aged 18-40 years) in terms of frequency of influenza-specific CD4 T-lymphocytes producing at least two different cytokines (CD40L, IL-2, TNF-α, IFN-γ).

Secondary Objectives

The secondary objectives are
(a) To evaluate the safety and reactogenicity of vaccination with candidate influenza vaccines adjuvanted during 21 days following the intramuscular administration of the vaccine in elderly subjects (aged 65 years and older). FLUARIX® is used as reference.
(b) To evaluate the humoral immune response (anti-haemagglutinin titre) 21, 90 and 180 days after vaccination with influenza candidate vaccines adjuvanted. FLUARIX® is used as reference.

Tertiary Objective

The tertiary objective is to evaluate the cell mediated immune response (production of IFN-γ, IL-2, CD40L, and TNF-α and memory B-cell response) 21, 90 and 180 days after vaccination with adjuvanted influenza-vaccines. FLUARIX® is used as reference.

XII.2. Vaccine Composition and Administration

The influenza vaccine adjuvanted with AS03+MPL(25 µg per dose) system is also used in study illustrated in Example XI. The influenza vaccine adjuvanted with AS03+MPL(50 µg per dose) system is of identical composition except that the concentration of MPL is doubled. The process is the same as the one described in Example VIII for the influenza vaccine adjuvanted with AS03+MPL, with as only difference that the concentration of MPL is doubled.

Control: full dose of FLUARIX® by IM administration.

Four scheduled visits per subject: at days 0, 21, 90 and 180 with blood sample collected at each visit to evaluate immunogenicity.

Vaccination schedule: one injection of influenza vaccine at day 0

XII.3. Immunogenicity Results

XII.3.1. CMI Endpoints and Results

Evaluation of the Primary Endpoint.

At day 21: CMI response in all subjects in terms of frequency of influenza-specific CD4 T-lymphocyte per $10^6$ in tests producing at least two different cytokines (IL-2, IFN-γ, TNF-α and CD40L)

For evaluation of CMI response, frequency of influenza-specific CD4 are analysed as follows: The GM ratio in term of influenza-specific CD4 frequency between groups vaccinated with adjuvanted vaccines and Flu YNG is obtained using an ANCOVA model on the logarithm-transformed titres. The ANCOVA model includes the vaccine group as fixed effect and the pre-vaccination log-transformed titre as regressor. The GM ratio and their 98.75% CI are derived as exponential-transformation of the corresponding group contrast in the model. The 98.75% CI for the adjusted GM is obtained by exponential-transformation of the 98.75% CI for the group least square mean of the above ANCOVA model.

Results—Inferential Analysis (Table 47)

The adjusted GM and GM ratios (with their 98.75% CI) of influenza-specific CD4 T-lymphocyte producing at least two cytokines (IL-2, IFN-γ, TNF-α and CD40L) at day 21, after in vitro restimulation with "pooled antigens II", are presented in Table 47. For each adjuvanted influenza vaccine, the upper limit of two-sided 98.75% CI of GM ratio is far below the clinical limit of 2.0. This shows the non-inferiority of both adjuvanted influenza vaccines administered to elderly subjects compared to the FLUARIX® vaccine administered in adults aged between 18 and 40 years in term of post-vaccination frequency of influenza-specific CD4.

TABLE 47

Adjusted GM ratio of influenza-specific CD4 producing at least
two cytokines, Day 21 (ATP cohort for immunogenicity)

| Flu YNG | | AS03 + MPL (conc. 1) | | Adjusted GM ratio (Flu YNG/AS03 + MPL (conc. 1)) | | |
|---|---|---|---|---|---|---|
| | Adjusted | | Adjusted | | 98.8% CI | |
| N | GM | N | GM | Value | LL | UL |
| 70 | 1995.3 | 72 | 2430.0 | 0.82 | 0.65 | 1.04 |

| Flu YNG | | AS03 + MPL (conc. 2) | | Adjusted GM ratio (Flu YNG/AS03 + MPL (conc. 2)) | | |
|---|---|---|---|---|---|---|
| | Adjusted | | Adjusted | | 98.8% CI | |
| N | GM | N | GM | Value | LL | UL |
| 70 | 1979.4 | 72 | 2603.8 | 0.76 | 0.59 | 0.98 |

Figure 26:
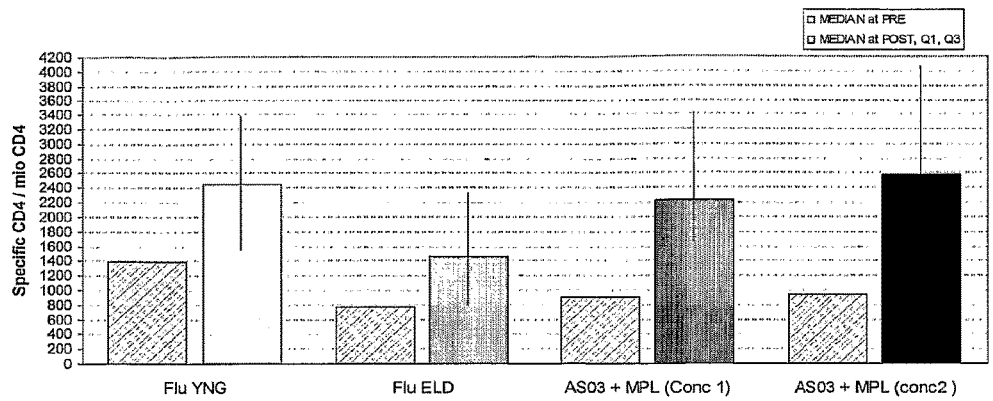

Adjusted GM = geometric mean antibody adjusted for baseline titre; N = Number of subjects with both pre- and post-vaccination results available; 98.8% CI = 98.8% confidence interval for the adjusted GM ratio (Ancova model: adjustment for baseline); LL = lower limit, UL = upper limit Results—Descriptive Analysis (FIG. 26)

The main findings were:

Before vaccination the CMI response if higher in young adults than in elderly

After vaccination,
there was a booster effect of the influenza vaccine on the CMI response in young adults (18-40 years)
CMI response in the elderly having received adjuvanted influenza vaccine is comparable to the CMI response of young adults.

The difference between pre and post-vaccination in CD4 T-lymphocytes responses for all cytokines investigated (IL-2, CD40L, TNF-α and IFN-γ) was significantly higher with the adjuvanted vaccines compared to FLUARIX® (18-40 years) for all tests excepted for IFNγ when we compare Fluarix (18-40 years) and Flu/AS03+MPL (conc. 1).

It should be noted that the in vitro stimulation was performed with the Flu strains (i) B/Jiangsu, (ii) A/H3N2/New-York and (iii) A/H3N2/Wyoming instead of A/H1N1/New-Caledonia included in the vaccine. However, preliminary data including the A/H1N1/New Caledonia vaccine strain from subsets of subjects indicate that the results will be similar.

Results—Evaluation of the Tertiary End-Point (Table 48)

In order to evaluate the tertiary end point, the frequency of influenza-specific CD4/CD8 T-lymphocytes and memory B-cells were measured at days 0, 21, 90 and 180. The frequency of influenza-specific cytokine-positive CD4/CD8 T-lymphocytes was summarised (descriptive statistics) for each vaccination group at days 0 and 21, for each antigen.

A Non-parametric test (Wilcoxon test) was used to compare the location of difference between the two groups (influenza adjuvanted vaccine versus FLUARIX®) and the statistical p-value is calculated for each antigen at each different test.

Descriptive statistics in individual difference between day 21/day 0 (Post-/Pre-vaccination) responses is calculated for each vaccination group and each antigen at each different test. A Non-parametric test (Wilcoxon test) is used to compare the individual difference Post-/Pre-vaccination) and the statistical p-value will be calculated for each antigen at each different test.

The p-values from Wilcoxon test used to compare the difference in the frequency of influenza-specific CD4 T-lymphocytes are presented in Table 48.

TABLE 48

Inferential statistics: p-values from Kruskal-Wallis Tests for
CD4 T cells at each time point (ATP Cohort for immunogenicity)

| | p-value | | | | | | | |
|---|---|---|---|---|---|---|---|---|
| | Group 1 and Flu ELD | | Group 2 and Flu ELD | | Group 1 and Flu YNG | | Group 2 and Flu YNG | |
| | day 0 | day 21 | day 0 | day 21 | day 0 | day 21 | day 0 | day 21 |
| ALL DOUBLES | 0.4380 | 0.0003 | 0.4380 | 0.0003 | 0.0000 | 0.9014 | 0.0005 | 0.4889 |
| CD40L | 0.3194 | 0.0002 | 0.3194 | 0.0002 | 0.0000 | 0.9841 | 0.0003 | 0.5412 |
| IFNγ | 0.5450 | 0.0004 | 0.5450 | 0.0004 | 0.0000 | 0.5397 | 0.0001 | 0.7895 |
| IL2 | 0.3701 | 0.0008 | 0.3701 | 0.0008 | 0.0003 | 0.8557 | 0.0022 | 0.4766 |
| TFNα | 0.3716 | 0.0004 | 0.3716 | 0.0004 | 0.0000 | 0.8730 | 0.0013 | 0.2114 |

Group 1: Influenza vaccine adjuvanted with AS03 + MPL (conc. 1)
Group 2: Influenza vaccine adjuvanted with AS03 + MPL (conc. 2)

The main conclusions are:
(a) Pre-vaccination GM frequencies of influenza-specific CD4 were similar in all groups of elderly subjects but superior in the adults aged between 18 and 40 years.
(b) Post-vaccination (day 21) frequency of influenza-specific CD4 T lymphocytes was similar in elderly subjects vaccinated with adjuvanted vaccines and in adults aged between 18 and 40 years vaccinated with FLUARIX®
(c) In elderly subjects, post-vaccination (day 21) frequency of influenza-specific CD4 T lymphocytes was significantly higher after vaccination with adjuvanted vaccines than with FLUARIX®.
(d) Pre-vaccination and post vaccination GM frequency of influenza-specific CD8 T cell was essentially similar in all groups.

Results—Evaluation of the Humoral Immune Response Endpoints
Observed Variables:
At days 0, 21, 90 and 180: serum haemagglutination-inhibition (HI) antibody titres, tested separately against each of the three influenza virus strains represented in the vaccine (anti-H1N1, anti-H3N2 & anti-B-antibodies).

The cut-off value for HI antibody against all vaccine antigens was defined by the laboratory before the analysis (and equals 1:10). A seronegative subject is a subject whose antibody titre is below the cut-off value. A seropositive subject is a subject whose antibody titre is greater than or equal to the cut-off value. Antibody titre below the cut-off of the assay is given an arbitrary value of half the cut-off.

Based on the HI antibody titres, the following parameters are calculated:
(j) Geometric mean titres (GMTs) of HI antibody at days 0 and 21, calculated by taking the anti-log of the mean of the log titre transformations.
(k) Seroconversion factors (SF) at day 21 defined as the fold increase in serum HI GMTs on day 21 compared to day 0.
(l) Seroconversion rates (SC) at day 21 defined as the percentage of vaccinees with either a pre-vaccination HI titre<1:10 and a post-vaccination titre≥1:40, or a pre-vaccination titre≥1:10 and a minimum 4-fold increase at post-vaccination titre.
(m) Seroprotection rates (SPR) at day 21 defined as the percentage of vaccinees with a serum HI titre≥1:40.

The 95% CI for GM is obtained within each group separately. The 95% CI for the mean of log-transformed titre is first obtained assuming that log-transformed titres are normally distributed with unknown variance. The 95% CI for the GM is then obtained by exponential-transformation of the 95% CI for the mean of log-transformed titre. Missing serological result for a particular antibody measurement is not replaced. Therefore a subject without serological result at a given time point do not contribute to the analysis of the assay for that time point.

Figure 27:
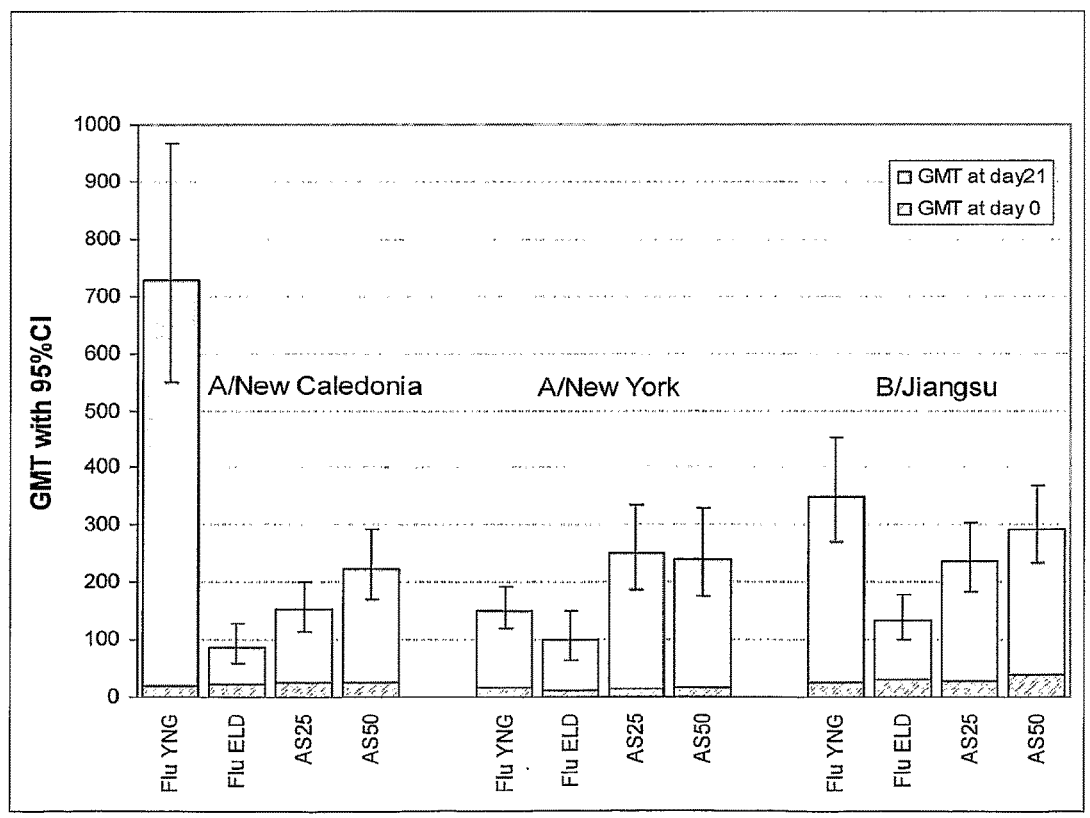

Humoral Immune Response Results (FIG. 27 and Table 49)
Pre-vaccination GMTs of HI antibodies for all 3 vaccine strains were within the same range in the 4 treatment groups. After vaccination, there is clear impact of the 2 adjuvants which increase the humoral response in elderly, compared to standard FLUARIX® in the same population.

GMTs are
significantly higher for H1N1 for AS03+MPL (conc. 2), significantly higher for H3N2 and for B for both adjuvants, Twenty one days after vaccination, the subjects of FLUARIX® (18-40 years) had a higher HI response for New Caledonia and B/Jangsu strains.

As shown in Table 49, the adjuvanted influenza vaccines exceeded the requirements of the European authorities for annual registration of split virion influenza vaccines ["Note for Guidance on Harmonization of Requirements for Influenza Vaccines for the immunological assessment of the annual strain changes" (CPMP/BWP/214/96)] in subjects aged over 60 years.

After vaccination, there was a statistically difference in terms of seroprotection rates of HI antibodies between FLUARIX® (≥65 years) group and
Flu AS03+MPL (conc 2) for A/New Caledonia strain
For each vaccine strain, the seroprotection rates for the 2 influenza adjuvanted vaccine groups are in the same range compared to FLUARIX® (18-40 years) group.

There was a statistically difference in terms of seroconversion rates of HI antibodies between FLUARIX® (65 years) group and
Flu AS03+MPL (conc 2) for A/New Caledonia strain
Flu AS03+MPL (conc 1) for B/Jiangsu strain
For each vaccine strain, the seroconversion rates for the 2 influenza adjuvanted vaccine groups are in the same range compared to FLUARIX® (18-40 years) group excepted for New Caledonia strain.

TABLE 49

Seroprotection rates seroconversion rates and conversion factors at day 21 (ATP cohort for immunogenicity)

| Strains | Group | N | Seroprotection rate (HI titre ≥40) % | Seroconversion rate (>4-fold increase) | Conversion factor [95% CI] |
|---|---|---|---|---|---|
| | EU standard (>60 years) | | >60% | >30% | >2.0 |
| | EU standard (<60 years) | | >70% | >40% | >2.5 |
| A/New Caledonia (H1N1) | Flu Yng | 75 | 100 [95.20-100] | 77.3 [66.2-86.2] | 35.1 [21.9-56.4] |
| | Flu Elderly | 49 | 71.4 [56.74-83.42] | 30.6 [18.3-45.4] | 3.7 [2.4-5.7] |
| | FluAS03 + MPL (conc. 1) | 75 | 90.5 [81.48-96.11] | 55.4 [43.4-67.0] | 6.4 [4.5-9.0] |
| | FluAS03 + MPL (conc. 2) | 75 | 98.7 [92.79-99.97] | 74.7 [63.3-84.0] | 9.2 [6.4-13.3] |
| A/New York (H3N2) | Flu Yng | 75 | 93.3 [85.12-97.80] | 76.0 [64.7-85.1] | 9.2 [7.1-11.8] |
| | Flu Elderly | 49 | 81.6 [67.98-91.24] | 69.4 [54.6-81.7] | 8.2 [5.7-11.8] |
| | FluAS03 + MPL (conc. 1) | 75 | 94.6 [86.73-98.51] | 90.5 [81.5-96.1] | 19.2 [14.6-25.3] |
| | FluAS03 + MPL (conc. 2) | 75 | 93.3 [85.12-97.80] | 82.7 [72.2-90.4] | 15.0 [11.2-20.2] |
| B/Jiangsu (B) | Flu Yng | 75 | 100 [95.20-100] | 80.0 [69.2-88.4] | 13.9 [10.1-19.1] |
| | Flu Elderly | 49 | 93.9 [83.13-98.72] | 81.3 [70.7-89.4] | 4.3 [3.0-6.1] |
| | FluAS03 + MPL (conc. 1) | 75 | 95.9 [88.61-99.16] | 73.0 [61.4-82.6] | 8.5 [6.5-11.2] |
| | FluAS03 + MPL (conc. 2) | 75 | 98.7 [92.79-99.97] | 66.7 [54.8-77.1] | 7.6 [5.6-10.2] |

N = total number of subject; % = Percentage of subjects with titre at day 21 within the specified range; CI = confidence interval XII.3.2. Immunogenicity Conclusions (a) Pre-vaccination frequency of influenza-specific CD4 was significantly inferior in elderly adults compared to adults aged between 18 and 40 years. After vaccination with FLUARIX® post-vaccination frequency (day 21) remained inferior in elderly adults compared to younger ones. On the contrary, the non-inferiority in term of frequency of post-vaccination frequency of influenza-specific CD4 after vaccination with adjuvanted vaccines of elderly subjects was demonstrated compared to vaccination with FLUARIX® in adults aged between 18 and 40 years.

(b) Regarding the humoral immune response in term of HI antibody response, all influenza vaccines fulfilled the requirements of the European authorities for annual registration of influenza inactivated vaccines ["Note for Guidance on Harmonisation of Requirements for Influenza Vaccines for the immunological assessment of the annual strain changes" (CPMP/BWP/214/96)]. In elderly adults, adjuvanted vaccines mediated at least a trend for a higher humoral immune response to influenza haemagglutinin than-FLUARIX®. Significant difference between the humoral immune response against each vaccine strain mediated in elderly subjects by adjuvanted vaccines compared to-FLUARIX® are summarised in Table 50. Compared to adults aged between 18 and 40 years vaccinated with FLUARIX®, elderly subjects vaccinated with the adjuvanted vaccines showed a trend for higher post-vaccination GMTs and seroconversion factor at day 21 against the A/New York strain.

TABLE 50

Significant difference in humoral immune response between adjuvanted vaccines and FLUARIX ® in elderly subjects

|  | Post-vacc GMT | Sero-conversion Factor | Sero-protection rate | Sero-conversion Rate |
|---|---|---|---|---|
| Flu AS03 + MPL (conc. 1) | A/New York B/Jiangsu | A/New York | — | B/Jiangsu |
| Flu AS03 + MPL (conc. 2) | A/New York B/Jiangsu A/New Caledonia | A/New Caledonia | A/New Caledonia | A/New Caledonia |

XII.4. Reactogenicity Results

XII.4.1. Recording of Adverse Events (AE)

Solicited symptoms (see Table 51) occurring during a 7-day follow-up period (day of vaccination and 6 subsequent days) were recorded. Unsolicited symptoms occurring during a 21-day follow-up period (day of vaccination and 20+3 subsequent days) were also recorded. Intensity of the following AEs was assessed as described in Table 52.

TABLE 51

Solicited local/general adverse events

| Solicited local AEs | Solicited general AEs |
|---|---|
| Pain at the injection site | Fatigue |
| Redness at the injection site | Fever |
| Swelling at the injection site | Headache |
| Haematoma | Muscle ache |
|  | Shivering |
|  | Joint pain in the arm of the injection |
|  | Joint pain at other locations |

N.B. Temperature was recorded in the evening. Should additional temperature measurements performed at other times of day, the highest temperature was recorded.

TABLE 52

Intensity scales for solicited symptoms in adults

| Adverse Event | Intensity grade | Parameter |
|---|---|---|
| Pain at injection site | 0 | Absent |
|  | 1 | on touch |
|  | 2 | when limb is moved |
|  | 3 | prevents normal activity |
| Redness at injection site |  | Record greatest surface diameter in mm |
| Swelling at injection site |  | Record greatest surface diameter in mm |
| Haematoma at injection site |  | Record greatest surface diameter in mm |
| Fever* |  | Record temperature in ° C./° F. |
| Headache | 0 | Absent |
|  | 1 | is easily tolerated |
|  | 2 | interferes with normal activity |
|  | 3 | prevents normal activity |
| Fatigue | 0 | Absent |
|  | 1 | is easily tolerated |
|  | 2 | interferes with normal activity |
|  | 3 | prevents normal activity |
| Joint pain at the injection site and other locations | 0 | Absent |
|  | 1 | is easily tolerated |
|  | 2 | interferes with normal activity |
|  | 3 | prevents normal activity |
| Muscle ache | 0 | Absent |
|  | 1 | is easily tolerated |
|  | 2 | interferes with normal activity |
|  | 3 | prevents normal activity |
| Shivering | 0 | Absent |
|  | 1 | is easily tolerated |
|  | 2 | interferes with normal activity |
|  | 3 | prevents normal activity |

*Fever is defined as axillary temperature ≥37.5° C. (99.5° F.)

The maximum intensity of local injection site redness/swelling is scored as follows:

0 is 0 mm; 1 is >0-≤20 mm; 2 is >20-≤50 mm; 3 is >50 mm.

The maximum intensity of fever is scored as follows:

1 is >37.5-≤38.0° C.; 2 is >38.0-≤39.0° C.; 3 is >39.0

The investigator makes an assessment of intensity for all other AEs, i.e. unsolicited symptoms, including SAEs reported during the study. The assessment is based on the investigator's clinical judgement. The intensity of each AE recorded is assigned to one of the following categories:

1 (mild)=An AE which is easily tolerated by the subject, causing minimal discomfort and not interfering with everyday activities;

2 (moderate)=An AE which is sufficiently discomforting to interfere with normal everyday activities;

3 (severe)=An AE which prevents normal, everyday activities (In adults/adolescents, such an AE would, for example, prevent attendance at work/school and would necessitate the administration of corrective therapy).

XII.4.2. Recording of Adverse Events (AE)

The reactogenicity observed in elderly subjects with adjuvanted vaccines, in terms of both local and general symptoms, was found to be higher than with FLUARIX® in the same population. However, it was shown to be similar to the level seen in the adult population. The incidence and the intensity of symptoms was increased after vaccination with adjuvanted vaccines compared to the reactogenity seen in elderly subjects with FLUARIX® (FIG. 28). In all cases, symptoms resolved rapidly.

Grade 3 symptoms showed a trend to be higher in the group who received the vaccine adjuvanted with the highest MPL concentration compared to the group who received the adjuvanted vaccine wherein the MPL is at a lower concentration. In all cases, symptoms however resolved rapidly.

We claim:

1. A method of vaccinating a human elderly against influenza, wherein the human elderly is at least 50 years of age, the method comprising: administering to the human elderly an immunogenic composition comprising
   (i) an influenza virus or antigenic preparation thereof and
   (ii) an oil-in-water emulsion adjuvant, wherein the oil-in-water emulsion adjuvant comprises a metabolisable oil, alpha-tocopherol, and an emulsifying agent;
   wherein the influenza virus or an antigenic preparation comprises antigen from an influenza virus strain to which the human elderly is immunologically naïve; wherein the influenza virus strain is selected from the group consisting of: H2, H5, H6, H7, and H9; and
   wherein the immunogenic composition comprises a haemagglutinin (HA) antigen from the influenza virus strain and contains 1 microgram to 7.5 micrograms of the HA antigen as measured by single radial immunodiffusion (SRD).

2. The method of claim 1, wherein the human elderly is at least 65 years of age.

3. The method of claim 1, wherein the metabolisable oil is squalene.

4. The method of claim 1, wherein the emulsifying agent is polysorbate 80.

5. The method of claim 1, wherein the metabolisable oil is squalene and the emulsifying agent is polysorbate 80.

6. The method of claim 1, wherein the immunogenic composition is multivalent.

7. The method of claim 1, wherein the immunogenic composition is trivalent.

8. The method of claim 1, wherein the influenza virus or antigenic preparation of the immunogenic composition is egg-derived or tissue-culture derived.

9. The method of claim 1, wherein the influenza virus or antigenic preparation of the immunogenic composition is selected from the group consisting of: a split influenza virus, a whole influenza virus, an influenza sub-unit, and an influenza virosome.

10. The method of claim 1, wherein the influenza virus of the immunogenic composition is a split influenza virus or antigenic preparation thereof.

11. The method of claim 1, wherein the oil-in-water emulsion adjuvant of the immunogenic composition comprises squalene in an amount of 0.5% to 20% of the total volume.

12. The method of claim 1, wherein the oil-in water emulsion adjuvant of the immunogenic composition contains oil droplets of which at least 80% by intensity are less than 300 nm in diameter.

13. The method of claim 1, wherein the emulsifying agent is present at an amount of 0.01% to 5.0% by weight (w/w) of said immunogenic composition.

14. The method of claim 1, wherein the alpha-tocopherol is present at an amount of 0.2% to 5.0% (v/v) of said immunogenic composition.

15. The method of claim 1, wherein the oil-in-water emulsion adjuvant of the immunogenic composition comprises 2.5% (v/v) squalene, 2.5% (v/v) alpha-tocopherol, and 0.9% (v/v) polysorbate 80.

16. The method of claim 1, wherein said immunogenic composition contains 3.5 micrograms to 5 micrograms of the HA antigen of the influenza virus as measured by single radial immunodiffusion (SRD).

17. The method of claim 1, wherein the immunogenic composition comprises an influenza virus or an antigenic preparation from an H5 influenza virus strain.

18. The method of claim 1, wherein the immunogenic composition comprises an influenza virus or an antigenic preparation from an influenza virus strain selected from the group consisting of: H5N1, H9N2, H7N7, and H2N2.

19. The method of claim 1, wherein the immunogenic composition comprises an influenza virus or an antigenic preparation from an H5N1 influenza virus strain.

20. The method of claim 1, wherein the immunogenic composition is monovalent.

21. The method of claim 1, wherein said immunogenic composition contains 3.75 micrograms of the HA antigen of the influenza virus as measured by single radial immunodiffusion (SRD).

* * * * *